United States Patent
Masci et al.

(10) Patent No.: US 11,103,560 B2
(45) Date of Patent: *Aug. 31, 2021

(54) CLOTTING COMPOSITION

(71) Applicant: Q-SERA PTY LTD., Melbourne (AU)

(72) Inventors: Paul Masci, Brisbane (AU); Kong-Nan Zhao, Brisbane (AU); Martin Lavin, Brisbane (AU); John De Jersey, Brisbane (AU); Goce Dimeski, Hamilton (AU)

(73) Assignee: Q-SERA PTY LTD., Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,543

(22) Filed: Aug. 4, 2020

(65) Prior Publication Data

US 2021/0000925 A1 Jan. 7, 2021

Related U.S. Application Data

(63) Continuation of application No. 15/518,215, filed as application No. PCT/AU2015/000629 on Oct. 23, 2015, now Pat. No. 10,786,553.

(30) Foreign Application Priority Data

Oct. 23, 2014 (AU) .............................. 2014904241

(51) Int. Cl.

| | | |
|---|---|---|
| A61K 38/36 | (2006.01) | |
| C12Q 1/56 | (2006.01) | |
| G01N 33/86 | (2006.01) | |
| A61K 38/17 | (2006.01) | |
| A61K 38/38 | (2006.01) | |
| A61K 38/48 | (2006.01) | |
| C12N 9/64 | (2006.01) | |
| A61K 38/00 | (2006.01) | |
| G01N 33/00 | (2006.01) | |

(52) U.S. Cl.
CPC .......... *A61K 38/36* (2013.01); *A61K 38/1703* (2013.01); *A61K 38/38* (2013.01); *A61K 38/4806* (2013.01); *C12N 9/6418* (2013.01); *C12Q 1/56* (2013.01); *C12Y 304/21006* (2013.01); *G01N 33/86* (2013.01); *A61K 38/00* (2013.01); *G01N 33/00* (2013.01)

(58) Field of Classification Search
CPC .................................................... A61K 38/36
See application file for complete search history.

(56) References Cited

U.S. PATENT DOCUMENTS

| | | | |
|---|---|---|---|
| 4,265,927 A | 5/1981 | Ericksson et al. | |
| 5,089,415 A | 2/1992 | La Duca | |
| 2013/0273584 A1 | 10/2013 | Masci et al. | |

FOREIGN PATENT DOCUMENTS

| | | | | |
|---|---|---|---|---|
| CN | 1520880 A | 8/2004 | | |
| EP | 0 585 504 A1 | 3/1994 | | |
| EP | 0585504 A1 | * 3/1994 | ............. | C07K 14/46 |
| GB | 2 433 592 A | 6/2007 | | |
| JP | 06-199673 A | 7/1994 | | |
| JP | 2004-524322 A | 8/2004 | | |
| JP | 2011-196996 A | 10/2011 | | |
| JP | 2013-537308 A | 9/2013 | | |
| WO | WO-01/44493 A2 | 6/2001 | | |
| WO | WO-2005/076002 A1 | 8/2005 | | |
| WO | WO-2007/072197 A1 | 6/2007 | | |
| WO | WO-2012/037609 A1 | 3/2012 | | |

OTHER PUBLICATIONS

Matafanov et al. Blood, Jul. 14, 2011. vol. 118, No. 2.*
"4.1 Surface Engineering of Blood Contacting Biomaterials" Surface Engineering of Polymeric Biomaterials, Smithers Rapra Technology Ltd., pp. 231-294 (Jan. 2013).
Erber et al., "Development of cryopelletization and formulation measures to improve stability of Echis carinatus venum protein for use in diagnostic rotational thromboelastometry", International Journal of Pharmaceutics 495: 692-700 (2015).
European Extended Search Report on Ep 15852949.5 dated Jun. 22, 2018.
European Extended Search Report, dated Jun. 22, 2018, issued in European Patent Application No. 15852949.5.
International Search Report and Written Opinion for PCT/AU2015/000629 dated Jan. 20, 2016.
Joseph et al., "Effect of snake venom procoagulants on snake plasma: implications for the coagulation cascade of snakes", Toxicon 40: 175-183 (2002).

* cited by examiner

*Primary Examiner* — Jeanette M Lieb
(74) *Attorney, Agent, or Firm* — Foley & Lardner LLP

(57) ABSTRACT

The present invention relates to improved clotting compositions for producing high quality blood serum samples for analyte testing, such as for pathology testing and other biological assays. In particular, the present invention relates to the use of prothrombin activators in combination with stabilizing agents such as colloids for producing high quality blood serum samples. The present invention also relates to associated methods for preparing clotting compositions, tubes, kits and methods of diagnosis, prognosis and monitoring for responsiveness to therapy.

3 Claims, 26 Drawing Sheets

Specification includes a Sequence Listing.

(A)

(B)

SEQUENCE LISTING

```
<160> NUMBER OF SEQ ID NOS: 57

<210> SEQ ID NO 1
<211> LENGTH: 609
<212> TYPE: PRT
<213> ORGANISM: Echis carinatus

<400> SEQUENCE: 1

Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val His Leu Glu Lys Asn Lys Glu Leu Phe Ser
65                  70                  75                  80

Glu Asp Tyr Ser Glu Thr His Tyr Ser Ser Asp Asp Arg Glu Ile Thr
                85                  90                  95

Thr Asn Pro Ser Val Glu Asp His Cys Tyr Tyr His Gly Arg Ile Gln
            100                 105                 110

Asn Asp Ala Glu Ser Thr Ala Ser Ile Ser Ala Cys Asn Gly Leu Lys
        115                 120                 125

Gly His Phe Lys Leu Arg Gly Glu Thr Tyr Phe Ile Glu Pro Leu Lys
    130                 135                 140

Ile Pro Asp Ser Glu His Ala Val Tyr Lys Tyr Glu Asn Ile Glu Asn
145                 150                 155                 160

Glu Asp Glu Ala Pro Lys Met Cys Gly Val Thr Gln Asp Asn Trp Glu
                165                 170                 175

Ser Asp Glu Pro Ile Lys Lys Thr Leu Gly Leu Ile Val Pro Pro His
            180                 185                 190

Glu Arg Lys Phe Glu Lys Lys Phe Ile Glu Leu Val Val Val Val Asp
        195                 200                 205

His Ser Met Val Thr Lys Tyr Asn Asn Asp Ser Thr Ala Ile Arg Thr
    210                 215                 220

Trp Ile Tyr Glu Leu Asn Thr Val Asn Glu Ile Tyr Leu Pro Phe Asn
225                 230                 235                 240

Ile Arg Val Ala Leu Val Gly Leu Glu Phe Trp Cys Asn Gly Asp Leu
                245                 250                 255
```

```
Ile Asn Val Thr Ser Thr Ala Asp Asp Thr Leu His Ser Phe Gly Glu
            260                 265                 270

Trp Arg Ala Ser Asp Leu Leu Asn Arg Lys Arg His Asp His Ala Gln
        275                 280                 285

Leu Leu Thr Asn Val Thr Leu Asp His Ser Thr Leu Gly Ile Thr Phe
    290                 295                 300

Val Tyr Gly Cys Lys Ser Asp Arg Ser Val Glu Leu Ile Leu Asp Tyr
305                 310                 315                 320

Ser Asn Ile Thr Phe Asn Met Ala Tyr Ile Ile Ala His Glu Met Gly
                325                 330                 335

His Ser Leu Gly Met Leu His Asp Thr Lys Phe Cys Thr Cys Gly Ala
            340                 345                 350

Lys Pro Cys Ile Met Phe Gly Lys Glu Ser Ile Pro Pro Pro Lys Glu
        355                 360                 365

Phe Ser Ser Cys Ser Tyr Asp Gln Tyr Asn Lys Tyr Leu Leu Lys Tyr
    370                 375                 380

Asn Pro Cys Ile Leu Asp Pro Pro Leu Arg Lys Asp Ile Ala Ser Pro
385                 390                 395                 400

Ala Val Cys Gly Asn Glu Ile Trp Glu Glu Gly Glu Glu Cys Asp Cys
                405                 410                 415

Gly Ser Pro Ala Asp Cys Arg Asn Pro Cys Cys Asp Ala Ala Thr Cys
            420                 425                 430

Lys Leu Lys Pro Gly Ala Glu Cys Gly Asn Gly Glu Cys Cys Asp Lys
        435                 440                 445

Cys Lys Ile Arg Lys Ala Gly Thr Glu Cys Arg Pro Ala Arg Asp Asp
450                 455                 460

Cys Val Ala Glu His Cys Thr Gly Gln Ser Ala Glu Cys Pro Arg Asn
465                 470                 475                 480

Glu Phe Gln Arg Asn Gly Gln Pro Cys Leu Asn Asn Ser Gly Tyr Cys
                485                 490                 495

Tyr Asn Gly Asp Cys Pro Ile Met Leu Asn Gln Cys Ile Ala Leu Phe
            500                 505                 510

Ser Pro Ser Ala Thr Val Ala Gln Asp Ser Cys Phe Gln Arg Asn Leu
        515                 520                 525

Gln Gly Ser Tyr Tyr Gly Tyr Cys Thr Lys Glu Ile Gly Tyr Tyr Gly
    530                 535                 540

Arg Phe Pro Cys Ala Pro Gln Asp Val Lys Cys Gly Arg Leu Tyr Cys
545                 550                 555                 560

Leu Asp Asn Ser Phe Lys Lys Asn Met Arg Cys Lys Asn Asp Tyr Ser
                565                 570                 575

Tyr Ala Asp Glu Asn Lys Gly Ile Val Glu Pro Gly Thr Lys Cys Glu
            580                 585                 590

Asp Gly Lys Val Cys Ile Asn Arg Lys Cys Val Asp Val Asn Thr Ala
        595                 600                 605

Tyr

<210> SEQ ID NO 2
<211> LENGTH: 63
<212> TYPE: PRT
<213> ORGANISM: Bothrops asper

<400> SEQUENCE: 2

Ser His Asp Asn Ala Gln Leu Leu Thr Ala Ile Lys Ala Tyr Ile Ala
1               5                   10                  15
```

Thr Met Cys Asp Pro Lys Met Ala Val Ile Met Ala His Glu Ile Gly
            20                  25                  30

His Gly Gly Tyr Tyr Gly Tyr Cys Arg Lys Ile Pro Cys Ala Pro Glu
        35                  40                  45

Asp Val Lys Asp Asp Ile Gly Met Val Leu Pro Gly Thr Lys
    50                  55                  60

<210> SEQ ID NO 3
<211> LENGTH: 32
<212> TYPE: PRT
<213> ORGANISM: Echis carinatus
<220> FEATURE:
<221> NAME/KEY: MOD_RES
<222> LOCATION: (23)..(23)
<223> OTHER INFORMATION: Any naturally occurring amino acid
<220> FEATURE:
<221> NAME/KEY: MOD_RES
<222> LOCATION: (25)..(25)
<223> OTHER INFORMATION: Any naturally occurring amino acid

<400> SEQUENCE: 3

Ser Arg Lys Gln Lys Phe Asp Lys Lys Phe Ile Lys Leu Val Ile Val
1               5                   10                  15

Val Asp His Ser Met Val Xaa Lys Xaa Asn Asn Asp Leu Ile Ala Ile
            20                  25                  30

<210> SEQ ID NO 4
<211> LENGTH: 29
<212> TYPE: PRT
<213> ORGANISM: Echis multisquamatus

<400> SEQUENCE: 4

Asp Cys Leu Pro Gly Trp Ser Val Tyr Glu Gly Arg Cys Tyr Lys Val
1               5                   10                  15

Phe Asn Gln Lys Thr Trp Lys Ala Ala Glu Lys Phe Cys
            20                  25

<210> SEQ ID NO 5
<211> LENGTH: 4737
<212> TYPE: DNA
<213> ORGANISM: Pseudonaja textilis

<400> SEQUENCE: 5
gagccacaga atacatttat gtggggaagt ggcaagttgc tgcaggcaga actgactttt      60
gtatatcttt cagcacatta gcctcaatgg aagatacag tgtgagccct gtccccaaat      120
gtcttctact gatgttcctg ggttggtcag ggctgaagta ttacgaagtg aatgcagctc      180
agctcaggga gtaccatata gctgctcagc tggaagactg ggattacaac ccccaacctg      240
aggagctatc cagattatca gagtcagatc ttacgtttaa aaaaattgtc tatagagaat      300
atgaactaga tttcaaacaa gagaagccaa gagatgagct ctcagggctc ctagggccaa      360
cactacgtgg agaagtggga gacatcctca aatttattt caagaatttt gctactcagc      420
ctgtgagcat tcacccgcag agtgccgtgt acaacaaatg gtcagaaggt tcttcatatt      480
ctgatggaac atcagatgtg gaagactgg atgatgctgt gcctccaggc cagtcgttca      540
agtatgtgtg gaatatcact gcagaaattg ggccaagaa agctgatcct ccctgtctca      600
cttatgcgta ctactcacat gtaaacatgg tgcgagactt taattctggt ctcattggtg      660
ctttgctgat atgtaaagaa ggaagcctga atgcaaatgg ttcacaaaaa ttcttcaaca      720
gagaatatgt gctgatgttt tctgtgtttg atgaaagcaa gaactggtac agaaagccct      780

```
cactacagta cacaattaat gggtttgcca atggaacatt gcctgatgtt caggcttgtg     840
cttatgatca tattagctgg catttgatag gaatgagttc cagtcctgag atcttctctg     900
ttcacttcaa tggacaaacc ttggaacaaa accattacaa agtgtcaacc atcaaccttg     960
tcggaggtgc ctcagtaaca gccaacatgt cagtgagcag acaggaaaaa tggctaatat    1020
cttctctggt tgcaaagcat ctacaagctg ggatgtatgg ttatctaaat atcaaagact    1080
gtggaaatcc agatacttta acaagaaagt tatcctttag agaactgagg aggattatga    1140
actgggaata tttcattgct gcagaagaaa tcacctggga ttatgctcca gaaattccta    1200
gcagtgttga cagaagatac aaagctcagt atctggataa ttttttcaaat tttattggca    1260 agaaatacaa aaaggcagtt ttcaggcaat ataaagacag caatttcact aaaccgacct    1320
atgccatttg gcccaaagaa cgtggaattc tgggccccgt tatcagagct aaagtcagag    1380
acacaataag tattgtattc aaaaatctgg ccagtcgacc ttacagcatt tatgtgcatg    1440
gagtttccgt ttcaaaagat gcagaaggag ctatttatcc ttcagatccc aaagagaata    1500
taactcatgg caaagcagtt gaaccaggac aggtctacac atataaatgg actgtgctgg    1560
atacagatga acctacagta aaggattctg agtgcattac taaattatat catagtgctg    1620
tggacatgac aagagatatt gcttcaggac ttattgggcc acttctggtt tgtaaacaca    1680
aggcactcag cgtcaagggc gtacagaata aagctgatgt ggaacagcat gcagtcttcg    1740
cagtgtttga tgaaaacaag agctggtact tggaagacaa tatcaagaaa tactgcagca    1800
atccttccac tgttaagaaa gatgacccta aattttacaa gtccaatgtt atgtacacac    1860
tcaatggcta tgcatcagat agaacagagg ttttggggtt tcatcagtct gaagttgttg    1920
aatggcacct caccagcgta ggtacagtgg atgagattgt tccagtacat ctttctggtc    1980
acaccttctt atccaaggga aaacatcaag atattttaaa tctttttcccc atgagtggtg    2040 aatcggctac tgtaacaatg gacaatctag gaacctggct tctgtcatca tggggctcct    2100
gtgagatgag caatggcatg agattgagat ttttggatgc caattatgat gatgaagatg    2160
agggaaatga agaagaggaa gaagatgatg gcgatatttt tgccgacatt ttcattcctc    2220
cagaagtagt aaaaaagaaa gaaaaggacc ccgtaaattt tgtatcagac ccagaatcgg    2280
ataagatagc aaaagaatta ggattattag atgacgagga taatcaagaa gagtcacaca    2340
atgtacagac agaggatgat gaagaacagc taatgatagc tacaatgctt gggtttcgat    2400
catttaaggg gtcagttgct gaagaagaat tgaatctcac agctctagct ttagaagaag    2460
atgcccatgc ttctgatcct cgaattgaca gtaatagtgc acgtaatcct gatgacatag    2520
ctggacgcta cctgcgtact atcaaccgtg aaataaaag gaggtactac attgcagcag    2580
aagaagtttt gtgggactac tcaccgatcg gaaaaagtca agtgagaagt cgcgcagcca    2640
agaccacatt caaaaaagct atttttccgaa gttatcttga tgatactttc cagacaccta    2700
gcactggagg agaatatgaa aagcatcttg gtatactggg tcctatcatt agggctgagg    2760
tggatgatgt aatcgaagtt cagttcagaa atttggcctc cagaccatac tcacttcatg    2820
ctcatggcct tctctatgag aaatcttctg aaggcagaag ctatgatgac aagtctcctg    2880
aattgttcaa aaaggatgat gctatcatgc caaacgcac atacatatat gtctggcaag    2940
tccctccacg gtcaggacca acagacaata cagaaaaatg taaatcatgg gcctattact    3000
ctggtgtaaa tccggaaaaa gatattcact ctggcttaat tggacctatt ttgatctgcc    3060
agaaaggcat gattgacaag tacaacagga caatagacat aagggaattt gtcttgtttt    3120
ttatggtctt tgatgaggag aaaagctggt actttccaaa atctgacaaa agcactcgtg    3180
```

```
cagagaaact tataggagtc caatctcgcc acacatttcc tgcaattaat gggatccctt      3240
atcagctgca aggcttgacg atgtacaaag atgagaatgt ccactggcat ttgctgaaca      3300
tgggtgggcc caaagatatc catgttgtta attttcatgg tcagacattc actgaagagg      3360
gaagggaaga taatcaactt ggagtccttc ctcttcttcc tggtacattc gcctccatca      3420
aaatgaaacc atccaaaatt ggcacatggc ttttagaaac agaagttggt gaaaatcagg      3480
aaagaggaat gcaggctctc tttactgtca ttgacaaaga ttgtaaatta ccaatgggac      3540
tggcaagtgg gataatacaa gactcacaga tcagtgcttc aggtcatgtt ggatattggg      3600
agcctaagct agcaagactg aataatactg gaaaatataa tgcttggagc atcataaaga      3660
aggaacatga acatccgtgg atccagatag acctacaaag acaagttgtc atcacaggca      3720
ttcagaccca aggagccatg caactactga acatttgta tactgtggaa tatttttta       3780 cctacagcaa agatgggcaa aactggatta cttttaaagg aagacattcc gaaacacaaa      3840
tgcattttga gggtaattca gatggcacca cagtaaaaga aaaccacatt gatcctccta      3900
ttattgccag atatattagg ctgcatccaa ccaagttcca caacagacct actttccgca      3960
ttgaactgtt aggttgtgaa gttgaaggct gctcagtgcc attgggaatg gaaagtgggg      4020
ctatcaagaa ttcagagatt acagcctctt cttataagaa gacttggtgg agttcatggg      4080
aaccatccct tgcacgactc aatctgaaag gacgaacaaa tgcttggcaa ccaaaggtaa      4140
acaacaaaga tcaatggcta caaattgacc tgcaacatct tacaaaaata acaagcataa      4200
taactcaagg agccacatca atgactacat caatgtatgt gaaaacattc tccatccatt      4260
atactgatga caattcaaca tggaagcctt atttggatgt tcgcacttcc atggaaaagg      4320
ttttcacagg aaatattaac agtgatggtc atgtcaaaca ttttttcaaa cccctatat      4380 tgtccaggtt cattcgtatc atccctaaaa catggaatca atatattgca ctccggatag      4440
aattgtttgg ttgtgaagtt ttttaaggct tggacagaag actatcaaat caagcaactt      4500
caatgtttca gttttcttta ttactaactc tgctttttaa aaggaaacaa aaacaaaagc      4560
ataataaaac tgtcttagca taaaaaagct atccttctca attttcagct atagctttca      4620
aatagctttg aaaatatcaa tcaaaatatc ataactgaag tgactttaca atgattaatt      4680
ctagtgccac tttaatcatg actgtaatcc taatacataa accttatttt ttttgcc           4737
```

<210> SEQ ID NO 6
<211> LENGTH: 4383
<212> TYPE: DNA
<213> ORGANISM: Pseudonaja textilis

<400> SEQUENCE: 6

```
atgggaagat acagtgtgag ccctgtcccc aaatgtcttc tactgatgtt cctgggttgg        60
tcagggctga agtattacca agtgaatgca gctcagctca gggagtacca tatagctgct       120
cagctggaag actgggatta caaccccaa cctgaggagc tatccagatt atcagagtca        180
gatcttacgt ttaaaaaaat tgtctataga gaatatgaac tagatttcaa acaagaggag        240
ccaagagatg cgctctcagg gctcctaggg ccaacactac gtggagaagt gggagacagc        300
ctcataattt atttcaagaa ttttgctact cagcctgtga gcattcaccc gcagagtgcc        360
gtgtacaaca atggtcaga aggttcttca tattctgatg aacatcaga tgtggaaaga         420 ctggatgatg ctgtgcctcc aggccagtcg ttcaagtatg tgtggaatat cactgcagaa        480
attgggccaa agaaagctga tcctccctgt ctcacttatg cgtactactc acatgtaaac        540
```

```
atggtgcgag actttaattc tggtctcatt ggtgctttgc tgatatgtaa agaaggaagc    600
ctgaatgcaa atggttcaca aaaattcttc aacagagaat atgtgctgat gttttctgtg    660
tttgatgaaa gcaagaactg gtacagaaag ccctcactac agtacacaat taatgggttt    720
gccaatggaa cattgcctga tgttcaggct tgtgcttatg atcatattag ctggcatttg    780
ataggaatga gttccagtcc tgagatcttc tctgttcact caatggaca aaccttggaa     840
caaaaccatt acaaagtgtc aaccatcaac cttgtcggag gtgcctcagt aacagccgac    900
atgtcagtga gcaggacagg aaaatggcta atatcttctc tggttgcaaa gcatctacaa    960
gctgggatgt atggttatct aaatatcaaa gactgtggaa atccagatac tttaacaaga   1020
aagttatcct ttagagaact gatgaagatt aagaactggg aatatttcat tgctgcagaa   1080
gaaatcacct gggattatgc tccagaaatt cctagcagtg ttgacagaag atacaaagct   1140
cagtatctgg ataattttc aaattttatt ggcaagaaat acaaaaaggc agttttcagg    1200
caatatgaag acggcaattt cactaaaccg acctatgcca tttggcccaa agaacgtgga   1260
attctgggcc ccgttatcaa agctaaagtc agagacacag taacaattgt attcaaaaat   1320
ctggccagtc gaccttacag cattatgtg catggagttt ccgtttcaaa agatgcagaa    1380
ggagctattt atccttcaga tcccaaagag aatataactc atggcaaagc agttgaacca   1440
ggacaggtct acacatataa atggactgtg ctggatacag atgaacctac agtaaaggat   1500
tctgagtgca ttactaaatt atatcatagt gctgtggaca tgacaagaga tattgcttca   1560
ggacttattg ggccacttct ggtttgtaaa cacaaggcac tcagcgtcaa gggggtacag   1620
aataaagctg atgtggaaca gcatgcagtc ttcgcagtgt ttgatgaaaa caagagctgg   1680
tacttggaag acaatatcaa gaaatactgc agcaatcctt ccgctgttaa gaaagatgac   1740
cctaaatttt acagtccaa tgttatgtac acactcaatg gctatgcatc agatagaaca    1800
gaggttttga ggtttcatca gtctgaagtt gttcaatggc acctcaccag cgtaggtaca   1860
gtggatgaga ttgttccagt acatctttct ggtcacacct tcttatccaa gggaaaacat   1920
caagatattt taaatctttt ccccatgagt ggtgaatctg ctactgtaac aatggacaat   1980
ctaggaacct ggcttctgtc atcatggggc tcctgtgaga tgagcaatgg catgagattg   2040
agatttttgg atgccaatta tgatgatgaa gatgagggaa atgaagaaga ggaagaagat   2100
gatggtgata ttttgccga cattttcatt ccttcagaag tagtaaaaaa gaagaagag    2160
gttcccgtaa attttgtacc agacccagaa tcggatgcgc tagcaaaaga attaggatta   2220
atagatgacg agggtaatcc aataatacag ccacgcaggg aacagacaga ggatgatgaa   2280
gaacagctaa tgaaagcttc aatgcttggg cttcgatcat ttaaggggtc agttgctgaa   2340
gaagaattga acacacagc tctagcttta aagaagatg cccatgcttc tgatcctcga    2400
attgacagta atagtgcacg taatcctgac gacatagctg gacgctacct gcgtactatc   2460
aaccgtggaa ataaaggag gtactacatt gcagcagaag aagttttgtg ggactactca   2520
ccgatcggaa aaagtcaagt gagaagtcgc gcagccaaga ccacattcaa aaaagctatt   2580
ttccgaagtt atcttgatga actttccag acacctagca ctggaggaga atatgaaaag    2640
catcttggta tactgggtcc tatcattagg gctgaggtgg atgatgtaat cgaaattcag   2700
ttcaaaaatt tggcctctag accatactca cttcatgctc atggccttct ctatgagaaa   2760
tcttctgaag cagaagcta tgacgacaag tctcctgaat tgttcaaaaa ggatgatgct   2820
atcatgccaa atggcacata cacatatgtc tggcaagtcc ctccacggtc aggaccaaca   2880
gacaatacag aaaaatgtaa atcatgggcc tattactctg gtgtaaatcc ggaaaaagat   2940
```

```
attcactctg gcttaattgg acctattttg atctgccaga aaggcatgat tgacaagtac   3000
aacaggacaa tagacataag ggaatttgtc ttgtttttta tggtctttga tgaggagaaa   3060
agctggtact ttccaaaatc tgacaaaagc acttgtgaag agaaacttat aggagtccaa   3120
tctctccaca catttcctgc aattaatggg atcccttatc agctgcaagg cttgacgatg   3180
tacaaagatg agaatgtcca ctggcatttg ctgaacatgg gtgggcccaa agatatccat   3240
gttgttaatt ttcatggtca gacattcact gaagagggaa gggaagataa tcaacttgga   3300
gtccttcctc ttcttcctgg tacattcgcc tccatcaaaa tgaaaccatc caaaattggc   3360
acatggcttt tagaaacaga agttggtgaa atcaggaaa gaggaatgca ggctctcttt   3420
actgtcattg acaaagattg taaattacca atgggactgg caagtgggat aatacaagac   3480
tcacagatca gtgcttcagg tcatgttgga tattgggagc taagctagc aagactgaat   3540 aatactggaa aatataatgc ttggagcatc ataagaagg aacatgaaca tccgtggatc   3600
cagatagacc tacaaagaca agttgtcatc acaggcattc agacccaagg aaccgtgcaa   3660
ctactgcaac attcgtatac tgtggaatat tttgttacct acagcgaaga tgggcaaaac   3720
tggattactt ttaaaggaag acattccgaa acacaaatgc attttgaggg taattcagat   3780
ggcaccacag taaagaaaaa ccacattgat cctcctatta ttgccagata tattagactg   3840
catccaacca agttctacaa cagacctact ttccgcattg aactgttagg ttgtgaagtt   3900
gaaggttgct cagtgccatt gggaatggaa agtgggcta tcaagaattc agagattaca   3960
gcctcttctt ataagaagac ttggtggagt tcatgggaac catcccttgc acgactcaat   4020
ctggaaggag gaacaaatgc ttggcaacca gaggtaaaca acaaagatca atggttacaa   4080
attgacctgc aacatcttac aaaaataaca agcataataa ctcaaggagc acatcaatg   4140 actacatcaa tgtatgtgaa acattctcc atccattata ctgatgacaa ttcaacatgg   4200
aagccttatt tggatgttcg cacttccatg gaaaaggttt tcacaggaaa tattaacagt   4260
gatggtcatg tcaaacattt tttcaaaccc cctatattgt ccaggttcat tcgtatcatc   4320
cctaaaacat ggaatcaata tattgcactc cggatagaat tgtttggttg tgaagttttt   4380
taa                                                                 4383
```

<210> SEQ ID NO 7
<211> LENGTH: 1459
<212> TYPE: PRT
<213> ORGANISM: Pseudonaja textilis

<400> SEQUENCE: 7

Met Gly Arg Tyr Ser Val Ser Pro Val Pro Lys Cys Leu Leu Leu Met
1               5                   10                  15

Phe Leu Gly Trp Ser Gly Leu Lys Tyr Tyr Glu Val Asn Ala Ala Gln
            20                  25                  30

Leu Arg Glu Tyr His Ile Ala Ala Gln Leu Glu Asp Trp Asp Tyr Asn
        35                  40                  45

Pro Gln Pro Glu Glu Leu Ser Arg Leu Ser Glu Ser Asp Leu Thr Phe
    50                  55                  60

Lys Lys Ile Val Tyr Arg Glu Tyr Glu Leu Asp Phe Lys Gln Glu Lys
65                  70                  75                  80

Pro Arg Asp Glu Leu Ser Gly Leu Leu Gly Pro Thr Leu Arg Gly Glu
                85                  90                  95

Val Gly Asp Ile Leu Ile Ile Tyr Phe Lys Asn Phe Ala Thr Gln Pro
            100                 105                 110

```
Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asn Gly Ser Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240

Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asn Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly Asn Pro Asp
                325                 330                 335

Thr Leu Thr Arg Lys Leu Ser Phe Arg Glu Leu Arg Ile Met Asn
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

Asn Phe Ser Asn Phe Ile Gly Lys Lys Tyr Lys Lys Ala Val Phe Arg
385                 390                 395                 400

Gln Tyr Lys Asp Ser Asn Phe Thr Lys Pro Thr Tyr Ala Ile Trp Pro
                405                 410                 415

Lys Glu Arg Gly Ile Leu Gly Pro Val Ile Arg Ala Lys Val Arg Asp
            420                 425                 430

Thr Ile Ser Ile Val Phe Lys Asn Leu Ala Ser Arg Pro Tyr Ser Ile
        435                 440                 445

Tyr Val His Gly Val Ser Val Ser Lys Asp Ala Glu Gly Ala Ile Tyr
    450                 455                 460

Pro Ser Asp Pro Lys Glu Asn Ile Thr His Gly Lys Ala Val Glu Pro
465                 470                 475                 480

Gly Gln Val Tyr Thr Tyr Lys Trp Thr Val Leu Asp Thr Asp Glu Pro
                485                 490                 495

Thr Val Lys Asp Ser Glu Cys Ile Thr Lys Leu Tyr His Ser Ala Val
            500                 505                 510

Asp Met Thr Arg Asp Ile Ala Ser Gly Leu Ile Gly Pro Leu Leu Val
        515                 520                 525
```

-continued

```
Cys Lys His Lys Ala Leu Ser Val Lys Gly Val Gln Asn Lys Ala Asp
    530                 535                 540

Val Glu Gln His Ala Val Phe Ala Val Phe Asp Glu Asn Lys Ser Trp
545                 550                 555                 560

Tyr Leu Glu Asp Asn Ile Lys Lys Tyr Cys Ser Asn Pro Ser Thr Val
                565                 570                 575

Lys Lys Asp Asp Pro Lys Phe Tyr Lys Ser Asn Val Met Tyr Thr Leu
            580                 585                 590

Asn Gly Tyr Ala Ser Asp Arg Thr Glu Val Leu Gly Phe His Gln Ser
        595                 600                 605

Glu Val Val Glu Trp His Leu Thr Ser Val Gly Thr Val Asp Glu Ile
610                 615                 620

Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655

Thr Met Asp Asn Leu Gly Thr Trp Leu Leu Ser Ser Trp Gly Ser Cys
            660                 665                 670

Glu Met Ser Asn Gly Met Arg Leu Arg Phe Leu Asp Ala Asn Tyr Asp
        675                 680                 685

Asp Glu Asp Glu Gly Asn Glu Glu Glu Asp Asp Gly Asp Ile
690                 695                 700

Phe Ala Asp Ile Phe Ile Pro Pro Glu Val Val Lys Lys Lys Glu Lys
705                 710                 715                 720

Asp Pro Val Asn Phe Val Ser Asp Pro Glu Ser Asp Lys Ile Ala Lys
                725                 730                 735

Glu Leu Gly Leu Leu Asp Asp Glu Asp Asn Gln Glu Glu Ser His Asn
            740                 745                 750

Val Gln Thr Glu Asp Asp Glu Glu Gln Leu Met Ile Ala Thr Met Leu
        755                 760                 765

Gly Phe Arg Ser Phe Lys Gly Ser Val Ala Glu Glu Leu Asn Leu
770                 775                 780

Thr Ala Leu Ala Leu Glu Glu Asp Ala His Ala Ser Asp Pro Arg Ile
785                 790                 795                 800

Asp Ser Asn Ser Ala Arg Asn Pro Asp Asp Ile Ala Gly Arg Tyr Leu
                805                 810                 815

Arg Thr Ile Asn Arg Gly Asn Lys Arg Tyr Ile Ala Ala Glu
            820                 825                 830

Glu Val Leu Trp Asp Tyr Ser Pro Ile Gly Lys Ser Gln Val Arg Ser
        835                 840                 845

Arg Ala Ala Lys Thr Thr Phe Lys Lys Ala Ile Phe Arg Ser Tyr Leu
850                 855                 860

Asp Asp Thr Phe Gln Thr Pro Ser Thr Gly Gly Tyr Glu Lys His
865                 870                 875                 880

Leu Gly Ile Leu Gly Pro Ile Ile Arg Ala Glu Val Asp Val Ile
                885                 890                 895

Glu Val Gln Phe Arg Asn Leu Ala Ser Arg Pro Tyr Ser Leu His Ala
            900                 905                 910

His Gly Leu Leu Tyr Glu Lys Ser Ser Glu Gly Arg Ser Tyr Asp Asp
        915                 920                 925

Lys Ser Pro Glu Leu Phe Lys Lys Asp Asp Ala Ile Met Pro Asn Gly
930                 935                 940

Thr Tyr Thr Tyr Val Trp Gln Val Pro Pro Arg Ser Gly Pro Thr Asp
```

-continued

```
                945                 950                 955                 960
            Asn Thr Glu Lys Cys Lys Ser Trp Ala Tyr Tyr Ser Gly Val Asn Pro
                            965                 970                 975
            Glu Lys Asp Ile His Ser Gly Leu Ile Gly Pro Ile Leu Ile Cys Gln
                            980                 985                 990
            Lys Gly Met Ile Asp Lys Tyr Asn Arg Thr Ile Asp Ile Arg Glu Phe
                            995                1000                1005
            Val Leu Phe Phe Met Val Phe Asp Glu Glu Lys Ser Trp Tyr Phe
                    1010                1015                1020
            Pro Lys Ser Asp Lys Ser Thr Arg Ala Glu Lys Leu Ile Gly Val
                    1025                1030                1035
            Gln Ser Arg His Thr Phe Pro Ala Ile Asn Gly Ile Pro Tyr Gln
                    1040                1045                1050
            Leu Gln Gly Leu Thr Met Tyr Lys Asp Glu Asn Val His Trp His
                    1055                1060                1065
            Leu Leu Asn Met Gly Gly Pro Lys Asp Ile His Val Val Asn Phe
                    1070                1075                1080
            His Gly Gln Thr Phe Thr Glu Glu Gly Arg Glu Asp Asn Gln Leu
                    1085                1090                1095
            Gly Val Leu Pro Leu Leu Pro Gly Thr Phe Ala Ser Ile Lys Met
                    1100                1105                1110
            Lys Pro Ser Lys Ile Gly Thr Trp Leu Leu Glu Thr Glu Val Gly
                    1115                1120                1125
            Glu Asn Gln Glu Arg Gly Met Gln Ala Leu Phe Thr Val Ile Asp
                    1130                1135                1140
            Lys Asp Cys Lys Leu Pro Met Gly Leu Ala Ser Gly Ile Ile Gln
                    1145                1150                1155
            Asp Ser Gln Ile Ser Ala Ser Gly His Val Gly Tyr Trp Glu Pro
                    1160                1165                1170
            Lys Leu Ala Arg Leu Asn Asn Thr Gly Lys Tyr Asn Ala Trp Ser
                    1175                1180                1185
            Ile Ile Lys Lys Glu His Glu His Pro Trp Ile Gln Ile Asp Leu
                    1190                1195                1200
            Gln Arg Gln Val Val Ile Thr Gly Ile Gln Thr Gln Gly Ala Met
                    1205                1210                1215
            Gln Leu Leu Lys His Leu Tyr Thr Val Glu Tyr Phe Phe Thr Tyr
                    1220                1225                1230
            Ser Lys Asp Gly Gln Asn Trp Ile Thr Phe Lys Gly Arg His Ser
                    1235                1240                1245
            Glu Thr Gln Met His Phe Glu Gly Asn Ser Asp Gly Thr Thr Val
                    1250                1255                1260
            Lys Glu Asn His Ile Asp Pro Pro Ile Ile Ala Arg Tyr Ile Arg
                    1265                1270                1275
            Leu His Pro Thr Lys Phe His Asn Arg Pro Thr Phe Arg Ile Glu
                    1280                1285                1290
            Leu Leu Gly Cys Glu Val Glu Gly Cys Ser Val Pro Leu Gly Met
                    1295                1300                1305
            Glu Ser Gly Ala Ile Lys Asn Ser Glu Ile Thr Ala Ser Ser Tyr
                    1310                1315                1320
            Lys Lys Thr Trp Trp Ser Ser Trp Glu Pro Ser Leu Ala Arg Leu
                    1325                1330                1335
            Asn Leu Lys Gly Arg Thr Asn Ala Trp Gln Pro Lys Val Asn Asn
                    1340                1345                1350
```

```
Lys Asp Gln Trp Leu Gln Ile Asp Leu Gln His Leu Thr Lys Ile
    1355                1360                1365

Thr Ser Ile Ile Thr Gln Gly Ala Thr Ser Met Thr Thr Ser Met
    1370                1375                1380

Tyr Val Lys Thr Phe Ser Ile His Tyr Thr Asp Asp Asn Ser Thr
    1385                1390                1395

Trp Lys Pro Tyr Leu Asp Val Arg Thr Ser Met Glu Lys Val Phe
1400                1405                1410

Thr Gly Asn Ile Asn Ser Asp Gly His Val Lys His Phe Phe Lys
    1415                1420                1425

Pro Pro Ile Leu Ser Arg Phe Ile Arg Ile Ile Pro Lys Thr Trp
    1430                1435                1440

Asn Gln Tyr Ile Ala Leu Arg Ile Glu Leu Phe Gly Cys Glu Val
    1445                1450                1455

Phe
```

<210> SEQ ID NO 8
<211> LENGTH: 1460
<212> TYPE: PRT
<213> ORGANISM: Pseudonaja textilis

<400> SEQUENCE: 8

```
Met Gly Arg Tyr Ser Val Ser Pro Val Pro Lys Cys Leu Leu Met
1               5                   10                  15

Phe Leu Gly Trp Ser Gly Leu Lys Tyr Tyr Gln Val Asn Ala Ala Gln
                20                  25                  30

Leu Arg Glu Tyr His Ile Ala Ala Gln Leu Glu Asp Trp Asp Tyr Asn
            35                  40                  45

Pro Gln Pro Glu Glu Leu Ser Arg Leu Ser Glu Ser Asp Leu Thr Phe
    50                  55                  60

Lys Lys Ile Val Tyr Arg Glu Tyr Glu Leu Asp Phe Lys Gln Glu Glu
65                  70                  75                  80

Pro Arg Asp Ala Leu Ser Gly Leu Leu Gly Pro Thr Leu Arg Gly Glu
                85                  90                  95

Val Gly Asp Ser Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
    115                 120                 125

Ser Ser Tyr Ser Asp Gly Thr Ser Asp Val Glu Arg Leu Asp Asp Ala
130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asn Gly Ser Gln Lys
    195                 200                 205

Phe Phe Asn Arg Glu Tyr Val Leu Met Phe Ser Val Phe Asp Glu Ser
210                 215                 220

Lys Asn Trp Tyr Arg Lys Pro Ser Leu Gln Tyr Thr Ile Asn Gly Phe
225                 230                 235                 240

Ala Asn Gly Thr Leu Pro Asp Val Gln Ala Cys Ala Tyr Asp His Ile
                245                 250                 255
```

-continued

Ser Trp His Leu Ile Gly Met Ser Ser Pro Glu Ile Phe Ser Val
            260             265             270

His Phe Asn Gly Gln Thr Leu Glu Gln Asn His Tyr Lys Val Ser Thr
        275             280             285

Ile Asn Leu Val Gly Gly Ala Ser Val Thr Ala Asp Met Ser Val Ser
    290             295             300

Arg Thr Gly Lys Trp Leu Ile Ser Ser Leu Val Ala Lys His Leu Gln
305             310             315             320

Ala Gly Met Tyr Gly Tyr Leu Asn Ile Lys Asp Cys Gly Asn Pro Asp
            325             330             335

Thr Leu Thr Arg Lys Leu Ser Phe Arg Glu Leu Met Lys Ile Lys Asn
        340             345             350

Trp Glu Tyr Phe Ile Ala Ala Glu Glu Ile Thr Trp Asp Tyr Ala Pro
            355             360             365

Glu Ile Pro Ser Ser Val Asp Arg Arg Tyr Lys Ala Gln Tyr Leu Asp
    370             375             380

Asn Phe Ser Asn Phe Ile Gly Lys Lys Tyr Lys Lys Ala Val Phe Arg
385             390             395             400

Gln Tyr Glu Asp Gly Asn Phe Thr Lys Pro Thr Tyr Ala Ile Trp Pro
            405             410             415

Lys Glu Arg Gly Ile Leu Gly Pro Val Ile Lys Ala Lys Val Arg Asp
            420             425             430

Thr Val Thr Ile Val Phe Lys Asn Leu Ala Ser Arg Pro Tyr Ser Ile
        435             440             445

Tyr Val His Gly Val Ser Val Ser Lys Asp Ala Glu Gly Ala Ile Tyr
        450             455             460

Pro Ser Asp Pro Lys Glu Asn Ile Thr His Gly Lys Ala Val Glu Pro
465             470             475             480

Gly Gln Val Tyr Thr Tyr Lys Trp Thr Val Leu Asp Thr Asp Glu Pro
            485             490             495

Thr Val Lys Asp Ser Glu Cys Ile Thr Lys Leu Tyr His Ser Ala Val
        500             505             510

Asp Met Thr Arg Asp Ile Ala Ser Gly Leu Ile Gly Pro Leu Leu Val
        515             520             525

Cys Lys His Lys Ala Leu Ser Val Lys Gly Val Gln Asn Lys Ala Asp
        530             535             540

Val Glu Gln His Ala Val Phe Ala Val Phe Asp Glu Asn Lys Ser Trp
545             550             555             560

Tyr Leu Glu Asp Asn Ile Lys Lys Tyr Cys Ser Asn Pro Ser Ala Val
            565             570             575

Lys Lys Asp Asp Pro Lys Phe Tyr Lys Ser Asn Val Met Tyr Thr Leu
        580             585             590

Asn Gly Tyr Ala Ser Asp Arg Thr Glu Val Leu Arg Phe His Gln Ser
    595             600             605

Glu Val Val Gln Trp His Leu Thr Ser Val Gly Thr Val Asp Glu Ile
    610             615             620

Val Pro Val His Leu Ser Gly His Thr Phe Leu Ser Lys Gly Lys His
625             630             635             640

Gln Asp Ile Leu Asn Leu Phe Pro Met Ser Gly Glu Ser Ala Thr Val
            645             650             655

Thr Met Asp Asn Leu Gly Thr Trp Leu Leu Ser Ser Trp Gly Ser Cys
        660             665             670

```
Glu Met Ser Asn Gly Met Arg Leu Arg Phe Leu Asp Ala Asn Tyr Asp
            675                 680                 685

Asp Glu Asp Glu Gly Asn Glu Glu Glu Glu Asp Asp Gly Asp Ile
    690                 695                 700

Phe Ala Asp Ile Phe Ile Pro Ser Glu Val Val Lys Lys Lys Glu Glu
705                 710                 715                 720

Val Pro Val Asn Phe Val Pro Asp Pro Glu Ser Asp Ala Leu Ala Lys
                725                 730                 735

Glu Leu Gly Leu Ile Asp Asp Glu Gly Asn Pro Ile Ile Gln Pro Arg
            740                 745                 750

Arg Glu Gln Thr Glu Asp Asp Glu Glu Gln Leu Met Lys Ala Ser Met
    755                 760                 765

Leu Gly Leu Arg Ser Phe Lys Gly Ser Val Ala Glu Glu Glu Leu Lys
    770                 775                 780

His Thr Ala Leu Ala Leu Glu Glu Asp Ala His Ala Ser Asp Pro Arg
785                 790                 795                 800

Ile Asp Ser Asn Ser Ala Arg Asn Pro Asp Asp Ile Ala Gly Arg Tyr
                805                 810                 815

Leu Arg Thr Ile Asn Arg Gly Asn Lys Arg Arg Tyr Tyr Ile Ala Ala
            820                 825                 830

Glu Glu Val Leu Trp Asp Tyr Ser Pro Ile Gly Lys Ser Gln Val Arg
    835                 840                 845

Ser Arg Ala Ala Lys Thr Thr Phe Lys Lys Ala Ile Phe Arg Ser Tyr
    850                 855                 860

Leu Asp Asp Thr Phe Gln Thr Pro Ser Thr Gly Gly Glu Tyr Glu Lys
865                 870                 875                 880

His Leu Gly Ile Leu Gly Pro Ile Ile Arg Ala Glu Val Asp Asp Val
                885                 890                 895

Ile Glu Ile Gln Phe Lys Asn Leu Ala Ser Arg Pro Tyr Ser Leu His
            900                 905                 910

Ala His Gly Leu Leu Tyr Glu Lys Ser Ser Glu Gly Arg Ser Tyr Asp
    915                 920                 925

Asp Lys Ser Pro Glu Leu Phe Lys Lys Asp Asp Ala Ile Met Pro Asn
    930                 935                 940

Gly Thr Tyr Thr Tyr Val Trp Gln Val Pro Pro Arg Ser Gly Pro Thr
945                 950                 955                 960

Asp Asn Thr Glu Lys Cys Lys Ser Trp Ala Tyr Tyr Ser Gly Val Asn
                965                 970                 975

Pro Glu Lys Asp Ile His Ser Gly Leu Ile Gly Pro Leu Ile Cys
            980                 985                 990

Gln Lys Gly Met Ile Asp Lys Tyr Asn Arg Thr Ile Asp Ile Arg Glu
    995                 1000                1005

Phe Val Leu Phe Phe Met Val Phe Asp Glu Glu Lys Ser Trp Tyr
    1010                1015                1020

Phe Pro Lys Ser Asp Lys Ser Thr Cys Glu Glu Lys Leu Ile Gly
    1025                1030                1035

Val Gln Ser Leu His Thr Phe Pro Ala Ile Asn Gly Ile Pro Tyr
    1040                1045                1050

Gln Leu Gln Gly Leu Thr Met Tyr Lys Asp Glu Asn Val His Trp
    1055                1060                1065

His Leu Leu Asn Met Gly Gly Pro Lys Asp Ile His Val Val Asn
    1070                1075                1080

Phe His Gly Gln Thr Phe Thr Glu Glu Gly Arg Glu Asp Asn Gln
```

```
                    1085                1090                1095
Leu Gly Val Leu Pro Leu Leu Pro Gly Thr Phe Ala Ser Ile Lys
    1100                1105                1110
Met Lys Pro Ser Lys Ile Gly Thr Trp Leu Leu Glu Thr Glu Val
    1115                1120                1125
Gly Glu Asn Gln Glu Arg Gly Met Gln Ala Leu Phe Thr Val Ile
    1130                1135                1140
Asp Lys Asp Cys Lys Leu Pro Met Gly Leu Ala Ser Gly Ile Ile
    1145                1150                1155
Gln Asp Ser Gln Ile Ser Ala Ser Gly His Val Gly Tyr Trp Glu
    1160                1165                1170
Pro Lys Leu Ala Arg Leu Asn Asn Thr Gly Lys Tyr Asn Ala Trp
    1175                1180                1185
Ser Ile Ile Lys Lys Glu His Glu His Pro Trp Ile Gln Ile Asp
    1190                1195                1200
Leu Gln Arg Gln Val Val Ile Thr Gly Ile Gln Thr Gln Gly Thr
    1205                1210                1215
Val Gln Leu Leu Gln His Ser Tyr Thr Val Glu Tyr Phe Val Thr
    1220                1225                1230
Tyr Ser Glu Asp Gly Gln Asn Trp Ile Thr Phe Lys Gly Arg His
    1235                1240                1245
Ser Glu Thr Gln Met His Phe Glu Gly Asn Ser Asp Gly Thr Thr
    1250                1255                1260
Val Lys Glu Asn His Ile Asp Pro Pro Ile Ile Ala Arg Tyr Ile
    1265                1270                1275
Arg Leu His Pro Thr Lys Phe Tyr Asn Arg Pro Thr Phe Arg Ile
    1280                1285                1290
Glu Leu Leu Gly Cys Glu Val Glu Gly Cys Ser Val Pro Leu Gly
    1295                1300                1305
Met Glu Ser Gly Ala Ile Lys Asn Ser Glu Ile Thr Ala Ser Ser
    1310                1315                1320
Tyr Lys Lys Thr Trp Trp Ser Ser Trp Glu Pro Ser Leu Ala Arg
    1325                1330                1335
Leu Asn Leu Glu Gly Gly Thr Asn Ala Trp Gln Pro Glu Val Asn
    1340                1345                1350
Asn Lys Asp Gln Trp Leu Gln Ile Asp Leu Gln His Leu Thr Lys
    1355                1360                1365
Ile Thr Ser Ile Ile Thr Gln Gly Ala Thr Ser Met Thr Thr Ser
    1370                1375                1380
Met Tyr Val Lys Thr Phe Ser Ile His Tyr Thr Asp Asp Asn Ser
    1385                1390                1395
Thr Trp Lys Pro Tyr Leu Asp Val Arg Thr Ser Met Glu Lys Val
    1400                1405                1410
Phe Thr Gly Asn Ile Asn Ser Asp Gly His Val Lys His Phe Phe
    1415                1420                1425
Lys Pro Pro Ile Leu Ser Arg Phe Ile Arg Ile Pro Lys Thr
    1430                1435                1440
Trp Asn Gln Tyr Ile Ala Leu Arg Ile Glu Leu Phe Gly Cys Glu
    1445                1450                1455
Val Phe
    1460

<210> SEQ ID NO 9
```

<211> LENGTH: 4380
<212> TYPE: DNA
<213> ORGANISM: Oxyuranus scutellatus

<400> SEQUENCE: 9

```
atgggaagat acagtgtgag ccctgtcccc aaatgtcttc tactgatgtt cctgggttgg     60
tcagggctga agtattacca agtgaatgca gctcagctca gggagtaccg tttagctgct    120
cagctggaag actgggatta caacccccaa cctgaggagc tatccagatt atcagagtca    180
gatcttacgt ttaaaaaaat tgtctataga gaatatgaac tagatttcaa acaagagaag    240
ccaagagatg agctctcagg gctcctaggg ccaacactac gtggagaagt gggagacagc    300
ctcataattt atttcaagaa ttttgctact cagcctgtga gcattcaccc gcagagtgcc    360
gtgtacaaca aatggtcaga aggttcttca tattctgatg gaacatcaga tgtggaaaga    420
ctggatgatg ctgtgcctcc aggccagtcg ttcaagtatg tgtggaatat cactgcagaa    480
attgggccaa agaaagctga tcctccctgt ctcacttatg cgtactactc acatgtaaac    540
atggtgcgag actttaattc tggtctcatt ggtgctttgc tgatatgtaa agaaggaagc    600
ctgaatgcag atggtgcaca aaaattcttc aacagagaat atgtgctgat gttttctgtg    660
tttgatgaaa gcaagaactg gtacagaaag ccctcattac agtacacaat taatgggttt    720
gccaatggaa cattgcctga tgttcaggct tgtgcttatg atcatattag ctggcatttg    780
ataggaatga gttccagtcc tgagatcttc tctgttcact tcaatggaca aaccttggaa    840
caaaaccatt acaaagtgtc aaccatcaac cttgtcggag gtgcctcagt aacagccaac    900
atgtcagtga gcaggacagg aaaatggcta atatcttctc tggttgcaaa gcatctacaa    960
gctgggatgt atggttatct aaatatcaaa gactgtggaa atccagatac tttaacaaga   1020
aagttatcct ttagagaacg gaggaggatt atgaaatggg aatatttcat tgctgcagaa   1080
gaaatcacct gggattatgc tccagaaatt cctagcagtg ttgacagaag atacaaagct   1140
cagtatctgg ataatttttc aaattttatt ggcaagaaat acaaaaaggc agttttcagg   1200
caatatgaag acagcaattt cactaaaccg acctatgcca tttggcccaa agaacgtgga   1260
attctgggcc ccgttatcaa agctaaagtc agagacacag taacaattgt attcaaaaat   1320
ctggccagtc gaccttacag catttatgtg catggagttt ccgtttcaaa agatgcagaa   1380
ggagctgttt atccttcaga tcccaaagag aatataactc atggcaaagc agttgaacca   1440
ggacaggtct acacatataa atggactgtg ctggatacag atgaacctac agtaaaggat   1500
tctgagtgca ttactaaatt atatcatagt gctgtggaca tgacaagaga tattgcttca   1560
ggacttattg ggccacctct ggtttgtaaa cgcaaggcac tcagcatcag gggggtacag   1620
aataaagctg atgtggaaca gcatgcagtc ttcgcagtgt ttgatgaaaa caagagctgg   1680
tacttggaag acaatatcaa gaaatactgc agcaatcctt ccagtgttaa gaaagatgac   1740
cctaaatttt acaagtccaa tgttatgtac acactcaatg gctatgcatc agatagaaca   1800
gaggtttggg ggtttcatca gtctgaagtt gttgaatggc acctcaccag cgtaggtaca   1860
gtggatgaga ttgttccagt acatctttct ggtcacacct tcttatccaa gggaaaacat   1920
caagatattt taaatctttt tcccatgagt ggtgaatcgg ctactgtaac aatggacaat   1980
ctaggaacct ggcttctgtc atcatggggc tcctgtgaga tgagcaatgg catgagattg   2040
agatttttgg atgccaatta tgatgatgaa gatgagggaa atgaagaaga ggaagaagat   2100
gatggtgata tttttgccga cattttcaat cctccagaag tagtaataaa gaaagaagag   2160
gttcccgtaa attttgtacc agacccagaa tcggatgcgc tagcaaaaga attaggatta   2220
```

```
tttgatgacg aggataatcc aaaacagtca cgcagtgaac agacagagga tgatgaagaa    2280
cagctaatga tagcttcaat gcttgggctt cgatcattta aggggtcagt tgctgaagaa    2340
gaattgaaac acacagctct agctttagaa gaagatgccc atgcttctga tcctcgaatt    2400
gacagtaata gtgcacataa ttctgacgac atagctggac gctacctgcg tactatcaac    2460
cgcagaaata aaaggaggta ctacattgca gcagaagaag ttttgtggga ctactcaccg    2520
atcggaaaaa gtcaagtgag aagtctccca gccaagacca cattcaaaaa agctattttc    2580
cgaagttatc ttgatgatac tttccagaca cctagcactg gaggagaata tgaaaagcat    2640
cttggtatac tgggtcctat cattagggct gaggtggatg atgtaatcga agttcagttc    2700
agaaatttgg cctctagacc atactcactt catgctcatg ccttctcta tgagaaatct    2760 tctgaaggca gaagctatga cgacaactct cctgaattgt tcaaaaaaga tgatgctatc    2820
atgccaaacg gcacatacac atatgtctgg caagtccctc cacggtcagg accaacagac    2880
aatacagaaa aatgtaaatc atgggcctat tactctggtg taaatccgga aaagatatt    2940 cactctggct taattggacc tattttgatc tgccagaaag gcatgattga caagtacaac    3000
aggacaatag acataaggga atttgtcttg ttttttatgg tctttgatga ggagaaaagc    3060
tggtactttc caaaatctga caaaagcact tgtgaagaga aacttatagg agtccaatct    3120
cgccacacat ttcctgcaat taatgggatc ccttatcagc tgcaaggctt gatgatgtac    3180
aaagatgaga atgtccactg gcatttgctg aacatgggtg ggcccaaaga tgtccatgtt    3240
gttaattttc atggtcagac attcactgaa gagggaaggg aagataatca acttggagtc    3300
cttcctcttc ttcctggtac attcgcctcc atcaaaatga aaccatccaa aattggcaca    3360
tggcttttag aaacagaagt tggtgaaaat caggaaagag gaatgcaggc tctctttact    3420
gtcattgaca aagattgtaa attaccaatg ggactggcaa gtgggataat acaagactca    3480
cagatcagtg cttcaggtca tgttggatat tgggagccta agctagcaag actgaataat    3540
actggaatgt ttaatgcttg gagcatcata agaaggaac atgaacatcc gtggatccag    3600
atagacctac aaagacaagt tgtcatcaca ggcattcaga cccagggaac cgtgcaacta    3660
ctgaaacatt cgtatactgt ggaatatttt gttacctaca gcaaagatgg gcaaaactgg    3720
attactttta aaggaagaca ttccaaaaca caaatgcatt ttgagggtaa ttcagatggc    3780
accacagtaa aagaaaacca cattgatcct cctattattg ccagatatat taggctgcat    3840
ccaaccaagt tctacaacac acctactttc cgcattgaac tgttaggttg tgaagttgaa    3900
ggttgctcag tgccattggg aatggaaagt ggggctatca aggattcaga gattacagcc    3960
tcttcttata aaagacttg gtggagttca tgggaaccat tccttgcacg actcaatctg    4020
aaaggacgaa caaatgcttg gcaaccaaag gtaaacaaca aagatcaatg gctacaaatt    4080
gacctgcaac atcttacaaa aataacaagc ataataactc aaggagccac atcaatgact    4140
acatcaatgt atgtgaaaac attctccatc cattatactg atgacaattc aacatggaag    4200
ccttatttgg atgttcgcac ttccatggaa aaggttttca caggaaatat taacagtgat    4260
ggtcatgtca acatttttt caacccccct atattgtcca ggttcattcg tatcatccct    4320
aaaacatgga atcaatatat tgcactccgg atagaattgt ttggttgtga agtttttaa    4380
```

<210> SEQ ID NO 10
<211> LENGTH: 4675
<212> TYPE: DNA
<213> ORGANISM: Oxyuranus scutellatus scutellatus

```
<400> SEQUENCE: 10
atgggaagat acagtgtgag ccctgtcccc aaatgtcttc tactgatgtt cctgggttgg      60
tcagggctga agtattacca agtgaatgca gctcagctca gggagtaccg tatagctgct     120
cagctggaag actgggatta caaccccaa cctgaggagc tatccagatt atcagagtca      180
gatcttacgt ttaaaaaaat tgtctataga gaatatgaac tagatttcaa acaagagaag     240
ccaagagatg agctctcagg gctcctaggg ccaacactac gtggagaagt gggagacagc     300
ctcataattt atttcaagaa ttttgctact cagcctgtga gcattcaccc gcagagtgcc     360
gtgtacaaca aatggtcaga aggttcttca tattctgatg aacatcaga tgtggaaaga      420 ctggatgatg ctgtgcctcc aggccagtcg ttcaagtatg tgtggaatat cactgcagaa     480
attgggccaa agaaagctga tcctccctgt ctcacttatg cgtactactc acatgtaaac     540
atggtgcgag actttaattc tggtctcatt ggtgctttgc tgatatgtaa agaaggaagc     600
ctgaatgcag atggtgcaca aaaattcttc aacagagaat atgtgctgat gttttctgtg     660
tttgatgaaa gcaagaactg gtacagaaag ccctcattac agtacacaat taatgggttt     720
gccaatggaa cattgcctga tgttcaggct tgtgcttatg atcatattag ctggcatttg     780
ataggaatga gttccagtcc tgagatcttc tctgttcact tcaatggaca aaccttggaa     840
caaaaccatt acaaagtgtc aaccatcaac cttgtcggag gtgcctcagt aacagccaac     900
atgtcagtga gcaggacagg aaaatggcta atatcttctc tggttgcaaa gcatctacaa     960
gctgggatgt atggttatct aatatcaaa gactgtggaa atccagatac tttaacaaga     1020
aagttatcct ttagagaatg gaggaggatt atgaaatggg aatatttcat tgctgcagaa     1080
gaaatcacct gggattatgc tccagaaatt cctagcagtg ttgacagaag atacaaagct     1140
cagtatctgg atttttcaaa ttttattggc aagaaataca aaaaggcagt tttcaggcaa     1200
tatgaagaca gcaatttcac taaaccgacc tatgccattt ggcccaaaga acgtggaatt     1260
ctgggccccg ttatcaaagc taaagtcaga gacacagtaa caattgtatt caaaaatctg     1320
gccagtcgac cttacagcat ttatgtgcat ggagtttccg tttcaaaaga tgcagaagga     1380 gctgttttatc cttcagatcc caaagagaat ataactcatg gcaaagcagt tgaaccagga     1440
caggtctaca catataaatg gactgtgctg gatacagatg aacctacagt aaaggattct     1500
gagtgcatta ctaaattata tcatagtgct gtggacatga caagagatat tgcttcagga     1560
cttattgggc cacttctggt ttgtaaacgc aaggcactca gcatcagggg ggtacagaat     1620
aaagctgatg tggaacagca tgcagtcttc gcagtgtttg atgaaaacaa gagctggtac     1680
ttggaagaca atatcaagaa atactgcagc aatccttcca gtgttaagaa agatgaccct     1740
aaattttaca gtccaatgt tatgtacaca ctcaatggct atgcatcaga tagaacagag     1800
gtttgggggt tcatcagtc tgaagttgtt gaatggcacc tcaccagcgt aggtacagtg     1860
gatgagattg ttccagtaca tctttctggt cacaccttct tatccaaggg aaaacatcaa     1920
gatattttaa atcttttttcc catgagtggt gaatccgcta ctgtaacaat ggacaatcta     1980
ggaacctggc ttctgtcatc atggggctcc tgtgagatga gcaatggcat gagattgaga     2040
tttttggatg ccaattatga tgatgaagat gagggaaatg aagaagagga agaagatgat     2100
ggtgatattt tgccgacat tttcaatcct ccagaagtag taataaagaa agaagaggtt     2160
cccgtaaatt ttgtaccaga cccagaatcg gatgcgctag caaaagaatt aggattatt      2220 gatgacgagg ataatccaaa acagtcacgc agtgaacaga cagaggatga tgaagaacag     2280
ctaatgatag cttcaatgct tgggcttcga tcatttaagg ggtcagttgc tgaagaagaa     2340
```

```
ttgaaacaca cagctctagc tttagaagaa gatgcccatg cttctgatcc tcgaattgac  2400
agtaatagtg cacataattc tgacgacata gctggacgct acctgcgtac tatctaccgc  2460
agaaataaaa ggaggtacta cattgcagca gaagaagttt tgtgggacta ctcaccgatc  2520
ggaaaaagtc aagtgagaag tctcccagcc aagaccacat tcaaaaaagc tattttccga  2580
agttatcttg atgatacttt ccagacacct agcactggag gagaatatga aaagcatctt  2640
ggtatactgg gtcctatcat tagggctgag gtggatgatg taatcgaagt tcagttcaga  2700
aatttggcct ctagaccata ctcacttcat gctcatggcc ttctctatga gaatcttct   2760 gaaggcagaa gctatgacga caactctcct gaattgttca aaaaggatga tgctatcatg  2820
ccaaacggca catacacata tgtctggcaa gtccctccac ggtcaggacc aacagacaat  2880
acagaaaaat gtaaatcatg ggcctattac tctggtgtaa atccggaaaa agatattcac  2940
tctgggctta ttggacctat tttgatctgc cagaaaggca tgattgacaa gtacaacagg  3000
acaatagaca taagggaatt tgtcttgttt tttatggtct ttgatgagga gaaaagctgg  3060
tactttccaa aatctgacaa aagcacttgt gaagagaaac ttataggagt ccaatctcgc  3120
cacacatttc ctgcaattaa tgggatccct tatcagctgc aaggcttgat gatgtacaaa  3180
gatgagaatg tccactggca tttgctgaac atgggtgggc ccaaagatgt ccatgttgtt  3240
aattttcatg gtcagacatt cactgaagag ggaagggaag ataatcaact tggagtcctt  3300
cctcttcttc ctggtacatt cgcctccatc aaaatgaaac catccaaaat tggcacatgg  3360
cttttagaaa cagaagttgg tgaaaatcag gaaagaggaa tgcaggctct ctttactgtc  3420
attgacaaag attgtaaatt accaatggga ctggcaagtg ggataataca agactcacag  3480
atcagtgctt caggtcatgt tggatattgg gagcctaagc tagcaagact gaataatact  3540
ggaatgttta atgcttggag catcataaag aaggaacatg aacatccgtg gatccagatc  3600
gacctacaaa gacaagttgt catcacaggc attcagaccc agggaaccgt gcacctactg  3660
aaacattcgt atactgtgga atattttgtt acctacagca agatgggca aaactggatt  3720 acttttaaag gaagacattc caaaacacaa atgcattttg agggtaattc agatggcacc  3780
acagtaaaag aaaaccacat tgatcctcct attattgcca gatatattag gctgcatcca  3840
accaagttct acaacacacc tactttccgc attgaactgt taggttgtga agttgaaggt  3900
tgctcagtgc cattgggaat ggaaagtggg gctatcaagg attcagagat tacagcctct  3960
tcttataaaa agacttggtg gagttcatgg gaaccattcc ttgcacgact caatctgaaa  4020
ggacgaacaa atgcttggca accaaaggta acaacaaag atcaatggct acaaattgac  4080
ctgcaacatc ttacaaaaat aacaagcata ataactcaag gagccacatc aatgactaca  4140
tcaatgtatg tgaaaacatt ctccatccat tatactgatg acaattcaac atggaagcct  4200
tatttggatg ttcgcacttc catggaaaag gttttcacag gaaatattaa cagtgatggt  4260
catgtcaaac atttttcaa ccccctata ttgtccaggt tcattcgtat catccctaaa  4320
acatggaatc aatatattgc actccggata gaattgtttg gttgtgaagt ttttaaggc   4380 ttggacagaa gactgtcaaa tcaagcaact tcaatgtttc aagttttctt attactaact  4440
ctgcttttta aaggaaaca aaaacaaaag cataataaaa ctgtcttagc ataaaaaaaa  4500
ctatccttct caattttcag ccatagcttt caaatagctt tgaaaatatc aatcaaaata  4560
tcataactga agtgacgttt acaatgatta ttcgtagtg ccacgtttaa tcatgaatgt  4620
aatcctaata caataaaatc gttattgttt ttgccccaaa aaaaaaaaaa aaaaa        4675
```

<210> SEQ ID NO 11
<211> LENGTH: 1458
<212> TYPE: PRT
<213> ORGANISM: Oxyuranus scutellatus scutellatus

<400> SEQUENCE: 11

Met Gly Arg Tyr Ser Val Ser Pro Val Pro Lys Cys Leu Leu Leu Met
1               5                   10                  15

Phe Leu Gly Trp Ser Gly Leu Lys Tyr Tyr Gln Val Asn Ala Ala Gln
            20                  25                  30

Leu Arg Glu Tyr Arg Ile Ala Ala Gln Leu Glu Asp Trp Asp Tyr Asn
        35                  40                  45

Pro Gln Pro Glu Glu Leu Ser Arg Leu Ser Glu Ser Asp Leu Thr Phe
    50                  55                  60

Lys Lys Ile Val Tyr Arg Glu Tyr Glu Leu Asp Phe Lys Gln Glu Lys
65                  70                  75                  80

Pro Arg Asp Glu Leu Ser Gly Leu Leu Gly Pro Thr Leu Arg Gly Glu
                85                  90                  95

Val Gly Asp Ser Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asp Gly Ala Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240

Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asn Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly Asn Pro Asp
                325                 330                 335

Thr Leu Thr Arg Lys Leu Ser Phe Arg Glu Trp Arg Arg Ile Met Lys
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

```
Phe Ser Asn Phe Ile Gly Lys Lys Tyr Lys Lys Ala Val Phe Arg Gln
385                 390                 395                 400

Tyr Glu Asp Ser Asn Phe Thr Lys Pro Thr Tyr Ala Ile Trp Pro Lys
            405                 410                 415

Glu Arg Gly Ile Leu Gly Pro Val Ile Lys Ala Lys Val Arg Asp Thr
                420                 425                 430

Val Thr Ile Val Phe Lys Asn Leu Ala Ser Arg Pro Tyr Ser Ile Tyr
            435                 440                 445

Val His Gly Val Ser Val Ser Lys Asp Ala Glu Gly Ala Val Tyr Pro
        450                 455                 460

Ser Asp Pro Lys Glu Asn Ile Thr His Gly Lys Ala Val Glu Pro Gly
465                 470                 475                 480

Gln Val Tyr Thr Tyr Lys Trp Thr Val Leu Asp Thr Asp Glu Pro Thr
                485                 490                 495

Val Lys Asp Ser Glu Cys Ile Thr Lys Leu Tyr His Ser Ala Val Asp
            500                 505                 510

Met Thr Arg Asp Ile Ala Ser Gly Leu Ile Gly Pro Leu Leu Val Cys
        515                 520                 525

Lys Arg Lys Ala Leu Ser Ile Arg Gly Val Gln Asn Lys Ala Asp Val
530                 535                 540

Glu Gln His Ala Val Phe Ala Val Phe Asp Glu Asn Lys Ser Trp Tyr
545                 550                 555                 560

Leu Glu Asp Asn Ile Lys Lys Tyr Cys Ser Asn Pro Ser Ser Val Lys
                565                 570                 575

Lys Asp Asp Pro Lys Phe Tyr Lys Ser Asn Val Met Tyr Thr Leu Asn
            580                 585                 590

Gly Tyr Ala Ser Asp Arg Thr Glu Val Trp Gly Phe His Gln Ser Glu
        595                 600                 605

Val Val Glu Trp His Leu Thr Ser Val Gly Thr Val Asp Glu Ile Val
        610                 615                 620

Pro Val His Leu Ser Gly His Thr Phe Leu Ser Lys Gly Lys His Gln
625                 630                 635                 640

Asp Ile Leu Asn Leu Phe Pro Met Ser Gly Glu Ser Ala Thr Val Thr
                645                 650                 655

Met Asp Asn Leu Gly Thr Trp Leu Leu Ser Ser Trp Gly Ser Cys Glu
            660                 665                 670

Met Ser Asn Gly Met Arg Leu Arg Phe Leu Asp Ala Asn Tyr Asp Asp
        675                 680                 685

Glu Asp Glu Gly Asn Glu Glu Glu Glu Asp Gly Asp Ile Phe
        690                 695                 700

Ala Asp Ile Phe Asn Pro Pro Glu Val Val Ile Lys Lys Glu Glu Val
705                 710                 715                 720

Pro Val Asn Phe Val Pro Asp Pro Glu Ser Asp Ala Leu Ala Lys Glu
                725                 730                 735

Leu Gly Leu Phe Asp Asp Glu Asp Asn Pro Lys Gln Ser Arg Ser Glu
            740                 745                 750

Gln Thr Glu Asp Asp Glu Glu Leu Met Ile Ala Ser Met Leu Gly
        755                 760                 765

Leu Arg Ser Phe Lys Gly Ser Val Ala Glu Glu Leu Lys His Thr
770                 775                 780

Ala Leu Ala Leu Glu Glu Asp Ala His Ala Ser Asp Pro Arg Ile Asp
785                 790                 795                 800

Ser Asn Ser Ala His Asn Ser Asp Asp Ile Ala Gly Arg Tyr Leu Arg
                805                 810                 815

Thr Ile Tyr Arg Arg Asn Lys Arg Arg Tyr Tyr Ile Ala Ala Glu Glu
            820                 825                 830

Val Leu Trp Asp Tyr Ser Pro Ile Gly Lys Ser Gln Val Arg Ser Leu
```

-continued

Gly Ile Leu Gly Pro Ile Ile Arg Ala Glu Val Asp Asp Val Ile Glu
            885                 890                 895

Val Gln Phe Arg Asn Leu Ala Ser Arg Pro Tyr Ser Leu His Ala His
            900                 905                 910

Gly Leu Leu Tyr Glu Lys Ser Ser Glu Gly Arg Ser Tyr Asp Asp Asn
            915                 920                 925

Ser Pro Glu Leu Phe Lys Lys Asp Ala Ile Met Pro Asn Gly Thr
            930                 935                 940

Tyr Thr Tyr Val Trp Gln Val Pro Pro Arg Ser Gly Pro Thr Asp Asn
945                 950                 955                 960

Thr Glu Lys Cys Lys Ser Trp Ala Tyr Tyr Ser Gly Val Asn Pro Glu
            965                 970                 975

Lys Asp Ile His Ser Gly Leu Ile Gly Pro Ile Leu Ile Cys Gln Lys
            980                 985                 990

Gly Met Ile Asp Lys Tyr Asn Arg Thr Ile Asp Ile Arg Glu Phe Val
            995                 1000                1005

Leu Phe Phe Met Val Phe Asp Glu Glu Lys Ser Trp Tyr Phe Pro
            1010                1015                1020

Lys Ser Asp Lys Ser Thr Cys Glu Glu Lys Leu Ile Gly Val Gln
            1025                1030                1035

Ser Arg His Thr Phe Pro Ala Ile Asn Gly Ile Pro Tyr Gln Leu
            1040                1045                1050

Gln Gly Leu Met Met Tyr Lys Asp Glu Asn Val His Trp His Leu
            1055                1060                1065

Leu Asn Met Gly Gly Pro Lys Asp Val His Val Val Asn Phe His
            1070                1075                1080

Gly Gln Thr Phe Thr Glu Glu Gly Arg Glu Asp Asn Gln Leu Gly
            1085                1090                1095

Val Leu Pro Leu Leu Pro Gly Thr Phe Ala Ser Ile Lys Met Lys
            1100                1105                1110

Pro Ser Lys Ile Gly Thr Trp Leu Leu Glu Thr Glu Val Gly Glu
            1115                1120                1125

Asn Gln Glu Arg Gly Met Gln Ala Leu Phe Thr Val Ile Asp Lys
            1130                1135                1140

Asp Cys Lys Leu Pro Met Gly Leu Ala Ser Gly Ile Ile Gln Asp
            1145                1150                1155

Ser Gln Ile Ser Ala Ser Gly His Val Gly Tyr Trp Glu Pro Lys
            1160                1165                1170

Leu Ala Arg Leu Asn Asn Thr Gly Met Phe Asn Ala Trp Ser Ile
            1175                1180                1185

Ile Lys Lys Glu His Glu His Pro Trp Ile Gln Ile Asp Leu Gln
            1190                1195                1200

Arg Gln Val Val Ile Thr Gly Ile Gln Thr Gln Gly Thr Val His
            1205                1210                1215

Leu Leu Lys His Ser Tyr Thr Val Glu Tyr Phe Val Thr Tyr Ser
            1220                1225                1230

Lys Asp Gly Gln Asn Trp Ile Thr Phe Lys Gly Arg His Ser Lys
            1235                1240                1245

Thr Gln Met His Phe Glu Gly Asn Ser Asp Gly Thr Thr Val Lys
            1250                1255                1260

Glu Asn His Ile Asp Pro Pro Ile Ile Ala Arg Tyr Ile Arg Leu
            1265                1270                1275

His Pro Thr Lys Phe Tyr Asn Thr Pro Thr Phe Arg Ile Glu Leu

-continued

```
                1280                1285                1290
Leu Gly Cys Glu Val Glu Gly Cys Ser Val Pro Leu Gly Met Glu
        1295                1300                1305
Ser Gly Ala Ile Lys Asp Ser Glu Ile Thr Ala Ser Ser Tyr Lys
        1310                1315                1320
Lys Thr Trp Trp Ser Ser Trp Glu Pro Phe Leu Ala Arg Leu Asn
        1325                1330                1335
Leu Lys Gly Arg Thr Asn Ala Trp Gln Pro Lys Val Asn Asn Lys
        1340                1345                1350
Asp Gln Trp Leu Gln Ile Asp Leu Gln His Leu Thr Lys Ile Thr
        1355                1360                1365
Ser Ile Ile Thr Gln Gly Ala Thr Ser Met Thr Thr Ser Met Tyr
        1370                1375                1380
Val Lys Thr Phe Ser Ile His Tyr Thr Asp Asp Asn Ser Thr Trp
        1385                1390                1395
Lys Pro Tyr Leu Asp Val Arg Thr Ser Met Glu Lys Val Phe Thr
        1400                1405                1410
Gly Asn Ile Asn Ser Asp Gly His Val Lys His Phe Phe Asn Pro
        1415                1420                1425
Pro Ile Leu Ser Arg Phe Ile Arg Ile Ile Pro Lys Thr Trp Asn
        1430                1435                1440
Gln Tyr Ile Ala Leu Arg Ile Glu Leu Phe Gly Cys Glu Val Phe
        1445                1450                1455

<210> SEQ ID NO 12
<211> LENGTH: 1459
<212> TYPE: PRT
<213> ORGANISM: Oxyuranus scutellatus

<400> SEQUENCE: 12

Met Gly Arg Tyr Ser Val Ser Pro Val Pro Lys Cys Leu Leu Leu Met
1               5                   10                  15
Phe Leu Gly Trp Ser Gly Leu Lys Tyr Tyr Gln Val Asn Ala Ala Gln
                20                  25                  30
Leu Arg Glu Tyr Arg Leu Ala Ala Gln Leu Glu Asp Trp Asp Tyr Asn
            35                  40                  45
Pro Gln Pro Glu Glu Leu Ser Arg Leu Ser Glu Ser Asp Leu Thr Phe
        50                  55                  60
Lys Lys Ile Val Tyr Arg Glu Tyr Glu Leu Asp Phe Lys Gln Glu Lys
65                  70                  75                  80
Pro Arg Asp Glu Leu Ser Gly Leu Leu Gly Pro Thr Leu Arg Gly Glu
                85                  90                  95
Val Gly Asp Ser Leu Ile Ile Tyr Phe Lys Asn Phe Ala Thr Gln Pro
            100                 105                 110
Val Ser Ile His Pro Gln Ser Ala Val Tyr Asn Lys Trp Ser Glu Gly
        115                 120                 125
Ser Ser Tyr Ser Asp Gly Thr Ser Asp Val Glu Arg Leu Asp Asp Ala
    130                 135                 140
Val Pro Pro Gly Gln Ser Phe Lys Tyr Val Trp Asn Ile Thr Ala Glu
145                 150                 155                 160
Ile Gly Pro Lys Lys Ala Asp Pro Pro Cys Leu Thr Tyr Ala Tyr Tyr
                165                 170                 175
Ser His Val Asn Met Val Arg Asp Phe Asn Ser Gly Leu Ile Gly Ala
            180                 185                 190
```

-continued

| | | | | | | | | | | | | | |
|---|---|---|---|---|---|---|---|---|---|---|---|---|---|
|Leu|Leu|Ile|Cys|Lys|Glu|Gly|Ser|Leu|Asn|Ala|Asp|Gly|Ala|Gln|Lys|
| | |195| | | |200| | | |205| | | |

Phe Phe Asn Arg Glu Tyr Val Leu Met Phe Ser Val Phe Asp Glu Ser
210                215                220

Lys Asn Trp Tyr Arg Lys Pro Ser Leu Gln Tyr Thr Ile Asn Gly Phe
225                230                235                240

Ala Asn Gly Thr Leu Pro Asp Val Gln Ala Cys Ala Tyr Asp His Ile
          245                250                255

Ser Trp His Leu Ile Gly Met Ser Ser Pro Glu Ile Phe Ser Val
          260                265                270

His Phe Asn Gly Gln Thr Leu Glu Gln Asn His Tyr Lys Val Ser Thr
     275                280                285

Ile Asn Leu Val Gly Gly Ala Ser Val Thr Ala Asn Met Ser Val Ser
290                295                300

Arg Thr Gly Lys Trp Leu Ile Ser Ser Leu Val Ala Lys His Leu Gln
305                310                315                320

Ala Gly Met Tyr Gly Tyr Leu Asn Ile Lys Asp Cys Gly Asn Pro Asp
               325                330                335

Thr Leu Thr Arg Lys Leu Ser Phe Arg Glu Arg Arg Ile Met Lys
          340                345                350

Trp Glu Tyr Phe Ile Ala Ala Glu Glu Ile Thr Trp Asp Tyr Ala Pro
     355                360                365

Glu Ile Pro Ser Ser Val Asp Arg Arg Tyr Lys Ala Gln Tyr Leu Asp
     370                375                380

Asn Phe Ser Asn Phe Ile Gly Lys Lys Tyr Lys Lys Ala Val Phe Arg
385                390                395                400

Gln Tyr Glu Asp Ser Asn Phe Thr Lys Pro Thr Tyr Ala Ile Trp Pro
               405                410                415

Lys Glu Arg Gly Ile Leu Gly Pro Val Ile Lys Ala Lys Val Arg Asp
               420                425                430

Thr Val Thr Ile Val Phe Lys Asn Leu Ala Ser Arg Pro Tyr Ser Ile
          435                440                445

Tyr Val His Gly Val Ser Val Ser Lys Asp Ala Glu Gly Ala Val Tyr
     450                455                460

Pro Ser Asp Pro Lys Glu Asn Ile Thr His Gly Lys Ala Val Glu Pro
465                470                475                480

Gly Gln Val Tyr Thr Tyr Lys Trp Thr Val Leu Asp Thr Asp Glu Pro
               485                490                495

Thr Val Lys Asp Ser Glu Cys Ile Thr Lys Leu Tyr His Ser Ala Val
          500                505                510

Asp Met Thr Arg Asp Ile Ala Ser Gly Leu Ile Gly Pro Pro Leu Val
     515                520                525

Cys Lys Arg Lys Ala Leu Ser Ile Arg Gly Val Gln Asn Lys Ala Asp
     530                535                540

Val Glu Gln His Ala Val Phe Ala Val Phe Asp Glu Asn Lys Ser Trp
545                550                555                560

Tyr Leu Glu Asp Asn Ile Lys Lys Tyr Cys Ser Asn Pro Ser Ser Val
               565                570                575

Lys Lys Asp Asp Pro Lys Phe Tyr Lys Ser Asn Val Met Tyr Thr Leu
               580                585                590

Asn Gly Tyr Ala Ser Asp Arg Thr Glu Val Trp Gly Phe His Gln Ser
     595                600                605

Glu Val Val Glu Trp His Leu Thr Ser Val Gly Thr Val Asp Glu Ile

-continued

```
                610                 615                 620
Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655

Thr Met Asp Asn Leu Gly Thr Trp Leu Leu Ser Ser Trp Gly Ser Cys
                660                 665                 670

Glu Met Ser Asn Gly Met Arg Leu Arg Phe Leu Asp Ala Asn Tyr Asp
                675                 680                 685

Asp Glu Asp Glu Gly Asn Glu Glu Glu Glu Asp Gly Asp Ile
690                 695                 700

Phe Ala Asp Ile Phe Asn Pro Pro Glu Val Val Ile Lys Lys Glu Glu
705                 710                 715                 720

Val Pro Val Asn Phe Val Pro Asp Pro Glu Ser Asp Ala Leu Ala Lys
                725                 730                 735

Glu Leu Gly Leu Phe Asp Asp Glu Asp Asn Pro Lys Gln Ser Arg Ser
                740                 745                 750

Glu Gln Thr Glu Asp Asp Glu Glu Gln Leu Met Ile Ala Ser Met Leu
                755                 760                 765

Gly Leu Arg Ser Phe Lys Gly Ser Val Ala Glu Glu Leu Lys His
                770                 775                 780

Thr Ala Leu Ala Leu Glu Glu Asp Ala His Ala Ser Asp Pro Arg Ile
785                 790                 795                 800

Asp Ser Asn Ser Ala His Asn Ser Asp Ile Ala Gly Arg Tyr Leu
                805                 810                 815

Arg Thr Ile Asn Arg Arg Asn Lys Arg Arg Tyr Tyr Ile Ala Ala Glu
                820                 825                 830

Glu Val Leu Trp Asp Tyr Ser Pro Ile Gly Lys Ser Gln Val Arg Ser
                835                 840                 845

Leu Pro Ala Lys Thr Thr Phe Lys Lys Ala Ile Phe Arg Ser Tyr Leu
                850                 855                 860

Asp Asp Thr Phe Gln Thr Pro Ser Thr Gly Gly Glu Tyr Glu Lys His
865                 870                 875                 880

Leu Gly Ile Leu Gly Pro Ile Ile Arg Ala Glu Val Asp Asp Val Ile
                885                 890                 895

Glu Val Gln Phe Arg Asn Leu Ala Ser Arg Pro Tyr Ser Leu His Ala
                900                 905                 910

His Gly Leu Leu Tyr Glu Lys Ser Ser Glu Gly Arg Ser Tyr Asp Asp
                915                 920                 925

Asn Ser Pro Glu Leu Phe Lys Lys Asp Asp Ala Ile Met Pro Asn Gly
930                 935                 940

Thr Tyr Thr Tyr Val Trp Gln Val Pro Pro Arg Ser Gly Pro Thr Asp
945                 950                 955                 960

Asn Thr Glu Lys Cys Lys Ser Trp Ala Tyr Tyr Ser Gly Val Asn Pro
                965                 970                 975

Glu Lys Asp Ile His Ser Gly Leu Ile Gly Pro Ile Leu Ile Cys Gln
                980                 985                 990

Lys Gly Met Ile Asp Lys Tyr Asn Arg Thr Ile Asp Ile Arg Glu Phe
                995                 1000                1005

Val Leu Phe Phe Met Val Phe Asp Glu Glu Lys Ser Trp Tyr Phe
1010                1015                1020

Pro Lys Ser Asp Lys Ser Thr Cys Glu Glu Lys Leu Ile Gly Val
                1025                1030                1035
```

```
Gln Ser Arg His Thr Phe Pro Ala Ile Asn Gly Ile Pro Tyr Gln
    1040            1045                1050

Leu Gln Gly Leu Met Met Tyr Lys Asp Glu Asn Val His Trp His
    1055            1060                1065

Leu Leu Asn Met Gly Gly Pro Lys Asp Val His Val Val Asn Phe
    1070            1075                1080

His Gly Gln Thr Phe Thr Glu Glu Gly Arg Glu Asp Asn Gln Leu
    1085            1090                1095

Gly Val Leu Pro Leu Leu Pro Gly Thr Phe Ala Ser Ile Lys Met
    1100            1105                1110

Lys Pro Ser Lys Ile Gly Thr Trp Leu Leu Glu Thr Glu Val Gly
    1115            1120                1125

Glu Asn Gln Glu Arg Gly Met Gln Ala Leu Phe Thr Val Ile Asp
    1130            1135                1140

Lys Asp Cys Lys Leu Pro Met Gly Leu Ala Ser Gly Ile Ile Gln
    1145            1150                1155

Asp Ser Gln Ile Ser Ala Ser Gly His Val Gly Tyr Trp Glu Pro
    1160            1165                1170

Lys Leu Ala Arg Leu Asn Asn Thr Gly Met Phe Asn Ala Trp Ser
    1175            1180                1185

Ile Ile Lys Lys Glu His Glu His Pro Trp Ile Gln Ile Asp Leu
    1190            1195                1200

Gln Arg Gln Val Val Ile Thr Gly Ile Gln Thr Gln Gly Thr Val
    1205            1210                1215

Gln Leu Leu Lys His Ser Tyr Thr Val Glu Tyr Phe Val Thr Tyr
    1220            1225                1230

Ser Lys Asp Gly Gln Asn Trp Ile Thr Phe Lys Gly Arg His Ser
    1235            1240                1245

Lys Thr Gln Met His Phe Glu Gly Asn Ser Asp Gly Thr Thr Val
    1250            1255                1260

Lys Glu Asn His Ile Asp Pro Pro Ile Ile Ala Arg Tyr Ile Arg
    1265            1270                1275

Leu His Pro Thr Lys Phe Tyr Asn Thr Pro Thr Phe Arg Ile Glu
    1280            1285                1290

Leu Leu Gly Cys Glu Val Glu Gly Cys Ser Val Pro Leu Gly Met
    1295            1300                1305

Glu Ser Gly Ala Ile Lys Asp Ser Glu Ile Thr Ala Ser Ser Tyr
    1310            1315                1320

Lys Lys Thr Trp Trp Ser Ser Trp Glu Pro Phe Leu Ala Arg Leu
    1325            1330                1335

Asn Leu Lys Gly Arg Thr Asn Ala Trp Gln Pro Lys Val Asn Asn
    1340            1345                1350

Lys Asp Gln Trp Leu Gln Ile Asp Leu Gln His Leu Thr Lys Ile
    1355            1360                1365

Thr Ser Ile Ile Thr Gln Gly Ala Thr Ser Met Thr Thr Ser Met
    1370            1375                1380

Tyr Val Lys Thr Phe Ser Ile His Tyr Thr Asp Asp Asn Ser Thr
    1385            1390                1395

Trp Lys Pro Tyr Leu Asp Val Arg Thr Ser Met Glu Lys Val Phe
    1400            1405                1410

Thr Gly Asn Ile Asn Ser Asp Gly His Val Lys His Phe Phe Asn
    1415            1420                1425
```

Pro Pro Ile Leu Ser Arg Phe Ile Arg Ile Ile Pro Lys Thr Trp
    1430                1435                1440

Asn Gln Tyr Ile Ala Leu Arg Ile Glu Leu Phe Gly Cys Glu Val
    1445                1450                1455

Phe

<210> SEQ ID NO 13
<211> LENGTH: 1460
<212> TYPE: PRT
<213> ORGANISM: Oxyuranus scutellatus

<400> SEQUENCE: 13

Met Gly Arg Tyr Ser Val Ser Pro Val Pro Lys Cys Leu Leu Leu Met
1               5                   10                  15

Phe Leu Gly Trp Ser Gly Leu Lys Tyr Tyr Gln Val Asn Ala Ala Gln
            20                  25                  30

Leu Arg Glu Tyr Arg Ile Ala Ala Gln Leu Glu Asp Trp Asp Tyr Asn
        35                  40                  45

Pro Gln Pro Glu Glu Leu Ser Arg Leu Ser Glu Ser Glu Leu Thr Phe
    50                  55                  60

Lys Lys Ile Val Tyr Arg Glu Tyr Glu Leu Asp Phe Lys Gln Glu Lys
65                  70                  75                  80

Pro Arg Asp Glu Leu Ser Gly Leu Leu Gly Pro Thr Leu Arg Gly Glu
                85                  90                  95

Val Gly Asp Ile Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asn Gly Ala Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240

Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asn Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly His Pro Asn
                325                 330                 335

```
Thr Leu Thr Arg Lys Leu Ser Phe Arg Glu Leu Arg Arg Ile Met Asn
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

Asn Phe Ser Asn Phe Ile Gly Lys Lys Tyr Lys Lys Ala Val Phe Arg
385                 390                 395                 400

Gln Tyr Glu Asp Gly Asn Phe Thr Lys Pro Thr Tyr Ala Ile Trp Pro
                405                 410                 415

Lys Glu Arg Gly Ile Leu Gly Pro Val Ile Lys Ala Lys Val Arg Asp
            420                 425                 430

Thr Val Thr Ile Val Phe Lys Asn Leu Ala Ser Arg Pro Tyr Ser Ile
        435                 440                 445

Tyr Val His Gly Val Ser Val Ser Lys Asp Ala Glu Gly Ala Ile Tyr
    450                 455                 460

Pro Ser Asp Pro Lys Glu Asn Ile Thr His Gly Lys Ala Val Glu Pro
465                 470                 475                 480

Gly Gln Val Tyr Thr Tyr Lys Trp Thr Val Leu Asp Thr Asp Glu Pro
                485                 490                 495

Thr Val Lys Asp Ser Glu Cys Ile Thr Lys Leu Tyr His Ser Ala Val
            500                 505                 510

Asp Met Thr Arg Asp Ile Ala Ser Gly Leu Ile Gly Pro Leu Leu Val
        515                 520                 525

Cys Lys Leu Lys Ala Leu Ser Val Lys Gly Val Gln Asn Lys Ala Asp
    530                 535                 540

Val Glu Gln His Ala Val Phe Ala Val Phe Asp Glu Asn Lys Ser Trp
545                 550                 555                 560

Tyr Leu Glu Asp Asn Ile Lys Lys Tyr Cys Ser Asn Pro Ser Ser Val
                565                 570                 575

Lys Lys Asp Asp Pro Lys Phe Tyr Lys Ser Asn Val Met Tyr Thr Leu
            580                 585                 590

Asn Gly Tyr Ala Ser Asp Arg Thr Glu Val Leu Gly Phe His Gln Ser
        595                 600                 605

Glu Val Val Gln Trp His Leu Thr Ser Val Gly Thr Val Asp Glu Ile
    610                 615                 620

Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655

Thr Met Asp Asn Leu Gly Thr Trp Leu Leu Ser Ser Trp Gly Ser Cys
            660                 665                 670

Glu Met Ser Asn Gly Met Arg Leu Arg Phe Leu Asp Ala Asn Tyr Asp
        675                 680                 685

Asp Glu Asp Glu Gly Asn Glu Glu Glu Asp Asp Gly Asp Ile
    690                 695                 700

Phe Ala Asp Ile Phe Ser Pro Pro Val Val Lys Lys Lys Glu Glu
705                 710                 715                 720

Val Pro Val Asn Phe Val Pro Asp Pro Glu Ser Asp Ala Leu Ala Lys
                725                 730                 735

Glu Leu Gly Leu Leu Asp Asp Glu Asp Asn Pro Glu Gln Ser Arg Ser
            740                 745                 750

Glu Gln Thr Glu Asp Asp Glu Glu Gln Leu Met Ile Ala Ser Val Leu
```

```
                755               760               765
Gly Leu Arg Ser Phe Lys Gly Ser Val Ala Glu Glu Leu Lys His
    770               775               780

Thr Ala Leu Ala Leu Glu Glu Asp Ala His Ala Ser Asp Pro Arg Ile
785               790               795               800

Asp Ser Asn Ser Ala Arg Asn Ser Asp Ile Ala Gly Arg Tyr Leu
                805               810               815

Arg Thr Ile Asn Arg Arg Asn Lys Arg Arg Tyr Tyr Ile Ala Ala Glu
            820               825               830

Glu Val Leu Trp Asp Tyr Ser Pro Ile Gly Lys Ser Gln Val Arg Ser
            835               840               845

Leu Pro Ala Lys Thr Thr Phe Lys Lys Ala Ile Phe Arg Ser Tyr Leu
    850               855               860

Asp Asp Thr Phe Gln Thr Pro Ser Thr Gly Gly Glu Tyr Glu Lys His
865               870               875               880

Leu Gly Ile Leu Gly Pro Ile Ile Arg Ala Glu Val Asp Asp Val Ile
            885               890               895

Glu Val Gln Phe Arg Asn Leu Ala Ser Arg Pro Tyr Ser Leu His Ala
                900               905               910

His Gly Leu Leu Tyr Glu Lys Ser Ser Glu Gly Arg Ser Tyr Asp Asp
            915               920               925

Asn Ser Pro Glu Leu Phe Lys Lys Asp Asp Ala Ile Met Pro Asn Gly
    930               935               940

Thr Tyr Thr Tyr Val Trp Gln Val Pro Pro Arg Ser Gly Pro Thr Asp
945               950               955               960

Asn Thr Glu Lys Cys Lys Ser Trp Ala Tyr Tyr Ser Gly Val Asn Pro
                965               970               975

Glu Lys Asp Ile His Ser Gly Leu Ile Gly Pro Ile Leu Ile Cys Gln
            980               985               990

Lys Gly Met Ile Asp Lys Tyr Asn Arg Thr Ile Asp Ile Arg Glu Phe
            995               1000              1005

Val Leu Phe Phe Met Val Phe Asp Glu Glu Lys Ser Trp Tyr Phe
    1010              1015              1020

Pro Lys Ser Asp Lys Ser Thr Cys Glu Glu Lys Leu Ile Gly Val
    1025              1030              1035

Gln Ser Ser His His Thr Phe Pro Ala Ile Asn Gly Ile Pro Tyr
    1040              1045              1050

Gln Leu Gln Gly Leu Met Met Tyr Lys Asp Glu Asn Val His Trp
    1055              1060              1065

His Leu Leu Asn Met Gly Gly Pro Lys Asp Ile His Val Val Asn
    1070              1075              1080

Phe His Gly Gln Thr Phe Thr Glu Glu Gly Arg Glu Asp Asn Gln
    1085              1090              1095

Leu Gly Val Leu Pro Leu Leu Pro Gly Thr Phe Ala Ser Ile Lys
    1100              1105              1110

Met Lys Pro Ser Lys Ile Gly Thr Trp Leu Leu Glu Thr Glu Val
    1115              1120              1125

Gly Glu Asn Gln Glu Arg Gly Met Gln Ala Leu Phe Thr Val Ile
    1130              1135              1140

Asp Lys Asp Cys Lys Leu Pro Met Gly Leu Ala Ser Gly Ile Ile
    1145              1150              1155

Gln Asp Ser Gln Ile Ser Ala Ser Gly His Val Glu Tyr Trp Glu
    1160              1165              1170
```

Pro Lys Leu Ala Arg Leu Asn Asn Thr Gly Met Phe Asn Ala Trp
    1175                1180                1185

Ser Ile Ile Lys Lys Glu His Glu His Pro Trp Ile Gln Ile Asp
    1190                1195                1200

Leu Gln Arg Gln Val Val Ile Thr Gly Ile Gln Thr Gln Gly Thr
    1205                1210                1215

Val Gln Leu Leu Lys His Ser Tyr Thr Val Glu Tyr Phe Val Thr
    1220                1225                1230

Tyr Ser Lys Asp Gly Gln Asn Trp Ile Thr Phe Lys Gly Arg His
    1235                1240                1245

Ser Glu Thr Gln Met His Phe Glu Gly Asn Ser Asp Gly Thr Thr
    1250                1255                1260

Val Lys Glu Asn His Ile Asp Pro Pro Ile Ile Ala Arg Tyr Ile
    1265                1270                1275

Arg Leu His Pro Thr Lys Phe Tyr Asn Thr Pro Thr Phe Arg Ile
    1280                1285                1290

Glu Leu Leu Gly Cys Glu Val Glu Gly Cys Ser Val Pro Leu Gly
    1295                1300                1305

Met Glu Ser Gly Ala Ile Lys Asn Ser Glu Ile Thr Ala Ser Ser
    1310                1315                1320

Tyr Lys Lys Thr Trp Trp Ser Ser Trp Glu Pro Phe Leu Ala Arg
    1325                1330                1335

Leu Asn Leu Glu Gly Gly Thr Asn Ala Trp Gln Pro Glu Val Asn
    1340                1345                1350

Asn Lys Asp Gln Trp Leu Gln Ile Asp Leu Gln His Leu Thr Lys
    1355                1360                1365

Ile Thr Ser Ile Ile Thr Gln Gly Ala Thr Ser Met Thr Thr Ala
    1370                1375                1380

Met Tyr Val Lys Thr Phe Ser Ile His Tyr Thr Asp Asp Asn Ser
    1385                1390                1395

Thr Trp Lys Pro Tyr Leu Asp Val Arg Thr Ser Met Glu Lys Val
    1400                1405                1410

Phe Thr Gly Asn Ile Asn Ser Asp Gly His Val Lys His Phe Phe
    1415                1420                1425

Lys Pro Pro Ile Leu Ser Arg Phe Ile Arg Ile Ile Pro Lys Thr
    1430                1435                1440

Trp Asn Gln Tyr Ile Ala Leu Arg Ile Glu Leu Phe Gly Cys Glu
    1445                1450                1455

Val Phe
    1460

<210> SEQ ID NO 14
<211> LENGTH: 4383
<212> TYPE: DNA
<213> ORGANISM: Oxyuranus microlepidotus

<400> SEQUENCE: 14
atgggaagat acagtgtgag ccctgtcccc aaatgtcttc tactgatgtt cctgggttgg      60
tcagggctga agtattacca agtgaatgca gctcagctca gggagtaccg tatagctgct 120
cagctggaag actgggatta caacccccaa cctgaggagc tatccagatt atcagagtca 180
gagcttacgt ttaaaaaaat tgtctataga gaatatgaac tagatttcaa acaagagaag 240
ccaagagatg agctctcagg gctcctaggg ccaacactac gtggagaagt gggagacatc 300

```
ctcataattt atttcaagaa ttttgctact cagcctgtga gcattcaccc gcagagtgcc    360
gtgtacaaca aatggtcaga aggttcttca tattctgatg aacatcaga tgtggaaaga     420
ctggatgatg ctgtgcctcc aggccagtcg ttcaagtatg tgtggaatat cactgcagaa   480
attgggccaa agaaagctga tcctccctgt ctcacttatg cgtactactc acatgtaaac   540
atggtgcgag actttaattc tggtctcatt ggtgctttgc tgatatgtaa agaaggaagc   600
ctgaatgcaa atggtgcaca aaaattcttc aacagagaat atgtgctgat gttttctgtg   660
tttgatgaaa gcaagaactg gtacagaaag ccctcactac agtacacaat taatgggttt   720
gccaatggaa cattgcctga tgttcaggct tgtgcttatg atcatattag ctggcatttg   780
ataggaatga gttccagtcc tgagatcttc tctgttcact caatggaca aaccttggaa     840
caaaaccatt acaaagtgtc aaccatcaac cttgtcggag gtgcctcagt aacagccaac   900
atgtcagtga gcaggacagg aaaatggcta atatcttctc tggttgcaaa gcatctacaa   960
gctgggatgt atggttatct aaatatcaaa gactgtggac atccaaatac tttaacaaga  1020
aagttatcct ttagagaact gaggaggatt atgaactggg aatatttcat tgctgcagaa  1080
gaaatcacct gggattatgc tccagaaatt cctagcagtg ttgacagaag atacaaagct  1140
cagtatctgg ataattttc aaattttatt ggcaagaaat acaaaaaggc agttttcagg   1200
caatatgaag acggcaattt cactaaaccg acctatgcca tttggcccaa agaacgtgga  1260
attctgggcc ccgttatcaa agctaaagtc agagacacag taacaattgt attcaaaaat  1320
ctggccagtc gaccttacag catttatgtg catggagttt ccgtttcaaa agatgcagaa  1380
ggagctattt atccttcaga tcccaaagag aatataactc atggcaaagc agttgaacca  1440
ggacaggtct acacatataa atggactgtg ctggatacag atgaacctac agtaaaggat  1500
tctgagtgta ttactaaatt atatcatagt gctgtggaca tgacaagaga tattgcttca  1560
ggacttattg ggccacttct ggtttgtaaa ctcaaggcac tcagcgtcaa gggggtacag  1620
aataaagctg atgtggaaca gcatgcagtc ttcgcagtgt ttgatgaaaa taagagctgg  1680
tacttggaag acaatatcaa gaaatactgc agcaatcctt ccagtgttaa gaaagatgac  1740
cctaaatttt acaagtccaa tgttatgtac acactcaatg ctatgcatc agatagaaca   1800
gaggttttgg ggtttcatca gtctgaagtt gttcaatggc acctcaccag cgtaggtaca  1860
gtggatgaga ttgttccagt acatctttct ggtcacacct tcttatccaa gggaaaacat  1920
caagatattt taaatctttt tcccatgagt ggtgaatcgg ctactgtaac aatggacaat  1980
ctaggaacct ggcttctgtc atcatggggc tcctgtgaga tgagcaatgg catgagattg  2040
agattttgg atgccaatta tgatgatgaa gatgagggaa atgaagaaga ggaagaagat  2100
gatggtgata ttttttgccga catttttcagt cctccagaag tagtaaaaaa gaaagaagag  2160
gttcccgtaa attttgtacc agacccagaa tcggatgcgc tagcaaaaga attaggatta  2220
ttagatgacg aggataatcc agaacagtca cgcagtgaac agacagagga tgatgaagaa  2280
cagctaatga tagcttcagt gcttgggctt cgatcattta gggggtcagt tgctgaagaa  2340
gaattgaaac acacagctct agctttagaa gaagatgccc atgcttctga tcctcgaatt  2400
gacagtaata gtgcacgtaa ttctgacgac atagctggac gctacctgcg tactatcaac  2460
cgcagaaata aaaggaggta ctacattgca gcagaagaag ttttgtggga ctactcaccg  2520
atcggaaaaa gtcaagtgag aagtctccca gccaagacca cattcaaaaa agctatttc   2580
cgaagttatc ttgatgatac tttccagaca cctagcactg gaggagaata tgaaaagcat  2640
cttggtatac tgggtcctat cattagggct gaggtggatg atgtaatcga agttcagttc  2700
```

| | | |
|---|---|---|
| agaaatttgg cctctagacc atactcactt catgctcatg gccttctcta tgagaaatct | | 2760 |
| tctgaaggca gaagctatga cgacaactct cctgaattgt tcaaaaagga tgatgctatc | | 2820 |
| atgccaaacg gcacatacac atatgtctgg caagtccctc cacggtcagg accaacagac | | 2880 |
| aatacagaaa aatgtaaatc atgggcctat tactctggtg taaatccgga aaagatatt | | 2940 |
| cactctggct taattggacc tattttgatc tgccagaaag gcatgattga caagtacaac | | 3000 |
| aggacaatag acataaggga atttgtcttg ttttttatgg tctttgatga ggagaaaagc | | 3060 |
| tggtactttc ccaaatctga caaaagcact tgtgaagaga aacttatagg agtccaatct | | 3120 |
| tctcaccaca catttcctgc aattaatggg atcccttatc agctgcaagg cttgatgatg | | 3180 |
| tacaaagatg agaatgtcca ctggcatttg ctgaacatgg gtgggcccaa agatatccat | | 3240 |
| gttgttaatt ttcatggtca gacattcact gaagagggaa gggaagataa tcaacttgga | | 3300 |
| gtccttcctc ttcttcctgg tacattcgcc tccatcaaaa tgaaaccatc caaaattggc | | 3360 |
| acatggcttt tagaaacaga agttggtgaa aatcaggaaa gaggaatgca ggctctcttt | | 3420 |
| actgtcattg acaaagattg taaattacca atgggactgg caagtgggat aatacaagac | | 3480 |
| tcacagatca gtgcttcagg tcatgttgaa tattgggagc taagctagc aagactgaat | | 3540 |
| aatactggaa tgtttaatgc ttggagcatc ataaagaagg aacatgaaca tccgtggatc | | 3600 |
| cagatagacc tacaaagaca agttgtcatc acaggcattc agacccaggg aaccgtgcaa | | 3660 |
| ctactgaaac attcgtatac tgtggaatat tttgttacct acagcaaaga tgggcaaaac | | 3720 |
| tggattactt ttaaaggaag acattccgaa acacaaatgc attttgaggg taattcagat | | 3780 |
| ggcaccacag taaaagaaaa ccacattgat cctcctatta ttgccagata tattaggctg | | 3840 |
| catccaacca agttctacaa cacacctact ttccgcattg aactgttagg ttgtgaagtt | | 3900 |
| gaaggttgct cagtgccatt gggaatggaa agtggggcta tcaagaattc agagattaca | | 3960 |
| gcctcttctt ataagaagac ttggtggagt tcatgggaac cattccttgc acgactcaat | | 4020 |
| ctggaaggag gaacaaatgc ttggcaacca gaggtaaaca acaaagatca atggctacaa | | 4080 |
| attgacctgc aacatcttac aaaaataaca agcataataa ctcaaggagc cacatcaatg | | 4140 |
| actacagcaa tgtatgtgaa acattctcc atccattata ctgatgacaa ttcaacatgg | | 4200 |
| aagccttatt tggatgttcg cacttccatg gaaaaggttt tcacaggaaa tattaacagt | | 4260 |
| gatggtcatg tcaaacattt tttcaaaccc cctatattgt ccaggttcat tcgtatcatc | | 4320 |
| cctaaaacat ggaatcaata tattgcactc cggatagaat tgtttggttg tgaagttttt | | 4380 |
| taa | | 4383 |

<210> SEQ ID NO 15
<211> LENGTH: 9179
<212> TYPE: DNA
<213> ORGANISM: Homo sapiens

<400> SEQUENCE: 15

| | | |
|---|---|---|
| gcaagaactg caggggagga ggacgctgcc acccacagcc tctagagctc attgcagctg | | 60 |
| ggacagcccg gagtgtggtt agcagctcgg caagcgctgc ccaggtcctg ggtggtggc | | 120 |
| agccagcggg agcaggaaag gaagcatgtt cccaggctgc ccacgcctct gggtcctggt | | 180 |
| ggtcttgggc accagctggg taggctgggg gagccaaggg acagaagcgg cacagctaag | | 240 |
| gcagttctac gtggctgctc agggcatcag ttggagctac cgacctgagc ccacaaactc | | 300 |
| aagtttgaat cttctgtaa cttccttaa gaaaattgtc tacagagagt atgaaccata | | 360 |

```
ttttaagaaa gaaaaaccac aatctaccat ttcaggactt cttgggccta ctttatatgc    420
tgaagtcgga gacatcataa aagttcactt taaaaataag gcagataagc ccttgagcat    480
ccatcctcaa ggaattaggt acagtaaatt atcagaaggt gcttcttacc ttgaccacac    540
attccctgcg gagaagatgg acgacgctgt ggctccaggc cgagaataca cctatgaatg    600
gagtatcagt gaggacagtg gacccaccca tgatgaccct ccatgcctca cacacatcta    660
ttactcccat gaaaatctga tcgaggattt caactcgggg ctgattgggc ccctgcttat    720
ctgtaaaaaa gggaccctaa ctgagggtgg gacacagaag acgtttgaca agcaaatcgt    780
gctactattt gctgtgtttg atgaaagcaa gagctggagc cagtcatcat ccctaatgta    840
cacagtcaat ggatatgtga atgggacaat gccagatata acagtttgtg cccatgacca    900
catcagctgg catctgctgg gaatgagctc ggggccagaa ttattctcca ttcatttcaa    960
cggccaggtc ctggagcaga accatcataa ggtctcagcc atcacccttg tcagtgctac   1020
atccactacc gcaaatatga ctgtgggccc agagggaaag tggatcatat cttctctcac   1080
cccaaaacat ttgcaagctg ggatgcaggc ttacattgac attaaaaact gcccaaagaa   1140
aaccaggaat cttaagaaaa taactcgtga gcagaggcgg cacatgaaga ggtgggaata   1200
cttcattgct gcagaggaag tcatttggga ctatgcacct gtaataccag cgaatatgga   1260
caaaaaatac aggtctcagc atttggataa tttctcaaac caaattggaa aacattataa   1320
gaaagttatg tacacacagt acgaagatga gtccttcacc aaacatacag tgaatcccaa   1380
tatgaaagaa gatgggattt tgggtcctat tatcagagcc caggtcagag acacactcaa   1440
aatcgtgttc aaaaatatgg ccagccgccc ctatagcatt taccctcatg gagtgacctt   1500
ctcgccttat gaagatgaag tcaactcttc tttcacctca ggcaggaaca acaccatgat   1560
cagagcagtt caaccagggg aaacctatac ttataagtgg aacatcttag agtttgatga   1620
acccacagaa aatgatgccc agtgcttaac aagaccatac tacagtgacg tggacatcat   1680
gagagacatc gcctctgggc taataggact acttctaatc tgtaagagca gatccctgga   1740
caggcgagga atacagaggg cagcagacat cgaacagcag gctgtgtttg ctgtgtttga   1800
tgagaacaaa agctggtacc ttgaggacaa catcaacaag ttttgtgaaa atcctgatga   1860
ggtgaaacgt gatgaccccca agttttatga atcaaacatc atgagcacta tcaatggcta   1920
tgtgcctgag agcataacta ctcttggatt ctgctttgat gacactgtcc agtggcactt   1980
ctgtagtgtg gggacccaga tgaaattttt gaccatccac ttcactgggc actcattcat   2040
ctatggaaag aggcatgagg acaccttgac cctcttcccc atgcgtggag aatctgtgac   2100
ggtcacaatg gataatgttg gaacttggat gttaacttcc atgaattcta gtccaagaag   2160
caaaaagctg aggctgaaat tcagggatgt taaatgtatc ccagatgatg atgaagactc   2220
atatgagatt tttgaacctc cagaatctac agtcatggct acacggaaaa tgcatgatcg   2280
tttagaacct gaagatgaag agagtgatgc tgactatgat taccagaaca gactggctgc   2340
agcattagga atcaggtcat tccgaaactc atcattgaat caggaagaag aagagttcaa   2400
tcttactgcc ctagctctgg agaatggcac tgaattcgtt tcttcaaaca cagatataat   2460
tgttggttca aattattctt ccccaagtaa tattagtaag ttcactgtca ataaccttgc   2520
agaacctcag aaagcccctt ctcaccaaca agccaccaca gctggttccc cactgagaca   2580
cctcattggc aagaactcag ttctcaattc ttccacagca gagcattcca gcccatattc   2640
tgaagaccct atagaggatc ctctacagcc agatgtcaca gggatacgtc tactttcact   2700
tggtgctgga gaattcaaaa gtcaagaaca tgctaagcat aagggaccca aggtagaaag   2760
```

-continued

| | |
|---|---|
| agatcaagca gcaaagcaca ggttctcctg gatgaaatta ctagcacata aagttgggag | 2820 |
| acacctaagc caagacactg gttctccttc cggaatgagg ccctgggagg accttcctag | 2880 |
| ccaagacact ggttctcctt ccagaatgag gccctggaag gaccctccta gtgatctgtt | 2940 |
| actcttaaaa caaagtaact catctaagat tttggttggg agatggcatt tggcttctga | 3000 |
| gaaaggtagc tatgaaataa tccaagatac tgatgaagac acagctgtta acaattggct | 3060 |
| gatcagcccc cagaatgcct cacgtgcttg gggagaaagc acccctcttg ccaacaagcc | 3120 |
| tggaaagcag agtggccacc caaagtttcc tagagttaga cataaatctc tacaagtaag | 3180 |
| acaggatgga ggaaagagta gactgaagaa aagccagttt ctcattaaga cacgaaaaaa | 3240 |
| gaaaaaagag aagcacacac accatgctcc tttatctccg aggacctttc accctctaag | 3300 |
| aagtgaagcc tacaacacat tttcagaaag aagacttaag cattcgttgg tgcttcataa | 3360 |
| atccaatgaa acatctcttc ccacagacct caatcagaca ttgccctcta tggattttgg | 3420 |
| ctggatagcc tcacttcctg accataatca gaattcctca aatgacactg gtcaggcaag | 3480 |
| ctgtcctcca ggtctttatc agacagtgcc cccagaggaa cactatcaaa cattccccat | 3540 |
| tcaagaccct gatcaaatgc actctacttc agacccagt cacagatcct cttctccaga | 3600 |
| gctcagtgaa atgcttgagt atgaccgaag tcacaagtcc ttccccacag atataagtca | 3660 |
| aatgtcccct tcctcagaac atgaagtctg gcagacagtc atctctccag acctcagcca | 3720 |
| ggtgaccctc tctccagaac tcagccagac aaacctctct ccagacctca gccacacgac | 3780 |
| tctctctcca gaactcattc agagaaacct ttccccagcc ctcggtcaga tgcccatttc | 3840 |
| tccagacctc agccatacaa cccttctcc agacctcagc catacaaccc tttctttaga | 3900 |
| cctcagccag acaaacctct ctccagaact cagtcagaca aacctttctc agccctcgg | 3960 |
| tcagatgccc ctttctccag acctcagcca tacaaccctt tctctagact tcagccagac | 4020 |
| aaacctctct ccagaactca gccatatgac tctctctcca gaactcagtc agacaaacct | 4080 |
| ttccccagcc ctcggtcaga tgcccatttc tccagacctc agccatacaa cccttctct | 4140 |
| agacttcagc cagacaaacc tctctccaga actcagtcaa acaaaccttt ccccagccct | 4200 |
| cggtcagatg ccccttctc cagacccag ccatacaacc ctttctctag acctcagcca | 4260 |
| gacaaacctc tctccagaac tcagtcagac aaacctttcc ccagacctca gtgagatgcc | 4320 |
| cctctttgca gatctcagtc aaattcccct taccccagac ctcgaccaga tgacactttc | 4380 |
| tccagacctt ggtgagacag atctttcccc aaactttggt cagatgtccc ttccccaga | 4440 |
| cctcagccag gtgactctct ctccagacat cagtgacacc acccttctcc cggatctcag | 4500 |
| ccagatatca cctcctccag accttgatca gatattctac ccttctgaat ctagtcagtc | 4560 |
| attgcttctt caagaattta atgagtcttt tccttatcca gaccttggtc agatgccatc | 4620 |
| tccttcatct cctactctca atgatacttt tctatcaaag gaatttaatc cactggttat | 4680 |
| agtgggcctc agtaaagatg gtacagatta cattgagatc attccaaagg aagaggtcca | 4740 |
| gagcagtgaa gatgactatg ctgaaattga ttatgtgccc tatgatgacc cctacaaaac | 4800 |
| tgatgttagg acaaacatca actcctccag agatcctgac aacattgcag catggtacct | 4860 |
| ccgcagcaac aatggaaaca gaagaaatta ttacattgct gctgaagaaa tatcctggga | 4920 |
| ttattcagaa tttgtacaaa gggaaacaga tattgaagac tctgatgata ttccagaaga | 4980 |
| taccacatat aagaaagtag tttttcgaaa gtacctcgac agcactttta ccaaacgtga | 5040 |
| tcctcgaggg gagtatgaag agcatctcgg aattcttggt cctattatca gagctgaagt | 5100 |

```
ggatgatgtt atccaagttc gttttaaaaa tttagcatcc agaccgtatt ctctacatgc    5160
ccatggactt tcctatgaaa aatcatcaga gggaaagact tatgaagatg actctcctga    5220
atggtttaag gaagataatg ctgttcagcc aaatagcagt tatacctacg tatggcatgc    5280
cactgagcga tcagggccag aaagtcctgg ctctgcctgt cgggcttggg cctactactc    5340
agctgtgaac ccagaaaaag atattcactc aggcttgata ggtcccctcc taatctgcca    5400
aaaaggaata ctacataagg acagcaacat gcctatggac atgagagaat tgtgtcttact   5460 atttatgacc tttgatgaaa agaagagctg gtactatgaa aagaagtccc gaagttcttg    5520
gagactcaca tcctcagaaa tgaaaaaatc ccatgagttt cacgccatta atgggatgat    5580
ctacagcttg cctggcctga aatgtatga gcaagagtgg gtgaggttac acctgctgaa    5640
cataggcggc tcccaagaca ttcacgtggt tcactttcac ggccagacct tgctggaaaa    5700
tggcaataaa cagcaccagt tagggtctg gccccttctg cctggttcat ttaaaactct    5760
tgaaatgaag gcatcaaaac ctggctggtg gctcctaaac acagaggttg gagaaaacca    5820
gagagcaggg atgcaaacgc catttcttat catggacaga gactgtagga tgccaatggg    5880
actaagcact ggtatcatat ctgattcaca gatcaaggct tcagagtttc tgggttactg    5940
ggagcccaga ttagcaagat aaacaatgg tggatcttat aatgcttgga gtgtagaaaa    6000
acttgcagca gaatttgcct ctaaaccttg gatccaggtg gacatgcaaa aggaagtcat    6060
aatcacaggg atccagaccc aaggtgccaa acactacctg aagtcctgct ataccacaga    6120
gttctatgta gcttacagtt ccaaccagat caactggcag atcttcaaag gaacagcac    6180 aaggaatgtg atgtatttta atggcaattc agatgcctct acaataaaag gaatcagtt    6240 tgacccacct attgtggcta gatatattag gatctctcca actcgagcct ataacagacc    6300
tacccttcga ttggaactgc aaggttgtga ggtaaatgga tgttccacac ccctgggtat    6360 ggaaatgga aagatagaaa acaagcaaat cacagcttct tcgtttaaga atcttggtg    6420 gggagattac tgggaacct tccgtgcccg tctgaatgcc cagggacgtg tgaatgcctg    6480
gcaagccaag gcaaacaaca taagcagtg gctagaaatt gatctactca agatcaagaa    6540
gataacggca attataacac agggctgcaa gtctctgtcc tctgaaatgt atgtaaagag    6600
ctataccatc cactacagtg agcagggagt ggaatggaaa ccatacaggc tgaaatcctc    6660
catggtggac aagattttg aaggaaatac taataccaaa ggacatgtga agaactttt    6720 caacccccca atcatttcca ggtttatccg tgtcattcct aaaacatgga atcaaagtat    6780
tgcacttcgc ctggaactct ttggctgtga tattactag aattgaacat tcaaaaccc    6840 ctggaagaga ctctttaaga cctcaaacca tttagaatgg gcaatgtatt ttacgctgtg    6900
ttaaatgtta acagttttcc actatttctc tttcttttct attagtgaat aaaattttat    6960
acaagaagct tttataatgt aactccttgc taccagtaag taagataatg gctattactt    7020
ctgcattaat ttgaatacag gtaggaaaat atcaagaacc aacaagaaaa gggcttatct    7080
ttcttaatga ttgaaaatgc tatgagtaa tatttatgta gttaaaatgc ttcattataa    7140
ctcttttaaa tcctttacac actagtaaaa cagatattac tttaaataat aattgataga    7200
cctggataac tttcacaaac acatgatttt ttaatggttt ttcttgagtg aagagaaaaa    7260
caatattatc aaatgaaata agtacttaaa atatcctgtc tttcccatat aacaatgatt    7320
tttctgactt tccatgagta aaaaaacagc caagcatctt tccagtagcc ccattgaaat    7380
tgtgaatccg tcctggtctc cctaaggact gcacacattg atattcaagg ttggtggtca    7440
ttagatatgg aacagaactg aaataaccat ggtagaactg aatgtgtaat gttggctta    7500
```

-continued

| | |
|---|---|
| ttctagctgg tactacatgg cacacagttt caaaacataa tttcacctac tggaaagctc | 7560 |
| agacctgtaa aacagagcat gggaactgct ggtctaaatg cagttgttcc tgctcaaaga | 7620 |
| gacctctggc caaactggca agcagttaaa gttttctttc agggccttcc tctctatggc | 7680 |
| ctcaacttcc tcctctctct tcttccagca acttccccct tcatcattcc tttccctggg | 7740 |
| gacttggcat tcagtgatcc tgtagatatt gcacaactgg ggaacctttta gacatcctta | 7800 |
| aaatcacatg agatagacag tcatttgggg tgtctgaaat aaaccacccc aaaacttagt | 7860 |
| gttaaaagag caaccaaaaa aaatttatgt gagattatgg atttgttact tagcttgatt | 7920 |
| taatcatcct gtaacgtgta catatatcaa aatgttatgt ataccataaa tatataaaat | 7980 |
| tttatcaacg aaattcataa caatctctca gaccacagag aaatcaaatt agaactgagg | 8040 |
| actaagaaac tcactcgaaa ccacacaact acatggaaac tgaacaaacct gctcctgaat | 8100 |
| gactactggg taaataatga aattaaggca gaaataaata agttccttaa aaccaatgag | 8160 |
| aacaaagaga caacatacca gaatctctag gagacagggc tttgcttttg ctgcattcta | 8220 |
| ttcgttgtga acacaaatta caggccagtc tcgattcagt gtagaaggga actgcataag | 8280 |
| gaccacatac caggaggcat aattcactgg gagcatcttt agaaactacc agagttacct | 8340 |
| gttgcccata ccagtggggt aagccctatg aatgtatatg agagtttcaa acatccacaa | 8400 |
| aacattggct ttctaatatt cgtattccca ctattccttt cttttcatga ttcatgtcat | 8460 |
| tgtcccatca acatttctaa gatttccatt ccgttaagag caaagagaa tgttggaagg | 8520 |
| tgggggaaaa catttctttg ttttctacag ggccagcttc ttggatgtgt gtgatctgtt | 8580 |
| cagttgcaaa gggtcacatg ctcagaagga ccgcatgcta aatttaatgc tttgcagtta | 8640 |
| ccctcttgaa atcctttatt ttttaagaag gaattcgaca tttccatttt tcaatgagcc | 8700 |
| ccacaaatta cgcagctagt cctgggcttc tctactctga aattgggcag gatctctctt | 8760 |
| gatctagaat ttactaaggc ataatagggg caagaaaatc ttatgaaata atgggggta | 8820 |
| gggaagagat gggaatggag catgagatcc agcttcgtta ttctctactt gagaaaaata | 8880 |
| aggcccaaaa gattaaacaa cttgcccaag gatattgctt gttagtgtca gaactgaaac | 8940 |
| cagaaaccaa atgatcatat ccctagactt ttagtctgct ttctcttcca taaaatgaaa | 9000 |
| cttataatgt ttctaatcca ttgctcagac aggtagacat gaatattaat tgataatgac | 9060 |
| tattaattga tctggaaaat acttgttttgg ggatcaataa tatgtttggg ctattatcta | 9120 |
| atgctgtgta gaaatattaa aaccctgtt attttgaaat aaaaaagata cccacttttt | 9179 |

<210> SEQ ID NO 16
<211> LENGTH: 2224
<212> TYPE: PRT
<213> ORGANISM: Homo sapiens

<400> SEQUENCE: 16

Met Phe Pro Gly Cys Pro Arg Leu Trp Val Leu Val Leu Gly Thr
1               5                   10                  15

Ser Trp Val Gly Trp Gly Ser Gln Gly Thr Glu Ala Ala Gln Leu Arg
                20                  25                  30

Gln Phe Tyr Val Ala Ala Gln Gly Ile Ser Trp Ser Tyr Arg Pro Glu
            35                  40                  45

Pro Thr Asn Ser Ser Leu Asn Leu Ser Val Thr Ser Phe Lys Lys Ile
        50                  55                  60

Val Tyr Arg Glu Tyr Glu Pro Tyr Phe Lys Lys Glu Lys Pro Gln Ser
65                  70                  75                  80

-continued

```
Thr Ile Ser Gly Leu Leu Gly Pro Thr Leu Tyr Ala Glu Val Gly Asp
                85                  90                  95

Ile Ile Lys Val His Phe Lys Asn Lys Ala Asp Lys Pro Leu Ser Ile
            100                 105                 110

His Pro Gln Gly Ile Arg Tyr Ser Lys Leu Ser Glu Gly Ala Ser Tyr
        115                 120                 125

Leu Asp His Thr Phe Pro Ala Glu Lys Met Asp Asp Ala Val Ala Pro
    130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
                165                 170                 175

Asn Leu Ile Glu Asp Phe Asn Ser Gly Leu Ile Gly Pro Leu Leu Ile
            180                 185                 190

Cys Lys Lys Gly Thr Leu Thr Glu Gly Gly Thr Gln Lys Thr Phe Asp
        195                 200                 205

Lys Gln Ile Val Leu Leu Phe Ala Val Phe Asp Glu Ser Lys Ser Trp
    210                 215                 220

Ser Gln Ser Ser Ser Leu Met Tyr Thr Val Asn Gly Tyr Val Asn Gly
225                 230                 235                 240

Thr Met Pro Asp Ile Thr Val Cys Ala His Asp His Ile Ser Trp His
                245                 250                 255

Leu Leu Gly Met Ser Ser Gly Pro Glu Leu Phe Ser Ile His Phe Asn
            260                 265                 270

Gly Gln Val Leu Glu Gln Asn His His Lys Val Ser Ala Ile Thr Leu
        275                 280                 285

Val Ser Ala Thr Ser Thr Thr Ala Asn Met Thr Val Gly Pro Glu Gly
    290                 295                 300

Lys Trp Ile Ile Ser Ser Leu Thr Pro Lys His Leu Gln Ala Gly Met
305                 310                 315                 320

Gln Ala Tyr Ile Asp Ile Lys Asn Cys Pro Lys Lys Thr Arg Asn Leu
                325                 330                 335

Lys Lys Ile Thr Arg Glu Gln Arg Arg His Met Lys Arg Trp Glu Tyr
            340                 345                 350

Phe Ile Ala Ala Glu Glu Val Ile Trp Asp Tyr Ala Pro Val Ile Pro
        355                 360                 365

Ala Asn Met Asp Lys Lys Tyr Arg Ser Gln His Leu Asp Asn Phe Ser
    370                 375                 380

Asn Gln Ile Gly Lys His Tyr Lys Lys Val Met Tyr Thr Gln Tyr Glu
385                 390                 395                 400

Asp Glu Ser Phe Thr Lys His Thr Val Asn Pro Asn Met Lys Glu Asp
                405                 410                 415

Gly Ile Leu Gly Pro Ile Ile Arg Ala Gln Val Arg Asp Thr Leu Lys
            420                 425                 430

Ile Val Phe Lys Asn Met Ala Ser Arg Pro Tyr Ser Ile Tyr Pro His
        435                 440                 445

Gly Val Thr Phe Ser Pro Tyr Glu Asp Glu Val Asn Ser Ser Phe Thr
    450                 455                 460

Ser Gly Arg Asn Asn Thr Met Ile Arg Ala Val Gln Pro Gly Glu Thr
465                 470                 475                 480

Tyr Thr Tyr Lys Trp Asn Ile Leu Glu Phe Asp Glu Pro Thr Glu Asn
                485                 490                 495
```

-continued

Asp Ala Gln Cys Leu Thr Arg Pro Tyr Tyr Ser Asp Val Asp Ile Met
            500                 505                 510
Arg Asp Ile Ala Ser Gly Leu Ile Gly Leu Leu Ile Cys Lys Ser
    515                 520                 525
Arg Ser Leu Asp Arg Arg Gly Ile Gln Arg Ala Ala Asp Ile Glu Gln
530                 535                 540
Gln Ala Val Phe Ala Val Phe Asp Glu Asn Lys Ser Trp Tyr Leu Glu
545                 550                 555                 560
Asp Asn Ile Asn Lys Phe Cys Glu Asn Pro Asp Glu Val Lys Arg Asp
                565                 570                 575
Asp Pro Lys Phe Tyr Glu Ser Asn Ile Met Ser Thr Ile Asn Gly Tyr
            580                 585                 590
Val Pro Glu Ser Ile Thr Thr Leu Gly Phe Cys Phe Asp Asp Thr Val
            595                 600                 605
Gln Trp His Phe Cys Ser Val Gly Thr Gln Asn Glu Ile Leu Thr Ile
    610                 615                 620
His Phe Thr Gly His Ser Phe Ile Tyr Gly Lys Arg His Glu Asp Thr
625                 630                 635                 640
Leu Thr Leu Phe Pro Met Arg Gly Glu Ser Val Thr Val Thr Met Asp
                645                 650                 655
Asn Val Gly Thr Trp Met Leu Thr Ser Met Asn Ser Ser Pro Arg Ser
            660                 665                 670
Lys Lys Leu Arg Leu Lys Phe Arg Asp Val Lys Cys Ile Pro Asp Asp
        675                 680                 685
Asp Glu Asp Ser Tyr Glu Ile Phe Glu Pro Pro Glu Ser Thr Val Met
    690                 695                 700
Ala Thr Arg Lys Met His Asp Arg Leu Glu Pro Glu Asp Glu Glu Ser
705                 710                 715                 720
Asp Ala Asp Tyr Asp Tyr Gln Asn Arg Leu Ala Ala Ala Leu Gly Ile
                725                 730                 735
Arg Ser Phe Arg Asn Ser Ser Leu Asn Gln Glu Glu Glu Phe Asn
            740                 745                 750
Leu Thr Ala Leu Ala Leu Glu Asn Gly Thr Glu Phe Val Ser Ser Asn
755                 760                 765
Thr Asp Ile Ile Val Gly Ser Asn Tyr Ser Ser Pro Ser Asn Ile Ser
770                 775                 780
Lys Phe Thr Val Asn Asn Leu Ala Glu Pro Gln Lys Ala Pro Ser His
785                 790                 795                 800
Gln Gln Ala Thr Thr Ala Gly Ser Pro Leu Arg His Leu Ile Gly Lys
                805                 810                 815
Asn Ser Val Leu Asn Ser Ser Thr Ala Glu His Ser Ser Pro Tyr Ser
            820                 825                 830
Glu Asp Pro Ile Glu Asp Pro Leu Gln Pro Asp Val Thr Gly Ile Arg
        835                 840                 845
Leu Leu Ser Leu Gly Ala Gly Glu Phe Lys Ser Gln Glu His Ala Lys
    850                 855                 860
His Lys Gly Pro Lys Val Glu Arg Asp Gln Ala Ala Lys His Arg Phe
865                 870                 875                 880
Ser Trp Met Lys Leu Leu Ala His Lys Val Gly Arg His Leu Ser Gln
                885                 890                 895
Asp Thr Gly Ser Pro Ser Gly Met Arg Pro Trp Glu Asp Leu Pro Ser
            900                 905                 910
Gln Asp Thr Gly Ser Pro Ser Arg Met Arg Pro Trp Lys Asp Pro Pro

```
                915                 920                 925
Ser Asp Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Glu Ser Thr Pro Leu Ala Asn Lys Pro
                980                 985                 990

Gly Lys Gln Ser Gly His Pro Lys  Phe Pro Arg Val Arg  His Lys Ser
                995                 1000                1005

Leu Gln  Val Arg Gln Asp Gly  Gly Lys Ser Arg Leu  Lys Lys Ser
    1010                1015                1020

Gln Phe  Leu Ile Lys Thr Arg  Lys Lys Lys Lys Glu  Lys His Thr
    1025                1030                1035

His His  Ala Pro Leu Ser Pro  Arg Thr Phe His Pro  Leu Arg Ser
    1040                1045                1050

Glu Ala  Tyr Asn Thr Phe Ser  Glu Arg Arg Leu Lys  His Ser Leu
    1055                1060                1065

Val Leu  His Lys Ser Asn Glu  Thr Ser Leu Pro Thr  Asp Leu Asn
    1070                1075                1080

Gln Thr  Leu Pro Ser Met Asp  Phe Gly Trp Ile Ala  Ser Leu Pro
    1085                1090                1095

Asp His  Asn Gln Asn Ser Ser  Asn Asp Thr Gly Gln  Ala Ser Cys
    1100                1105                1110

Pro Pro  Gly Leu Tyr Gln Thr  Val Pro Pro Glu Glu  His Tyr Gln
    1115                1120                1125

Thr Phe  Pro Ile Gln Asp Pro  Asp Gln Met His Ser  Thr Ser Asp
    1130                1135                1140

Pro Ser  His Arg Ser Ser Ser  Pro Glu Leu Ser Glu  Met Leu Glu
    1145                1150                1155

Tyr Asp  Arg Ser His Lys Ser  Phe Pro Thr Asp Ile  Ser Gln Met
    1160                1165                1170

Ser Pro  Ser Ser Glu His Glu  Val Trp Gln Thr Val  Ile Ser Pro
    1175                1180                1185

Asp Leu  Ser Gln Val Thr Leu  Ser Pro Glu Leu Ser  Gln Thr Asn
    1190                1195                1200

Leu Ser  Pro Asp Leu Ser His  Thr Thr Leu Ser Pro  Glu Leu Ile
    1205                1210                1215

Gln Arg  Asn Leu Ser Pro Ala  Leu Gly Gln Met Pro  Ile Ser Pro
    1220                1225                1230

Asp Leu  Ser His Thr Thr Leu  Ser Pro Asp Leu Ser  His Thr Thr
    1235                1240                1245

Leu Ser  Leu Asp Leu Ser Gln  Thr Asn Leu Ser Pro  Glu Leu Ser
    1250                1255                1260

Gln Thr  Asn Leu Ser Pro Ala  Leu Gly Gln Met Pro  Leu Ser Pro
    1265                1270                1275

Asp Leu  Ser His Thr Thr Leu  Ser Leu Asp Phe Ser  Gln Thr Asn
    1280                1285                1290

Leu Ser  Pro Glu Leu Ser His  Met Thr Leu Ser Pro  Glu Leu Ser
    1295                1300                1305

Gln Thr  Asn Leu Ser Pro Ala  Leu Gly Gln Met Pro  Ile Ser Pro
    1310                1315                1320
```

-continued

```
Asp Leu Ser His Thr Thr Leu Ser Leu Asp Phe Ser Gln Thr Asn
1325                1330                1335

Leu Ser Pro Glu Leu Ser Gln Thr Asn Leu Ser Pro Ala Leu Gly
1340                1345                1350

Gln Met Pro Leu Ser Pro Asp Pro Ser His Thr Thr Leu Ser Leu
1355                1360                1365

Asp Leu Ser Gln Thr Asn Leu Ser Pro Glu Leu Ser Gln Thr Asn
1370                1375                1380

Leu Ser Pro Asp Leu Ser Glu Met Pro Leu Phe Ala Asp Leu Ser
1385                1390                1395

Gln Ile Pro Leu Thr Pro Asp Leu Asp Gln Met Thr Leu Ser Pro
1400                1405                1410

Asp Leu Gly Glu Thr Asp Leu Ser Pro Asn Phe Gly Gln Met Ser
1415                1420                1425

Leu Ser Pro Asp Leu Ser Gln Val Thr Leu Ser Pro Asp Ile Ser
1430                1435                1440

Asp Thr Thr Leu Leu Pro Asp Leu Ser Gln Ile Ser Pro Pro Pro
1445                1450                1455

Asp Leu Asp Gln Ile Phe Tyr Pro Ser Glu Ser Ser Gln Ser Leu
1460                1465                1470

Leu Leu Gln Glu Phe Asn Glu Ser Phe Pro Tyr Pro Asp Leu Gly
1475                1480                1485

Gln Met Pro Ser Pro Ser Ser Pro Thr Leu Asn Asp Thr Phe Leu
1490                1495                1500

Ser Lys Glu Phe Asn Pro Leu Val Ile Val Gly Leu Ser Lys Asp
1505                1510                1515

Gly Thr Asp Tyr Ile Glu Ile Ile Pro Lys Glu Glu Val Gln Ser
1520                1525                1530

Ser Glu Asp Asp Tyr Ala Glu Ile Asp Tyr Val Pro Tyr Asp Asp
1535                1540                1545

Pro Tyr Lys Thr Asp Val Arg Thr Asn Ile Asn Ser Ser Arg Asp
1550                1555                1560

Pro Asp Asn Ile Ala Ala Trp Tyr Leu Arg Ser Asn Asn Gly Asn
1565                1570                1575

Arg Arg Asn Tyr Tyr Ile Ala Ala Glu Glu Ile Ser Trp Asp Tyr
1580                1585                1590

Ser Glu Phe Val Gln Arg Glu Thr Asp Ile Glu Asp Ser Asp Asp
1595                1600                1605

Ile Pro Glu Asp Thr Thr Tyr Lys Lys Val Val Phe Arg Lys Tyr
1610                1615                1620

Leu Asp Ser Thr Phe Thr Lys Arg Asp Pro Arg Gly Glu Tyr Glu
1625                1630                1635

Glu His Leu Gly Ile Leu Gly Pro Ile Ile Arg Ala Glu Val Asp
1640                1645                1650

Asp Val Ile Gln Val Arg Phe Lys Asn Leu Ala Ser Arg Pro Tyr
1655                1660                1665

Ser Leu His Ala His Gly Leu Ser Tyr Glu Lys Ser Ser Glu Gly
1670                1675                1680

Lys Thr Tyr Glu Asp Asp Ser Pro Glu Trp Phe Lys Glu Asp Asn
1685                1690                1695

Ala Val Gln Pro Asn Ser Ser Tyr Thr Tyr Val Trp His Ala Thr
1700                1705                1710
```

```
Glu Arg Ser Gly Pro Glu Ser Pro Gly Ser Ala Cys Arg Ala Trp
1715                1720                1725

Ala Tyr Tyr Ser Ala Val Asn Pro Glu Lys Asp Ile His Ser Gly
1730                1735                1740

Leu Ile Gly Pro Leu Leu Ile Cys Gln Lys Gly Ile Leu His Lys
1745                1750                1755

Asp Ser Asn Met Pro Val Asp Met Arg Glu Phe Val Leu Leu Phe
1760                1765                1770

Met Thr Phe Asp Glu Lys Lys Ser Trp Tyr Tyr Glu Lys Lys Ser
1775                1780                1785

Arg Ser Ser Trp Arg Leu Thr Ser Ser Glu Met Lys Lys Ser His
1790                1795                1800

Glu Phe His Ala Ile Asn Gly Met Ile Tyr Ser Leu Pro Gly Leu
1805                1810                1815

Lys Met Tyr Glu Gln Glu Trp Val Arg Leu His Leu Leu Asn Ile
1820                1825                1830

Gly Gly Ser Gln Asp Ile His Val Val His Phe His Gly Gln Thr
1835                1840                1845

Leu Leu Glu Asn Gly Asn Lys Gln His Gln Leu Gly Val Trp Pro
1850                1855                1860

Leu Leu Pro Gly Ser Phe Lys Thr Leu Glu Met Lys Ala Ser Lys
1865                1870                1875

Pro Gly Trp Trp Leu Leu Asn Thr Glu Val Gly Glu Asn Gln Arg
1880                1885                1890

Ala Gly Met Gln Thr Pro Phe Leu Ile Met Asp Arg Asp Cys Arg
1895                1900                1905

Met Pro Met Gly Leu Ser Thr Gly Ile Ile Ser Asp Ser Gln Ile
1910                1915                1920

Lys Ala Ser Glu Phe Leu Gly Tyr Trp Glu Pro Arg Leu Ala Arg
1925                1930                1935

Leu Asn Asn Gly Gly Ser Tyr Asn Ala Trp Ser Val Glu Lys Leu
1940                1945                1950

Ala Ala Glu Phe Ala Ser Lys Pro Trp Ile Gln Val Asp Met Gln
1955                1960                1965

Lys Glu Val Ile Ile Thr Gly Ile Gln Thr Gln Gly Ala Lys His
1970                1975                1980

Tyr Leu Lys Ser Cys Tyr Thr Thr Glu Phe Tyr Val Ala Tyr Ser
1985                1990                1995

Ser Asn Gln Ile Asn Trp Gln Ile Phe Lys Gly Asn Ser Thr Arg
2000                2005                2010

Asn Val Met Tyr Phe Asn Gly Asn Ser Asp Ala Ser Thr Ile Lys
2015                2020                2025

Glu Asn Gln Phe Asp Pro Pro Ile Val Ala Arg Tyr Ile Arg Ile
2030                2035                2040

Ser Pro Thr Arg Ala Tyr Asn Arg Pro Thr Leu Arg Leu Glu Leu
2045                2050                2055

Gln Gly Cys Glu Val Asn Gly Cys Ser Thr Pro Leu Gly Met Glu
2060                2065                2070

Asn Gly Lys Ile Glu Asn Lys Gln Ile Thr Ala Ser Ser Phe Lys
2075                2080                2085

Lys Ser Trp Trp Gly Asp Tyr Trp Glu Pro Phe Arg Ala Arg Leu
2090                2095                2100

Asn Ala Gln Gly Arg Val Asn Ala Trp Gln Ala Lys Ala Asn Asn
```

```
                2105                2110                2115
Asn Lys Gln Trp Leu Glu Ile Asp Leu Leu Lys Ile Lys Lys Ile
        2120                2125                2130

Thr Ala Ile Ile Thr Gln Gly Cys Lys Ser Leu Ser Ser Glu Met
        2135                2140                2145

Tyr Val Lys Ser Tyr Thr Ile His Tyr Ser Glu Gln Gly Val Glu
        2150                2155                2160

Trp Lys Pro Tyr Arg Leu Lys Ser Ser Met Val Asp Lys Ile Phe
        2165                2170                2175

Glu Gly Asn Thr Asn Thr Lys Gly His Val Lys Asn Phe Phe Asn
        2180                2185                2190

Pro Pro Ile Ile Ser Arg Phe Ile Arg Val Ile Pro Lys Thr Trp
        2195                2200                2205

Asn Gln Ser Ile Ala Leu Arg Leu Glu Leu Phe Gly Cys Asp Ile
        2210                2215                2220

Tyr

<210> SEQ ID NO 17
<211> LENGTH: 6910
<212> TYPE: DNA
<213> ORGANISM: Bos Taurus

<400> SEQUENCE: 17
agcctctggg agctcactgc agcccggcct gcggacagcc tcgcagaggc agccctaacc      60
caccccgggg gtggtggcgg caggcaagag aaggaaagga accatgttcc tcgcttgccc     120
tggcttctgg gtcctcgtgg tcctaggcag cagctgggca ggctgggga acctaggggc     180 tgaagcagca aagctaaggc agttctacgt agctgctcag agcatcagat ggaactaccg     240
ccccgagtcc acacacctca gttcgaaacc ttttgaaacc tcctttaaga aaattgtcta     300
cagggagtat gaagcatatt ttcagaaaga aaaaccacaa tccagaactt caggacttct     360
tgggcctact ttgtatgctg aagttggaga catcatgaaa gttcactta agaataaagc      420 acacaagccc ttaagcatcc atgctcaagg aattaagtac agtaaattct cagaaggtgc     480
gtcttactct gaccacacac tccccatgga aagatggat gatgctgtag ctccgggcca     540
agaatatacc tatgagtgga ttatcagtga gcacagtggg cccacccacg atgaccctcc     600
atgcctcaca cacatctatt actcctatgt aaatctggtg gaggacttca actctggact     660
gattggacct ctgcttattt gtaagaaagg cacccctaacc gaggatggaa ctcagaaaat     720
gtttgagaag caacatgtac tgatgtttgc tgtgtttgat gaaagtaaaa gctgaaacca     780
gacatcatcc ttaatgtaca cagtcaatgg ctatgtgaat gggacgatgc cagatataac     840
agtctgtgcc catgaccaca tcagttggca tctgattgga atgagctctg gccagaact      900 gttctccatc catttcaatg gtcaggtcct ggagcagaac catcataaga tctcagccat     960
cactctcgtc agcgccacgt ccacaaccgc aaacatgacc gtgagccccg agggaaggtg    1020
gaccatagct tctctcatcc ccagacattt tcaagctggg atgcaggctt acatagacat    1080
taaaaactgt gcaaagaaaa ccagaaatcc taagaaacta actcgagacc agaggcggca    1140
cattaagaga tgggaatact tcattgctgc agaggaagtc atttgggact atgcacctat    1200
aataccagca acatggacaa aaatatacag atctctgcat ttggataatt tctcaaaccg    1260
aattggaaaa cattataaga aggttgtcta caaacagtac caagatgact ccttcaccaa    1320
acgcctggag gatcccagta gtgaaggaga tgggatcttg ggcccatta tcagagccca    1380
```

-continued

```
ggtcagagac acactgaaaa tcgtgttcaa aaatatggcc agccgctcct acagcattta    1440
ccctcacggt gtgacattct ctccttatga caatgaagta aactcttcct caacctcagg    1500
cagcaacacc atgatcagag cagttcgacc aggggaaacc tacacttata agtggaacat    1560
cctagaatct gatgaaccca cagaaaatga tgctcagtgc ttaacaagac catactacag    1620
taatgtggac atcacaaggg accttgcttc tggactgata gggcttcttc taatttgtaa    1680
gagcagatcc ttggatagac gaggcataca gagggcagca gacatcgagc agcaggctgt    1740
gtttgccgtg tttgacgaga acaagagctg gtacattgag acaacatct acaagttttg    1800
tgaaaatcct gagaaagtga aacgtgatga ccccaagttt tatgagtcaa acatcatgag    1860
taatttcact cttccagcta ttaacggcta tgtgcctgag agtatacccca tactagggtt    1920
ctgctttgat gacactgtcc agtggcactt ctgcagtgtg ggaacccaga atgacatttt    1980
gaccattcac ttcactgggc actcattcat ctatggaaag aggcacgagg acaccttgac    2040
ccttttcccc atgcagggggg aatccgtgac tgtcacaatg gataatgttg gaacttggat    2100
gttaaccacc atgaattcca atccaagaag caaaaaacta cggctgaggt tcagggatgc    2160
taagtgtatc cggaatgatg atgatgactc ctatgagatt atatatgaac cttcaggatc    2220
tacagccatg actacaaaga aaattcatga ttcttcagaa atcgaagatg aaaatgatgc    2280
tgactctgat taccaggacg aactggcttt aatactaggt cttaggtcat tcagaaattc    2340
atcactgaat caggagaaag atgagctcaa tcttaccgcc ctagctctgg agaaagactc    2400
tgaattcatt cctccgagtg ccaacagatc tcttgattca aattcttctt cccgaagtca    2460
tgttagcagg cttattgcca aaaactttgc agaatctctg aaaactcttc tgcacctgga    2520
agcccctgca gctggttccc ccctggaaca cgctggctta gataagaact cagctctcaa    2580
ccctcccatg gcagagcatt ccagccctta ttctgaagac cctagagaag atcatccact    2640
ctcagatgtc acaggggtaa gcctacttcc atttggcaca ggattcaaaa atcgaaaacc    2700
tgccaaacat caaagattcc aggtaggaag aggccaagca gcaaagcata agttctccca    2760
gacgcgattc ccagcacata aaaccaggac acgtttaagc caagacaact cttcttcttc    2820
cagaatgggg ccctgggagg acattcccag tgatctgtta ctcttacaac aaaaggatcc    2880
atataagatt ctgaatggag aatggcattt ggtttctgag aaaggcagtt atgaaataat    2940
ccaagatgct aatgaaaaca agactgttaa taagttgcca acagcccccc agaatgactc    3000
aaggacttgg ggagaaaaca tccctttcaa aaacagtcat ggaaagcaga gtggccaccc    3060
aacattttttg gtaactagac gtaaacctct acaagacaga caggatagaa gaaatagtag    3120
attgaaggaa ggccttccgt taattaggac acgaagaaag aaaaaggaag agaagcctgc    3180
ataccatgtt cctctatctc caaggagttt tcatcctctg agaggagagg tcaatgcctc    3240
attttcagac agaagacata atcattcatt gttactccat gcgtccaatg aaacatctct    3300
ttccatagac ctcaatcaga cattcccctc tatgaatctt agccttgcag cctcacttcc    3360
tgaccatgac cagacctcac caaatgacac caccagtcag actagctccc ctccagatct    3420
ttatccgaca gtgagcccag aggaacacta tcaaatattc cctattcaag actctgatcc    3480
aacacattct actacagccc ccagtaacag atctcctgat ccaacacatt ctactacagc    3540
ccccagtaac agatctcctc ccacacagcc cagccagata cccaactatg acctaagaaa    3600
cagggccatc cctactgatg tgagtcaaat tttcccttcc ttggaactcg aagtctggca    3660
gacagctacc tctctagacc tcagtcaacc atccatctcc ccagacctttg ccagatggc    3720
actttccccca gaccccggcc aggagtctct ctctccagac cttggccaga cgtccctctc    3780
```

```
tccagacctc agccaggagt ctctctcccc agaccttggc cagacagccc tttcccaga    3840
ccccagccag gagtctctct ccccagacct tggccagaca gcccttttcc cagacccag    3900
ccaggagtct ctctccccag accttggcca gacagccctt tccccagacc ccggccagga    3960
gtctctctct ccagaccttg gccagacgtc cctctctcca gacctcagcc aggagtctct    4020
ctccccagac cttggccaga cagccctttc cccagacccc agccaggagt ctctctcccc    4080
agaccttggc cagacagccc tttccccaga ccccagccag gagtctctct ctccagacct    4140
tggccagacg tccctctctc cagaccttgg ccaggagtct ctctcccag accttggcca    4200
gacagccctt tccccagacc ccagccagga gtctctctct ccagaccttg gccagacgtc    4260
cctctctcca gaccttggcc aggagtctct ctccccagac cttggccaga cagccctttc    4320
cccagacctc agccaggagt ctctctcctcc agatcttggc cagacacccc tctctccaga    4380
cctcagcctg gagtctcttt ctccagacct cagccagctt gatctcaagc agacatcacc    4440
tcctctagat cttaatcaga catcccacac ttctgaatca agtcagtcat tgcctcttcc    4500
agaatttggt cagactttcc ctaatgcaga tattggtcag atgccatctc ctccaccaga    4560
ctctacacta ataacactt ttataccaga agaatttaat ccgctggttg tagtaggcct    4620
cagtagagat gatggagatt atattgaaat tattccaagg cagaaggaag agagcagtga    4680
agaagactat ggtgaatttg agtttgtagc ctataatgac ccttaccaaa ctgatcttag    4740
gacagatatc aactcctcca gaaatcctga caacattgca gcatggtacc tccgcagcaa    4800
cactggaaac agaaaatatt attacattgc agctgaagaa atatcctggg attattcaaa    4860
atttgtgcaa agtgatgacg ttgactatgt tccagaggac accgtataca agaaagtagt    4920
tttccgaaag tacttgata gcacttttac caaacttgat cctcaggggg agtatgaaga    4980
gcatcttggc atacttggtc cagtcattag agctgaagtg gatgatgtta ccaagttcg    5040
ttttaaaaat ttagcatcca gaccatattc tcttcatgcc catgggcttt cctatgaaaa    5100
atcatcagaa ggaaagactt atgaagatga ctctcctgaa tggtttaagg aggacaatgc    5160
tattcagccc aataaaaactt acacctatgt atggcacgcc actacgcgat ccgggccaga    5220
aaaccctgga tctgcctgtc gggcttgggc ctactactca gcagtgaacc cagaaaaga    5280
catccattca ggcttgatag ggcctcttct gatctgccga aaagggacac ttgataagga    5340
gaccaacatg cctgtggaca tgagagaatt tgtcctgctt tttatggtct ttgatgaaaa    5400
gaagagctgg tattatgaca agaagcccac aaggtcttgg agacgtgcat cctcagaagt    5460
aaaaaactcc catgagtttc atgccatcaa tgggatgatc tacaacttgc ctggcttgag    5520
aatgtacgag caagagtggg tgaggttgca cctgctgaac ttaggcggct cccgagacat    5580
tcacgtggtt cactttcatg gccagacctt gctagaaaac ggcactcaac agcaccagtt    5640
agggtctgg ccccttctgc ctggttcatt taaaactctt gaatgaagg catcaaaacc    5700
tggctggtgg ctcctagaca cggaagttgg agaaattcag agagcaggga tgcagacacc    5760
atttctcatt gtagacagag aatgtaagat gccaatggga ctaagcactg gcctgatagc    5820
tgactcacag atccaggctt ctgagttttg gggttattgg gaacccaaat tagcaaggtt    5880
aaacaatggt ggatcataca atgcttggat tgcagaaaaa ctttcaacgg aatttaaccc    5940
tgaaccttgg atccaggtag acatgcaaaa ggaagtcctg ctcacgggga tccagaccca    6000
gggcgccaaa cactacctga agccctacta caccaccgag ttctgtgtgg cttacagctt    6060
ggatcggaaa aactggcgta tcttcaaagg gaacagcaca aggaatgtga tgtatttgg    6120
```

-continued

```
tggcaattca gatgcttcta caataaaaga gaatcagatt gacccacctg ttgtggctag    6180
atacattagg atctctccaa ctggatccta taacaaacct gcccttcgat tggagctgca    6240
aggttgtgag gttaatggat gctccacacc gctgggtatg gaaagtggaa agatagaaaa    6300
caagcaaatc accgcttcct cgtttaaaaa gtcttggtgg ggaaattact gggaacccctt   6360 ccttgcacgt cttaatgccc agggccgtgt aaatgcctgg caagctaagg caaacaacaa    6420
caatcagtgg ttacaaattg atctgctcaa aatcaagaag ataactgcga ttgtaacaca    6480
aggatgcaag tctctgtcct ctgaaatgta tgtgaagagc tacaccatcc actacagtga    6540
ccagggaacg gactggaaac cttacaggga gaaatcctca atggtggaca agattttcga    6600
aggaaataat aatgtcagag acatgtgaa gaacttttc aacccaccaa tcatctccag     6660
gtttatacgc atcattccta aaacatgaa tcagagtatt gcacttcgct tggaactctt     6720
tggctgtgat atgtactaga attgaatatt ttaaaagata ggagggactc aaagatatca    6780
aaccacttag agtgggcaat gcattttgta gctattttaa gtataaaaaa atttccatta    6840
tttctctttt ttctattaga gaataaaatt ttatatgcaa aacctttatg atataactcc    6900
tgataaccac                                                          6910
```

<210> SEQ ID NO 18
<211> LENGTH: 2211
<212> TYPE: PRT
<213> ORGANISM: Bos Taurus

<400> SEQUENCE: 18

```
Met Phe Leu Ala Cys Pro Gly Phe Trp Val Leu Val Leu Gly Ser
1               5                   10                  15

Ser Trp Ala Gly Trp Gly Asn Leu Gly Ala Glu Ala Ala Lys Leu Arg
            20                  25                  30

Gln Phe Tyr Val Ala Ala Gln Ser Ile Arg Trp Asn Tyr Arg Pro Glu
        35                  40                  45

Ser Thr His Leu Ser Ser Lys Pro Phe Glu Thr Ser Phe Lys Lys Ile
    50                  55                  60

Val Tyr Arg Glu Tyr Glu Ala Tyr Phe Gln Lys Glu Lys Pro Gln Ser
65                  70                  75                  80

Arg Thr Ser Gly Leu Leu Gly Pro Thr Leu Tyr Ala Glu Val Gly Asp
                85                  90                  95

Ile Met Lys Val His Phe Lys Asn Lys Ala His Lys Pro Leu Ser Ile
            100                 105                 110

His Ala Gln Gly Ile Lys Tyr Ser Lys Phe Ser Glu Gly Ala Ser Tyr
        115                 120                 125

Ser Asp His Thr Leu Pro Met Glu Lys Met Asp Asp Ala Val Ala Pro
    130                 135                 140

Gly Gln Glu Tyr Thr Tyr Glu Trp Ile Ile Ser Glu His Ser Gly Pro
145                 150                 155                 160

Thr His Asp Asp Pro Pro Cys Leu Thr His Ile Tyr Tyr Ser Tyr Val
                165                 170                 175

Asn Leu Val Glu Asp Phe Asn Ser Gly Leu Ile Gly Pro Leu Leu Ile
            180                 185                 190

Cys Lys Lys Gly Thr Leu Thr Glu Asp Gly Thr Gln Lys Met Phe Glu
        195                 200                 205

Lys Gln His Val Leu Met Phe Ala Val Phe Asp Glu Ser Lys Ser Trp
    210                 215                 220

Asn Gln Thr Ser Ser Leu Met Tyr Thr Val Asn Gly Tyr Val Asn Gly
```

```
                225                 230                 235                 240
        Thr Met Pro Asp Ile Thr Val Cys Ala His Asp His Ile Ser Trp His
                        245                 250                 255
        Leu Ile Gly Met Ser Ser Gly Pro Glu Leu Phe Ser Ile His Phe Asn
                        260                 265                 270
        Gly Gln Val Leu Glu Gln Asn His Lys Ile Ser Ala Ile Thr Leu
                        275                 280                 285
        Val Ser Ala Thr Ser Thr Thr Ala Asn Met Thr Val Ser Pro Glu Gly
                290                 295                 300
        Arg Trp Thr Ile Ala Ser Leu Ile Pro Arg His Phe Gln Ala Gly Met
        305                 310                 315                 320
        Gln Ala Tyr Ile Asp Ile Lys Asn Cys Ala Lys Lys Thr Arg Asn Pro
                        325                 330                 335
        Lys Lys Leu Thr Arg Asp Gln Arg Arg His Ile Lys Arg Trp Glu Tyr
                        340                 345                 350
        Phe Ile Ala Ala Glu Glu Val Ile Trp Asp Tyr Ala Pro Ile Ile Pro
                        355                 360                 365
        Ala Asn Met Asp Lys Lys Tyr Arg Ser Leu His Leu Asp Asn Phe Ser
                370                 375                 380
        Asn Arg Ile Gly Lys His Tyr Lys Lys Val Val Tyr Lys Gln Tyr Gln
        385                 390                 395                 400
        Asp Asp Ser Phe Thr Lys Arg Leu Glu Asp Pro Ser Ser Glu Gly Asp
                        405                 410                 415
        Gly Ile Leu Gly Pro Ile Ile Arg Ala Gln Val Arg Asp Thr Leu Lys
                        420                 425                 430
        Ile Val Phe Lys Asn Met Ala Ser Arg Ser Tyr Ser Ile Tyr Pro His
                        435                 440                 445
        Gly Val Thr Phe Ser Pro Tyr Asp Asn Glu Val Asn Ser Ser Ser Thr
                        450                 455                 460
        Ser Gly Ser Asn Thr Met Ile Arg Ala Val Arg Pro Gly Glu Thr Tyr
        465                 470                 475                 480
        Thr Tyr Lys Trp Asn Ile Leu Glu Ser Asp Glu Pro Thr Glu Asn Asp
                        485                 490                 495
        Ala Gln Cys Leu Thr Arg Pro Tyr Tyr Ser Asn Val Asp Ile Thr Arg
                        500                 505                 510
        Asp Leu Ala Ser Gly Leu Ile Gly Leu Leu Ile Cys Lys Ser Arg
                        515                 520                 525
        Ser Leu Asp Arg Arg Gly Ile Gln Arg Ala Ala Asp Ile Glu Gln Gln
                530                 535                 540
        Ala Val Phe Ala Val Phe Asp Glu Asn Lys Ser Trp Tyr Ile Glu Asp
        545                 550                 555                 560
        Asn Ile Tyr Lys Phe Cys Glu Asn Pro Glu Lys Val Lys Arg Asp Asp
                        565                 570                 575
        Pro Lys Phe Tyr Glu Ser Asn Ile Met Ser Asn Phe Thr Leu Pro Ala
                        580                 585                 590
        Ile Asn Gly Tyr Val Pro Glu Ser Ile Pro Ile Leu Gly Phe Cys Phe
                        595                 600                 605
        Asp Asp Thr Val Gln Trp His Phe Cys Ser Val Gly Thr Gln Asn Asp
                        610                 615                 620
        Ile Leu Thr Ile His Phe Thr Gly His Ser Phe Ile Tyr Gly Lys Arg
        625                 630                 635                 640
        His Glu Asp Thr Leu Thr Leu Phe Pro Met Gln Gly Glu Ser Val Thr
                        645                 650                 655
```

```
Val Thr Met Asp Asn Val Gly Thr Trp Met Leu Thr Thr Met Asn Ser
            660                 665                 670

Asn Pro Arg Ser Lys Leu Arg Leu Arg Phe Arg Asp Ala Lys Cys
        675                 680                 685

Ile Arg Asn Asp Asp Asp Ser Tyr Glu Ile Ile Tyr Glu Pro Ser
    690                 695                 700

Gly Ser Thr Ala Met Thr Thr Lys Lys Ile His Asp Ser Ser Glu Ile
705                 710                 715                 720

Glu Asp Glu Asn Asp Ala Asp Ser Asp Tyr Gln Asp Glu Leu Ala Leu
                725                 730                 735

Ile Leu Gly Leu Arg Ser Phe Arg Asn Ser Ser Leu Asn Gln Glu Lys
            740                 745                 750

Asp Glu Leu Asn Leu Thr Ala Leu Ala Leu Glu Lys Asp Ser Glu Phe
        755                 760                 765

Ile Pro Pro Ser Ala Asn Arg Ser Leu Asp Ser Asn Ser Ser Ser Arg
    770                 775                 780

Ser His Val Ser Arg Leu Ile Ala Lys Asn Phe Ala Glu Ser Leu Lys
785                 790                 795                 800

Thr Leu Leu His Leu Glu Ala Pro Ala Ala Gly Ser Pro Leu Glu His
                805                 810                 815

Ala Gly Leu Asp Lys Asn Ser Ala Leu Asn Pro Pro Met Ala Glu His
            820                 825                 830

Ser Ser Pro Tyr Ser Glu Asp Pro Arg Glu Asp His Pro Leu Ser Asp
        835                 840                 845

Val Thr Gly Val Ser Leu Leu Pro Phe Gly Thr Gly Phe Lys Asn Arg
    850                 855                 860

Lys Pro Ala Lys His Gln Arg Phe Gln Val Gly Arg Gly Gln Ala Ala
865                 870                 875                 880

Lys His Lys Phe Ser Gln Thr Arg Phe Pro Ala His Lys Thr Arg Thr
                885                 890                 895

Arg Leu Ser Gln Asp Asn Ser Ser Ser Arg Met Gly Pro Trp Glu
            900                 905                 910

Asp Ile Pro Ser Asp Leu Leu Leu Gln Gln Lys Asp Pro Tyr Lys
        915                 920                 925

Ile Leu Asn Gly Glu Trp His Leu Val Ser Lys Gly Ser Tyr Glu
    930                 935                 940

Ile Ile Gln Asp Ala Asn Glu Asn Lys Thr Val Asn Lys Leu Pro Asn
945                 950                 955                 960

Ser Pro Gln Asn Asp Ser Arg Thr Trp Gly Glu Asn Ile Pro Phe Lys
                965                 970                 975

Asn Ser His Gly Lys Gln Ser Gly His Pro Thr Phe Leu Val Thr Arg
            980                 985                 990

Arg Lys Pro Leu Gln Asp Arg Gln Asp Arg Arg Asn Ser Arg Leu Lys
        995                 1000                1005

Glu Gly Leu Pro Leu Ile Arg Thr Arg Arg Lys Lys Lys Glu Glu
    1010                1015                1020

Lys Pro Ala Tyr His Val Pro Leu Ser Pro Arg Ser Phe His Pro
    1025                1030                1035

Leu Arg Gly Glu Val Asn Ala Ser Phe Ser Asp Arg Arg His Asn
    1040                1045                1050

His Ser Leu Leu Leu His Ala Ser Asn Glu Thr Ser Leu Ser Ile
    1055                1060                1065
```

-continued

```
Asp Leu Asn Gln Thr Phe Pro Ser Met Asn Leu Ser Leu Ala Ala
    1070                1075                1080

Ser Leu Pro Asp His Asp Gln Thr Ser Pro Asn Asp Thr Thr Ser
    1085                1090                1095

Gln Thr Ser Ser Pro Pro Asp Leu Tyr Pro Thr Val Ser Pro Glu
    1100                1105                1110

Glu His Tyr Gln Ile Phe Pro Ile Gln Asp Ser Asp Pro Thr His
    1115                1120                1125

Ser Thr Thr Ala Pro Ser Asn Arg Ser Pro Asp Pro Thr His Ser
    1130                1135                1140

Thr Thr Ala Pro Ser Asn Arg Ser Pro Pro Thr Gln Pro Ser Gln
    1145                1150                1155

Ile Pro Asn Tyr Asp Leu Arg Asn Arg Ala Ile Pro Thr Asp Val
    1160                1165                1170

Ser Gln Ile Phe Pro Ser Leu Glu Leu Glu Val Trp Gln Thr Ala
    1175                1180                1185

Thr Ser Leu Asp Leu Ser Gln Pro Ser Ile Ser Pro Asp Leu Gly
    1190                1195                1200

Gln Met Ala Leu Ser Pro Asp Pro Gly Gln Glu Ser Leu Ser Pro
    1205                1210                1215

Asp Leu Gly Gln Thr Ser Leu Ser Pro Asp Leu Ser Gln Glu Ser
    1220                1225                1230

Leu Ser Pro Asp Leu Gly Gln Thr Ala Leu Ser Pro Asp Pro Ser
    1235                1240                1245

Gln Glu Ser Leu Ser Pro Asp Leu Gly Gln Thr Ala Leu Ser Pro
    1250                1255                1260

Asp Pro Ser Gln Glu Ser Leu Ser Pro Asp Leu Gly Gln Thr Ala
    1265                1270                1275

Leu Ser Pro Asp Pro Gly Gln Glu Ser Leu Ser Pro Asp Leu Gly
    1280                1285                1290

Gln Thr Ser Leu Ser Pro Asp Leu Ser Gln Glu Ser Leu Ser Pro
    1295                1300                1305

Asp Leu Gly Gln Thr Ala Leu Ser Pro Asp Pro Ser Gln Glu Ser
    1310                1315                1320

Leu Ser Pro Asp Leu Gly Gln Thr Ala Leu Ser Pro Asp Pro Ser
    1325                1330                1335

Gln Glu Ser Leu Ser Pro Asp Leu Gly Gln Thr Ser Leu Ser Pro
    1340                1345                1350

Asp Leu Gly Gln Glu Ser Leu Ser Pro Asp Leu Gly Gln Thr Ala
    1355                1360                1365

Leu Ser Pro Asp Pro Ser Gln Glu Ser Leu Ser Pro Asp Leu Gly
    1370                1375                1380

Gln Thr Ser Leu Ser Pro Asp Leu Gly Gln Glu Ser Leu Ser Pro
    1385                1390                1395

Asp Leu Gly Gln Thr Ala Leu Ser Pro Asp Leu Ser Gln Glu Ser
    1400                1405                1410

Leu Ser Pro Asp Leu Gly Gln Thr Pro Leu Ser Pro Asp Leu Ser
    1415                1420                1425

Leu Glu Ser Leu Ser Pro Asp Leu Ser Gln Leu Asp Leu Lys Gln
    1430                1435                1440

Thr Ser Pro Pro Leu Asp Leu Asn Gln Thr Ser His Thr Ser Glu
    1445                1450                1455

Ser Ser Gln Ser Leu Pro Leu Pro Glu Phe Gly Gln Thr Phe Pro
```

```
              1460                1465                1470

Asn Ala Asp Ile Gly Gln Met Pro Ser Pro Pro Asp Ser Thr
         1475                1480                1485

Leu Asn Asn Thr Phe Ile Pro Glu Glu Phe Asn Pro Leu Val Val
         1490                1495                1500

Val Gly Leu Ser Arg Asp Asp Gly Asp Tyr Ile Glu Ile Ile Pro
         1505                1510                1515

Arg Gln Lys Glu Glu Ser Ser Glu Glu Asp Tyr Gly Glu Phe Glu
         1520                1525                1530

Phe Val Ala Tyr Asn Asp Pro Tyr Gln Thr Asp Leu Arg Thr Asp
         1535                1540                1545

Ile Asn Ser Ser Arg Asn Pro Asp Asn Ile Ala Ala Trp Tyr Leu
         1550                1555                1560

Arg Ser Asn Thr Gly Asn Arg Lys Tyr Tyr Ile Ala Ala Glu
         1565                1570                1575

Glu Ile Ser Trp Asp Tyr Ser Lys Phe Val Gln Ser Asp Asp Val
         1580                1585                1590

Asp Tyr Val Pro Glu Asp Thr Val Tyr Lys Lys Val Val Phe Arg
         1595                1600                1605

Lys Tyr Leu Asp Ser Thr Phe Thr Lys Leu Asp Pro Gln Gly Glu
         1610                1615                1620

Tyr Glu Glu His Leu Gly Ile Leu Gly Pro Val Ile Arg Ala Glu
         1625                1630                1635

Val Asp Asp Val Ile Gln Val Arg Phe Lys Asn Leu Ala Ser Arg
         1640                1645                1650

Pro Tyr Ser Leu His Ala His Gly Leu Ser Tyr Glu Lys Ser Ser
         1655                1660                1665

Glu Gly Lys Thr Tyr Glu Asp Asp Ser Pro Glu Trp Phe Lys Glu
         1670                1675                1680

Asp Asn Ala Ile Gln Pro Asn Lys Thr Tyr Thr Tyr Val Trp His
         1685                1690                1695

Ala Thr Thr Arg Ser Gly Pro Glu Asn Pro Gly Ser Ala Cys Arg
         1700                1705                1710

Ala Trp Ala Tyr Tyr Ser Ala Val Asn Pro Glu Lys Asp Ile His
         1715                1720                1725

Ser Gly Leu Ile Gly Pro Leu Leu Ile Cys Arg Lys Gly Thr Leu
         1730                1735                1740

Asp Lys Glu Thr Asn Met Pro Val Asp Met Arg Glu Phe Val Leu
         1745                1750                1755

Leu Phe Met Val Phe Asp Glu Lys Lys Ser Trp Tyr Tyr Asp Lys
         1760                1765                1770

Lys Pro Thr Arg Ser Trp Arg Arg Ala Ser Ser Glu Val Lys Asn
         1775                1780                1785

Ser His Glu Phe His Ala Ile Asn Gly Met Ile Tyr Asn Leu Pro
         1790                1795                1800

Gly Leu Arg Met Tyr Glu Gln Glu Trp Val Arg Leu His Leu Leu
         1805                1810                1815

Asn Leu Gly Gly Ser Arg Asp Ile His Val Val His Phe His Gly
         1820                1825                1830

Gln Thr Leu Leu Glu Asn Gly Thr Gln Gln His Gln Leu Gly Val
         1835                1840                1845

Trp Pro Leu Leu Pro Gly Ser Phe Lys Thr Leu Glu Met Lys Ala
         1850                1855                1860
```

```
Ser Lys Pro Gly Trp Trp Leu Leu Asp Thr Glu Val Gly Glu Ile
    1865             1870                1875
Gln Arg Ala Gly Met Gln Thr Pro Phe Leu Ile Val Asp Arg Glu
    1880             1885                1890
Cys Lys Met Pro Met Gly Leu Ser Thr Gly Leu Ile Ala Asp Ser
    1895             1900                1905
Gln Ile Gln Ala Ser Glu Phe Trp Gly Tyr Trp Glu Pro Lys Leu
    1910             1915                1920
Ala Arg Leu Asn Asn Gly Gly Ser Tyr Asn Ala Trp Ile Ala Glu
    1925             1930                1935
Lys Leu Ser Thr Glu Phe Asn Pro Glu Pro Trp Ile Gln Val Asp
    1940             1945                1950
Met Gln Lys Glu Val Leu Leu Thr Gly Ile Gln Thr Gln Gly Ala
    1955             1960                1965
Lys His Tyr Leu Lys Pro Tyr Tyr Thr Thr Glu Phe Cys Val Ala
    1970             1975                1980
Tyr Ser Leu Asp Arg Lys Asn Trp Arg Ile Phe Lys Gly Asn Ser
    1985             1990                1995
Thr Arg Asn Val Met Tyr Phe Gly Gly Asn Ser Asp Ala Ser Thr
    2000             2005                2010
Ile Lys Glu Asn Gln Ile Asp Pro Pro Val Val Ala Arg Tyr Ile
    2015             2020                2025
Arg Ile Ser Pro Thr Gly Ser Tyr Asn Lys Pro Ala Leu Arg Leu
    2030             2035                2040
Glu Leu Gln Gly Cys Glu Val Asn Gly Cys Ser Thr Pro Leu Gly
    2045             2050                2055
Met Glu Ser Gly Lys Ile Glu Asn Lys Gln Ile Thr Ala Ser Ser
    2060             2065                2070
Phe Lys Lys Ser Trp Trp Gly Asn Tyr Trp Glu Pro Phe Leu Ala
    2075             2080                2085
Arg Leu Asn Ala Gln Gly Arg Val Asn Ala Trp Gln Ala Lys Ala
    2090             2095                2100
Asn Asn Asn Asn Gln Trp Leu Gln Ile Asp Leu Leu Lys Ile Lys
    2105             2110                2115
Lys Ile Thr Ala Ile Val Thr Gln Gly Cys Lys Ser Leu Ser Ser
    2120             2125                2130
Glu Met Tyr Val Lys Ser Tyr Thr Ile His Tyr Ser Asp Gln Gly
    2135             2140                2145
Thr Asp Trp Lys Pro Tyr Arg Glu Lys Ser Ser Met Val Asp Lys
    2150             2155                2160
Ile Phe Glu Gly Asn Asn Asn Val Arg Gly His Val Lys Asn Phe
    2165             2170                2175
Phe Asn Pro Pro Ile Ile Ser Arg Phe Ile Arg Ile Ile Pro Lys
    2180             2185                2190
Thr Trp Asn Gln Ser Ile Ala Leu Arg Leu Glu Leu Phe Gly Cys
    2195             2200                2205
Asp Met Tyr
    2210
```

<210> SEQ ID NO 19
<211> LENGTH: 1031
<212> TYPE: DNA
<213> ORGANISM: Pseudonaja textilis

```
<400> SEQUENCE: 19
cgacggcccg ggctggtctg ccaggaagat ttcatgggac tccttatttg cggagacttt    60 gccccctgtgg atccagagag tagaaactct cactcatctc ctcatagggt gtcctttcta   120
tgatgctcca agatgtgttt taatcacacc aatcatttcc aaataaggct gcagagataa   180
atgttatgtt tattatattt caaaggtaac ctcacactca catatcagat ggccaaatat   240
cttcgagttc tacaactacc caaaactttt aattaaatat attgttttat tgccccgttc   300
tttcctattc tcaataacaa atgttgtgtt aaactatttc tctcttcact gtactgtaaa   360
agtactgtac tatacttttta ttgtgaaggc tgatcaaaga ttgtaatcaa gatattttag   420
ttgaaaaaaa tatgttttac tgtgctctac tttctgctgc ttttttgagat gtgtgagaga   480 gagatgcaaa atgcaattct ctctcatgtt caaatattgc agaaatatac ttacgatagg   540
tagtagcatt agcatttgct aggtcttcct taggaacaag ttgctctgga tgtaggatgt   600
ttctttaagg tttctttatg aaaaactcag agaggaggca gtgaagctct tcccctaagt   660
acaatctgtt ttcaacttct gggtgagctt cctttcaagg tcactatctg tgcttagcag   720 tgagggcag ctctccttttg aggtatccat cccacacccc atactattaa tcttgtactg   780
actcaaatga ccttacttgg taaagacccg catttttgaat tagtcagcac aatgatctga   840
agcatccata gtcaaacaca aacaggcttt ggaggacatg ataagggctg gagcagaaca   900
acaggaagct tgattgcttg aaccttgttc atagccagcc ctgaaagaga acaaactgtt   960
cttttccatc gataggcacc atggcccctc agctactcct ctgtctgatc ctcactttttc  1020 tagggagtct c                                                        1031

<210> SEQ ID NO 20
<211> LENGTH: 1010
<212> TYPE: DNA
<213> ORGANISM: Pseudonaja textilis

<400> SEQUENCE: 20
cgacggcccg ggctggtctg ccaggaagat ttcatgggac tccttatttg cggagacttt    60 gccccctgtgg atccagagag tagaaactct cactcatctc ctcatagggt gtcctttcta   120
tgatgctcca agatgtgttt taatcacacc aatcatttcc aaataaggct gcagagataa   180
atgttatgtt tattatattt caaaggtaac ctcacactca catatcagat ggccaaatat   240
cttcgagttc tacaactacc caaaactttt aattaaatat attgttttat tgccccgttc   300
tttcctattc tcaataacaa atgttgtgtt aaactatttc tctcttcact gtactgtaaa   360
agtactgtac tatacttttta ttgtgaaggc tgatcaaaga ttgtaatcaa gatattttag   420
ttgaaaaaaa tatgttttac tgtgctctac tttctgctgc ttttttgagat gtgtgagaga   480 gagatgcaaa atgcaattct ctctcatgtt caaatattgc agaaatatac ttacgatagg   540
tagtagcatt agcatttgct aggtcttcct taggaacaag ttgctctgga tgtaggatgt   600
ttctttatga aaactcagag aggaggcagt gaagctcttc ccctaagtac aatctgtttt   660
caacttctgg gtgagcttcc tttcaaggtc actatctgtg cttagcagtg aggggcagct   720
ctcctttgag gtatccatcc cacacccccat actattaatc ttgtactgac tcaaatgacc   780
ttacttggta aagacccgca ttttgaatta gtcagcacaa tgatctgaag catccatagt   840
caaacacaaa caggctttgg aggacatgat aagggctgga gcagaacaac aggaagcttg   900
attgcttgaa ccttgttcat agccagccct gaaagagaac aaactgttct tttccatcga   960
taggcaccat ggcccctcag ctactcctct gtctgatcct cactttttcta              1010
```

<210> SEQ ID NO 21
<211> LENGTH: 1299
<212> TYPE: DNA
<213> ORGANISM: Pseudonaja textilis

<400> SEQUENCE: 21

```
cgacggcccg ggctggtctg ccaggaagat ttcatgggac tccttatttg cggagacttt     60
gcccctgtgg atccagagag tagaaactct cactcatctc ctcatagggt gtcctttcta    120
tgatgctcca agatgtgttt taatcacacc aatcatttcc aaataaggct gcagagataa    180
atgttatgtt tattatattt caaaggtaac ctcacactca catatcagat ggccaaatat    240
cttcgagttc tacaactacc caaaactttt aattaaatat attgttttat tgccccgttc    300
tttcctattc tcaataacaa atgttgtgtt aaactatttc tctcttcact gtactgtaaa    360
agtactgtac tatactttta ttgtgaaggc tgatcaaaga ttgtaatcaa gatattttag    420
ttgaaaaaaa tatgttttac tgtgctctac tttctgctgc tttttgggat gtgtgagaga    480
gagatgcaaa atgcaattct ctctcatgtt caaatattgc agaaatatac ttacgatagg    540
tagtagcatt agcatttgct aggtcttcct taggaaccag gtgctctgga tgtagggtgt    600
ttctttaagg tttctttatg aagaactcag agaggaggca gggaagctct tccccctaag    660
taatctgttt tcaacttctg ggtgagcttc ctttcaaggt cactatctgt gcttagcagt    720
gaggggcagc tctcctttga ggtatccatc ccacgcccca tactattaat cttgtactga    780
ctcaaatgac cttacttggt aaagacccgc attttgaatt agtcagcaca atgatctgaa    840
gcatccatag ccaaactcaa acaggctttg gaggacatga taagggctgg agcagaacaa    900
caggaagctt gattgcttga accttgttca tagccagccc tgtagtgtac ttgtttgcat    960
actcataata ctgcattcct attggacaga tactatcgct taacgattgg tagataacaa   1020
cagttctaat tggacgccta agcagtggga gttttaaata aatgccattg gttgcgagcc   1080
gcgagcagcc gctataaaag ggactgccgc ggctcgactt tagttgaagt tactgacagt   1140
taataaagag ctgaattcaa ctccggtctc gagtctgctt tgttctggcg atagaacaag   1200
aacaagaact gaaagagaac aaaccgttct tttccatcga taggcaccat ggctcctcaa   1260
ctactcctct gtctgatcct cacttttcta tggagtctc                          1299
```

<210> SEQ ID NO 22
<211> LENGTH: 2231
<212> TYPE: DNA
<213> ORGANISM: Pseudonaja textilis textilis

<400> SEQUENCE: 22

```
acgcggggga agttactgac agttaataaa gagctgaatt aactccggtc tcgagtctgc     60
tttgttctgg cgatagaaca agaacaagaa ctgaaagaga acaaactgtt cttttccatc    120
gataggcacc atggctcctc aactactcct ctgtctgatc ctcacttttc tgtggagtct    180
cccagaggct gaaagtaatg tattcttaaa aagcaaagtg gcaaatagat tttgcaaag     240
aacaaaacga gctaattcac tggttgagga atttaaatct ggaaacattg aaagggaatg    300
cattgaggag agatgttcaa aagaagaagc cagggaggta tttgaagatg acgagaaaac    360
tgagaccttc tggaatgttt atgtagatgg ggatcagtgt tcatcaaacc cctgtcatta    420
tcgcgggata tgcaaagatg gcattggtag ctatacctgt acctgcttgt ctggctatga    480
agggaaaaac tgtgaacgtg tcttatataa gtcctgcaga gtggacaatg gtaactgttg    540
```

| | |
|---|---|
| gcacttctgc aaatctgttc aaaacgatat tcaatgttca tgcgctgaag gttaccttt | 600 |
| gggagaggat gggcactctt gtgttgctgg aggtaacttt tcatgtggta gaaatatcaa | 660 |
| aacaaggaac aagagggaag caagtctgcc tgactttgtg cagtcccata atgcaacttt | 720 |
| gctgaaaaaa tctgataatc caagccctga tatcagaatt gttaacgaaa tggactgcaa | 780 |
| actgggtgaa tgtccgtggc aggcagctct ggtagatgac aagaaaggtg tgttttgtgg | 840 |
| aggaacaatt ttgagtccca tctatgtgct tactgcagcc cactgcatta atgagaccga | 900 |
| gacgatttca gttgttgtag agaaatagaa cagatcaaga gcagaaaccg gacctcttct | 960 |
| ttctgtggat aaagtatatg tgcataaaaa atttgttcct cccaaaaaaa gccaggaatt | 1020 |
| ctatgaaaag tttgatcttg tcagctatga ctatgatata gccatcatcc aaatgaagac | 1080 |
| ccctatccag ttctctgaaa atgtggttcc tgcctgcctt cccacagctg attttgccaa | 1140 |
| ccaagtcctc atgaaacaag attttggcat cgttagtgga tttgggggta ttttcgaaag | 1200 |
| aggaccgaac tctaaaacac ttaaagtcct taaggttcct tatgtggaca ggcacacctg | 1260 |
| catgcttttcc agcaattttc caattactcc aactatgttc tgtgctggct atgatactct | 1320 |
| gcctcaagat gcatgccaag gagacagcgg ggggccccac atcactgcat acagagatac | 1380 |
| ccactttatt actgggattg tcagctgggg gaaggatgt gcacggaaag cagatatgg | 1440 |
| tatttacaca aaattgtcca aattcatccc ttggataaaa agaataatgc gtcaaaagct | 1500 |
| acccagtaca gagtcaagca ctggtcggct ctaaaaatca tccagtgaca tatttcatgc | 1560 |
| agctataatg cattgggtta gaacattcat gatatccact ttggttcaga actcttcaga | 1620 |
| tgtagggcca ttttaaaata taacattcaa gtcatgtagc tttcctattt atcgagacct | 1680 |
| ttttcttct ggtattaatc ccttctggaa catagaatga gtaggcgatt tcatttcagc | 1740 |
| tcttgtctct cgtgtcctat cttttatgac cttttctaaa gatttataaa ggtttataat | 1800 |
| ttataatcct tcaaatagaa gctcagcagg aatatttggt cccttttgtaa tgcaacctcc | 1860 |
| agttcccttg agaccatcag ttgggttaat caaggtagtg cccaattcag ctgaattgtt | 1920 |
| gtccaattta atttacctca aaccaagcct tcagtactgt tgccttctac ttctatggag | 1980 |
| ggggagttag ggacgtcata aaaccttgct ctccgaatcc aacacttcat gtcaaaaatt | 2040 |
| tcttgaagaa agtgtacaga attctgtatt tcccaaatgg ttattccact cgcgtgctca | 2100 |
| catttttgggt tattttgtgt gatcaaaatt tccagtgaca ggatctgatt gagatgatca | 2160 |
| ctaactgggt tataggaccc gaataaaagt gatatattct aaaaaaaaaa aaaaaaaaa | 2220 |
| aaaaaaaaa a | 2231 |

<210> SEQ ID NO 23
<211> LENGTH: 2219
<212> TYPE: DNA
<213> ORGANISM: Pseudonaja textilis textilis

<400> SEQUENCE: 23

| | |
|---|---|
| acgcgggga agttactgac agttaataaa gagctgaatt aactccggtc tcgagtctgc | 60 |
| tttgttctgg cgatagaaca agaacaagaa ctgaaagaga acaaactgtt cttttccatc | 120 |
| gataggcacc atggctcctc aactactcct ctgtctgatc ctcactttc tgtggagtct | 180 |
| cccagaggct gaaagtaatg tattcttaaa aagcaaagtg gcaaatagat ttttgcaaag | 240 |
| aacagaacga gctaattcac tggttgagga atttaaatct ggaaacattg aaagggaatg | 300 |
| cattgaggag agatgttcaa agaagaagc cagggaggta tttgaagatg acgagaaaac | 360 |
| tgagaccttc tggaatgttt atgtagatgg ggatcagtgt tcatcaaacc cctgtcatta | 420 |

```
tcgcgggata tgcaaagatg gcattggtag ctatacctgt acctgcttgt ctggctatga      480
agggaaaaac tgtgaacgtg tcttatataa gtcctgcaga gtggacaatg gtaactgttg      540
gcacttctgc aaacatgttc aaaatgatat tcagtgttca tgtgctgaag gttaccttt       600 gggagaggat gggcactctt gtgttgctgg aggtaacttt tcatgtggta gaaatatcaa      660
aacaaggaac aagagggaag caaatctgcc tgactttgtg cagtcccaga atgcaacttt      720
gctgaaaaaa tctgataatc caagccctga tatcagaatt gttaatggaa tggattgcaa      780
actgggtgaa tgtccgtggc aggcagctct ggtagatgaa aaggaaggtg tgttttgtgg      840
aggaacaatt ttgagtccca tctatgtgct tactgcagcc cactgcatta atgagaccga      900
gacgatttca gttgttgtag gggaaataga caaatcaaga atagaaaccg gacctcttct      960
ttctgtggat aaaatatatg tgcataaaaa atttgttcct cctcaaaaag cctataagtt     1020
tgatcttgcc gcctatgact atgacatagc catcatccaa atgaagaccc ctatccagtt     1080
ctctgaaaat gtggttcctg cctgccttcc cacagctgat tttgccaacc aagtcctcat     1140
gaaacaagat tttggcatcg ttagtggatt tgggcgtatt gtcgaaaaag gaccaaaatc     1200
taaaacactt aaagtcctta aggttcctta tgtggacagg cacacctgca tggttttccag    1260 cgaaactcca attactccaa atatgttctg tgctggctat gatactctgc ctcgagatgc     1320
atgccaggga gacagtgggg ggccccacac cactgtatac agagatacccc actttattac    1380 tgggattgtc agctcggggg aaggatgtgc aaggaatggc aaatatggta attacacaaa     1440
actgtccaaa ttcatccctt ggataaaaag aataatgcgt caaaagctac ccagtacaga     1500
gtcaagcact ggtcggctct aaaaatcatc cagtgacata tttcatgcag ctataatgca     1560
ttgggttaga acattcatga tatccacttt ggttcagaac tcttcagatg tagggccatt     1620
tttaaatata acattcaagt catgtagctt tcctatttat cgagaccttt tttcttctgg     1680
tattaatccc ttctggaaca tagaatgagt aggcgatttc atttcagctc ttgtctctcg     1740
tgtcctatct tttatgacct tttctaaaga tttataaagg tttataattt ataatccttc     1800
aaatagaagc tcagcaggaa tatttggtcc cttttgtaatg caacctccag ttcccttgag    1860
accatcagtt gggttaatca aggtagtgcc caattcagct gaattgttgt ccaatttaat     1920
ttacctcaaa ccaagccttc agtactgttg ccttctactt ctatggaggg ggagttaggg    1980
acgtcataaa accttgctct ccgaatccaa cacttcatgt caaaaatttc ttgaagaaag    2040
tgtacagaat tctgtatttc ccaaatggtt attccactcg cgtgctcaca ttttgggtta    2100
ttttgtgtga tcaaaatttc cagtgacagg atctgattga gatgatcact aactgggtta    2160
taggacccga ataaaagtga tatattctaa aaaaaaaaa aaaaaaaaa aaaaaaaa        2219
```

<210> SEQ ID NO 24
<211> LENGTH: 1392
<212> TYPE: DNA
<213> ORGANISM: Pseudonaja textilis

<400> SEQUENCE: 24

```
atggctcctc agctactcct ctgtctgatc ctcactttc tgtggagtct cccagaggct       60
gaaagtaatg tattcttaaa aagcaaagtg gcaaatagat ttttgcaaag aacaaaacga     120
gctaattcac tggttgagga atttaaatct ggaaacattg aaagggaatg cattgaggag     180
agatgttcaa agaagaaagc cagggaggca tttgaagatg acgagaaaac tgagaccttc     240
tggaatgttt atgtagatgg ggatcagtgt tcatcaaacc cctgtcatta tcgcgggata     300
```

```
tgcaaagatg gcattggtag ctatacctgt acctgcttgt ctggctatga agggaaaaac      360
tgtgaacgtg tcttatataa gtcctgcaga gtggacaatg gtaactgttg gcacttctgc      420
aaacatgttc aaaatgatat tcagtgttca tgtgctgaag gttaccttt gggagaggat      480 gggcactctt gtgttgctgg aggtaacttt tcatgtggta gaaatatcaa acaaggaac      540 aagagggaag caaatctgcc tgactttgtg cagtcccaga atgcaacttt gctgaaaaaa      600
tctgataatc aagccctga tatcagaatt gttaatggaa tggattgcaa actgggtgaa      660
tgtccgtggc aggcagctct ggtagatgaa aaggaaggtg tgttttgtgg aggaacaatt      720
ttgagtccca tctatgtgct tactgcagcc cactgcatta atgagaccga acgatttca      780 gttgttgtag gggaaataga caaatcaaga atagaaaccg acctcttct ttctgtggat      840 aaaatatatg tgcataaaaa atttgttcct cctcaaaaag cctataagtt tgatcttgcc      900
gcctatgact atgacatagc catcatccaa atgaagaccc ctatccagtt ctctgaaaat      960
gtggttcctg cctgccttcc cacagctgat tttgccaacc aagtcctcat gaaacaagat     1020
tttggcatcg ttagtggatt tgggcgtatt ttcgaaaaag accaaaaatc taaaacactt     1080
aaagtcctta aggttcctta tgtggacagg cacacctgca tggtttccag cgaaactcca     1140
attactccaa atatgttctg tgctggctat gatactctgc ctcgagatgc atgccaggga     1200
gacagtgggg ggccccacac cactgtatac agagataccc actttattac tgggattgtc     1260
agctcggggg aaggatgtgc aaggaatggc aaatatggta tttacacaaa actgtccaaa     1320
ttcatcccct tggataaaag aataatgcgt caaaagctac ccagtacaga gtcaagcacc     1380
ggtcggctct aa                                                          1392

<210> SEQ ID NO 25
<211> LENGTH: 1452
<212> TYPE: DNA
<213> ORGANISM: Pseudonaja textilis

<400> SEQUENCE: 25
atggctcctc agctactcct ctgtctgatc ctcactttc tgtggagtct cccagaggct       60
gaaagtaatg tattcttaaa aagcaaagtg gcaaatagat ttttgcaaag aacaaaacga      120
gccaattcac tgtttgagga atttaaatct ggaaacattg aaagggaatg cattgaggag      180
agatgttcaa agaagaagc cagggaggca tttgaagatg acgagaaaac tgagaccttc      240
tggaatgttt atgtagatgg ggatcagtgt tcatcaaacc cctgtcatta tggcgggaca      300
tgcaaagatg gcattggtag ctatacctgt acctgcttgt ctggctatga agggaaaaac      360
tgtgaatatg tcttatataa gtcctgcaga gtggacaatg gtgactgttg gcacttctgc      420
aaacctgttc aaaacggaat tcagtgttca tgtgctgaaa gttaccttt gggagaggat      480 gggcactctt gtgttgctgg aggtgacttt tcatgtggta gaaatataaa acaaggaac      540 aagcgggaag caaatctgcc tgactttcaa acagattttt ctgatgacta cgatgagatt      600
gatgaaaata tttttgttga aactcctaca aatttctctg cttagttct cactgtgcag      660 tcccagaatg caactttgct gaaaaaatct gataatccaa gccctgatat cagagttgtt      720 aatgaacag actgcaaact aggtgaatgt ccatggcagg cacttctgct aaatgatgaa      780
ggagatgggt tttgtggagg aacaattttg agtccatct atgtgcttac tgcagcccac      840
tgcattaacc agaccaagta cattacagtt gttgtagggg aaatagacat atcaagcaaa      900 aaaccggac gtcttcattc tgtggataaa atatatgtgc atcaaaaatt tgttcctgcc      960
acgtatgact atgacatagc catcatccaa ctgaagaccc ctatccagtt ctctgaaaat     1020
```

-continued

```
gtggttcctg cctgccttcc cactgctgat tttgccaacc aagtcctcat gaaacaaaat    1080
tttggcatcg ttagtggatt tgggcgtact cgagaaagag gaaagacctc taacacactt    1140
aaagttgtta cgcttcctta tgtggacagg cacacctgca tgctttccag caattttcca    1200
attactcaaa atatgttctg tgctggctat gatactctgc ctcaagatgc atgccaggga    1260
gacagcggag ggccccacat cactgcatac agagataccc actttattac tgggattgtc    1320 agctggggg aaggatgtgc acagacaggc aaatatggtg tttacacaaa agtgtccaaa    1380
ttcatccttt ggataaaaag aataatacgt caaaagcaac ccagtacaga gtcaagcacc    1440
ggtcggctct aa                                                        1452
```

<210> SEQ ID NO 26
<211> LENGTH: 483
<212> TYPE: PRT
<213> ORGANISM: Pseudonaja textilis

<400> SEQUENCE: 26

Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Phe Glu Glu Phe
        35                  40                  45

Lys Ser Gly Asn Ile Glu Arg Glu Cys Ile Glu Glu Arg Cys Ser Lys
    50                  55                  60

Glu Glu Ala Arg Glu Ala Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Gly Gly Thr Cys Lys Asp Gly Ile Gly Ser Tyr Thr Cys Thr Cys
            100                 105                 110

Leu Ser Gly Tyr Glu Gly Lys Asn Cys Glu Tyr Val Leu Tyr Lys Ser
        115                 120                 125

Cys Arg Val Asp Asn Gly Asp Cys Trp His Phe Cys Lys Pro Val Gln
    130                 135                 140

Asn Gly Ile Gln Cys Ser Cys Ala Glu Ser Tyr Leu Leu Gly Glu Asp
145                 150                 155                 160

Gly His Ser Cys Val Ala Gly Gly Asp Phe Ser Cys Gly Arg Asn Ile
                165                 170                 175

Lys Thr Arg Asn Lys Arg Glu Ala Asn Leu Pro Asp Phe Gln Thr Asp
            180                 185                 190

Phe Ser Asp Asp Tyr Asp Glu Ile Asp Glu Asn Asn Phe Val Glu Thr
        195                 200                 205

Pro Thr Asn Phe Ser Gly Leu Val Leu Thr Val Gln Ser Gln Asn Ala
    210                 215                 220

Thr Leu Leu Lys Lys Ser Asp Asn Pro Ser Asp Ile Arg Val Val
225                 230                 235                 240

Asn Gly Thr Asp Cys Lys Leu Gly Glu Cys Pro Trp Gln Ala Leu Leu
                245                 250                 255

Leu Asn Asp Glu Gly Asp Gly Phe Cys Gly Gly Thr Ile Leu Ser Pro
            260                 265                 270

Ile Tyr Val Leu Thr Ala Ala His Cys Ile Asn Gln Thr Lys Tyr Ile
        275                 280                 285

```
Thr Val Val Gly Glu Ile Asp Ile Ser Ser Lys Lys Thr Gly Arg
    290                 295                 300

Leu His Ser Val Asp Lys Ile Tyr Val His Gln Lys Phe Val Pro Ala
305                 310                 315                 320

Thr Tyr Asp Tyr Asp Ile Ala Ile Ile Gln Leu Lys Thr Pro Ile Gln
                325                 330                 335

Phe Ser Glu Asn Val Val Pro Ala Cys Leu Pro Thr Ala Asp Phe Ala
                340                 345                 350

Asn Gln Val Leu Met Lys Gln Asn Phe Gly Ile Val Ser Gly Phe Gly
                355                 360                 365

Arg Thr Arg Glu Arg Gly Lys Thr Ser Asn Thr Leu Lys Val Val Thr
    370                 375                 380

Leu Pro Tyr Val Asp Arg His Thr Cys Met Leu Ser Ser Asn Phe Pro
385                 390                 395                 400

Ile Thr Gln Asn Met Phe Cys Ala Gly Tyr Asp Thr Leu Pro Gln Asp
                405                 410                 415

Ala Cys Gln Gly Asp Ser Gly Gly Pro His Ile Thr Ala Tyr Arg Asp
                420                 425                 430

Thr His Phe Ile Thr Gly Ile Val Ser Trp Gly Glu Gly Cys Ala Gln
                435                 440                 445

Thr Gly Lys Tyr Gly Val Tyr Thr Lys Val Ser Lys Phe Ile Leu Trp
    450                 455                 460

Ile Lys Arg Ile Ile Arg Gln Lys Gln Pro Ser Thr Glu Ser Ser Thr
465                 470                 475                 480

Gly Arg Leu

<210> SEQ ID NO 27
<211> LENGTH: 463
<212> TYPE: PRT
<213> ORGANISM: Pseudonaja textilis

<400> SEQUENCE: 27

Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ala Asn Ser Leu Val Glu Glu Phe
    35                  40                  45

Lys Ser Gly Asn Ile Glu Arg Glu Cys Ile Glu Glu Arg Cys Ser Lys
50                  55                  60

Glu Glu Ala Arg Glu Ala Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
                100                 105                 110

Leu Ser Gly Tyr Glu Gly Lys Asn Cys Glu Arg Val Leu Tyr Lys Ser
                115                 120                 125

Cys Arg Val Asp Asn Gly Asn Cys Trp His Phe Cys Lys His Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175
```

```
Lys Thr Arg Asn Lys Arg Glu Ala Asn Leu Pro Asp Phe Val Gln Ser
                180                 185                 190

Gln Asn Ala Thr Leu Leu Lys Lys Ser Asp Asn Pro Ser Pro Asp Ile
            195                 200                 205

Arg Ile Val Asn Gly Met Asp Cys Lys Leu Gly Glu Cys Pro Trp Gln
        210                 215                 220

Ala Ala Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Gly Glu Ile Asp Lys Ser Arg Ile Glu
            260                 265                 270

Thr Gly Pro Leu Leu Ser Val Asp Lys Ile Tyr Val His Lys Lys Phe
        275                 280                 285

Val Pro Pro Gln Lys Ala Tyr Lys Phe Asp Leu Ala Ala Tyr Asp Tyr
        290                 295                 300

Asp Ile Ala Ile Ile Gln Met Lys Thr Pro Ile Gln Phe Ser Glu Asn
305                 310                 315                 320

Val Val Pro Ala Cys Leu Pro Thr Ala Asp Phe Ala Asn Gln Val Leu
                325                 330                 335

Met Lys Gln Asp Phe Gly Ile Val Ser Gly Phe Gly Arg Ile Phe Glu
            340                 345                 350

Lys Gly Pro Lys Ser Lys Thr Leu Lys Val Leu Lys Val Pro Tyr Val
        355                 360                 365

Asp Arg His Thr Cys Met Val Ser Ser Glu Thr Pro Ile Thr Pro Asn
        370                 375                 380

Met Phe Cys Ala Gly Tyr Asp Thr Leu Pro Arg Asp Ala Cys Gln Gly
385                 390                 395                 400

Asp Ser Gly Gly Pro His Thr Thr Val Tyr Arg Asp Thr His Phe Ile
                405                 410                 415

Thr Gly Ile Val Ser Ser Gly Glu Gly Cys Ala Arg Asn Gly Lys Tyr
            420                 425                 430

Gly Ile Tyr Thr Lys Leu Ser Lys Phe Ile Pro Trp Ile Lys Arg Ile
        435                 440                 445

Met Arg Gln Lys Leu Pro Ser Thr Glu Ser Ser Thr Gly Arg Leu
    450                 455                 460

<210> SEQ ID NO 28
<211> LENGTH: 467
<212> TYPE: PRT
<213> ORGANISM: Pseudonaja textilis textilis

<400> SEQUENCE: 28

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Val Glu Glu Phe
        35                  40                  45

Lys Ser Gly Asn Ile Glu Arg Glu Cys Ile Glu Arg Cys Ser Lys
    50                  55                  60

Glu Glu Ala Arg Glu Val Phe Glu Asp Glu Lys Thr Glu Thr Phe
65                  70                  75                  80

Trp Asn Val Tyr Val Asp Gly Asp Gln Cys Ser Ser Asn Pro Cys His
                85                  90                  95
```

```
Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
            115                 120                 125

Cys Arg Val Asp Asn Gly Asn Cys Trp His Phe Cys Lys Ser Val Gln
            130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

His Asn Ala Thr Leu Leu Lys Lys Ser Asp Asn Pro Ser Pro Asp Ile
            195                 200                 205

Arg Ile Val Asn Gly Met Asp Cys Lys Leu Gly Glu Cys Pro Trp Gln
            210                 215                 220

Ala Ala Leu Val Asp Asp Lys Lys Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Val Gly Glu Ile Asp Arg Ser Arg Ala Glu
            260                 265                 270

Thr Gly Pro Leu Leu Ser Val Asp Lys Val Tyr Val His Lys Lys Phe
            275                 280                 285

Val Pro Pro Lys Lys Ser Gln Glu Phe Tyr Lys Phe Asp Leu Val
            290                 295                 300

Ser Tyr Asp Tyr Asp Ile Ala Ile Ile Gln Met Lys Thr Pro Ile Gln
305                 310                 315                 320

Phe Ser Glu Asn Val Val Pro Ala Cys Leu Pro Thr Ala Asp Phe Ala
                325                 330                 335

Asn Gln Val Leu Met Lys Gln Asp Phe Gly Ile Val Ser Gly Phe Gly
            340                 345                 350

Gly Ile Phe Glu Arg Gly Pro Asn Ser Lys Thr Leu Lys Val Leu Lys
            355                 360                 365

Val Pro Tyr Val Asp Arg His Thr Cys Met Leu Ser Ser Asn Phe Pro
370                 375                 380

Ile Thr Pro Thr Met Phe Cys Ala Gly Tyr Asp Thr Leu Pro Gln Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Arg
            420                 425                 430

Lys Gly Arg Tyr Gly Ile Tyr Thr Lys Leu Ser Lys Phe Ile Pro Trp
            435                 440                 445

Ile Lys Arg Ile Met Arg Gln Lys Leu Pro Ser Thr Glu Ser Ser Thr
450                 455                 460

Gly Arg Leu
465

<210> SEQ ID NO 29
<211> LENGTH: 463
<212> TYPE: PRT
<213> ORGANISM: Pseudonaja textilis textilis
```

```
<400> SEQUENCE: 29

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Glu Arg Ala Asn Ser Leu Val Glu Glu Phe
        35                  40                  45

Lys Ser Gly Asn Ile Glu Arg Glu Cys Ile Glu Arg Cys Ser Lys
    50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys His Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Asn Phe Ser Cys Gly Arg Asn Ile
                165                 170                 175

Lys Thr Arg Asn Lys Arg Glu Ala Asn Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Ala Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Gly Glu Ile Asp Lys Ser Arg Ile Glu
            260                 265                 270

Thr Gly Pro Leu Leu Ser Val Asp Lys Ile Tyr Val His Lys Lys Phe
        275                 280                 285

Val Pro Pro Gln Lys Ala Tyr Lys Phe Asp Leu Ala Ala Tyr Asp Tyr
    290                 295                 300

Asp Ile Ala Ile Ile Gln Met Lys Thr Pro Ile Gln Phe Ser Glu Asn
305                 310                 315                 320

Val Val Pro Ala Cys Leu Pro Thr Ala Asp Phe Ala Asn Gln Val Leu
                325                 330                 335

Met Lys Gln Asp Phe Gly Ile Val Ser Gly Phe Gly Arg Ile Val Glu
            340                 345                 350

Lys Gly Pro Lys Ser Lys Thr Leu Lys Val Leu Lys Val Pro Tyr Val
        355                 360                 365

Asp Arg His Thr Cys Met Val Ser Ser Glu Thr Pro Ile Thr Pro Asn
    370                 375                 380

Met Phe Cys Ala Gly Tyr Asp Thr Leu Pro Arg Asp Ala Cys Gln Gly
385                 390                 395                 400

Asp Ser Gly Gly Pro His Thr Thr Val Tyr Arg Asp Thr His Phe Ile
                405                 410                 415
```

```
Thr Gly Ile Val Ser Ser Gly Glu Gly Cys Ala Arg Asn Gly Lys Tyr
            420                 425                 430

Gly Asn Tyr Thr Lys Leu Ser Lys Phe Ile Pro Trp Ile Lys Arg Ile
            435                 440                 445

Met Arg Gln Lys Leu Pro Ser Thr Glu Ser Ser Thr Gly Arg Leu
    450                 455                 460

<210> SEQ ID NO 30
<211> LENGTH: 449
<212> TYPE: PRT
<213> ORGANISM: Pseudonaja textilis

<400> SEQUENCE: 30

Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ala Asn Ser Leu Val Glu Phe
            35                  40                  45

Lys Ser Gly Asn Ile Glu Arg Glu Cys Ile Glu Glu Arg Cys Ser Lys
    50                  55                  60

Glu Glu Ala Arg Glu Ala Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
            115                 120                 125

Cys Arg Val Asp Asn Gly Asn Cys Trp His Phe Cys Lys Ser Val Gln
130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

Gln Asn Ala Pro Leu Leu Lys Ile Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Ala Leu Val Asp Asp Lys Lys Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Gly Glu Ile Asp Arg Ser Arg Ala Glu
            260                 265                 270

Thr Gly Pro Leu Leu Ser Val Asp Lys Val Tyr Val His Lys Lys Phe
        275                 280                 285

Val Pro Pro Lys Lys Ser Gln Glu Phe Tyr Glu Lys Phe Asp Leu Val
    290                 295                 300

Ser Tyr Asp Tyr Asp Ile Ala Ile Ile Gln Met Lys Thr Pro Ile Gln
305                 310                 315                 320

Phe Ser Glu Asn Val Val Pro Ala Cys Leu Pro Thr Ala Asp Phe Ala
```

```
                325                 330                 335

Asn Gln Val Leu Met Lys Gln Asp Phe Gly Ile Val Ser Gly Phe Gly
            340                 345                 350

Gly Ile Phe Glu Arg Gly Pro Asn Ser Lys Thr Leu Lys Val Leu Lys
        355                 360                 365

Val Pro Tyr Val Asp Arg His Thr Cys Met Leu Ser Ser Asn Phe Pro
    370                 375                 380

Ile Thr Pro Thr Met Phe Cys Ala Gly Tyr Asp Thr Leu Pro Gln Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Arg
            420                 425                 430

Lys Gly Arg Tyr Gly Ile Tyr Thr Lys Leu Ser Lys Phe Ile Pro Trp
        435                 440                 445

Ile
```

<210> SEQ ID NO 31
<211> LENGTH: 1404
<212> TYPE: DNA
<213> ORGANISM: Oxyuranus scutellatus

<400> SEQUENCE: 31

```
atggctcctc aactactcct ctgtctgatc ctcacttttc tgtggagtct cccagaggcc     60
gaaagtaatg tattcttaaa aagcaaagtg gcaaatagat tttgcaaag aacaaaacga     120 gctaattcac tgtatgagga atttagatct ggaaacattg aaagggaatg cattgaggag    180
agatgttcaa aagaagaagc cagggaggta tttgaagatg acgagaaaac tgagaccttc    240
tggaatgttt atgtagatgg ggatcagtgt tcatcaaacc cctgtcatta tcgcgggaca    300
tgcaaagatg gcattggtag ctatacctgt acctgcttgt ctggctatga agggaaaaac    360
tgtgaacgtg tcttatataa gtcctgcaga gtggacaatg gtaactgttg gcacttctgc    420
aaacctgttc aaaacgatat tcagtgttca tgtgctgaag gttacctttt gggagaggat    480
gggcactctt gtgttgctgg aggtaacttt tcatgtggta gaaatatcaa aacaaggaac    540
aagagggaag caagtctgcc tgactttgtg cagtcccaga atgcaatttt gctgaaaaaa    600
tctgataatc caagccctga tatcagaatt gttaatggaa tggactgcaa actgggtgaa    660
tgtccgtggc aggcagttct ggtagatgaa aaggaagatg cgttttgtgg aggaacaatt    720
ttgagtccca tctatgtgct tactgcagcc cactgcatta accagaccaa gatgatttca    780
gttgttgtag gggaaataaa catatcaaga aaaaaccccg gacgtcttct ttctgtggat    840
aaaatatatg tgcatcaaaa atttgttcct cccaaaaaag gctatgaatt ctatgaaaag    900
tttgatcttg tcagctatga ctatgatata gccatcctcc aaatgaagac ccctatccag    960
ttctctgaaa atgtggttcc tgcctgcctt cccacagctg attttgccaa ccaagtcctc   1020
atgaaacaag attttggcat cgttagtgga tttgggcgta ttttcgaaaa aggacctcaa   1080
tctaaaacac ttaaagtcct taaggttcct tatgtggaca ggcacacctg catgctttcc   1140
agcgaatctc caattactcc aactatgttc tgtgctggct atgatactct gcctcgagat   1200
gcatgccagg gagacagtgg ggggccccac atcactgcat acagagatac ccactttatt   1260
actgggattg tcagctgggg ggaaggatgt gcacagacag gcaaatatgg tgtttacaca   1320
aaagtgtcca aattcatcct ttggataaaa agaataatgc gtcaaaagct acccagtaca   1380
```
gagtcaagca ctggtcggct ctaa                                                            1404

<210> SEQ ID NO 32
<211> LENGTH: 467
<212> TYPE: PRT
<213> ORGANISM: Oxyuranus scutellatus

<400> SEQUENCE: 32

```
Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Tyr Glu Glu Phe
        35                  40                  45

Arg Ser Gly Asn Ile Glu Arg Glu Cys Ile Glu Glu Ar

```
Val Pro Tyr Val Asp Arg His Thr Cys Met Leu Ser Ser Glu Ser Pro
    370                 375                 380

Ile Thr Pro Thr Met Phe Cys Ala Gly Tyr Asp Thr Leu Pro Arg Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Gln
                420                 425                 430

Thr Gly Lys Tyr Gly Val Tyr Thr Lys Val Ser Lys Phe Ile Leu Trp
            435                 440                 445

Ile Lys Arg Ile Met Arg Gln Lys Leu Pro Ser Thr Glu Ser Ser Thr
450                 455                 460

Gly Arg Leu
465

<210> SEQ ID NO 33
<211> LENGTH: 1404
<212> TYPE: DNA
<213> ORGANISM: Oxyuranus microlepidotus

<400> SEQUENCE: 33
atggctcctc aactactcct ctgtctgatc ctcacttttc tgtggagtct cccagaggct      60
gaaagtaatg tattcttaaa aagcaaagtg gcaaatagat ttttgcaaag aacaaaacga     120
gctaattcac tgtttgagga atttagatct ggaaacattg aaagggaatg cattgaggag     180
agatgttcaa agaagaagc cagggaggta tttgaagatg acgagaaaac tgagaccttc     240
tggaatgttt atgtagatgg ggatcagtgt tcatcaaacc cctgtcatta tcgcgggaca     300
tgcaaagatg gcattggtag ctatacctgt acctgcttgt ttggctatga agggaaaaac     360
tgtgaacgtg tcttatataa gtcctgcaga gtggacaatg gtaactgttg gcacttctgc     420
aaacctgttc aaaacgatat tcagtgttca tgtgctgaag gttacctttt gggagaggat     480
gggcactctt gtgttgctgg aggtaacttt tcatgtggta gaaatatcaa acaaggaac     540 aagagggaag caagtctgcc tgactttgtg cagtcccaga atgcaacttt gctgaaaaaa     600
tctgataatc aagccctga tatcagaatt gttaatggaa tggactgcaa actgggtgaa     660
tgtccgtggc aggcagttct ggtagatgaa aaggaaggtg tgttttgtgg aggaacaatt     720
ttgagtccca tctatgtgct tactgcagcc cactgcatta ccagaccga aagatttca     780 gttgttgtag ggaaatagaa caaatcaaga gtagaaaccg acatcttct ttctgtggat     840 aaaatatatg tgcataaaaa atttgttcct cccaaaaaag gctataaatt ctatgaaaag     900
tttgatcttg tcagctatga ctatgatata gccatcatcc aaatgaagac ccctatccag     960
ttctctgaaa atgtggttcc tgcctgcctt cccacagctg attttgccaa ccaagtcctc    1020
atgaaacaag attttggcat cattagtgga tttgggcgta ttttcgaaaa aggaccgaaa    1080
tctaacacac ttaaagtcct taaggttcct tatgtggaca ggcacacctg catggtttcc    1140
agcgaatctc caattactcc aactatgttc tgtgctggct atgatactct gcctcgagat    1200
gcatgccagg gagacagtgg ggggcccac atcactgcat acagagatac ccactttatt    1260
actgggattg tcagctgggg ggaaggatgt gctaagaaag caaatatgg tatttacaca    1320 aaagtgtcca aattcatcct ttggataaaa agaataatgc gtcaaaagct acccagtaca    1380
gagtcaagca ctggtcggct ctaa                                            1404

<210> SEQ ID NO 34
```

```
<211> LENGTH: 467
<212> TYPE: PRT
<213> ORGANISM: Oxyuranus microlepidotus

<400> SE

Ala Cys Gln Gly Asp Ser Gly Gly Pro His Ile Thr Ala Tyr Arg Asp
385                 390                 395                 400
                405                 410                 415

Thr His Phe Ile Thr Gly Ile Val Ser Trp Gly Glu Gly Cys Ala Lys
                420                 425                 430

Lys Gly Lys Tyr Gly Ile Tyr Thr Lys Val Ser Lys Phe Ile Leu Trp
                435                 440                 445

Ile Lys Arg Ile Met Arg Gln Lys Leu Pro Ser Thr Glu Ser Ser Thr
450                 455                 460

Gly Arg Leu
465

<210> SEQ ID NO 35
<211> LENGTH: 1365
<212> TYPE: DNA
<213> ORGANISM: Pseudechis porphyriacus

<400> SEQUENCE: 35

| | | |
|---|---|---|
| atggctcctc aactactcct ctgtctgatc ctcactttc tctggagtct cccggaggct | 60 |
| gaaagtaatg tattcttaaa aagcaaagag gcaaatagat ttttgcaaag aacaaaacga | 120 |
| tctaattcac tgtttgagga atttagacct ggaaacattg aaagggaatg cattgaggag | 180 |
| aaatgttcaa agaagaagc cagggagata tttaaagata cgagaaaac tgaggccttt | 240 |
| tggaatgttt atgtagatgg ggatcagtgt tcatcaaacc cctgtcatta tggtgggaca | 300 |
| tgcaaagatg gcattggtag ctatacctgt acctgcttgc ctaactatga agggaaaaac | 360 |
| tgtgaacatc tcttatttaa gtcctgcaga ttttcaatg gtaactgttg gcacttctgc | 420 |
| aaacctgttc aaaacgacac tcagtgttca tgtgctgaaa gttaccgttt gggagatgat | 480 |
| gggcactctt gtgttgctga aggtgacttt tcatgtggta gaaatataaa agcaaggaac | 540 |
| aagagggaag caagtctgcc tgactttgtg cagtcccaga atgcaacttt gctgaaaaaa | 600 |
| tctgataatc aagccctga tatcagaatt attaatggaa tggactgcaa actgggtgaa | 660 |
| tgtccatggc aggcagttct gctagataaa gaaggagatg tgtttttgtgg aggaacaatt | 720 |
| ttgagtccca tctatgtgct tactgcagcc cactgcatta cccagtccaa gcacatttca | 780 |
| gttgttgtag ggaaaataga tatatcaaga aaagaaacca gacatcttct ttctgtagat | 840 |
| aaagcatatg tgcatacaaa atttgttctt gccacctatg actatgatat gccatcatc | 900 |
| caattgaaga cccctatcca gttctctgaa aatgtggttc ctgcctgtct tcccactgct | 960 |
| gattttgcca ccaagtcct catgaaacaa gattttggca tcattagtgg atttgggcat | 1020 |
| actcgatctg gaggacagac ctctaacaca cttaaagtcg ttacgattcc ttatgtggac | 1080 |
| aggcacacct gcatgctttc cagcgatttt cgaattactc caaatatgtt ctgtgctggt | 1140 |
| tatgatactc tgcctcgaga tgcatgccag ggagacagtg ggggccccca catcactgca | 1200 |
| tacagagata cccactttat tactgggatt atcagctggg gggaaggatg tgcaaagaaa | 1260 |
| ggcaaatatg gtgtttacac aaaagtgtcc aacttcatcc cttggataaa agcagtaatg | 1320 |
| cgtaaacatc aacccagtac agagtcaagc actggtcggc tctaa | 1365 |

<210> SEQ ID NO 36
<211> LENGTH: 450
<212> TYPE: PRT
<213> ORGANISM: Pseudechis porphyriacus

<400> SEQUENCE: 36

-continued

```
Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Glu Ala Asn
            20                  25                  30

Arg Phe Leu Gln Arg Thr Lys Arg Ser Asn Ser Leu Phe Glu Glu Phe
        35                  40                  45

Arg Pro Gly Asn Ile Glu Arg Glu Cys Ile Glu Glu Lys Cys Ser Lys
    50                  55                  60

Glu Glu Ala Arg Glu Ile Phe Lys Asp Asn Glu Lys Thr Glu Ala Phe
65                  70                  75                  80

Trp Asn Val Tyr Val Asp Gly Asp Gln Cys Ser Ser Asn Pro Cys His
                85                  90                  95

Tyr Gly Gly Thr Cys Lys Asp Gly Ile Gly Ser Tyr Thr Cys Thr Cys
            100                 105                 110

Leu Pro Asn Tyr Glu Gly Lys Asn Cys Glu His Leu Leu Phe Lys Ser
        115                 120                 125

Cys Arg Phe Phe Asn Gly Asn Cys Trp His Phe Cys Lys Pro Val Gln
    130                 135                 140

Asn Asp Thr Gln Cys Ser Cys Ala Glu Ser Tyr Arg Leu Gly Asp Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Ile Asn Gly Met Asp Cys Lys Leu Gly Glu Cys Pro Trp Gln
    210                 215                 220

Ala Val Leu Leu Asp Lys Glu Gly Asp Val Phe Cys Gly Gly Thr Ile
225                 230                 235                 240

Leu Ser Pro Ile Tyr Val Leu Thr Ala Ala His Cys Ile Thr Gln Ser
                245                 250                 255

Lys His Ile Ser Val Val Val Gly Glu Ile Asp Ile Ser Arg Lys Glu
            260                 265                 270

Thr Arg His Leu Leu Ser Val Asp Lys Ala Tyr Val His Thr Lys Phe
        275                 280                 285

Val Leu Ala Thr Tyr Asp Tyr Asp Ile Ala Ile Ile Gln Leu Lys Thr
    290                 295                 300

Pro Ile Gln Phe Ser Glu Asn Val Val Pro Ala Cys Leu Pro Thr Ala
305                 310                 315                 320

Asp Phe Ala Asn Gln Val Leu Met Lys Gln Asp Phe Gly Ile Ile Ser
                325                 330                 335

Gly Phe Gly His Thr Arg Ser Gly Gly Gln Thr Ser Asn Thr Leu Lys
            340                 345                 350

Val Val Thr Ile Pro Tyr Val Asp Arg His Thr Cys Met Leu Ser Ser
        355                 360                 365

Asp Phe Arg Ile Thr Pro Asn Met Phe Cys Ala Gly Tyr Asp Thr Leu
    370                 375                 380

Pro Arg Asp Ala Cys Gln Gly Asp Ser Gly Gly Pro His Ile Thr Ala
385                 390                 395                 400

Tyr Arg Asp Thr His Phe Ile Thr Gly Ile Ile Ser Trp Gly Glu Gly
                405                 410                 415

Cys Ala Lys Lys Gly Lys Tyr Gly Val Tyr Thr Lys Val Ser Asn Phe
```

```
                420                425                430
Ile Pro Trp Ile Lys Ala Val Met Arg Lys His Gln Pro Ser Thr Glu
        435                440                445

Ser Ser
    450
```

<210> SEQ ID NO 37
<211> LENGTH: 1368
<212> TYPE: DNA
<213> ORGANISM: Hoplocephalus stephensii

<400> SEQUENCE: 37

```
atggctcctc aactactcct ctgtctgatc ctcactttc tgtggagtgt cccagaggct    60
gaaagtaatg tattcttaaa aagcaaagtg gcaaatagat ttttgcaaag aacaaaacga   120
tctaattcac tgtttgagga aattagacct ggaaacattg aaagggaatg cattgaggag   180
aaatgttcaa agaagaagc cagggaggta tttgaagata cgagaaaac tgagaccttc    240
tggaatgttt atgtagatgg ggatcagtgt tcatcaaacc cctgtcatta tcacgggaca   300
tgcaaagatg gcattggtag ctataccgt acctgcttgc ctaactatga agggaaaaac    360
tgtgaaaaag tcttatttaa gtcctgcaga gcgttcaatg gtaactgttg gcacttctgc   420
aaacgtgttc aaagtgaaac tcagtgttca tgtgctgaaa gttaccgttt gggagttgat   480
gggcactctt gtgttgctga aggtgacttt tcatgtggta gaaatataaa agcaaggaac   540
aagagggaag caagtctgcc tgactttgtg cagtcccaga aggcaacttt gctgaaaaaa   600
tctgataatc caagccctga tatcagaatt gttaatggaa tggactccaa actgggtgaa   660
tgtccatggc aggcagttct gataaatgaa aaggagaag tgttttgtgg aggaacaatt   720
ttgagtccca tccatgtgct tactgcagcc cactgcatta accagaccaa gagcgtttca   780
gttattgtag gggaaataga catatcaaga aaagaaacca gacgtcttct ttctgtggat   840
aaaatatatg tgcatacaaa atttgttcct cccaactatt actatgggca tcaaaacttt   900
gatcgtgtcg cctatgacta tgatatagcc atcatccgaa tgaagacccc tatccagttc   960
tctgaaaatg tggttcctgc ctgccttccc actgctgatt tgccaacga agtcctcatg  1020
aaacaagatt ctggcatcgt tagtggattt gggcgtattc gatttaaaga accgacctct  1080
aacacactta agtcattac ggttccttat gtggacaggc acacctgcat gctttccagt  1140
gattttcgaa ttactcaaaa tatgttctgt gctggctatg atactctgcc tcaagatgca  1200
tgcgagggag acagtggggg gcccacatc actgcatacg gagataccca ctttattact  1260
gggattgtca gctgggggga aggatgtgca cggaaaggca aatatggtgt ttacacaaaa  1320
gtgtccagat tcatcccttg gataaaaaaa ataatgagtc taaagtaa             1368
```

<210> SEQ ID NO 38
<211> LENGTH: 455
<212> TYPE: PRT
<213> ORGANISM: Hoplocephalus stephensii

<400> SEQUENCE: 38

```
Met Ala Pro Gln Leu Leu Leu Cys Leu Ile Leu Thr Phe Leu Trp Ser
1               5                  10                  15

Val Pro Glu Ala Glu Ser Asn Val Phe Leu Lys Ser Lys Val Ala Asn
            20                  25                  30

Arg Phe Leu Gln Arg Thr Lys Arg Ser Asn Ser Leu Phe Glu Glu Ile
        35                  40                  45
```

```
Arg Pro Gly Asn Ile Glu Arg Glu Cys Ile Glu Glu Lys Cys Ser Lys
 50                  55                  60

Glu Glu Ala Arg Glu Val Phe Glu Asp Asn Glu Lys Thr Glu Thr Phe
 65                  70                  75                  80

Trp Asn Val Tyr Val Asp Gly Asp Gln Cys Ser Ser Asn Pro Cys His
                 85                  90                  95

Tyr His Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Phe Lys Ser
            115                 120                 125

Cys Arg Ala Phe Asn Gly Asn Cys Trp His Phe Cys Lys Arg Val Gln
130                 135                 140

Ser Glu Thr Gln Cys Ser Cys Ala Glu Ser Tyr Arg Leu Gly Val Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Lys Ala Thr Leu Leu Lys Ser Asp Asn Pro Ser Pro Asp Ile
            195                 200                 205

Arg Ile Val Asn Gly Met Asp Ser Lys Leu Gly Glu Cys Pro Trp Gln
210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
            245                 250                 255

Lys Ser Val Ser Val Ile Val Gly Glu Ile Asp Ile Ser Arg Lys Glu
            260                 265                 270

Thr Arg Arg Leu Leu Ser Val Asp Lys Ile Tyr Val His Thr Lys Phe
            275                 280                 285

Val Pro Pro Asn Tyr Tyr Tyr Gly His Gln Asn Phe Asp Arg Val Ala
            290                 295                 300

Tyr Asp Tyr Asp Ile Ala Ile Ile Arg Met Lys Thr Pro Ile Gln Phe
305                 310                 315                 320

Ser Glu Asn Val Val Pro Ala Cys Leu Pro Thr Ala Asp Phe Ala Asn
                325                 330                 335

Glu Val Leu Met Lys Gln Asp Ser Gly Ile Val Ser Gly Phe Gly Arg
            340                 345                 350

Ile Arg Phe Lys Glu Pro Thr Ser Asn Thr Leu Lys Val Ile Thr Val
            355                 360                 365

Pro Tyr Val Asp Arg His Thr Cys Met Leu Ser Ser Asp Phe Arg Ile
            370                 375                 380

Thr Gln Asn Met Phe Cys Ala Gly Tyr Asp Thr Leu Pro Gln Asp Ala
385                 390                 395                 400

Cys Glu Gly Asp Ser Gly Gly Pro His Ile Thr Ala Tyr Gly Asp Thr
                405                 410                 415

His Phe Ile Thr Gly Ile Val Ser Trp Gly Glu Gly Cys Ala Arg Lys
            420                 425                 430

Gly Lys Tyr Gly Val Tyr Thr Lys Val Ser Arg Phe Ile Pro Trp Ile
            435                 440                 445

Lys Lys Ile Met Ser Leu Lys
450                 455
```

<210> SEQ ID NO 39
<211> LENGTH: 1362
<212> TYPE: DNA
<213> ORGANISM: Notechis scutatus

<400> SEQUENCE: 39

```
atggctcctc aactactcct ctgtctgatc ctcactttc tgtggagtct cccagaggct        60
gaaagtaatg tattcttaaa aagcaaagtg gcaaatagat ttttgcaaag aacaaaacga       120
tctaattcac tgtttgagga aattagacct ggaaacattg aaagggaatg cattgaggag       180
aaatgttcaa agaagaagc cagggaggta tttgaagata cgagaaaac tgagaccttc        240 tggaatgttt atgtagatgg ggatcagtgt tcatcaaacc cctgtcatta tcgcgggaca       300
tgcaaagatg gcattggtag ctatacctgt acctgcttgc ctaactatga agggaaaaac       360
tgtgaaaaag tcttatttaa gtcctgcaga gcattcaatg gtaactgttg gcacttctgc       420
aaacgtgttc aaagtgaaac tcagtgttca tgtgctgaaa gttaccttt gggagttgat       480 gggcactctt gtgttgctga aggtgacttt tcatgtggta gaaatataaa agcaaggaac       540
aagagggaag caagtctgcc tgactttgtg cagtcccaga aggcaactgt gctgaaaaaa       600
tctgataatc aagccctga tatcagaatt gttaatggaa tggactgcaa actgggtgaa        660
tgtccatggc aggcagttct gataaatgaa aaggagaag tgttttgtgg aggaacaatt        720
ttgagcccca tccatgtgct tactgcagcc cactgcatta accagaccaa gagcgtttca       780
gttattgtag gggaaataga catatcaaga aaagaaacca gacgtcttct ttctgtggat       840
aaaatatatg tgcataaaaa atttgttcct cccaactctt actatcaaaa cattgatcgt       900
ttcgcctatg actatgatat agccatcatc cgaatgaaga cccctatcca gttctctgaa       960
aatgtggttc ctgcctgcct tcccactgct gattttgcca aggaagtcct catgaaacaa      1020
gattctggca tcgttagtgg atttgggcgt actcaatcta taggatatac ctctaacata      1080
cttaaagtca ttacggttcc ttatgtggac aggcacacct gcatgctttc cagtaattt       1140 cgaattactc aaaatatgtt ctgtgctggc tatgatactc tgcctcaaga tgcatgccag      1200
ggagacagtg gggggcccca catcactgca tacggagata cccactttgt tactgggatt      1260
atcagctggg gggaaggatg tgcacggaaa ggcaaatatg gtgtttacac aaaagtgtcc      1320
aatttcatcc cttggataaa aaaataatg agtctaaagt aa                         1362
```

<210> SEQ ID NO 40
<211> LENGTH: 453
<212> TYPE: PRT
<213> ORGANISM: Notechis scutatus

<400> SEQUENCE: 40

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ser Asn Ser Leu Phe Glu Glu Ile
            35                  40                  45

Arg Pro Gly Asn Ile Glu Arg Glu Cys Ile Glu Glu Lys Cys Ser Lys
        50                  55                  60

Glu Glu Ala Arg Glu Val Phe Glu Asp Asn Glu Lys Thr Glu Thr Phe
65                  70                  75                  80

Trp Asn Val Tyr Val Asp Gly Asp Gln Cys Ser Ser Asn Pro Cys His
                85                  90                  95

```
Tyr Arg Gly Thr Cys Lys Asp Gly Ile Gly Ser Tyr Thr Cys Thr Cys
                100                 105                 110

Leu Pro Asn Tyr Glu Gly Lys Asn Cys Glu Lys Val Leu Phe Lys Ser
            115                 120                 125

Cys Arg Ala Phe Asn Gly Asn Cys Trp His Phe Cys Lys Arg Val Gln
130                 135                 140

Ser Glu Thr Gln Cys Ser Cys Ala Glu Ser Tyr Leu Leu Gly Val Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Lys Ala Thr Val Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
                245                 250                 255

Lys Ser Val Ser Val Ile Val Gly Glu Ile Asp Ile Ser Arg Lys Glu
            260                 265                 270

Thr Arg Arg Leu Leu Ser Val Asp Lys Ile Tyr Val His Lys Lys Phe
        275                 280                 285

Val Pro Pro Asn Ser Tyr Tyr Gln Asn Ile Asp Arg Phe Ala Tyr Asp
290                 295                 300

Tyr Asp Ile Ala Ile Ile Arg Met Lys Thr Pro Ile Gln Phe Ser Glu
305                 310                 315                 320

Asn Val Val Pro Ala Cys Leu Pro Thr Ala Asp Phe Ala Lys Glu Val
                325                 330                 335

Leu Met Lys Gln Asp Ser Gly Ile Val Ser Gly Phe Gly Arg Thr Gln
            340                 345                 350

Ser Ile Gly Tyr Thr Ser Asn Ile Leu Lys Val Ile Thr Val Pro Tyr
        355                 360                 365

Val Asp Arg His Thr Cys Met Leu Ser Ser Asn Phe Arg Ile Thr Gln
370                 375                 380

Asn Met Phe Cys Ala Gly Tyr Asp Thr Leu Pro Gln Asp Ala Cys Gln
385                 390                 395                 400

Gly Asp Ser Gly Gly Pro His Ile Thr Ala Tyr Gly Asp Thr His Phe
                405                 410                 415

Val Thr Gly Ile Ile Ser Trp Gly Glu Gly Cys Ala Arg Lys Gly Lys
            420                 425                 430

Tyr Gly Val Tyr Thr Lys Val Ser Asn Phe Ile Pro Trp Ile Lys Lys
        435                 440                 445

Ile Met Ser Leu Lys
    450

<210> SEQ ID NO 41
<211> LENGTH: 1368
<212> TYPE: DNA
<213> ORGANISM: Tropidechis carinatus

<400> SEQUENCE: 41
atggctcctc aactactcct ctgtctgatc ctcactttc tgtggagtct cccagaggct      60
```

```
gaaagtaatg tattcttaaa aagcaaagtg gcaaatagat ttttgcaaag aacaaaacga    120
tctaattcac tgtttgagga aattagacct ggaaacattg aaagggaatg cattgaggag    180
aaatgttcaa agaagaagc cagggaggta tttgaagata cgagaaaac tgagaccttc     240 tggaatgttt atgtagatgg ggatcagtgt tcatcaaacc cctgtcatta tcgcgggaca    300
tgcaaagatg gcattggtag ctatacctgt acctgcttgc ctaactatga agggaaaaac    360
tgtgaaaaag tcttatatca gtcctgcaga gtggacaatg gtaactgttg gcacttctgc    420
aaacgtgttc aaagtgaaac tcagtgttca tgtgctgaaa gttaccgttt gggagttgat    480
gggcactctt gtgttgctga aggtgacttt tcatgtggta gaaatataaa agcaaggaac    540
aagagggaag caagtctgcc tgactttgtg cagtcccaaa aggcaacttt gctgaaaaaa    600
tctgataatc aagccctga tatcagaatt gttaatggaa tggactgcaa actgggtgaa     660
tgtccatggc aggcagttct gataaatgaa aaggagaag tgttttgtgg aggaacaatt    720
ttgagtccca tccatgtgct tactgcagcc cactgcatta accagaccaa gagcgtttca    780
gttattgtag gggaaataga catatcaaga aaagaaacca gacgtcttct ttctgtggat    840
aaaatatatg tgcatacaaa atttgttcct cccaactatt actatgtgca tcaaaacttt    900
gatcgtgtcg cctatgacta tgatatagcc atcatccgaa tgaagacccc tatccagttc    960
tctgaaaatg tggttcctgc ctgccttccc actgctgatt tgccaacga agtcctcatg    1020 aaacaagatt ctggcatcgt tagtggattt gggcgtattc aatttaaaca accgacctct    1080
aacacactta agtcattac ggttccttat gtggacaggc acacctgcat gctttccagt    1140
gattttcgaa ttactcaaaa tatgttctgt gctggctatg atactctgcc tcaagatgca    1200
tgccagggag acagtggggg gccccacatc actgcataca gagataccca ctttattact    1260
gggattatca gctgggggga aggatgtgca cggaaaggca aatatggtgt ttacacaaaa    1320
gtgtccaaat tcatcccttg gataaaaaaa ataatgagtc taaagtaa              1368
```

<210> SEQ ID NO 42
<211> LENGTH: 455
<212> TYPE: PRT
<213> ORGANISM: Tropidechis carinatus

<400> SEQUENCE: 42

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ser Asn Ser Leu Phe Glu Glu Ile
        35                  40                  45

Arg Pro Gly Asn Ile Glu Arg Glu Cys Ile Glu Glu Lys Cys Ser Lys
    50                  55                  60

Glu Glu Ala Arg Glu Val Phe Glu Asp Asn Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Tyr Gln Ser
        115                 120                 125

Cys Arg Val Asp Asn Gly Asn Cys Trp His Phe Cys Lys Arg Val Gln
    130                 135                 140
```

-continued

```
Ser Glu Thr Gln Cys Ser Cys Ala Glu Ser Tyr Arg Leu Gly Val Asp
145                 150                 155                 160

Gly His Ser Cys Val Ala Glu Gly Asp Phe Ser Cys Gly Arg Asn Ile
            165                 170                 175

Lys Ala Arg Asn Lys Arg Glu Ala Ser Leu Pro Asp Phe Val Gln Ser
        180                 185                 190

Gln Lys Ala Thr Leu Leu Lys Lys Ser Asp Asn Pro Ser Pro Asp Ile
    195                 200                 205

Arg Ile Val Asn Gly Met Asp Cys Lys Leu Gly Glu Cys Pro Trp Gln
210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
            245                 250                 255

Lys Ser Val Ser Val Ile Val Gly Glu Ile Asp Ile Ser Arg Lys Glu
        260                 265                 270

Thr Arg Arg Leu Leu Ser Val Asp Lys Ile Tyr Val His Thr Lys Phe
    275                 280                 285

Val Pro Pro Asn Tyr Tyr Val His Gln Asn Phe Asp Arg Val Ala
290                 295                 300

Tyr Asp Tyr Asp Ile Ala Ile Ile Arg Met Lys Thr Pro Ile Gln Phe
305                 310                 315                 320

Ser Glu Asn Val Val Pro Ala Cys Leu Pro Thr Ala Asp Phe Ala Asn
            325                 330                 335

Glu Val Leu Met Lys Gln Asp Ser Gly Ile Val Ser Gly Phe Gly Arg
        340                 345                 350

Ile Gln Phe Lys Gln Pro Thr Ser Asn Thr Leu Lys Val Ile Thr Val
    355                 360                 365

Pro Tyr Val Asp Arg His Thr Cys Met Leu Ser Ser Asp Phe Arg Ile
370                 375                 380

Thr Gln Asn Met Phe Cys Ala Gly Tyr Asp Thr Leu Pro Gln Asp Ala
385                 390                 395                 400

Cys Gln Gly Asp Ser Gly Gly Pro His Ile Thr Ala Tyr Arg Asp Thr
            405                 410                 415

His Phe Ile Thr Gly Ile Ile Ser Trp Gly Glu Gly Cys Ala Arg Lys
        420                 425                 430

Gly Lys Tyr Gly Val Tyr Thr Lys Val Ser Lys Phe Ile Pro Trp Ile
    435                 440                 445

Lys Lys Ile Met Ser Leu Lys
450                 455

<210> SEQ ID NO 43
<211> LENGTH: 671
<212> TYPE: DNA
<213> ORGANISM: Demansia vestigiata

<400> SEQUENCE: 43
atggctcctc aactactcct ctgtctgatc cagactttc tgtggagtct cccagaggct      60
gaaagtaatg tattcttaaa aagcaatgtg gcaaatagat ttttgcaaag aacaaaacga    120
gctaattcag ggtttgagga aatttaccct gcaaactttg aaagggaatg cgttgaggag    180
agatgttcaa agaagaagc cagggaggta tttgaagatg acgagaaaac tgaggccttc    240
tggactgttt atgtagatgg ggatcagtgt ttatcaaacc cctgtcatta tggcgggaca    300
tgcaaagatg gcattggtag ctataccctgt acctgcttgg ctggctatga agggaaaaac    360
```

```
tgtgaacatg acttacttaa gtcctgcaga gtggacaatg gtaactgttg gcacttctgc      420
aaacctgttc aaaacgacac tcagtgttca tgtgctgaag gttaccgttt gggagataat      480
gggttctctt gtattgctga aggtgagttt tcatgtggca gaaatataaa atcaaggaac      540
aagagggaag caagtctgcc tgactttcaa acagattttt ctgatgacta tgatgcgatt      600
gatgaaaata atttgattga aactgtgcag tcccagagtg caactttgct gaaaaaatct      660
gataatccaa a                                                           671
```

<210> SEQ ID NO 44
<211> LENGTH: 473
<212> TYPE: PRT
<213> ORGANISM: Demansia vestigiata

<400> SEQUENCE: 44

```
Met Ala Pro Gln Leu Leu Cys Leu Ile Gln Thr Phe Leu Trp Ser
1               5                   10                  15

Leu Pro Glu Ala Glu Ser Asn Val Phe Leu Lys Ser Asn Val Ala Asn
            20                  25                  30

Arg Phe Leu Gln Arg Thr Lys Arg Ala Asn Ser Gly Phe Glu Glu Ile
        35                  40                  45

Tyr Pro Ala Asn Phe Glu Arg Glu Cys Val Glu Glu Arg Cys Ser Lys
    50                  55                  60

Glu Glu Ala Arg Glu Val Phe Glu Asp Asp Glu Lys Thr Glu Ala Phe
65                  70                  75                  80

Trp Thr Val Tyr Val Asp Gly Asp Gln Cys Leu Ser Asn Pro Cys His
                85                  90                  95

Tyr Gly Gly Thr Cys Lys Asp Gly Ile Gly Ser Tyr Thr Cys Thr Cys
            100                 105                 110

Leu Ala Gly Tyr Glu Gly Lys Asn Cys Glu His Asp Leu Leu Lys Ser
        115                 120                 125

Cys Arg Val Asp Asn Gly Asn Cys Trp His Phe Cys Lys Pro Val Gln
    130                 135                 140

Asn Asp Thr Gln Cys Ser Cys Ala Glu Gly Tyr Arg Leu Gly Asp Asn
145                 150                 155                 160

Gly Phe Ser Cys Ile Ala Glu Gly Glu Phe Ser Cys Gly Arg Asn Ile
                165                 170                 175

Lys Ser Arg Asn Lys Arg Glu Ala Ser Leu Pro Asp Phe Gln Thr Asp
            180                 185                 190

Phe Ser Asp Asp Tyr Asp Ala Ile Asp Glu Asn Asn Leu Ile Glu Thr
        195                 200                 205

Val Gln Ser Gln Ser Ala Thr Leu Leu Lys Lys Ser Asp Asn Pro Asn
    210                 215                 220

Pro Asp Ile Arg Ile Val Asn Gly Leu Asp Cys Lys Leu Gly Glu Cys
225                 230                 235                 240

Pro Trp Gln Ala Val Leu Ile Asp Glu Lys Gly Thr Ala Phe Gly Gly
                245                 250                 255

Gly Thr Ile Leu Ser Pro Tyr Phe Val Leu Thr Ala Ala His Cys Ile
            260                 265                 270

Asn Lys Thr Lys Ser Ile Ala Val Val Gly Gln Val Asp Ile Ser
        275                 280                 285

Arg Lys Glu Thr Arg Arg Leu Leu Ser Val Asp Lys Val Tyr Thr His
    290                 295                 300

Pro Lys Tyr Val His Val Thr Asn Asp Tyr Asp Ile Ala Ile Ile Gln
```

|        |        |        |        |        |        |        |        |        |        |        |        |
|--------|--------|--------|--------|--------|--------|--------|--------|--------|--------|--------|--------|
| 305    |        |        |        | 310    |        |        |        | 315    |        |        | 320    |
| Leu    | Lys    | Thr    | Pro    | Ile    | Gln    | Phe    | Ser    | Glu    | Asn    | Val    | Val    | Pro    | Ala    | Cys    | Leu    |

Leu Lys Thr Pro Ile Gln Phe Ser Glu Asn Val Val Pro Ala Cys Leu
305             310             315             320

Pro Thr Ala Asp Phe Ala Asn His Val Leu Met Lys Gln Asp Phe Gly
        325             330             335

Ile Val Ser Gly Phe Gly Arg Ile Glu Glu Lys Gly Pro Thr Ser Asn
340             345             350

Ile Leu Lys Val Val Met Val Pro Tyr Val Asp Arg His Thr Cys Ile
355             360             365

Leu Ser Thr Lys Ile Pro Ile Thr Arg Asn Met Phe Cys Ala Gly Tyr
370             375             380

Gly Asn Gln Pro Glu Asp Ala Cys Glu Gly Asp Ser Gly Gly Pro His
385             390             395             400

Ile Thr Ala Tyr Lys Asp Thr His Phe Leu Thr Gly Ile Val Ser Trp
        405             410             415

Gly Glu Gly Cys Gly Arg Asp Gly Lys Tyr Gly Ile Tyr Thr Lys Val
420             425             430

Ser Asn Phe Leu Pro Trp Ile Lys Thr Ile Met Arg Arg Lys Gln Pro
435             440             445

Ser Thr Glu Ser Ser Thr Gly Arg Leu
450             455             460

465             470

<210> SEQ ID NO 45
<211> LENGTH: 1416
<212> TYPE: DNA
<213> ORGANISM: Demansia vestigiata

<400> SEQUENCE: 45

```
atggctcctc aactactcct ctgtctgatc ctcacttttc tgtggagtct cccagaggct    60
gaaagtaatg tattcttaaa aagcaatgtg gcaaatagat ttttgcaaag aacaaaacga   120
gctaattcaa tatttgaaga aattagacct ggaaacattg aaagggaatg cgttgaggaa   180
aaatgttcaa agaagaagc cagggaggta tttcaagata tgagaaaac tgaggccttc    240
tggactgttt atgtagatgg ggatcagtgt ttatcaaacc cctgtcatta tcgtgggaca   300
tgcaaagatg gcattggtag ctatacctgt acctgcttgc ctggctatga agggaaaaac   360
tgtgaacatg tcgtagttaa gtcctgcaga ctgttcaatg gtaactgttg gcacttctgc   420
aaaactgttc aaaacgacac tcagtgttca gtgctgaag gttaccgttt gggagttgat   480
gggttctcct gtattgctga aggtgacttt tcatgtggca gaattataaa atcaaggaac   540
aagagggaag caagtctgcc tgactttcat ttttctgatg actatgatgc gattgatgaa   600
ataaatttgg ttgaaactgt gcagtcccag agtgcaactt tgctgaaaaa atctgataat   660
ccaagccctg atatcagaat tgttagtgga ttggactgca aactgggtga atgtccatgg   720
caggcagttc tgatagatga acatggaaaa gcgtttggtg gaggaacaat tttgagtccc   780
tactttgtgc ttactgcagc ccactgcctt aaccagacca aaagcattgc agttgttgta   840
gggcaagtag acatatcaag aaaagaaacc agacatcttc tccatgtgga taaagcatat   900
atgcattcaa aatatgttcg tgccacctat gaccatgata tagccatcct cagactgagg   960
accccctatc agttctctga aaatgtggtt cctgcctgcc ttcccactgc tgattttgcc  1020
gacgaagtcc tcatgaaaca agattttggc atcgttagtg gatttgggcg tttgcatgaa  1080
agaggatcga cctctgacat acttaaagtc attagggttc cttatgtgga caggtacacc  1140
tgcatgcttt ccagcaacta tcgaattact ccaagtatgt tctgtgctgg ctatggtaat  1200
```

```
cagcctcaag atgcatgcca gggagacagt ggggggcccc acatcactgc atacggagat   1260 acccactta ttactgggat tatcagctgg ggggaaggtt gtggaaggaa aggcaaatat    1320
ggtatttaca caaaagtgtc caatttcatc ccttggataa aaacaataat gcgtcgaaat   1380
caacccagta cagagtcaag cactggtcgg ctctaa                             1416
```

<210> SEQ ID NO 46
<211> LENGTH: 471
<212> TYPE: PRT
<213> ORGANISM: Demansia vestigiata

<400> SEQUENCE: 46

```
Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Asn Val Ala Asn
            20                  25                  30

Arg Phe Leu Gln Arg Thr Lys Arg Ala Asn Ser Ile Phe Glu Glu Ile
        35                  40                  45

Arg Pro Gly Asn Ile Glu Arg Glu Cys Val Glu Glu Lys Cys Ser Lys
    50                  55                  60

Glu Glu Ala Arg Glu Val Phe Gln Asp Asn Glu Lys Thr Glu Ala Phe
65                  70                  75                  80

Trp Thr Val Tyr Val Asp Gly Asp Gln Cys Leu Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Gly Tyr Glu Gly Lys Asn Cys Glu His Val Val Lys Ser
        115                 120                 125

Cys Arg Leu Phe Asn Gly Asn Cys Trp His Phe Cys Lys Thr Val Gln
    130                 135                 140

Asn Asp Thr Gln Cys Ser Cys Ala Glu Gly Tyr Arg Leu Gly Val Asp
145                 150                 155                 160

Gly Phe Ser Cys Ile Ala Glu Gly Asp Phe Ser Cys Gly Arg Ile Ile
                165                 170                 175

Lys Ser Arg Asn Lys Arg Glu Ala Ser Leu Pro Asp Phe His Phe Ser
            180                 185                 190

Asp Asp Tyr Asp Ala Ile Asp Glu Asn Asn Leu Val Glu Thr Val Gln
        195                 200                 205

Ser Gln Ser Ala Thr Leu Leu Lys Lys Ser Asp Asn Pro Ser Pro Asp
    210                 215                 220

Ile Arg Ile Val Ser Gly Leu Asp Cys Lys Leu Gly Glu Cys Pro Trp
225                 230                 235                 240

Gln Ala Val Leu Ile Asp Glu His Gly Lys Ala Phe Gly Gly Gly Thr
                245                 250                 255

Ile Leu Ser Pro Tyr Phe Val Leu Thr Ala Ala His Cys Leu Asn Gln
            260                 265                 270

Thr Lys Ser Ile Ala Val Val Gly Gln Val Asp Ile Ser Arg Lys
        275                 280                 285

Glu Thr Arg His Leu Leu His Val Asp Lys Ala Tyr Met His Ser Lys
    290                 295                 300

Tyr Val Arg Ala Thr Tyr Asp His Asp Ile Ala Ile Leu Arg Leu Arg
305                 310                 315                 320

Thr Pro Ile Gln Phe Ser Glu Asn Val Val Pro Ala Cys Leu Pro Thr
                325                 330                 335
```

```
Ala Asp Phe Ala Asp Glu Val Leu Met Lys Gln Asp Phe Gly Ile Val
            340                 345                 350
Ser Gly Phe Gly Arg Leu His Glu Arg Gly Ser Thr Ser Asp Ile Leu
        355                 360                 365
Lys Val Ile Arg Val Pro Tyr Val Asp Arg Tyr Thr Cys Met Leu Ser
    370                 375                 380
Ser Asn Tyr Arg Ile Thr Pro Ser Met Phe Cys Ala Gly Tyr Gly Asn
385                 390                 395                 400
Gln Pro Gln Asp Ala Cys Gln Gly Asp Ser Gly Pro His Ile Thr
                405                 410                 415
Ala Tyr Gly Asp Thr His Phe Ile Thr Gly Ile Ile Ser Trp Gly Glu
            420                 425                 430
Gly Cys Gly Arg Lys Gly Lys Tyr Gly Ile Tyr Thr Lys Val Ser Asn
        435                 440                 445
Phe Ile Pro Trp Ile Lys Thr Ile Met Arg Arg Asn Gln Pro Ser Thr
    450                 455                 460
Glu Ser Ser Thr Gly Arg Leu
465                 470
```

<210> SEQ ID NO 47
<211> LENGTH: 33731
<212> TYPE: DNA
<213> ORGANISM: Homo sapiens

<400> SEQUENCE: 47

| | | | | | |
|---|---|---|---|---|---|
| ctgtctgacc | gcagctctca | agtgtctcag | gggctgtggc | tctgggcttc | gtgctgtcac | 60 |
| ttccacagac | agacagacat | ccccaaaagg | ggagcaacca | tgctgggcac | gactgctgtg | 120 |
| gccaccgtgc | tctcagccac | tttcccatgc | caaataaaa | cgataaaaga | ctggggggctt | 180 |
| ctgcccatcc | tgcctcactt | gaccaagagc | ccagaagagg | atgcgacacc | cagggcctca | 240 |
| tgggaccacc | ggctggcagg | ggttctgctc | actgggttta | tgggtgagac | gagcactccc | 300 |
| aggagggcca | ctgggccggg | aagaactgtg | agaatcggg | gcacgccctg | tcctcccagc | 360 |
| tgccagggca | cagcatccct | tccccacctc | aacacccaga | ccccagattc | acccagttc | 420 |
| acttgtcccc | acacgagcca | caggctgcca | cctggggcag | gctggcccca | ccttggggtt | 480 |
| agatgcaggt | ccccttgccc | cagaaggaga | ctgcagcccc | tgcagaccta | gaaatggcca | 540 |
| cagcccatcc | ccatgcacca | gggggtgagg | tggcaggtgg | tggaaagggc | ctgagggggg | 600 |
| cttcttcctt | ccaggcgagc | acgacctcag | cgagcacgac | ggggatgagc | agagccggcg | 660 |
| ggtggcgcag | gtcatcatcc | ccagcacgta | cgtcccgggc | accaccaacc | acgacatcgc | 720 |
| gctgctccgc | ctgcaccagc | ccgtggtcct | cactgaccat | gtggtgcccc | tctgcctgcc | 780 |
| cgaacggacg | ttctctgaga | ggacgctggc | cttcgtgcgc | ttctcattgg | tcagcggctg | 840 |
| gggccagctg | ctggaccgtg | gcgccacggc | cctggagctc | atggtcctca | acgtgccccg | 900 |
| gctgatgacc | caggactgcc | tgcagcagtc | acggaaggtg | ggagactccc | caaatatcac | 960 |
| ggagtacatg | ttctgtgccg | gctactcgga | tggcagcaag | gactcctgca | aggggacag | 1020 |
| tggaggccca | catgccaccc | actaccgggg | cacgtggtac | ctgacgggca | tcgtcagctg | 1080 |
| gggccagggc | tgcgcaaccg | tgggccactt | tggggtgtac | accagggtct | cccagtacat | 1140 |
| cgagtggctg | caaaagctca | tgcgctcaga | gccacgccca | ggagtcctcc | tgcgagcccc | 1200 |
| atttccctag | cccagcagcc | ctggcctgtg | gagagaaagc | caaggctgcg | tcgaactgtc | 1260 |
| ctggcaccaa | atcccatata | ttcttctgca | gttaatgggg | tagaggaggg | catgggaggg | 1320 |

```
agggagaggt ggggagggag acagagacag aaacagagag agacagagac agagagagac   1380
tgagggagag actctgagga catggagaga gactcaaaga gactccaaga ttcaaagaga   1440
ctaatagaga cacagagatg gaatagaaaa gatgagaggc agaggcagac aggcgctgga   1500
cagaggggca ggggagtgcc aaggttgtcc tggaggcaga cagcccagct gagcctcctt   1560
acctcccttc agccaagccc acctgcacgt gatctgctgg cctcaggctg ctgctctgcc   1620
ttcattgctg gagacagtag aggcatgaac acacatggat gcacacacac acacgccaat   1680
gcacacacac agagatatgc acacacacgg atgcacacac agatggtcac acagagatac   1740
gcaaacacac cgatgcacac gcacatagag atatgcacac acagatgcac acacagatat   1800
acacatggat gcacgcacat gccaatgcac gcacacatca gtgcacacgg atgcacagag   1860
atatgcacac accgatgtgc gcacacacag atatgcacac acatggatga gcacacacac   1920
accaatgcgc acacacaccg atgtacacac acagatgcac acacagatgc acacacaccg   1980
atgctgactc catgtgtgct gtcctctgaa ggcggttgtt tagctctcac ttttctggtt   2040
cttatccatt atcatcttca cttcagacaa ttcagaagca tcaccatgca tggtggcgaa   2100
tgccccaaaa ctctccccca aatgtatttc tcccttcgct gggtgccggg ctgcacagac   2160
tattccccac ctgcttccca gcttcacaat aaacggctgc gtctcctccg cacacctgtg   2220
gtgcctgcca cccactgggt tgcccatgat tcattttttgg agcccccggt gctcatcctc   2280
tgagatgctc ttttctttca caattttcaa catcactgaa atgaaccctc acatggaagc   2340
tattttttaa aaacaaaagc tgtttgatag atgtttgagg ctgtagctcc caggatcctg   2400
tggaattgga tgttctctcc ctgccacagc ccttgtcaat gatatttcac agagaccctg   2460
ggagcacctg ctcaagagtc agggacacac gcatcactaa atgcaagttc ccaggccctg   2520
gctgcagtgg gaggacctgg caagctgcac tcttgctgag tccccagggt ggtggaagaa   2580
gaatgagaaa cacatgaaca gagaaatggg gaggtgacaa acagtgcccc cactcagact   2640
ccggcaagca cggctcagag agtggactcg atgccatccc tgcagggccg tcctgggcac   2700
cactggcact cacagcagca aggtgggcac cattggcact cacagcagca aggcaggcac   2760
cagcaaccca cctcggggcc actcaggcat catctacttc agagcagaca gggtctatga   2820
actacagccg tgggctgctt ccaaggcacc ctgctcttgt aaataaagtt ttatgggaac   2880
acacccatat tagtgtccat ggagtggccg tggcagagac gtccagccgg acagaccagc   2940
tgacccgcca agcccagcat ggttagtgtc aggacctctg ctgaagatgc ttgctgaccc   3000
tggccagacc ccgttcctta atgccccctta acgggacgg gagccagtgg cgggccctga   3060
tccaggtcag agctggctct gctttctctt ttgtccgagt gaccatgcct cagtttcctc   3120
atgtgtaaaa caggagccca ccgtgatgct tatggtggga tgagatcagc atggatggaa   3180
caaggccctg gaagggccca tgccatggtc atcgacagca aagccactct gcagacagat   3240
gcttcagtga attggtagaa aattctgcaa ccagaatgcc cggggctcct gagggcctaa   3300
gcccagccca gggttctgga agccactctg acttcttggg agtggaagtt ggcaggactc   3360
ttcctgggaa gaagcggagg gtggggatga gaggacagtt caggagccca cccagaccca   3420
caggaggaaa ctagggagt catgcggggt cctggtggag cgccagcctc ccttcctgcc   3480
aatgggaaat gcaggcgccc acctcatggt gctgccggag gagggggccc gggactcccc   3540
agaggcttcg ctgaagggcc tgggcgcccc caaaggctac atgtttcata tgggacgtgc   3600
cacctgccac ggctcagctc cagctttctg tgagtggcga gatagaatac ggggaggcca   3660
```

```
ctggccatgg gcctgggaca gggtgggatg aggcggcagg cttgggccac caaagccagc    3720
atcgccaccc agcattgatg acaaagactg cgtgtctgcc atgagcatcc tgctgttggt    3780
gcacacaccg cattggtctc tccatacaaa catgcctaga ggcgatgtca gagggtggag    3840
accaggagag gcaggagtca gacatctggt gccaccagga aggcccttct cagaggacca    3900
ggctgtgcgt ggtgcccgcc gtgggaggcc agcctggcgt tggcatccag catcatcagt    3960
ttgtgcagtc gggtggggct cagtgagtgc ctcctgtgtg ccaggcacaa tgacgcacaa    4020
tgtgtgcaca ccaggctcat gtgcaggtgg ctgcgagaca gggcgaccca tcaaggcaga    4080
tgcaccatga ggcagtggcc agtgctgtgg gtgttagggg cattgctccc cggccactac    4140
ggcatagcag gcagtgatcg ccacactggc caagctttag accatttatt ccagagaccc    4200
cagaggcaaa aagcccggct gcacctccca gtgactccca cagccattga gcagagacac    4260
tcaggacctt gtgatgggag gtttctgcac tggagaacga gcccagaagc cctctcagcc    4320
tcggaacagt gtggccagtg gtgggcaggt caggaggggc ttcagacaca gcctgtccct    4380
ccagatggtc acgggaaggt cactccccac agaagtacgt tttggggcca tgcgggcaca    4440
gaaggtttgg gggtgggtgg ggcaggtgcc agcctggcct gtgggaggcc atggtgcaga    4500
tgccaagccc cccccgtgac atgagaccac ctgataccac ccagagagtg gctgtgagcg    4560
gaagggcccg cccagaaaca gcagggccct tggggcagaa gtcctgggct cagatcccac    4620
gctcactgcc agcggcctcg gctcaggctt ctgcgctctc taaacttagt tttctcttct    4680
ggaaaaatga tgggaaaat gatatttgta tgtgaggact gagagttaaa tgtaaacatc    4740
tggaaactac aaaatgagca cgaaatgatg tttttattct tagaacagaa agtccccaca    4800
cccgcggccc tggtgactga tgaggatgag gttctgcggg gcctctctgg ccgcccagct    4860
ctgcctgggg aaggtggggc cagagtggat gtgttcccag cgtggtcact cccctgcctc    4920
gccagcaggt ctcggctcca atcaggaggc ctaagccaag tgataagcag ccagacaaca    4980
gccatcccag ctggggcgtg gactttgctc cagcagcctg tcccagtgag gacagggaca    5040
cagtactcgg ccacaccatg gggcgcccac tgcacctcgt cctgctcagt gcctccctgg    5100
ctggcctcct gctgctcggg gaaagtcgta agtgcccctc gccttcaga cccaaaagca    5160
gcgccaggga gcagggaggg gcggcagttg gggaaaccct ctcatctctg cagcctggac    5220
ggtgggtgcc ttgagtgctg ccagaggctg ggctcggatg gctgggcttg gccttttccag   5280
ccaacggcat cctcaaggcc agctgtggct ccctgggggct gagagtcaga cgggcggatc    5340
agaggtcaca gagacaaaaa cacaaggaca gagtcagaga gagaaaggga gagggaagga    5400
gaaacggaga cacagtgaga tgggaggcca agaggcagag acagaggtag aaagacggag    5460
acagagagag agggaggggt tggggcaggc agagacagga cagttagcca tctgccacca    5520
cagggaggca caggacgagg ggcacagcag aggagctccc agggaggagg aggctgagcc    5580
gagccagtgc caccactctc ggactggctc cgtcggggaa ggagctgcct aatgcacagc    5640
tggacaggtg ggggcagcag ggctgtccag gacccccggg tctgtccaaa agcagaggcc    5700
cagacaggac agaagccagg caagcctggg gacagcggag gaagaggagg cccctctggt    5760
ggggacacga gagacaggga ccctagactt gtttgcatcc tggacaaagt ggacaggcag    5820
gggcaccaag gggacccagg cctgggaagg gaatgtgtga gggagagacg gagcagggg    5880
agaccctcgt ggggtggaaa ggggagaccc ctgggaaggc tgagtggatc ctcagtgcat    5940
cactgaccta aacggcccct ccgcctggtg acttggagct ccagtcacat cacacgggg    6000
tcttctccat cccacccctca accccctgcc ctccccagcc tctgtcccct gagccacatc    6060
```

-continued

```
ttcctgtctc ccacgcggaa cgggactccc gtcttcatgg ggtactgtgt ggctccaact    6120
cgcccagcct tcttcctccc cctcaggcca cactgccccc tgcaggagcc cactgtgatg    6180
cttgtggtgg gatgagatca gcgtgggtgg aacaaggccc tggaaggacc catgccatca    6240
tcatcgacag caaagctact ctgcaaacag acagatgctt ccgcgaattg gtagaaaatt    6300
ctgcagccgg aatgctctag gatcctgagg ccctaagccc ggcccggggc tcccgaggcc    6360
ctaagcccgg cccgggactc tggaagctgc tctggcttat tgggaatgga agttggcagg    6420
actcctcttc ctgggaagaa gcagagggtg gggatgagaa gacaggccag gagcccaccc    6480
agacccacag gaggaaacta ggggagttat gcagagtcct ggtggagcgc cagcttccct    6540
tcctgccaat gggaaatgca ggcgcccacc tcgcggacct ctgggtccac agggtattgg    6600
cacccttagc tgtgtgatgc gggcctggct cataaccatg gcctgtggtg tccccggggg    6660
ccggcctgga ccctgggtgg acatggccag ccccggagag ccagggccag gccatctctc    6720
tcccctactc tgcctcagag gcctcggcag ctgcactgtg gggtgggtgg ggctgaacac    6780
aggtcccaga aggtcccact caggaccctg ctgtgcacac ttttgatttt aataaaatca    6840
gaatgcgcac agcatctgca gtctagcctt taaacgagca cagctgtcct ggcagtcacg    6900
gaagttcttc tggggcggtg ggacctcagc attcctttgc tggtactgct acaagaaagg    6960
acaatggacc aagtagctta aagcaacaga aacatttctc ccacagctct ggaggctgga    7020
agttcaaaat caaggcgtca gcggggctgg ttcctccaga ggctgggaga gagtctgctc    7080
taggcctgtt tcctgcctc ggggtgccag cggcctcaca gcccatggct tgtgggagca    7140
ttgctcccat cgctgcctcc atcatcgcat ggggttctca ccatggctgt ttttctgtct    7200
tcttttctct cagaaggaca ccagtcattg gatttagggc tcactctact cccataaaat    7260
gtcttcctaa ctaaatacat cacaaaagtt ctatttccaa ttaaggtcag gttctgaggt    7320
tctgggaaag acatgaattt ggagggacat tattcagccc tgtcctgcca cctgtgagtg    7380
ttttctgcaa tccaactttt tattttaata aaatcagaat acgcagagca cctgcagtgc    7440
cagcctttaa actactgctg ttgtactggc aatcattaaa gctacgtggc ttcagtttca    7500
atctttacat tcaacaagtt taaacccatt cttcatgagt ttggacctta ctgactgaaa    7560
attttgcttg ctggtaaaac ttgctcaaat gcagttgctg actgtggaat tcactgatgt    7620
tgccaaaaca acaaacacaa ctgtgtgctc gaggattgca atgctcccaa cagcttctga    7680
agaaacaaac cacacgacaa atgtctacca atctggatgc tccatatcag agttctagag    7740
tgttccatta atttcttgag acaagtgcct aaaaaccttg ttttaatttc gttttgccaa    7800
aatcccattt tactcacatc agaaagtgtg gccacgtggc ccagacccgg cctgctcagt    7860
ctgactgaag cgttgatgcg actcagccat aacagatagc agaagcgccc agattcagtc    7920
cagagggctg agccaggcac gccatctttc cttcattccc tcaacacata ttggttaagt    7980
tccggccgtg ctaggcacgg gcatacagct gtgaccaaac acgtcaagtc tttttccagc    8040
ggagggaagg ataagcctgt cagcatgtaa tgtcagagag gggttgggtg ctagaagaca    8100
aatagcacag tgtaagggga tgaaagagac acgagtgggg gcaacgtcag agggcgtggt    8160
cagggagggt gtctcggagg gcgctgggcc tgagccactt gggtatctgt ggaaagaatg    8220
ttccagacag ggaggtgact ggtgcaaaag tcctggggtg tgagtgttgg gctcagccag    8280
ggtcagcgca gagcccagtg tggcagagag aggtgaatga gggcagagtt gaaggtggtg    8340
aggcctggga ggcctggcca tgggaagacc ctgggctctg ttctaagacc actagaggca    8400
```

```
gattctgggt agtccttgac ttccttgcat caccctttcc accccgtgcc tgccacctgt    8460
accctcttcc tcacacagtc cagctcaacc ttataggccg tgtcctaccc ccatgagctg    8520
gggagagctg agcaggcttc agggagatgg gaaaaggcgg gaactggaca ggggctgcaa    8580
aggaaaggtg acttcttact ggtcaatcag cctggggatg ctcggggtg gatgccaagg     8640 ggaacagagc tgtggccgct atcacagaac agcgagttcc tctaagaggt cagaggaggc    8700
gcaagggatc gaccagagac agtgagggcg tcaggctcca gttgagtggg gaccaatcct    8760
tgtggcaagt ctgtgaacca tcactgtggc tctagggtag cagagaaaaa agcaggcata    8820
tgtccatctg gccacaagga aggagaccaa ggggaagaga gaaggtacca agagaggtgt    8880
tcacatggag gtgcgtcaga acaccgaggg caaggcagaa cgcggtcttc agaccccaac    8940
tggagcccag gaggcccgcg agtcccagtt tgggaaacac taagccaggc ttggataact    9000
tgtctgaggc tgtggtcatc ccaacatgag agccagaggc cccaagggag atgggcattc    9060
cccacccctc agcttcctca gtgccttttg tggagtggag gtgacatgag gctgcaggtt    9120
gcagggagcc acgtgtgggc tgcatttcag agcaagtgtg tgggagtgga gcagacacgc    9180
agagtaatgg ggcagggtca agaaataata aatctaagtc tagcgttggt gggataatgt    9240
cggtgtcact aaaagaaatg gggaatttgg aaggtaaagt aactggaggt aggaatgaac    9300
ccaagattta ctaagcacct tctgtatacc aaactcaaca ctaggagttt atacaatctt    9360
taaaacagct ctaagagtag atattataat tcccttctgc caataataaa taataagtga    9420
ctaaggtgtt tttgaagctc aagattgctt gattctgcag tcttgttta aattttggac     9480 atggagagtt tggagttctg agatgaggga aggcatctgt catagtgaga gagctgaaaa    9540
catggagctc aggacaaaag tcagtgctag agagatcagt tggaagagtt atctttattg    9600
tagtgagaca ttgaattttt cagtggaaaa aaagcacaga aaaagactac agagggccaa    9660
gaaaagaaac tgaggctgtc aaaatgaaaa gaggaggagg agtgggtgag agacaaagga    9720
gacacaggca gagagatgtg gacagcacag cccacagaca cacactctac aagggacaca    9780
gactctcgga tccagggcat tttaaccagc agatcaagac tcatttgcca gtcatgaaat    9840
caactcagta ttttttttta aaagagtaga atcaaataga aaactttgta ctaagtactg    9900
tattttagga aatactaata aatactattt cttgaaagtt ggcatgtatg tgtgtcctgg    9960
cacttcataa attgtactat tatagtttgt aattgaaaca gcatcaccaa tccccacata    10020
acaaagagca gagaccttaa agacgagtgg ggccaggctg aaggggcaca gcttgagcca    10080
aagcacagaa cagtgggctg aaagcaccct agggagggag aattcaagga aggggcttg     10140 ggtggccagg ctgagccagc gtgagcatgt gaggaggctg gtgagctgat tgggtgggat    10200
gtgtctactt ctccagagaa gggtgcatgg gtctagagca ggtgcctcat gctgtacctc    10260
atagagaact gggggagg gggaaatggg catttccctc cacagccccc aaagtgcctg       10320
aggaaagtgt tgataaagaa gccaaactct gtaaaatatt tgaagagatt tattctgagc    10380
caaatgtgag gaccacgacc catgacacag ccttggaagg tcctgagaac atgtgtccaa    10440
ggtagttggg tcacagcttg attttatgta tttttagggg acagaagtta catacagaca    10500
ccaatcaata agcataagtt gtacactggt tcgttccaga aaaggggaag gtgggggctt    10560
ccaggtcata ggtggcttca agatattct gattggcaat cagttgaaag agttattatc      10620
taaagacctg gaataaatgg aaaggagtat ctgggttaag ataagaggtt gtggagacca    10680
aggttcttgt tatgtagatg aagactcata ggtggccacc cttagaggga atagatgca     10740 actgtttcct cttcagacct ttaaaaggtg ctacacacat ggccaggcgc cttggctcat    10800
```

```
cctgtaatcc cagcactttg ggaggctgag gcaggtggat cacttaaggt caggagttca    10860
agaccagcct ggccaacatg gtgaaactcc atctctacta aaatacaaa aattagccgg     10920 gtgtggtggt gcttgcctgt agtttcagct actcgggagg ctgagacagt agaatctcct   10980
cctgaggcag gacaatggct tgaacctggg aggcagatgt tgcagtgagc tgagattgtg   11040
ccattgcact ccagcctgga tgacagagca aaacaccatc ttaaagagaa aaaaaaaaa    11100 aaaaaaaaa aaaggtgcta gactctcagc tcagaaaaag acctggaatg gtaaggggt    11160 tctctacaga atgtggattt ccctgagata gctttgcagg gccatttcaa aatatgtcaa   11220
acaaatacaa tttggagtaa aatcatttat tttagggcct gctatatgtc atgtgatcct   11280
atactagaga agtcaggttg gaaactggta tcttattgct acaaagactc tgtttggtca   11340
gcctcaaggt ctcttaacgt gaatgctggt cagctgtgcc cgaattccaa aggaagaaat   11400
aatgaggcgt gtgggacctg cttcccctca tggcctcaac tagtctttca ggttcctatg   11460
gaattccctt ggcagagagg acgggtccac tcagtgagtt gggggcttag aatttatt    11520 ttggtttaca agagagtgat ccgccttttg tgatctggat atggcaaggg acatggcagt   11580
cagggagcat aggtgagggg gagcctgggt gagggtgacc agagctttta accctgtcct   11640
ccctgccttc cagtgttcat ccgcagggag caggccaaca acatcctggc gagggtcacg   11700
agggccaatt cctttcttga agagatgaag aaaggacacc tcgaaagaga gtgcatggaa   11760
gagacctgct catacgaaga ggcccgcgag gtctttgagg acagcgacaa gacggtaagg   11820
gctggggata gcctggctgt tggtaaggag ctcaggccac agcgccctcg ctggccccgc   11880
tgctccgtcc atccaggggg gcggcctgga ggaagggca gcgtgcgcga aggctttcag   11940
gggcggggcc cagcaaatcg aggcctcggc ggagtcctgc ccacagggac atcagtgccg   12000 ccccgcgct gactccttcc cggcgaggac tcagcgggga gggatgcgcc caagtccctt   12060
gagggtcaca gggcttctgc cagagttaag ttctatttaa aaataaaatg ttaacctaaa   12120
aaccaatagt catggtctcg ccagcgcct cgccgagttg cagtgagctg agatcgtgcc    12180
ctcccacgcc cgcagcccgc gtcctgcctt ggcctccgta gtcgctgaga gccacagcct   12240
agagcgccag cgcgcaggcg cacaactgac gccaggccac gaacccagta ctgctcctgc   12300
acagcagaag cactagcact gaggccgggc ggcgaacccg gcactgcgcc tgcgcagcaa   12360
aaggacacgc actgaggcca ggccgcgaac ccagcacggt gcctgcgcag caggaagacc   12420
ggcatccaca ccggacgacg aacccagcat cgcgcctgcg cagtaggagg agagcaatgc   12480
caccaggccg cgattgcgca gccgcagcag ccccgcgcgg aagacgctac cctcctctcc   12540
cccgaagagg cggggcttcg aacgaacctg gaaatggccg aggggtctcg acttcctcac   12600
cccaggcatc aggaaaggtg cctgcaggac agggctctga agtggaagtg ggcggtggtg   12660
atgccgaact gacaagaatg agctgaagag aagaaagtag ccgagaaggg ggccaagccg   12720
gagctcagtg agcaacagct aggccagccg cggctggtgc catcagccac accactaact   12780
gtggacccaa atggaaactt tgaggcccct tacaggtccc ccagcgcagg ccaccgccga   12840
aggttactgg ggaagacccc tgcagcttcc atgtggacat tactcgcttg cttcatcccg   12900
gagtgcagtc acctgcagcc tgggaccacc tgactgatgt caccctggag atccatgcca   12960
aaagagctgg ggaaagttca ccttctaatg accccctgcgg accagggtga agttacaagt   13020
tatggccagg tcaaggaatt ataagtcaat aaataaactg cctcagggag acgtactcag   13080
agtccaggaa aatctaggaa acaccaagaa gggcgagcgc agcatcagcc cctgcaaaat   13140
```

-continued

```
tgcactgctg cctcctggct cacatgttgc cccatcctta ctttagcctc aaaggcaagg   13200
agacccaata ttatttgagt acttggattt gatcctgagt gactttctga gaaagcagtg   13260
tatcatctgc cctaagatca ccacatatat gacaaggttt ttggatgagt tgagatttct   13320
agacattgaa accctcatga tgaacgtcat cccgggtagc aggggctaag cctttcatca   13380
cctgctacaa caagctggac attaacttgt atttgagaat tgctccagga ctctaccttc   13440
agatgctggt tagtagcatt gactggattt atgaaattgg atgccagtta aggaataaga   13500
gaatgtattt gatttgccac cctatatggt ctgtgcagac tgtcatgatc tcattgaaat   13560
ccaagaaaag attatgtcag ggatgaagca catcacaggt ggttacaagg tcacccacca   13620
tccagatggc tcagaaagcc aaacctatgg gttgacttct cctcacccgt ctggagaatc   13680
agtgtggtag aagagcttga aaagtgctgg ggtgtgacgc tgccagaaac taacctcttt   13740
ggaactgaag aaactcaaaa aattattggt gatatctatg taacaaaagc ttttgaaagt   13800
cttctacctc agaacatatt caggcgcctt gataaacttg tcaaggagtt cctgaaagtg   13860
acttacatca gtcccacatt tatctgttat cacctgcaga taatgagctc tttgaccaaa   13920
tgatctctct aagagggtct cactgagcac tttgagctat ttgtcatgaa gatagctgaa   13980
tgtttccatg cagcaacagc agcagctgtt gacaaacaag acaaggccag caaagatgat   14040
gaggccacat tcatagatga aagcttccat gcaaccctgg aatatgggct tccgcccaca   14100
gctggttgga gcgtgacaat caaatgtgtt accatgtttc tcacagactc ccacaacatc   14160
aaggaaatat ttctgactcc tggcatgaaa cttgaagaaa gagaatgtag cagccactaa   14220
tacaatggaa agcgcaacat tgacacgtct atctagaaaa ttttaattgt ctaagttgtg   14280
tgactcagat atctttgcat ttctgcaaaa gatcaaggtc tactctaatt cttaattaaa   14340
ttaagaattc ctttttatta cttgttagca aataaatggc ttgtctctaa cagaaaaaat   14400
ttagaatttt cggaaatatt ttcaaatact tcttatatat acatatattt ttttccactg   14460
gtagaatttt tctttagtaa aagtaaataa tgctgatcca agtttatgtt tcactcagca   14520
tcgtttctca aacactcttc tttacttata tatagctacc ctatagctaa gctatatttt   14580
attgtatgat gcatttactc ttttcagagt ttggccatat aagttatttc taaatattgc   14640
tattaggaaa acacatatgc atgcatttct tctagattat catctaagag tggcttctcc   14700
agagagagac gactgaatta aaggttatca acaagttcca attccagata agatgaagaa   14760
atcacattcc acactgcctc tcccactgag tgtagctcca aaacatggat agaatgcatg   14820
tagcagctat ttgacgaccc taaaaagtaa atcgcagtgt attgcagaat aagactacaa   14880
ttagatgtat gatatgatac aactggctgt gagtttatca ttttttcctc cagtcttcca   14940
gacatcactt gacctgaatc taatggacat ttataggatt ctcaacaata gcaaagtaca   15000
ctttccttcc acatatggaa aattcctcaa ggtagactat atcctgtgtc ttaaagcata   15060
cctcaataaa aagattgaac tcacataaag tatgttttct gaccataatg gaattaaagt   15120
aaaaattact aacagaaaaa taactggaaa cttccctaag tactcggaaa ttaagtcaca   15180
catgtataaa taatctgtga gtcaaagaga aaattttaag gggagtaaga aagtattttg   15240
agctgaacaa aaatgaatat gtaacataaa atctgtggga tgcagctaaa aaagcagtgt   15300
ttcaagggaa atttatagca ttaaatgctc acatgggaaa agaaagacgg tctcaaattg   15360
tttatgtaag cttccacttt aataaactag aaaaaagaa aaaataaac caaaggaaa    15420 ttgaaaaagc agaaatcaaa gaatttaaa acaaaaata tagacaaaat taataagctg    15480
atgaaactca acaagactg acaggaataa aaacaaacaa acaaaaacaa gaaaaaggac   15540
```

```
ctatgttgga aatggaagag aggggacatc actacagaaa ctgtagatgt taaatgtata   15600
ataagaaaat actttgaaca actctgcata tataaatttg catgagattt gaacttggat   15660
gaaatgagcc tattcttcaa taccacaagc caccaaaaca tacacaaggt gaaagagata   15720
cctgccaatt caattcttaa tttaaaacct tctgaaaaag taatgttcag gtacagatgg   15780
tttcactggt agaattttac caaacatttc aaaagaaca ccaattctat acaactcttc    15840
cagaacatag aagagggaac acttcttagt ttgtcttagg ccagcattac cctgatgtca   15900
aaaccagaca aatactgaaa acaaaaacca ccctacgtaa caatatctct catgaatcta   15960
gacataaaaa tcctcaacaa aatattagca aacggtgcag caatatattt ttaaaagagt   16020
aataatacac catgaccaag tgagttttc tggggcacac atgactggct caatatttaa    16080
aaataattat gtaatccacc atataaacaa aagagaacat ccacataatc atgtcaattg   16140
atgcaacaaa caaatctggc aaaatttaac atccatttat gattttataa aaacctatc    16200
agcagaatat gaataggagg gaattttatg aacataataa agttcatcta caaagagtct   16260
acagttgata ttatacttaa aggtgaaaac tgaaggtttt ctccctgaga ctggaacaac   16320
acaagaatgt ccattcccaa cactcctaat tcaacattat actggaagtc ctagctctaa   16380
ggaaggcctt cagtaagtca agaaaaagaa ataaagttat cactatttga agatgacatg   16440
atcatgcata tagaaaatcc taagaatgt gaaggggaaa aaagcttgtt ttagtccctt     16500
ctcacgctgc tgtgaagaac tacccgagac tgggtaattt ataaaggaaa aaggtttaa    16560
ttgactcagt tctacatgtc taaggagacc tcagtaaact acaatcatg gcagaaaagg    16620
aagcaaacgt gctcttcttc acatggctgt aggagggaga agaatgagag ccgagcaaaa   16680
ggggaatcct cttaaaaaaa atcagatctc atgagaacat actcccacga gaacagcatg   16740
gaggaaccac cctcacgatt cagttacctc ccacttggtc cctctcacta cacatgggga   16800
ttatgggaac tacaattcaa gatgagattt gggtggggac agagccaaac catatcaatg   16860
ctcctaaaat ttgcaaatga gtgtaacaag gtcacagaat acaaggtcag cacatgtgtt   16920
aatcacattt ttatgtaata gcaatgcaca gttatttgta agccaaaaat ttttaaatgc   16980
catttacaat tgcttcaaag aaaattatat acttatatgt aaagctaata aaacatatac   17040
aggatcttta tcccaaaatc tacaaaattc caatgaaagt atttaaacag acctaaataa   17100
atagagacac atacagtgtt catggattga aagactcaac atattaagat atcaattttc   17160
ggccgggcgc ggtggctcat gcctgtaatc ccagcacttt gggagaccga ggtgggtgga   17220
tcacctaagg tcgggagttc gagaccagcc tggccaacat ggtgaaaccc cgtctctact   17280
aaaaaatac aaaaattagc tgggcgtggt ggtgtgcgcc tgtaatccca gctactcggg    17340
aggctgaggc aggagaatca cttgaacctg ggaggtgaag gttgcagtga gccaagatca   17400
agccattgca ctccagcctg ggcaacaaga gcgaaactct gtctccaaaa aaaaaaaac    17460
aaaagaaaag aaagaattgt ctttttcaac aaattatatt agtctcagtc tgtttgtgct   17520
tctataacaa aatagatcag actgggtaaa ttataaacag aataaggtta ttgctcacag   17580
ttatggaggc tgggaagtcc tccaagatca agaaaccagc agatatgggg cctgatgagg   17640
gcctggtctc tgcttccaag acggtgcctc atggctgtat cctcacctga cagaaggcag   17700
aagcacagaa gggacaaaca ctgtgtgaag cctctttat aaggacatta atcctattca    17760
caagggcaga gccttcatgg cctaatcacc tcctaaagat ctcacccta atactattac    17820
attgtcgatt aaatttttaac atatgtatgg ggggcatgtt gagaccatag cagtgttgga   17880
```

-continued

```
acaattatat atttatatgc aaaaaaatga acctgaccta aacttcacaa ttatacaaaa    17940
attaacacaa tatagataat agatccaaac ataaaataca aaactataaa acttttagga    18000
gaaaatacaa caaaatttat gacatggagc taggcaaaaa ttcttagaca ttgacaccaa    18060
aagaatgatt aataaaagaa aaaagtcata aattggactt tatcaaaatt aaaacctttt    18120
gcacttcaga aataaacact gttaagagga tgaaaataca agctacaaac taagagaaaa    18180
tatttgcaaa tcacatatcc aacaaaggaa tcatattcgg aatatataaa gaaatcttaa    18240
cagatcagaa gaagaaaata aacactcagt taaacaaaag accttaacag ccaactcgcc    18300
aaagaggata tatggataga aaataaacat gtgagaagat actcaacatt attagctctt    18360
acagaaatgc agataaaaac cacaataaga acgactatat actcatagag taaaaaacac    18420
tgacacagaa cagcgctggt taagacacgg agaaagcaga actttgatac actgctcgtg    18480
ggaatgcaaa atggcacggc cactttgaaa aggaatttga cagtttctta taaagttata    18540
taaggttacc acaggactcg gcaatcccat ttctgggcat ttaccctaga gaatgaaaa     18600 cttatttcca cataaaatcc tgtacataaa tgtctatagc aactctagtc ttttttttt     18660 tttttaattt ttattttttg agacagagtc ttcccgttgc ccaggctggg gtgcaatggc    18720
acaatctcgg ctcactacaa cctcctcctc tcaggttcaa gtgattctcc tgcctcagcc    18780
tcccaagtag ctgggattac aggtgtgtgc caccatggca ggctaattct tgtactttt     18840 tttttttttt tttttttttt tttttttttt gagacggagt ctcgctctgt cgcccaggct    18900
ggagtgcagt ggcgggatct cggctcactg caagctccgc ctcccgggtt cacgccattc    18960
tcctgcctca gcctcccaag tagctgggac tacaggcgcc cgccactacg cccggctaat    19020 ttttgtatt tttagtagag acggggtttc accgttttag ctgggatggt ctcgatctcc     19080
tgacctcgtg atccgcccgc ctcggcctcc caaagtgctg ggattacagg cgtgagccac    19140
cgcgcccggc caattcttgt acttttagta gagatggggt ttcaccatgt tggccaggct    19200
ggtctcgaac tcctgacctc aagtgatcca cccgcctcag cctcccaaag tgctgggatt    19260
ataggcgtga ggcaccacgc ctggccagca actctattct taattgccaa agctggaag    19320 taagataaat gtcttttgct gggtgtaccc atacaatata acagttgtca gcaacaacaa    19380
gtaagaaagt attgatacaa cttgcatgaa tttcaaaggc tttgtattga atgaaaagct    19440
agtttcacaa ggtcctataa taaacacttt catttacatg acatgctcaa taggttgtta    19500
tcattgtgat aaagaataga ttagtggtgg gacagggttt gccaagggtt ggcaggtggg    19560
ggagatggca tggggtattt gggggggaag gatggacctg tactgcatcc tgatgatgct    19620
ggtggctaca gaagtctctc catgtgttga aattcataga agtgtacacc aaaacattgg    19680
ttttgctgtg tgagaatttt aaaagtaaaa agtaagaag atagtgtatt tgcttcctag     19740
ggcaaccata acaaagcact acaaacgcct taaaataaca gggatttatt gtcgcagctt    19800
tggagacaag tctgaaatta gggtgtcagc agtgttggtt ccttctggag gctctgggag    19860
agtctctgtc ccaggctctc tgctcgcttc caggagcacc cggcaatcat gggcatcctt    19920
gggctgcgga cgcgtcgctc ctgtctctgc tttcatcttc gcatggcctt ctctctctgt    19980
gcctctgtgt gacttttct gtctcttata aggactttct cctttattta gggcccacac    20040
tgacccagca tgatctcttc tacagccttg gcttagttaa catctgcaaa gacccgattt    20100
ccaattaagg ttctattctg aggctgcagg tggacctgaa ttagcaggga gggcactatt    20160
caaccaactg tagagagtta aaaaacaata agcctgtgga cattttttag cgtaatctag    20220
gctcttgatg acctgtttta aactaatcag caatgaatat ttttcagcta acgtaatgac    20280
```

```
tattgacaag cacgtgaccc ttgtctgaat gttaactcag gcatagcaac taaaaaccat   20340
ccattgacca gctcgggagt agcaaacaga gcaagccatt cttggtgcaa cctgtttcta   20400
ggtaattaac ttgaaaatat tttcaatatt caacaaagat ggttcattta agatgactga   20460
agccacatct tcacagatgc agaagatctg aatagctttc ctctttagat tgaatagttc   20520
tagaacaatt cattcctaaa agtgacttcc attggggaaa atatcctatt cagcttgagt   20580
cacttaatta tggttgttat tggtataaaa tgtctctgtt ttccctaata tattttaaa    20640 tttcttttt ccttttagaa tgaattctgg aataaataca aaggtcagta tttttttctgt   20700 tttaaccttc agtgagaggg gttcatcagg atatttgaat tttgaaaata gttcctgaat   20760
ttcctttctg cttttgttct catttttactc atttaagact ttttccctca gggtgtttcc   20820
ataatagtta ttgtaaaaga gttttagag taatttttata ctaatcctag ttttgttatt   20880
gagttagaga tatatattta aatcagttca ttctcatttg aggataccaa attccatgat   20940 aactttctt aaataaaagt gtattcggta aaagcaaaaa acagagtctg aaagattaga   21000
ttcccgacta aggtaaccac cttgatttaa tgcttaatag catctgaagt ggcctcagtc   21060
atgactacct ggtaacagta ttcacatttc tcaaaatgac aactgggcct atctctaaat   21120
gagattgtgt aaatcctcca agaaatggga agcccgtgt tagtgtttgc cttctccttt    21180
tgccccagga tgatttggaa agaggaaccc taacctcctc tcccgtcaag gcccagccca   21240
gaaatgagca tcaggctctc acctttcctc catccttcca gttggtccct gtggtcacct   21300
ctgactgtaa acacactgca aaacaccggc aaaaatcaaa aagctgggcc ggtgatccac   21360
ctagataaag gcatcacgta cacatggcca caaaagggggg tggatcaaat aaagtccaaa   21420
gagggggagt tgtttacaga gaaaccggaa gactcttcca gttatctgaa cggcagggcc   21480
aaggttagca cagcaaaact gtttccatga tgccggaaac agcttgcaga ctccagtttc   21540
gaaatcctct ctttgcagat ggcgaccagt gtgagaccag tccttgccag aaccagggca   21600
aatgtaaaga cggcctcggg gaatacacct gcacctgttt agaaggattc gaaggcaaaa   21660
actgtgaatt atgtaggttc ctctgcttgg tataccttca gatcagatgc ccctgaagag   21720
tggcaggtgg gcgggggaag aagtgaaaac gcctaatgaa acaatcttaa gtcatttctg   21780
atttacaaag tctgggctct attataccta ttatactgtg ccactatagc aatagaaaaa   21840
aaagccccaa tatgtccccc aaacgattcg gtttggggg c atgatgagag agacacagtc   21900
acttctctgc tcctccgaga gagactgtag aacattgatg aagcgtgtga tccattcatg   21960
tgtaaacagg agtggactct ctgttttcct tggggccaag tgcattgccc tgttattcct   22020
gctccttgtg accctgtgca gtgattctaa atcacctctt atttatgtgt atggatgcag   22080
gtgtcaatat ttgtgaatat ttgtgattgg ccaattataa aaatttgata catttaatta   22140
gttctacgtg gaaaaatcac taagtgcttt ctctaatgtg gtgattaagt tttaaataaa   22200
aagttaggct actgttagat caatttccct aaggaaaaag atttgcattt cttttaaagt   22260
acttaattga tcatcttttt tttttttttt tttgagatgg agtctcgctc tgtggcccag   22320
gctagagtgc agtggcacga tctcagctca ccgcaagctc cgcctgccag gttcacgcca   22380
ttctcctgcc tcagcctccc aagtagctgg gactataggc cccggccacc agtcccggct   22440 aattttttt tttttttaatt ttttagtgga gacggggttt caccgtgtta gccaggatgg   22500
tctcgatctc ctgaccctgg tgatccgccc g cttcgacctc ccaaagtgct gggattacag   22560
gcgtgaggca cagcgccggc ctaattgatc atctttagac tgtgttctta gattggatta   22620
```

```
cttttgagtt ttccctgatg agaatatcaa ttacgcatca ttccattcca agtccgcagt   22680
cgcctccctg gaacaccatt tggtaactta tgaggcataa ccctgttcag gctcccaggg   22740
ctattatgca cattttctaa aatttcaggc atgttgatct ttgcactgtg attacttttt   22800
catcaaaagc cacacagagg gatgtggagt gaccgtaatg tgagtgctgc tggggcaggg   22860
ggtaccggcc atcccggagg tgtgaggggc aggtacctgg agcctggctt ctggctacac   22920
cgggcactgc accatgagct ccccgtgacc cgtgaggttg cccttcaagg caagtgtacc   22980
tgtcgcctgg ctctggccct ttgctcaacc caatggccgc tttgtggctg acaggcaagt   23040
ggatgtagct ggcacccttg gccagccca  gcctccattt ctccagctgt ccccagagcc   23100
aacgtgcctc tcctttgcag tcacacggaa gctctgcagc ctggacaacg gggactgtga   23160
ccagttctgc cacgaggaac agaactctgt ggtgtgctcc tgcgcccgcg gtacaccct   23220
ggctgacaac ggcaaggcct gcattccac  aggtaggagg cacgttgggc cacagccacc   23280
cgctgccgct gggccgggcc agggaggaca agcccgtgcc aggggtggg  gacacaggca   23340
tgttctgggc gggcctggca ggtaacagtg acaccaagag gacaggactg agccctgggc   23400
tccgggccca ggtggttcaa acatgaagac catgaggttt ggaaacagac ccattatttc   23460
tgtaagccag atctgctgtt taacctcagc ttccccatct gacaaatggg accaacacta   23520
ttgcctgact gcttgggtga tccctggagc actttgcatg atgcctggcc caccgcaggc   23580
cctcagtctg cattgggact gtgggggat  ccagtgcaag ggctcaaagc accagggcag   23640
gcaaagggca gagctggccc gaggaactgg agctaaggtg cggggctggg ataggagtca   23700
ggggacgctc aggctctgag ctccttttac caggaccagt gttcattgaa cgtagttttt   23760
cttttccttg atgaatgtgg acaacaggcg gccagagggc agtgagcaca ggacaggcag   23820
gggactgggc agggtgggga cgagcctccc tgtcctgacc ccgtgggcat tgcctacgct   23880
gggcttgcct ggctgccggc acttccacac ggccagcaca catgaggccc tcgaaggcgg   23940
ggcctaggcg tcacagctgc accttgcaca gcaaccccac tcccactcat agctggcccg   24000
acccgcagcg ttggcctcac ccgggggcat attcgaaggg cagagttcca ggcccgcctt   24060
ttcaagagcc tggtgaccca gctcaccttc cggcttcagg tgcggctcag ccccagacc   24120
gtgttctgcc cccggctacc atgactgtcc cctccagaca caggttactc ccgagtgttc   24180
tgtcactctt cctttcatat ccttcttacc gaaaacaatt tacttccaaa gatgagtgat   24240
cacgaaaaga ccgggttcca tatgcatcct tcaagcgctg cttcaattat gtgcctgaaa   24300
catctcagca agtgaaagac actgtggctg accttgctac tggcaatgac attcaagctt   24360
aagctggtta aaaaatattt taactgaagt catttcttga catacacacg aatatttttt   24420
aattctagaa acaatcacaa atccatttaa aaccaagtgt gggccgggtg cagtagctca   24480
tgcctgtaat cccagcattt gggaggcca  aggcgggcgg atcatgaggt cagggagatcg   24540
agaccatcct ggccaacaca gtgaaacccc gtctctagta aaaatacaaa aaaaaaaaa    24600
aattagctgg gcatggtggt gcacgcctgt agtcccagct gctcaggagg ctgaggcaag   24660
agaatggcgt gaacctggaa ggcggagctt gcactgagca ctgagccgag attgcgccac   24720
tgcgctccag cctgggcaac agaatgagac tctgtctcaa aaaaaaaaaa aaaaaaaaa    24780
tcaaaaggca aatgtgatgt gtgaaaataa aattacataa tctactttgt agtgcaaaaa   24840
gttcaggctg gcaaggtgg  ctcacgcctg taatcccagc actttgggaa gccaaggtgg   24900
gtggatcacc tgaggtcagg agttcaagac cagcctggcc aacatggtga aaccctgtct   24960
ctataaaaaa aaaaatacaa aaacttagct gggcgtggtg gcgcacgcct gtaatcccag   25020
```

```
ctactcggga ggctgaggca ggagaatcgc ctgaacccag gaggtggagg ttgcaatgag   25080
ccaagatcat gccattgcac tccagcctgg gagacaagag agaaactcca tctcaaaaaa   25140
aaaaaaaagt tcagttccaa ataatggatg aactcagaac ttggaagggt ggtgactgca   25200
cacatggaca gagctgaggc acggcggggt ggaggcccct gcggctggca gattcaccgg   25260
agcctcctca gactgcgcag gagcacagca agtaaacagc taagctgtgc ccatctgacc   25320
ccagacacgt gtggccacag agaagcccct tgccatccat tcccccctcc tctcctctcc   25380
tgctccccca caccccctgcc ttcctccaac atgtttcagc cattctcttg gccttggtgc   25440
cctaattggc cgttatacaa aaggaagctt cctaacatct cggcgtggcc tctctgggag   25500
ctgtgctatt ccagacgctc tcctgtgcct ccagttgttt gcgtgcgcca ttccttctgc   25560
ctgaaaactt tttttcttc aatgtttcat taggaaaagt tttccaacac acagcacact   25620
ggaaagaatt ttgcagggag tcgcacacgc ccagcacttg ggttctcctg ttggcatcct   25680
ccggccagat gcattcatcc catttcgccc ggcccgtttg tctctgtcca tccgtcaagc   25740
tttcttgact tcttggtgca ttttcaggca aaccgcagac gccaacactc ccctcgctgc   25800
ctgggttgct gcctggcgtc cattgttcac aggcggtcac ctgaggggag gccaacgctc   25860
ggacagctgc gctcacctgc agatccgacc cctgccgacg acgtggggcc tcgccctgca   25920
agcccgctgc ccctccgggt gcccctgcgc tctgcctccc ggctctctga ctcttctccc   25980
tcagggtgag ctgtgcaggc tatggggagc ctctctctgt gctgaaggcc ccggccgtcc   26040
tctttctttc agggccctac ccctgtggga aacagaccct ggaacgcagg aagaggtcag   26100
tggcccaggc caccagcagc agcggggagg cccctgacag catcacatgg aagccatatg   26160
atgcagccga cctggacccc accgagaacc ccttcgacct gcttgacttc aaccagacgc   26220
agcctgagag gggcgacaac aacctcacca ggatcgtggg aggccaggaa tgcaaggacg   26280
gggagtgtcc ctggcaggta acagtaggat gtccccctcgg gcctgctgga gagaccacct   26340
gtcccgctgt gcacctcggg gaggccagcc tgacacttgg aatagcaatc cgggaaggaa   26400
ctgttccgaa ctaggacaga ggggctccgg cacccaagcc tgcctgcctg tcccctccct   26460
ccgggcagcc aaggaggctg tgagctccac agggaagtgg ccggggctga gggagaggct   26520
gggcccaggc aacgccccc tcagcccctt cccactgggc atttccatgg ctgcccgtgg   26580
catgcccagg acgatgctgt cctgtgaaac agaagagagg gagaaggcgc agccacacgc   26640
tcaagtgtcc tcaaacctcc cctacaccag gagacaaggc taaagccagg gagccaccca   26700
cactgcaggg gcatcagcgg gcaggaggac ggtgccgggt gggcaaggcc tccatctgct   26760
cttctgtttg acgggaggca gaaagagttg gtgtcctcgc ttcatttcta attttggaat   26820
ttttttaccc aaaacacctaa atccatgga ggtagatagt accttagaga aaaacacatc   26880
tacttatttt caaaggtaaa aaagaaaatc actctttgag gctttttgt taagagacag   26940 taccttgctc tgttgcccag gctggagtgc agtgtcgcga tctcggctca ctgcaacctc   27000
cacctcctgg gttcaagcga ttctcatgcc tcagactccc aagtagctgg aattacgggc   27060
gcccgctact tacgcctggc taatttttt tttttttga cggagtctc cactctgtcg   27120 cccaggctgg agtgcagtgg cgcgatctcg gctcactgca acctccacct cccaggttca   27180
tgtcattctc ctgcttcagc ctcccgagta gctgggacta caggcgcctg ccaccacgcc   27240
cagctaattt tttttgtatt tttagtagag acggggtttc accgtgttag ccaggatggt   27300
ctccatctcc tgacctggtg atctgcccac ctcagcctcc caaagtgctg ggattacagg   27360
```

```
cgtgagacaa tgtgcccggc catgcctggc taatttttt atttttaata gagacaggaa   27420
tttcaccatg ttggccaggc tggtctcaaa ctccaggcct catgtgatcc accctcctca   27480
gccacccaaa gtgctggagt tacaggtgtg agccactata ccaggtccta atctttgatt   27540
gttgatttgg actaatgctg ccagattaaa caaataaaag cacaatactt tcaattaaat   27600
ttcaatttca cataaactag aaatacatta aacaaaagca caatactttc aattaaattt   27660
caatttcaca taaactagaa atactttcag tgtaagtatg ttccaagtat cgcatgaagc   27720
atacatatgc gaaaaattat tgctgtttta tctgattcaa gtcaaactag gtgtattagt   27780
cagttttcac actgctgaca catacatacc cgagactggg taatttataa agaaaaagag   27840
gttgaatgaa ctcacagttc cacgtggctg gggaggcctc accgtcacgg tggaaggcgc   27900
aaggcacgtc ttacatggcg gcagcaagac agagaatgag agaacaagca aaggggttt    27960
cccctttagaa aaccatcagc tcttgtgaga cttattcact tccaccagaa cagcatgggg   28020
aaaccgccct cacgattcag ttacctccca ccaggtccct cccacaacac acgggaaata   28080
tgggagctac agtttgagat gagatttggg tggggacaca gccaaacctt gttgctgggc   28140
atcctgtatt ttctctggca atcctcactt ggacttgaat tttcagcgcc caaaaccaga   28200
atgtcctctc ctacaagcaa gaatctcaga gctgccagcg cccccatgaa ttcccccagg   28260
tcttccccca ccccagaccg tgtggcgggt gagcctctgt ctaactataa agagccaagc   28320
gagagaggga tgcactgagg tggctctgca atgcatgttt gttgagggcc ttctgtgtgt   28380
caggcactga gccgggtgct gtgtaggtgg gatatgaaac catgaagcct ctctgtgacc   28440
aatacacaga aatctcaacc tagttaggga gctgagaccg aaatcctccc agtcccaggc   28500
actgtgtggt tggggcaaga acctcgatgc aggagacccc accgaggatg agcaggaaaa   28560
gcctcttgtg gggctgagga gctggacttg gagctgcagg cggggttttg gaggggttcc   28620
tgggctgggg gaccagggtg gggcgccctg gagggctcac tggagggcc ctcgcccagc    28680
ctgttgaggt ttgcgattct tgtttcctgg ttcgagtctt ggcaagtggg cctcatctgc   28740
atctttagga agaatggttg gtgttcgtgt cttagaaagc ctgacttttcc ctcatgtaag   28800
ctggatgatg agttgacaaa ttatgcaaaa aagaggcaaa aacatgaccc cttttctagc    28860
catgaatgtt ttaagaaatg ttttaagact cggtattgtc agtagtttca ttggtctgta   28920
catgtgccca gccactatca caggacggga aactccccag agaaaagaaa accaaaatat   28980
gcccgggctc caaacttgca agtccagctc cctagggaca gcatgtggca cccctgtcag   29040
tgcttgctcc cctgggaccg tgttccaagt cctggcaggt aggagaccct tcacaggagc   29100
tgccacaggg accccagga agtcacctgg gatggaggtg tccgtgcacc atgggggaca    29160
ggctcacact gctgaaccgt cgggacacca ggcaggcaca ccggttgagg cagatgatgt   29220
ttctgcacag actggcgtct cctggtccca ggtagaaatc ctgccacaga gacgggaaag   29280
gctgctccca cagggagcat cttttccaaa gcatggacag atgtgtcgtg tgcatgagac   29340
tttagagagc tctgtgatgg agttggtaga aagaagagat gactccctat atcagtgagt   29400
gtgtggcaca ggcagagaaa agagacagac aaggaactgt ccttgggtgg atggcaggag   29460
accgaagagc acagcttggc atggggaggg ccggcagtg ccacctgaag agctggcttc    29520
tcagtcaggc aacacctgtc cacctggcca gccacactga gcctgtcacg tctgtcacag   29580
gccctgctca tcaatgagga aaacgagggt ttctgtggtg gaaccattct gagcgagttc   29640
tacatcctaa cggcagccca ctgtctctac caagccaaga gattcaaggt gagggtaggt   29700
aagtgaccaa cagcccccag ggccgtggtg aggggcaccg tcactgtctg cttttcagaa   29760
```

```
accactaaag ctgatggaat ttgttgggaa cactggttga aatcctgaaa tcctatttgt    29820
aggggttagg ggcatttcac agaggaagaa gatgaggaag cagaggaagg ggaagagtgg    29880
ggaggaggac ggggagggga ggcgaaccag cccagcccct ctcccactgg gtgtccaggt    29940
ctcgggtctc cgagtctctg gtcccgggt ctctgggtct gcatgtccag ctaatgttct     30000
gtgtctcagt gtcttttatt gggagccttc cagacctccc tttctcttta acatactctg    30060
aacaccaagc acctctgtct cttctatttt tatttgtggg attgtttcat taacatctgt    30120
ctttgtccac tagaccctag agctgctcag tacaaaccca acacaagcta caaatgcaag    30180
caatatatgt aaactgatat ttttctaaca ttaaatgttc tattatacat tttaaaatat    30240
aaaaaaacag gctgggtgtg gtggctcatg cctgtaatcc cagcactttg ggaggctgag    30300
gcgggcagat cacctgaggt caggagtttg agatcagcct ggccagcatg gcgaaacccc    30360
atctctacta aaaatacaa aaattagccg ggcatggtgg cacgggcctg taatcccagc     30420
tacttgggaa gctgaggcag gagaaccact tgaacccggg aggtggaggt tgcagtgagc    30480
tgagattgtg ccattgcact ccagcccggg aacagagca aaactctgtc tcaaaaaaaa     30540
aaaaaaaata tatatatata tatatgtata tatatgtgt tatatatata tacatatata     30600
tacacacaca cacacaattt ccataatata tcttatttaa ctcaacatat tgaaaatatt    30660 acttttttcca tgtgtaatca tgttaaaggt gtaataacac attccgcaca ttttctttca   30720
tgctaagtct ctattttacg ttcatggcac aactatttta cactctcagc cagcggccac    30780
accgcacaac ctgggtctgg gatgccaaaa gccttcggtc ctgggacgcc tcgttggtgc    30840
ccacgactgg cacagacgat gcacccgcca aaggacacag gagtggcggc cgtctaaaga    30900
accaaacgtg tgagacagga ccagtggttc cctgggcagc aaggctgaca ggcactttta    30960
tttgctgctt tgcacttccc tctattttc aaattttcaa aagtgatcac gtgccatttt     31020
taatttaaaa aaatatatat aacttcctta aaaagcaacg gatgtgcgag agcatgtccc    31080
tggctgagct gagcacagtc ccactcgtct gtcccagggg accggaacac ggagcaggag    31140
gagggcggtg aggcggtgca cgaggtggag gtggtcatca agcacaaccg gttcacaaag    31200
gagacctatg acttcgacat cgccgtgctc cggctcaaga ccccatcac cttccgcatg     31260 aacgtggcgc ctgcctgcct ccccgagcgt gactgggccg agtccacgct gatgacgcag    31320
aagacgggga ttgtgagcgg cttcgggcgc acccacgaga agggccggca gtccaccagg    31380
ctcaagatgc tggaggtgcc ctacgtggac cgcaacagct gcaagctgtc cagcagcttc    31440
atcatcaccc agaacatgtt ctgtgccggc tacgacacca gcaggagga tgcctgccag     31500 ggggacagcg ggggcccgca cgtcacccgc ttcaaggaca cctacttcgt gacaggcatc    31560
gtcagctggg gagagggctg tgcccgtaag gggaagtacg ggatctacac caaggtcacc    31620
gccttcctca agtggatcga caggtccatg aaaaccaggg gcttgcccaa ggccaagagc    31680
catgccccgg aggtcataac gtcctctcca ttaaagtgag atcccactca aggcctggtt    31740
tgtctctcga ttgccgcctt gccctggctt ctcccgccct gttgaggtgg aaggtgaag    31800 tgtctgtctg gaacaccagc ttccgcccctt cccagctagg ctggggattc ctccagggaa   31860
tattctagtc tgtgggggca ggatggaggc tccaggggatg atactgtgcc atgactgcca    31920
tgggcattcc tttccccaga taccttcctg catctgggtc acgcccagag gcagatggga    31980
gcctgtgcag gccccgtggc gtcgggaggg gcccacacgt tggcgcagcc tccccaagac    32040
cccccacttg gcctggtctc tcttgttcct cttgggaatt ggacacctcc ccggtgactg    32100
```

-continued

```
cctatgaccc gcagactccc tgggagggaa acgtccagaa agcttctcat tggggcggac    32160
attttacatt aacttaaaca accaggtgct cttcaactgc acggtgccag cccccacccc    32220
agctcaggct tgtgtggtgg gggccacagg catccccgg gcaggtgacc tgctcaccag     32280
gcagcgacct gacctggcac agttggcccc caccgtggcc acccttagaa ccccctgtgg    32340
gctttagcat gcctgcatcc aggccacagc ctggccactg aaatcagtct ctggagtgaa    32400
gctggccagg agcttctgga agcttctgga gctcctcagg tgctgagtgg tggtggcgtg    32460
gcaggcgggg cttcgggggg ctcctcctct cctagggtcc agatgtttag tccttgccct    32520
gctgcaatcc ggcactgtcc ctaggcctca agttaactgg ccatgaaaat caaatgaact    32580
ttcggtaaac agaaaagatt ccggacaagg cctgccgtgt gtctcccaaa cgtctcctgc    32640
agtttgcgtc ttgtgtaatg tccctaagca aagttcaaca gttctagtac aaaaactccc    32700
caaaaaagtc atgagctggg caaaaccgtt cgtaaacaga tgttgcgaag tcagggaaaa    32760
tcaaagtgga caggtgttcg acctcccaga aacggtctga ggaggggccg gtctcccagg    32820
gtgggcggga gggcattcct ggcctgcccg ctctgaggcc ttctccgtgg agctggctgt    32880
cgggctcctc gccggcccgtt cctggagaaa aggcttctgc ctcggagcta gcctgctgtt    32940
gggctgcgtt tcctaggcag ccacgtggtc cccagggccc cagaggtaaa ccctggactt    33000
ggattcccgt ttctggaaat caaaggttga gtggggtcca gagagaactc tgggaaaata    33060
attacaattg aaaccccca tcgccatcac tgtctgcacc ctggttcctg ccgcactggg    33120
tgtctggtgc ccgtgcccgt ctcaggatag aaaggaaact ggaggctgca gagagaagga    33180
cctgatgggt cgtagctcag catctgccga agccccatct agaaataggt tctcgtcctg    33240
ggaggtgtgg gagggagcct cgggagggag acagcaggag gagaggcccc agtcctggac    33300
acgcgctggg ggttgaagtc tcggctctgc aggctcctgt gctgcgtggc agggattttc    33360
tctctgccta aatatcgtct tcataagtaa aggcaagtgg gctaaaccta tgtcatctcc    33420
gtgttaactc agaatagtct aggcctgggc caggggacac tttgtgatct gagaccccca    33480
gaattccctg agggaggccc agctctgttt cgggaaataa ctgaagcggc tgtttgtgcg    33540
aggtgagacc ctgaggaccg agagcagcag gaggtcatgg tggggagcaa aaacgggaaa    33600
agtgattccg cctgagactg agggagagag aacccaggtg agaccctgag gactgtgagc    33660
agcaggaggt cacggtgggg agtaaagatg ggaaaagtga ttccgcctga gagtgaggga    33720
gagagaacag a    33731
```

<210> SEQ ID NO 48
<211> LENGTH: 467
<212> TYPE: PRT
<213> ORGANISM: Homo sapiens
<400> SEQUENCE: 48

```
Leu Leu Gly Glu Ser Leu Phe Ile Arg Arg Glu Gln Ala Asn Asn Ile
1               5                   10                  15

Leu Ala Arg Val Thr Arg Ala Asn Ser Phe Leu Glu Glu Met Lys Lys
            20                  25                  30

Gly His Leu Glu Arg Glu Cys Met Glu Glu Thr Cys Ser Tyr Glu Glu
        35                  40                  45

Ala Arg Glu Val Phe Glu Asp Ser Asp Lys Thr Asn Glu Phe Trp Asn
    50                  55                  60

Lys Tyr Lys Asp Gly Asp Gln Cys Glu Thr Ser Pro Cys Gln Asn Gln
65                  70                  75                  80
```

```
Gly Lys Cys Lys Asp Gly Leu Gly Glu Tyr Thr Cys Thr Cys Leu Glu
             85                  90                  95

Gly Phe Glu Gly Lys Asn Cys Glu Leu Phe Thr Arg Lys Leu Cys Ser
            100                 105                 110

Leu Asp Asn Gly Asp Cys Asp Gln Phe Cys His Glu Glu Gln Asn Ser
        115                 120                 125

Val Val Cys Ser Cys Ala Arg Gly Tyr Thr Leu Ala Asp Asn Gly Lys
    130                 135                 140

Ala Cys Ile Pro Thr Gly Pro Tyr Pro Cys Gly Lys Gln Thr Leu Glu
145                 150                 155                 160

Arg Arg Lys Arg Ser Val Ala Gln Ala Thr Ser Ser Ser Gly Glu Ala
                165                 170                 175

Pro Asp Ser Ile Thr Trp Lys Pro Tyr Asp Ala Ala Asp Leu Asp Pro
            180                 185                 190

Thr Glu Asn Pro Phe Asp Leu Leu Asp Phe Asn Gln Thr Gln Pro Glu
        195                 200                 205

Arg Gly Asp Asn Asn Leu Thr Arg Ile Val Gly Gly Gln Glu Cys Lys
    210                 215                 220

Asp Gly Glu Cys Pro Trp Gln Ala Leu Leu Ile Asn Glu Glu Asn Glu
225                 230                 235                 240

Gly Phe Cys Gly Gly Thr Ile Leu Ser Glu Phe Tyr Ile Leu Thr Ala
                245                 250                 255

Ala His Cys Leu Tyr Gln Ala Lys Arg Phe Glu Gly Asp Arg Asn Thr
            260                 265                 270

Glu Gln Glu Glu Gly Gly Glu Ala Val His Glu Val Glu Val Val Ile
        275                 280                 285

Lys His Asn Arg Phe Thr Lys Glu Thr Tyr Asp Phe Asp Ile Ala Val
    290                 295                 300

Leu Arg Leu Lys Thr Pro Ile Thr Phe Arg Met Asn Val Ala Pro Ala
305                 310                 315                 320

Cys Leu Pro Glu Arg Asp Trp Ala Glu Ser Thr Leu Met Thr Gln Lys
                325                 330                 335

Thr Gly Ile Val Ser Gly Phe Gly Arg Thr His Glu Lys Gly Arg Gln
            340                 345                 350

Ser Thr Arg Leu Lys Met Leu Glu Val Pro Tyr Val Asp Arg Asn Ser
        355                 360                 365

Cys Lys Leu Ser Ser Ser Phe Ile Ile Thr Gln Asn Met Phe Cys Ala
    370                 375                 380

Gly Tyr Asp Thr Lys Gln Glu Asp Ala Cys Gln Gly Asp Ser Gly Gly
385                 390                 395                 400

Pro His Val Thr Arg Phe Lys Asp Thr Tyr Phe Val Thr Gly Ile Val
                405                 410                 415

Ser Trp Gly Glu Gly Cys Ala Arg Lys Gly Lys Tyr Gly Ile Tyr Thr
            420                 425                 430

Lys Val Thr Ala Phe Leu Lys Trp Ile Asp Arg Ser Met Lys Thr Arg
        435                 440                 445

Gly Leu Pro Lys Ala Lys Ser His Ala Pro Glu Val Ile Thr Ser Ser
450                 455                 460

Pro Leu Lys
465

<210> SEQ ID NO 49
<211> LENGTH: 1529
<212> TYPE: DNA
```

<213> ORGANISM: Bos Taurus

<400> SEQUENCE: 49

```
ctcagcaccg cccctgggcgg cctcctgcgg ccggcgggga gcgtgttcct gccccgggac    60
caggcccacc gtgtcctgca gagagcccgc agggccaact cattcttgga ggaggtgaag   120
cagggaaacc tggagcgaga gtgcctggag gaggcctgct cactagagga ggcccgcgag   180
gtcttcgagg acgcagagca gacggatgaa ttctggagta aatacaaaga tggagaccag   240
tgtgaaggcc acccgtgcct gaatcagggc cactgtaaag acggcatcgg agactacacc   300
tgcacctgtg cggaagggtt tgaaggcaaa aactgcgagt ctccacgcg tgagatctgc    360
agcctggaca atgggggctg cgaccagttc tgcagggagg agcgcagcga ggtgcggtgc   420
tcctgcgcgc acggctacgt gctgggcgac gacagcaagt cctgcgtgtc cacagagcgc   480
ttcccctgtg ggaagttcac gcagggacgc agccggcggt gggccatcca ccagcgag    540
gacgcgcttg acgccagcga gctggagcac tacgaccctg cagacctgag ccccacagag   600
agctccttgg acctgctggg cctcaacagg accgagccca cgccgggga ggacggcagc    660
caggtggtcc ggatagtggg cggcagggac tgcgcggagg gcgagtgccc atggcaggct   720
ctgctggtca acgaagagaa cgagggattc tgcggggca ccatcctgaa cgagttctac    780
gtcctcacgg ctgcccactg cctgcaccag gccaagaggt tcacggtgag gtcggcgac    840
cggaacacag agcaggagga gggcaacgag atggcacacg aggtggagat gactgtgaag   900
cacagccgct ttgtcaagga gacctacgac ttcgacatcg cggtgctgag gctcaagacg   960
cccatccggt tccgccggaa cgtggcgccc gcctgcctgc ccgagaagga ctgggcggag  1020
gccacgctga tgacccagaa gacgggcatc gtcagcggct cgggcgcac gcacgagaag  1080
ggccgcctgt cgtccacgct caagatgctg gaggtgccct acgtggaccg cagcacctgt  1140
aagctgtcca gcagcttcac catcacgccc aacatgttct gcgccggcta cgacacccag  1200
cccgaggacg cctgccaggg cgacagtggc ggccccacg tcacccgctt caaggacacc  1260
tacttcgtca caggcatcgt cagctgggga aagggtgcg cgcgcaaggg caagttcggc   1320
gtctacacca aggtctccaa cttcctcaag tggatcgaca agatcatgaa ggccagggca  1380
ggggccgcgg cagccgcgg ccacagtgaa gcccctgcca cctggacggt cccgccccc   1440
cttccgctct gagcgggctc cctccctgcc tgattagagc tgtgtcctct ccttaaaaaa  1500
aaaaaaaaaa aaaaaaaaaa aaaaaaaaa                                    1529
```

<210> SEQ ID NO 50
<211> LENGTH: 492
<212> TYPE: PRT
<213> ORGANISM: Bos Taurus

<400> SEQUENCE: 50

```
Met Ala Gly Leu Leu His Leu Val Leu Leu Ser Thr Ala Leu Gly Gly
1               5                   10                  15

Leu Leu Arg Pro Ala Gly Ser Val Phe Leu Pro Arg Asp Gln Ala His
                20                  25                  30

Arg Val Leu Gln Arg Ala Arg Arg Ala Asn Ser Phe Leu Glu Glu Val
            35                  40                  45

Lys Gln Gly Asn Leu Glu Arg Glu Cys Leu Glu Glu Ala Cys Ser Leu
        50                  55                  60

Glu Glu Ala Arg Glu Val Phe Glu Asp Ala Glu Gln Thr Asp Glu Phe
65                  70                  75                  80
```

```
Trp Ser Lys Tyr Lys Asp Gly Asp Gln Cys Glu Gly His Pro Cys Leu
                85                  90                  95

Asn Gln Gly His Cys Lys Asp Gly Ile Gly Asp Tyr Thr Cys Thr Cys
            100                 105                 110

Ala Glu Gly Phe Glu Gly Lys Asn Cys Glu Phe Ser Thr Arg Glu Ile
            115                 120                 125

Cys Ser Leu Asp Asn Gly Gly Cys Asp Gln Phe Cys Arg Glu Glu Arg
            130                 135                 140

Ser Glu Val Arg Cys Ser Cys Ala His Gly Tyr Val Leu Gly Asp Asp
145                 150                 155                 160

Ser Lys Ser Cys Val Ser Thr Glu Arg Phe Pro Cys Gly Lys Phe Thr
                165                 170                 175

Gln Gly Arg Ser Arg Arg Trp Ala Ile His Thr Ser Glu Asp Ala Leu
            180                 185                 190

Asp Ala Ser Glu Leu Glu His Tyr Asp Pro Ala Asp Leu Ser Pro Thr
            195                 200                 205

Glu Ser Ser Leu Asp Leu Leu Gly Leu Asn Arg Thr Glu Pro Ser Ala
210                 215                 220

Gly Glu Asp Gly Ser Gln Val Val Arg Ile Val Gly Arg Asp Cys
225                 230                 235                 240

Ala Glu Gly Glu Cys Pro Trp Gln Ala Leu Leu Val Asn Glu Glu Asn
                245                 250                 255

Glu Gly Phe Cys Gly Gly Thr Ile Leu Asn Glu Phe Tyr Val Leu Thr
            260                 265                 270

Ala Ala His Cys Leu His Gln Ala Lys Arg Phe Thr Val Arg Val Gly
            275                 280                 285

Asp Arg Asn Thr Glu Gln Glu Glu Gly Asn Glu Met Ala His Glu Val
            290                 295                 300

Glu Met Thr Val Lys His Ser Arg Phe Val Lys Glu Thr Tyr Asp Phe
305                 310                 315                 320

Asp Ile Ala Val Leu Arg Leu Lys Thr Pro Ile Arg Phe Arg Arg Asn
                325                 330                 335

Val Ala Pro Ala Cys Leu Pro Glu Lys Asp Trp Ala Glu Ala Thr Leu
            340                 345                 350

Met Thr Gln Lys Thr Gly Ile Val Ser Gly Phe Gly Arg Thr His Glu
            355                 360                 365

Lys Gly Arg Leu Ser Ser Thr Leu Lys Met Leu Glu Val Pro Tyr Val
            370                 375                 380

Asp Arg Ser Thr Cys Lys Leu Ser Ser Ser Phe Thr Ile Thr Pro Asn
385                 390                 395                 400

Met Phe Cys Ala Gly Tyr Asp Thr Gln Pro Glu Asp Ala Cys Gln Gly
                405                 410                 415

Asp Ser Gly Gly Pro His Val Thr Arg Phe Lys Asp Thr Tyr Phe Val
            420                 425                 430

Thr Gly Ile Val Ser Trp Gly Glu Gly Cys Ala Arg Lys Gly Lys Phe
            435                 440                 445

Gly Val Tyr Thr Lys Val Ser Asn Phe Leu Lys Trp Ile Asp Lys Ile
            450                 455                 460

Met Lys Ala Arg Ala Gly Ala Ala Gly Ser Arg Gly His Ser Glu Ala
465                 470                 475                 480

Pro Ala Thr Trp Thr Val Pro Pro Leu Pro Leu
                485                 490
```

```
<210> SEQ ID NO 51
<211> LENGTH: 30
<212> TYPE: PRT
<213> ORGANISM: Echis carinatus

<400> SEQUENCE: 51

Asp Cys Leu Pro Gly Trp Ser Ser His Glu Gly His Cys Tyr Lys Val
1               5                   10                  15

Phe Asn Gln Glu Met Tyr Trp Ala Asp Ala Glu Lys Phe Cys
            20                  25                  30

<210> SEQ ID NO 52
<211> LENGTH: 30
<212> TYPE: PRT
<213> ORGANISM: Echis carinatus

<400> SEQUENCE: 52

Asp Cys Leu Pro Asp Trp Phe His Tyr Glu Gly His Cys Tyr Arg Val
1               5                   10                  15

Phe Asp Glu Pro Lys Lys Trp Ala Asp Ala Glu Lys Phe Cys
            20                  25                  30

<210> SEQ ID NO 53
<211> LENGTH: 616
<212> TYPE: PRT
<213> ORGANISM: Echis carinatus

<400> SEQUENCE: 53

Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val Leu His Leu Glu Lys Asn Lys Glu Leu Phe
65                  70                  75                  80

Ser Glu Asp Tyr Ser Glu Thr His Tyr Ser Ser Asp Arg Glu Ile
                85                  90                  95

Thr Thr Asn Pro Ser Val Glu Asp His Cys Tyr Tyr His Gly Arg Ile
                100                 105                 110

Gln Asn Asp Ala Glu Ser Thr Ala Ser Ile Ser Ala Cys Asn Gly Leu
            115                 120                 125

Lys Gly His Phe Lys Leu Arg Gly Glu Thr Tyr Phe Ile Glu Pro Leu
130                 135                 140

Lys Ile Pro Asp Ser Glu Ala His Ala Val Tyr Lys Tyr Glu Asn Ile
145                 150                 155                 160

Glu Asn Glu Asp Glu Ala Pro Lys Met Cys Gly Val Thr Gln Asp Asn
                165                 170                 175

Trp Glu Ser Asp Glu Pro Ile Lys Lys Thr Leu Gly Leu Ile Val Pro
            180                 185                 190

Pro His Glu Arg Lys Phe Glu Lys Lys Phe Ile Glu Leu Val Val Val
        195                 200                 205

Val Asp His Ser Met Val Thr Lys Tyr Asn Asn Asp Ser Thr Ala Ile
    210                 215                 220

Arg Thr Trp Ile Tyr Glu Met Leu Asn Thr Val Asn Glu Ile Tyr Leu
225                 230                 235                 240
```

```
Pro Phe Asn Ile Arg Val Ala Leu Val Gly Leu Glu Phe Trp Cys Asn
            245                 250                 255

Gly Asp Leu Ile Asn Val Thr Ser Thr Ala Asp Asp Thr Leu His Ser
        260                 265                 270

Phe Gly Glu Trp Arg Ala Ser Asp Leu Leu Asn Arg Lys Arg His Asp
    275                 280                 285

His Ala Gln Leu Leu Thr Asn Val Thr Leu Asp His Ser Thr Leu Gly
290                 295                 300

Ile Thr Phe Val Tyr Gly Met Cys Lys Ser Asp Arg Ser Val Glu Leu
305                 310                 315                 320

Ile Leu Asp Tyr Ser Asn Ile Thr Phe Asn Met Ala Tyr Ile Ile Ala
                325                 330                 335

His Glu Met Gly His Ser Leu Gly Met Leu His Asp Thr Lys Phe Cys
            340                 345                 350

Thr Cys Gly Ala Lys Pro Cys Ile Met Phe Gly Lys Glu Ser Ile Pro
        355                 360                 365

Pro Pro Lys Glu Phe Ser Ser Cys Ser Tyr Asp Gln Tyr Asn Lys Tyr
370                 375                 380

Leu Leu Lys Tyr Asn Pro Lys Cys Ile Leu Asp Pro Pro Leu Arg Lys
385                 390                 395                 400

Asp Ile Ala Ser Pro Ala Val Cys Gly Asn Glu Ile Trp Glu Glu Gly
                405                 410                 415

Glu Glu Cys Asp Cys Gly Ser Pro Ala Asp Cys Arg Asn Pro Cys Cys
            420                 425                 430

Asp Ala Ala Thr Cys Lys Leu Lys Pro Gly Ala Glu Cys Gly Asn Gly
        435                 440                 445

Glu Cys Cys Asp Lys Cys Lys Ile Arg Lys Ala Gly Thr Glu Cys Arg
450                 455                 460

Pro Ala Arg Asp Asp Cys Asp Val Ala Glu His Cys Thr Gly Gln Ser
465                 470                 475                 480

Ala Glu Cys Pro Arg Asn Glu Phe Gln Arg Asn Gly Gln Pro Cys Leu
                485                 490                 495

Asn Asn Ser Gly Tyr Cys Tyr Asn Gly Asp Cys Pro Ile Met Leu Asn
            500                 505                 510

Gln Cys Ile Ala Leu Phe Ser Pro Ser Ala Thr Val Ala Gln Asp Ser
        515                 520                 525

Cys Phe Gln Arg Asn Leu Gln Gly Ser Tyr Tyr Gly Tyr Cys Thr Lys
530                 535                 540

Glu Ile Gly Tyr Tyr Gly Lys Arg Phe Pro Cys Ala Pro Gln Asp Val
545                 550                 555                 560

Lys Cys Gly Arg Leu Tyr Cys Leu Asp Asn Ser Phe Lys Lys Asn Met
                565                 570                 575

Arg Cys Lys Asn Asp Tyr Ser Tyr Ala Asp Glu Asn Lys Gly Ile Val
            580                 585                 590

Glu Pro Gly Thr Lys Cys Glu Asp Gly Lys Val Cys Ile Asn Arg Lys
        595                 600                 605

Cys Val Asp Val Asn Thr Ala Tyr
    610                 615
```

<210> SEQ ID NO 54
<211> LENGTH: 603
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 54

```
Ile Ile Leu Gly Ser Gly Asn Val Asn Asp Tyr Glu Val Val Tyr Pro
1               5                   10                  15

Gln Lys Val Thr Ala Leu Pro Lys Gly Ala Val Gln Gln Pro Glu Gln
                20                  25                  30

Lys Tyr Glu Asp Ala Met Gln Tyr Glu Phe Glu Val Lys Gly Glu Pro
            35                  40                  45

Val Val Leu His Leu Glu Lys Asn Lys Glu Leu Phe Ser Glu Asp Tyr
        50                  55                  60

Ser Glu Thr His Tyr Ser Ser Asp Arg Glu Ile Thr Thr Asn Pro
65                  70                  75                  80

Ser Val Glu Asp His Cys Tyr Tyr His Gly Arg Ile Gln Asn Asp Ala
                85                  90                  95

Glu Ser Thr Ala Ser Ile Ser Ala Cys Asn Gly Leu Lys Gly His Phe
            100                 105                 110

Lys Leu Arg Gly Glu Thr Tyr Phe Ile Glu Pro Leu Lys Ile Pro Asp
        115                 120                 125

Ser Glu Ala His Ala Val Tyr Lys Tyr Glu Asn Ile Glu Asn Glu Asp
    130                 135                 140

Glu Ala Pro Lys Met Cys Gly Val Thr Gln Asp Asn Trp Glu Ser Asp
145                 150                 155                 160

Glu Pro Ile Lys Lys Thr Leu Gly Leu Ile Glu Asn Leu Tyr Phe Gln
                165                 170                 175

Ser Val Pro Pro His Glu Arg Lys Phe Glu Lys Lys Phe Ile Glu Leu
            180                 185                 190

Val Val Val Val Asp His Ser Met Val Thr Lys Tyr Asn Asn Asp Ser
        195                 200                 205

Thr Ala Ile Arg Thr Trp Ile Tyr Glu Met Leu Asn Thr Val Asn Glu
    210                 215                 220

Ile Tyr Leu Pro Phe Asn Ile Arg Val Ala Leu Val Gly Leu Glu Phe
225                 230                 235                 240

Trp Cys Asn Gly Asp Leu Ile Asn Val Thr Ser Thr Ala Asp Asp Thr
                245                 250                 255

Leu His Ser Phe Gly Glu Trp Arg Ala Ser Asp Leu Leu Asn Arg Lys
            260                 265                 270

Arg His Asp His Ala Gln Leu Leu Thr Asn Val Thr Leu Asp His Ser
        275                 280                 285

Thr Leu Gly Ile Thr Phe Val Tyr Gly Met Cys Lys Ser Asp Arg Ser
    290                 295                 300

Val Glu Leu Ile Leu Asp Tyr Ser Asn Ile Thr Phe Asn Met Ala Tyr
305                 310                 315                 320

Ile Ile Ala His Glu Met Gly His Ser Leu Gly Met Leu His Asp Thr
                325                 330                 335

Lys Phe Cys Thr Cys Gly Ala Lys Pro Cys Ile Met Phe Gly Lys Glu
            340                 345                 350

Ser Ile Pro Pro Pro Lys Glu Phe Ser Ser Cys Ser Tyr Asp Gln Tyr
        355                 360                 365

Asn Lys Tyr Leu Leu Lys Tyr Asn Pro Lys Cys Ile Leu Asp Pro Pro
    370                 375                 380

Leu Arg Lys Asp Ile Ala Ser Pro Ala Val Cys Gly Asn Glu Ile Trp
385                 390                 395                 400
```

-continued

```
Glu Glu Gly Glu Glu Cys Asp Cys Gly Ser Pro Ala Asp Cys Arg Asn
                405                 410                 415

Pro Cys Cys Asp Ala Ala Thr Cys Lys Leu Lys Pro Gly Ala Glu Cys
            420                 425                 430

Gly Asn Gly Glu Cys Cys Asp Lys Cys Lys Ile Arg Lys Ala Gly Thr
            435                 440                 445

Glu Cys Arg Pro Ala Arg Asp Asp Cys Asp Val Ala Glu His Cys Thr
450                 455                 460

Gly Gln Ser Ala Glu Cys Pro Arg Asn Glu Phe Gln Arg Asn Gly Gln
465                 470                 475                 480

Pro Cys Leu Asn Asn Ser Gly Tyr Cys Tyr Asn Gly Asp Cys Pro Ile
                485                 490                 495

Met Leu Asn Gln Cys Ile Ala Leu Phe Ser Pro Ser Ala Thr Val Ala
            500                 505                 510

Gln Asp Ser Cys Phe Gln Arg Asn Leu Gln Gly Ser Tyr Tyr Gly Tyr
            515                 520                 525

Cys Thr Lys Glu Ile Gly Tyr Tyr Gly Lys Arg Phe Pro Cys Ala Pro
            530                 535                 540

Gln Asp Val Lys Cys Gly Arg Leu Tyr Cys Leu Asp Asn Ser Phe Lys
545                 550                 555                 560

Lys Asn Met Arg Cys Lys Asn Asp Tyr Ser Tyr Ala Asp Glu Asn Lys
                565                 570                 575

Gly Ile Val Glu Pro Gly Thr Lys Cys Glu Asp Gly Lys Val Cys Ile
            580                 585                 590

Asn Arg Lys Cys Val Asp Val Asn Thr Ala Tyr
            595                 600

<210> SEQ ID NO 55
<211> LENGTH: 426
<212> TYPE: PRT
<213> ORGANISM: Echis carinatus

<400> SEQUENCE: 55

Val Pro Pro His Glu Arg Lys Phe Glu Lys Phe Ile Glu Leu Val
1               5                   10                  15

Val Val Val Asp His Ser Met Val Thr Lys Tyr Asn Asn Asp Ser Thr
            20                  25                  30

Ala Ile Arg Thr Trp Ile Tyr Glu Met Leu Asn Thr Val Asn Glu Ile
        35                  40                  45

Tyr Leu Pro Phe Asn Ile Arg Val Ala Leu Val Gly Leu Glu Phe Trp
50                  55                  60

Cys Asn Gly Asp Leu Ile Asn Val Thr Ser Thr Ala Asp Asp Thr Leu
65                  70                  75                  80

His Ser Phe Gly Glu Trp Arg Ala Ser Asp Leu Leu Asn Arg Lys Arg
                85                  90                  95

His Asp His Ala Gln Leu Leu Thr Asn Val Thr Leu Asp His Ser Thr
            100                 105                 110

Leu Gly Ile Thr Phe Val Tyr Gly Met Cys Lys Ser Asp Arg Ser Val
        115                 120                 125

Glu Leu Ile Leu Asp Tyr Ser Asn Ile Thr Phe Asn Met Ala Tyr Ile
            130                 135                 140

Ile Ala His Glu Met Gly His Ser Leu Gly Met Leu His Asp Thr Lys
145                 150                 155                 160

Phe Cys Thr Cys Gly Ala Lys Pro Cys Ile Met Phe Gly Lys Glu Ser
```

```
                     165                 170                 175

Ile Pro Pro Pro Lys Glu Phe Ser Ser Cys Ser Tyr Asp Gln Tyr Asn
                180                 185                 190

Lys Tyr Leu Leu Lys Tyr Asn Pro Lys Cys Ile Leu Asp Pro Pro Leu
            195                 200                 205

Arg Lys Asp Ile Ala Ser Pro Ala Val Cys Gly Asn Glu Ile Trp Glu
        210                 215                 220

Glu Gly Glu Glu Cys Asp Cys Gly Ser Pro Ala Asp Cys Arg Asn Pro
225                 230                 235                 240

Cys Cys Asp Ala Ala Thr Cys Lys Leu Lys Pro Gly Ala Glu Cys Gly
                245                 250                 255

Asn Gly Glu Cys Cys Asp Lys Cys Lys Ile Arg Lys Ala Gly Thr Glu
            260                 265                 270

Cys Arg Pro Ala Arg Asp Asp Cys Asp Val Ala Glu His Cys Thr Gly
        275                 280                 285

Gln Ser Ala Glu Cys Pro Arg Asn Glu Phe Gln Arg Asn Gly Gln Pro
    290                 295                 300

Cys Leu Asn Asn Ser Gly Tyr Cys Tyr Asn Gly Asp Cys Pro Ile Met
305                 310                 315                 320

Leu Asn Gln Cys Ile Ala Leu Phe Ser Pro Ser Ala Thr Val Ala Gln
                325                 330                 335

Asp Ser Cys Phe Gln Arg Asn Leu Gln Gly Ser Tyr Tyr Gly Tyr Cys
            340                 345                 350

Thr Lys Glu Ile Gly Tyr Tyr Gly Lys Arg Phe Pro Cys Ala Pro Gln
        355                 360                 365

Asp Val Lys Cys Gly Arg Leu Tyr Cys Leu Asp Asn Ser Phe Lys Lys
    370                 375                 380

Asn Met Arg Cys Lys Asn Asp Tyr Ser Tyr Ala Asp Glu Asn Lys Gly
385                 390                 395                 400

Ile Val Glu Pro Gly Thr Lys Cys Glu Asp Gly Lys Val Cys Ile Asn
                405                 410                 415

Arg Lys Cys Val Asp Val Asn Thr Ala Tyr
            420                 425

<210> SEQ ID NO 56
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ile Ile Leu Gly Ser Gly Asn Val Asn Asp Tyr Glu Val Val Tyr Pro
1               5                   10                  15

Gln Lys Val Thr Ala Leu Pro Lys Gly Ala Val Gln Pro Glu Gln
            20                  25                  30

Lys Tyr Glu Asp Ala Met Gln Tyr Glu Phe Glu Val Lys Gly Glu Pro
        35                  40                  45

Val Val Leu His Leu Glu Lys Asn Lys Glu Leu Phe Ser Glu Asp Tyr
    50                  55                  60

Ser Glu Thr His Tyr Ser Ser Asp Asp Arg Glu Ile Thr Thr Asn Pro
65                  70                  75                  80

Ser Val Glu Asp His Cys Tyr Tyr His Gly Arg Ile Gln Asn Asp Ala
                85                  90                  95
```

-continued

Glu Ser Thr Ala Ser Ile Ser Ala Cys Asn Gly Leu Lys Gly His Phe
                100                 105                 110

Lys Leu Arg Gly Glu Thr Tyr Phe Ile Glu Pro Leu Lys Ile Pro Asp
            115                 120                 125

Ser Glu Ala His Ala Val Tyr Lys Tyr Glu Asn Ile Glu Asn Glu Asp
        130                 135                 140

Glu Ala Pro Lys Met Cys Gly Val Thr Gln Asp Asn Trp Glu Ser Asp
145                 150                 155                 160

Glu Pro Ile Lys Lys Thr Leu Gly Leu Ile Glu Asn Leu Tyr Phe Gln
                165                 170                 175

Ser Val Pro Pro His Glu Arg Lys Phe Glu Lys Lys Phe Ile Glu Leu
            180                 185                 190

Val Val Val Val Asp His Ser Met Val Thr Lys Tyr Asn Asn Asp Ser
        195                 200                 205

Thr Ala Ile Arg Thr Trp Ile Tyr Glu Met Leu Asn Thr Val Asn Glu
210                 215                 220

Ile Tyr Leu Pro Phe Asn Ile Arg Val Ala Leu Val Gly Leu Glu Phe
225                 230                 235                 240

Trp Cys Asn Gly Asp Leu Ile Asn Val Thr Ser Thr Ala Asp Asp Thr
                245                 250                 255

Leu His Ser Phe Gly Glu Trp Arg Ala Ser Asp Leu Leu Asn Arg Lys
            260                 265                 270

Arg His Asp His Ala Gln Leu Leu Thr Asn Val Thr Leu Asp His Ser
        275                 280                 285

Thr Leu Gly Ile Thr Phe Val Tyr Gly Met Cys Lys Ser Asp Arg Ser
290                 295                 300

Val Glu Leu Ile Leu Asp Tyr Ser Asn Ile Thr Phe Asn Met Ala Tyr
305                 310                 315                 320

Ile Ile Ala His Glu Met Gly His Ser Leu Gly Met Leu His Asp Thr
                325                 330                 335

Lys Phe Cys Thr Cys Gly Ala Lys Pro Cys Ile Met Phe Gly Lys Glu
            340                 345                 350

Ser Ile Pro Pro Pro Lys Glu Phe Ser Ser Cys Ser Tyr Asp Gln Tyr
        355                 360                 365

Asn Lys Tyr Leu Leu Lys Tyr Asn Pro Lys Cys Ile Leu Asp Ser Pro
370                 375                 380

Leu Arg Lys Asp Ile Ala Ser Pro Ala Val Cys Gly Asn Glu Ile Trp
385                 390                 395                 400

Glu Glu Gly Glu Glu Cys Asp Cys Gly Ser Pro Ala Asp Cys Arg Asn
                405                 410                 415

Pro Cys Cys Asp Ala Ala Thr Cys Lys Leu Lys Pro Gly Ala Glu Cys
            420                 425                 430

Gly Asn Gly Glu Cys Cys Asp Lys Cys Lys Ile Arg Lys Ala Gly Thr
        435                 440                 445

Glu Cys Arg Pro Ala Arg Asp Asp Cys Asp Val Ala Glu His Cys Thr
450                 455                 460

Gly Gln Ser Ala Glu Cys Pro Arg Asn Glu Phe Gln Arg Asn Gly Gln
465                 470                 475                 480

Pro Cys Leu Asn Asn Ser Gly Tyr Cys Tyr Asn Gly Asp Cys Pro Ile
                485                 490                 495

Met Leu Asn Gln Cys Ile Ala Leu Phe Ser Pro Ser Ala Thr Val Ala
            500                 505                 510

Gln Asp Ser Cys Phe Gln Arg Asn Leu Gln Gly Ser Tyr Tyr Gly Tyr

```
            515                 520                 525
Cys Thr Lys Glu Ile Gly Tyr Tyr Gly Lys Arg Phe Pro Cys Ala Pro
        530                 535                 540

Gln Asp Val Lys Cys Gly Arg Leu Tyr Cys Leu Asp Asn Ser Phe Lys
545                 550                 555                 560

Lys Asn Met Arg Cys Lys Asn Asp Tyr Ser Tyr Ala Asp Glu Asn Lys
                565                 570                 575

Gly Ile Val Glu Pro Gly Thr Lys Cys Glu Asp Gly Val Cys Ile
            580                 585                 590

Asn Arg Lys Cys Val Asp Val Asn Thr Ala Tyr
            595                 600

<210> SEQ ID NO 57
<211> LENGTH: 426
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Val Pro Pro His Glu Arg Lys Phe Glu Lys Phe Ile Glu Leu Val
1               5                   10                  15

Val Val Val Asp His Ser Met Val Thr Lys Tyr Asn Asn Asp Ser Thr
            20                  25                  30

Ala Ile Arg Thr Trp Ile Tyr Glu Met Leu Asn Thr Val Asn Glu Ile
        35                  40                  45

Tyr Leu Pro Phe Asn Ile Arg Val Ala Leu Val Gly Leu Glu Phe Trp
    50                  55                  60

Cys Asn Gly Asp Leu Ile Asn Val Thr Ser Thr Ala Asp Asp Thr Leu
65                  70                  75                  80

His Ser Phe Gly Glu Trp Arg Ala Ser Asp Leu Leu Asn Arg Lys Arg
                85                  90                  95

His Asp His Ala Gln Leu Leu Thr Asn Val Thr Leu Asp His Ser Thr
            100                 105                 110

Leu Gly Ile Thr Phe Val Tyr Gly Met Cys Lys Ser Asp Arg Ser Val
        115                 120                 125

Glu Leu Ile Leu Asp Tyr Ser Asn Ile Thr Phe Asn Met Ala Tyr Ile
    130                 135                 140

Ile Ala His Glu Met Gly His Ser Leu Gly Met Leu His Asp Thr Lys
145                 150                 155                 160

Phe Cys Thr Cys Gly Ala Lys Pro Cys Ile Met Phe Gly Lys Glu Ser
                165                 170                 175

Ile Pro Pro Pro Lys Glu Phe Ser Ser Cys Ser Tyr Asp Gln Tyr Asn
            180                 185                 190

Lys Tyr Leu Leu Lys Tyr Asn Pro Lys Cys Ile Leu Asp Ser Pro Leu
        195                 200                 205

Arg Lys Asp Ile Ala Ser Pro Ala Val Cys Gly Asn Glu Ile Trp Glu
    210                 215                 220

Glu Gly Glu Glu Cys Asp Cys Gly Ser Pro Ala Asp Cys Arg Asn Pro
225                 230                 235                 240

Cys Cys Asp Ala Ala Thr Cys Lys Leu Lys Pro Gly Ala Glu Cys Gly
                245                 250                 255

Asn Gly Glu Cys Cys Asp Lys Cys Lys Ile Arg Lys Ala Gly Thr Glu
            260                 265                 270
```

-continued

```
Cys Arg Pro Ala Arg Asp Asp Cys Asp Val Ala Glu His Cys Thr Gly
        275                 280                 285

Gln Ser Ala Glu Cys Pro Arg Asn Glu Phe Gln Arg Asn Gly Gln Pro
    290                 295                 300

Cys Leu Asn Asn Ser Gly Tyr Cys Tyr Asn Gly Asp Cys Pro Ile Met
305                 310                 315                 320

Leu Asn Gln Cys Ile Ala Leu Phe Ser Pro Ser Ala Thr Val Ala Gln
            325                 330                 335

Asp Ser Cys Phe Gln Arg Asn Leu Gln Gly Ser Tyr Tyr Gly Tyr Cys
            340                 345                 350

Thr Lys Glu Ile Gly Tyr Tyr Gly Lys Arg Phe Pro Cys Ala Pro Gln
        355                 360                 365

Asp Val Lys Cys Gly Arg Leu Tyr Cys Leu Asp Asn Ser Phe Lys Lys
    370                 375                 380

Asn Met Arg Cys Lys Asn Asp Tyr Ser Tyr Ala Asp Glu Asn Lys Gly
385                 390                 395                 400

Ile Val Glu Pro Gly Thr Lys Cys Glu Asp Gly Lys Val Cys Ile Asn
            405                 410                 415

Arg Lys Cys Val Asp Val Asn Thr Ala Tyr
            420                 425
```

CLOTTING COMPOSITION

FIELD OF THE INVENTION

The present invention relates to improved clotting compositions for producing high quality blood serum samples for analyte testing. In particular, the present invention relates to the use of prothrombin activators in combination with stabilizing agents such as colloids for producing high quality blood serum samples for analyte testing, such as for pathology testing and other biological assays. The present invention also relates to associated methods for preparing clotting compositions, tubes, kits and methods of diagnosis, prognosis and monitoring for responsiveness to therapy.

CROSS REFERENCE TO RELATED APPLICATIONS

The present application is a continuation of U.S. patent application Ser. No. 15/518,215, filed Apr. 10, 2017, which is a national stage of International Application No. PCT/AU2015/000629, filed Oct. 23, 2015, which claims priority to Australian Patent Application No. 2014904241, filed Oct. 23, 2014, all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 29, 2020, is named 116073-0102_SL.txt and is 312 KB in size.

STATEMENT REGARDING FEDERALLY FUNDED RESEARCH

Not applicable.

BACKGROUND TO THE INVENTION

Serum is typically produced by allowing a blood sample to clot and then centrifuging the sample to separate the blood clot, including cells, from the serum. Plastic tubes (in place of glass) are now typically used and require procoagulants, also known as clot activators, to enhance the clotting process. Procoagulants use either intrinsic or extrinsic pathways to achieve clot formation.

Clot formation by the intrinsic pathway is surface-dependent, whereby a greater density of activating surface sites enhances clotting time. Typically, siliceous substances such as glass, silica, kaolin, bentonite and diatomaceous earth are used in plastic tubes to accelerate clot formation through the intrinsic pathway to achieve contact activation. However, clotting via the intrinsic pathway is relatively slow, typically requiring 30 to 60 minutes.

Clot activation via the extrinsic pathway involves coagulation that is initiated by adding substances that are extrinsic to blood and which involve a biochemical reaction in a concentration-dependent manner. Clot activators that operate via the extrinsic pathway include ellagic acid, thrombin, snake venom components and thromboplastin. Although these clot activators produce rapid clotting in 10 to 20 minutes, the clots that are formed are often gelatinous and do not easily separate from serum.

Serum is usually preferred over plasma for analyte testing unless urgent results are required, in which case the clotting time for a serum tube is considered too long. Even with existing procoagulants, in most commercial tubes the minimum required clotting time recommended by manufacturers is 30 minutes for blood samples from normal patients, and much longer (typically 60 minutes or longer) for samples from patients taking anti-clotting therapeutic agents such as heparin. For patient samples from emergency situations (emergency departments, intensive care, operating theatres etc.) and samples from catherisation laboratories, the time is too long and therefore plasma, which can be produced much faster, is often preferred over serum.

Plasma is formed by collecting blood in tubes containing anticoagulants followed by centrifugation which can be performed immediately after collection to separate the cells and thus obtain plasma for analysis. Lithium heparin is the most commonly used anticoagulant in these tubes. Citrate, sodium fluoride/potassium oxalate and EDTA are other anticoagulants that are used in some tubes to produce plasma for estimation of a small number of other analytes.

The coagulation process in preparing a serum sample consumes fibrinogen and entraps platelets and other cells within a network of fibrin. Upon centrifugation, the serum is separated from the clot, either by a serum separator in the collection device or by aliquoting the serum into a secondary container, to prevent contact with the cells. This separation permits the sample to remain stable for extended periods of time. This stability is particularly important if samples are not analysed immediately, or if re-analysis or additional analyses are required.

For some serum samples, coagulation remains incomplete after the recommended waiting times. This problem of incomplete clotting, or latent clotting, in samples is especially prevalent in patients on anti-clotting therapy or specimens collected from anticoagulated taps or cannulae. Such blood can take much longer than the manufacturers recommended waiting time to clot, or in fact may never fully clot in a standard serum tube (e.g. blood from cardiac surgery patients who are fully heparinised).

If a serum sample is centrifuged before clotting is complete, clotting can continue in the serum, as the remaining fibrinogen is converted to fibrin, leading to clots, microclots or formation of fibrin strings capable of causing analyser or analyte-specific problems. The formation of microclots and fibrinogen strings during sample preparation may also occur in plasma tubes due to the lack of timely inversion of lithium heparin tubes after blood collection. While heparin prevents clot formation, it cannot disintegrate clots upon contact. Hence, clots will remain in the tube regardless of further contact with heparin. Likewise clotting can also occur in other anticoagulated tubes (e.g. EDTA). Lithium heparin plasma tubes can also allow formation of insoluble fibrin as result of the stimulation of platelet factor 4 (PL4) from alpha granules of platelets during platelet aggregation, thereby neutralising heparin.

Additionally, other patient factors such as disease state and medication can both diminish the efficacy of heparin activity and lead to increased fibrin formation. Over time, heparin activity in stored lithium heparin blood specimens is decreased, mainly due to PL4 activity. The formation of insoluble fibrin is enhanced when plasma is stored at low temperatures.

Even the smallest clots are capable of producing clinically significant errors and/or cause automatic analysers to clog. Indeed, this problem is becoming more prevalent as the volumes used in new automated analysers are continually reducing over time plus the increasing number of patients on anticoagulants. Clogging of analysers means that laboratory workflow is disrupted, and analysers are subject to down time and require cleaning and may require replacement of affected parts. Thus, for accuracy, samples must be manually checked by eye or using automated detection systems if available to ensure they are free of fibrin strands or clots. If strands or clots of insoluble material are present, the sample requires sub-sampling into a new container and re-centrifugation prior to test analysis. Samples that exhibit repeated latent clotting may need to be transferred to a lithium heparin tube to stop ongoing clotting. These actions take additional time. Further, fibrin strands or clots are not always detected (e.g. they may even occur after analyser sampling), and consequential sampling errors may lead to patient care decisions being made on inaccurate results.

Specimens obtained in plasma tubes, specifically lithium heparin plasma, may also be contaminated with cells. Lithium heparin gel tubes when centrifuged will always present a small "buffy coat like layer" on top of the gel at the bottom of the plasma. This layer contains fibrin, cells and cell stroma. The rapid gel movement during centrifugation leaves some cells in the plasma The rapid gel and blood cell movement during centrifugation causes the gel to form the barrier between the cells and the plasma and leaves some cells in the plasma. If the plasma specimen is mixed (e.g. during sub-sampling or handling), it will become turbid due to suspension of cell-containing material and fibrin, which decreases the specimen integrity. In addition, platelet aggregates can form which may also contain fibrin and/or white blood cells. These aggregates can be large enough to be visible to the unaided eye and have been termed "white particulate matter" due to their typical white colour, and present similar problems to incomplete clotting discussed above. The presence of cells in the sample can therefore affect analyte concentrations. Certain analytes (e.g. glucose) may be decreased by cell activity and others may be increased by leakage or cell lysis (e.g. lactate dehydrogenase, potassium or phosphate).

Although generally there is no difference in concentration of analytes measured in serum or plasma tubes, there are some exceptions. Plasma tubes that use heparin are not suitable for heparin analysis or cell-based assays. Lithium heparin plasma tubes are not suitable for lithium analysis. Plasma may be unreliable for additional testing or re-testing, due to the presence of cells and insoluble fibrin formation upon prolonged storage at 2-8° C. Further, some serum or plasma tubes may produce inaccurate results of analyte levels due to interaction with procoagulant or anticoagulant agents within the tubes.

It is also desirable to reduce the sample size needed for testing, especially in critically ill patients, patients receiving blood transfusions, and infants, in order to reduce the volume of blood taken from a patient. It is therefore optimal to be able to run all necessary tests using a sample taken in a single blood collection tube. To achieve this, testing methods have been developed using very small sample volumes (e.g. 2 µL) so that typically one serum or plasma tube is used for at least 21 tests, but can be used for between 50-60 or even 70-80 tests, depending on the volume of sample needed for each test. However, where there is doubt over the accuracy of measuring a particular analyte in a serum or plasma tube, it may be necessary to take both a serum tube and a plasma tube from the patient, and doing so defeats the goal of reducing the volume of blood taken from the patient.

Thrombin-containing tubes have been developed as faster clotting tubes. Thrombin possesses both procoagulant and proteolytic activity, and thrombin is known to have high specificity for cutting bonds in fibrinogen, activated protein C (APC) and Factor Va. However, it has been found that thrombin-containing tubes cannot be used with all blood samples. Thrombin is known to be rapidly and completely inhibited by the heparin-antithrombin III complex present in heparinised blood samples. For example, it has been reported that BD RST tubes are ineffective in clotting patient samples containing high doses of heparin (see, for example, Dimeski et al., 2010).

Problems arising from the use of current methodologies for serum and plasma preparation from blood show that improvements are required to achieve timely, reliable analytical results from a wider variety of blood samples generally.

In response to this need, it was previously shown in International patent application no. PCT/AU2011/001221, published as WO 2012/037609 (the entire contents of which is incorporated herein by reference), that the use of prothrombin activators isolated from snake venom are able to clot blood samples to produce high quality serum for use in analyte testing procedures.

It has now been demonstrated that the use of prothrombin activators isolated from snake venom, when formulated as a clotting composition in combination with one or more additional agents such as a colloid, significantly increases the stability of the clotting composition. This increased stability is significant because of the capacity to manufacture, sterilize, transport and store clotting compositions (for example, in the form of a collection tube) without significant loss of clotting activity under conditions that would previously have compromised the efficacy of such compositions. For example, the compositions of the present invention are stable after sterilisation involving irradiation, storage at elevated temperatures and storage for extended periods of time.

SUMMARY OF THE INVENTION

In a first aspect of the present invention, there is provided a clotting composition for preparing a serum sample, wherein the clotting composition comprises a prothrombin activator and a stabilizing agent. In some embodiments, the stabilizing agent may be a colloid.

In a second aspect of the present invention, there is provided a method for preparing the clotting composition of the first aspect, wherein the method comprises providing a prothrombin activator and a stabilizing agent. In some embodiments, the stabilizing agent may be a colloid.

In a third aspect of the present invention, there is provided a kit for preparing a serum sample, wherein the kit comprises a prothrombin activator and a stabilizing agent. In some embodiments, the stabilizing agent may be a colloid.

In a fourth aspect of the present invention, there is provided a container comprising a clotting composition for preparing a serum sample, wherein the clotting composition comprises a prothrombin activator and a stabilizing agent. In some embodiments, the stabilizing agent may be a colloid. In particular embodiments, the container is a blood collection tube, the prothrombin activator is OsPa or Ecarin and the colloid is gelofusine or Bovine Serum Albumin.

In a fifth aspect of the present invention, there is provided a method for preparing a serum sample, wherein the method comprises contacting a blood sample with the clotting composition of the first aspect for a time and under conditions sufficient to cause clotting of the blood sample, and optionally, separating serum from clotted cells, thereby preparing a serum sample. The clotted cells may include red blood cells, white blood cells, platelets and cellular stroma.

In a sixth aspect of the present invention, there is provided a serum sample produced by the method of the fifth aspect.

In a seventh aspect of the present invention, there is provided a method for diagnosing a disease or condition in a subject, wherein the method comprises providing a blood sample from the subject, preparing a serum sample from the blood sample in accordance with the fifth aspect of the present invention, and testing the serum sample for the presence or absence of an analyte in the serum sample, or for an indicative level or concentration of an analyte in the serum sample, wherein the presence, absence or indicative level or concentration of the analyte is indicative of the disease or condition in the subject.

In an eighth aspect of the present invention, there is provided a method for providing a prognosis for a subject, wherein the method comprises providing a blood sample from the subject, preparing a serum sample from the blood sample in accordance with the fifth aspect of the present invention, and testing the serum sample for the presence or absence of an analyte in the serum sample, or for an indicative level or concentration of an analyte in the serum sample, wherein the presence, absence or indicative level or concentration of the analyte is indicative of the prognosis for the subject.

In a ninth aspect of the present invention, there is provided a method for monitoring the responsiveness of a subject to a therapy, wherein the method comprises providing a blood sample from the subject, preparing a serum sample from the blood sample in accordance with the fifth aspect of the present invention, and testing the serum sample for the presence or absence of an analyte in the serum sample, or for an indicative level or concentration of an analyte in the serum sample, wherein the presence, absence or indicative level or concentration of the analyte is indicative of the responsiveness of the subject to the therapy.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much 15, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference or full-length polynucleotide or polypeptide sequence, refers to a fragment that has at least about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of the activity of a reference sequence. Included within the scope of the present invention are biologically active fragments, including those of at least about 18, 19, 20, 21, 22, 23, 24, 25, 26, 27, 28, 29, 30, 40, 50, 60, 70, 80, 90, 100, 120, 140, 160, 180, 200, 250, 300, 400, 500, 600, 700, 800, 900, 1,000, 1,500, 2,000 nucleotides or residues in length, which comprise or encode an activity of a reference polynucleotide or polypeptide. Representative biologically active fragments generally participate in an interaction, e.g. an intramolecular or an inter-molecular interaction. An inter-molecular interaction can be a specific binding interaction or an enzymatic interaction (e.g., the interaction can be transient and a covalent bond is formed or broken). Biologically active fragments of a full-length polypeptide include peptides that may comprise amino acid sequences sufficiently similar to or derived from the amino acid sequences of a (putative) full-length polypeptide. Typically, biologically active fragments comprise a domain or motif with at least one activity of a full-length polypeptide. Suitably, the biologically-active fragment has no less than about 1%, 10%, 25% or 50% of an activity of the full-length polypeptide from which it is derived.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridisation between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "derivable" includes, and may be used interchangeably with, the terms "obtainable" and "isolatable". Compositions or other subject matter of the present invention that is "derivable", "obtainable" or "isolatable" from a particular source or process include not only compositions or other matter derived, obtained or isolated from that source or process, but also the same compositions or matter however sourced or produced, for example, through recombinant DNA technology or other genetic engineering methods.

As used herein, the term "detecting an analyte" means determining the presence, absence, amount, level or concentration of one or more analytes in a sample.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of nucleic or amino acids that are identical or constitute conservative substitutions. Homology may be determined using sequence comparison programs such as GAP (Devereux et al., 1984) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

By "isolated" is meant material that is substantially or essentially free from components that normally accompany it in its native state. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances.

The terms "derived from" and "derivable" include, and may be used interchangeably with, the terms "obtained", "obtainable", "isolated" and "isolatable". Compositions or other matter of the present invention that are "derived from", "derivable", "obtained", "obtainable", "isolated" or "isolatable" from a particular source or process include not only compositions or other matter so derived, obtained or isolated from that source or process, but also the same compositions or matter however sourced or produced. For example, a prothrombin activator derived or derivable from snake venom may include not only a prothrombin activator that is isolated from snake venom, but also the same prothrombin activator expressed from a vector or other expression system through recombinant DNA technology.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "patient", "subject" and "individual" are used interchangeably and refer to patients, subjects and individuals of human or other mammals and includes any one for whom it is desired to detect analyte levels or to diagnose the presence, absence or severity of a disease or condition using the invention. However, it will be understood that "patient" does not imply that symptoms are present. Suitable mammals that fall within the scope of the invention include, but are not restricted to, primates (e.g. humans, chimpanzees) livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes).

The term "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridise with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "polypeptide variant" refers to polypeptides that are distinguished from a reference polypeptide by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridise and serve as a site for the initiation of synthesis. By "substantially complementary", it is meant that the primer is sufficiently complementary to hybridise with a target polynucleotide. Preferably, the primer contains no mismatches with the template to which it is designed to hybridise but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridisation conditions. Probes can be labelled directly or indirectly.

The term "recombinant" when used with reference, for example, to a cell, nucleic acid, protein or vector, indicates that the cell, nucleic acid, protein or vector has been modified by the introduction of a heterologous nucleic acid or protein or by the alteration of a native nucleic acid or protein, or that the cell is derived from a cell so modified. Accordingly, "recombinant" cells express genes that are not found within the native (non-recombinant) form of the cell or express native genes that are otherwise abnormally expressed, under expressed or not expressed at all. By the term "recombinant nucleic acid" is meant a nucleic acid, originally formed in vitro, in general, by the manipulation of a nucleic acid, for example, using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered "recombinant" for the purposes of this invention. It is understood that once a recombinant nucleic acid is made and reintroduced into a host cell or organism, it will replicate non-recombinantly, i.e., using the in vivo cellular machinery of the host cell rather than in vitro manipulations. However, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "reference result" includes a result taken from the same subject at a different time, a result from a normal subject or a group of normal subjects, or a reference standard used in an analytical test.

By "regulatory element" or "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" may be understood to mean the "match percentage" calculated by the DNASIS computer program (Version 2.5 for Windows; available from Hitachi Software Engineering Co., Ltd., South San Francisco, Calif., USA) using standard defaults as used in the reference material accompanying the software.

The term "sequence similarity" refers to the percentage number of amino acids that are identical or constitute conservative substitutions as defined in Table 2 infra. Similarity may be determined using sequence comparison programs such as GAP (Devereux et al., 1984). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997. A detailed discussion of sequence analysis can be found in Unit 19.3 of Ausubel et al., "Current Protocols in Molecular Biology", John Wiley & Sons Inc, 1994-1998, Chapter 15.

The phrase "stabilizing agent" as used herein includes any molecule that is capable of contributing to the stability of a clotting composition comprising a prothrombin activator, such as by preserving, increasing, prolonging or otherwise enhancing the ability of a clotting composition to clot blood relative to a given unit of time. Such stabilization may therefore result in a clotting composition that is able to clot blood in less time than it would take to clot blood in the absence of the stabilizing agent. The time taken for the clotting composition, in combination with the stabilizing agent, to clot blood may be less time than it would take to clot blood in the absence of the stabilizing agent due to a range of factors, including, but not limited to, preserving, increasing, prolonging or otherwise enhancing the clotting activity of the clotting composition by the stabilizing agent, especially in circumstances where the clotting activity of the clotting composition would otherwise be compromised, for example, due to exposure of the clotting composition to various environmental conditions, such as during the process of manufacturing the clotting composition, including exposure to heat and sterilizing radiation, as well as the storage time and storage conditions of the clotting composition, including temperature and humidity, and in addition the transportation conditions of the clotting composition, including temperature, humidity and atmospheric pressure.

"Stringency" as used herein, refers to the temperature and ionic strength conditions, and presence or absence of certain organic solvents, during hybridisation and washing procedures. The higher the stringency, the higher will be the degree of complementarity between immobilized target nucleotide sequences and the labelled probe polynucleotide sequences that remain hybridised to the target after washing. The term "high stringency" refers to temperature and ionic conditions under which only nucleotide sequences having a high frequency of complementary bases will hybridise. The stringency required is nucleotide sequence dependent and depends upon the various components present during hybridisation. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridises to a complementary probe.

The term "transformation" means alteration of the genotype of an organism, for example a bacterium, yeast, mammal, avian, reptile, fish or plant, by the introduction of a foreign or endogenous nucleic acid.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integral with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

The reference to any prior art in this specification is not, and should not be taken as an acknowledgement or any form of suggestion that prior art forms part of the common general knowledge of the person skilled in the art.

The entire content of all publications, patents, patent applications and other material recited in this specification is incorporated herein by reference.

BRIEF DESCRIPTION OF THE SEQUENCE LISTING

SEQ ID NO: 1 is a polypeptide sequence for ecarin from *Echis carinatus*.

SEQ ID NO: 2 is a partial polypeptide sequence for basparin from *Bothrops asper* venom.

SEQ ID NO: 3 is a partial polypeptide sequence for carinactivase-1 from *Echis carinatus* venom (prepared as described in Yamada, D., et al., (1996))—62 kDa subunit.

SEQ ID NO: 4 is a partial polypeptide sequence for multactivase from *Echis multisquamatus* venom (prepared as described in Yamada, D., et al., (1997)).

SEQ ID NO: 5 is a nucleotide sequence encoding Factor V-like component of PtPA (or pseutarin C) from *Pseudonaja textilis*.

SEQ ID NO: 6 is a nucleotide sequence encoding Factor V-like component of PtPA (or pseutarin C) from *Pseudonaja textilis*.

SEQ ID NO: 7 is a polypeptide sequence for Factor V-like component of PtPA (or pseutarin C) from *Pseudonaja textilis*.

SEQ ID NO: 8 is a polypeptide sequence for Factor V-like component of PtPA (or pseutarin C) from *Pseudonaja textilis*.

SEQ ID NO: 9 is a nucleotide sequence encoding Factor V-like component of OsPA (or oscutarin C) from *Oxyuranus scutellatus*.

SEQ ID NO: 10 is a nucleotide sequence encoding Factor V-like component of OsPA (or oscutarin C) from *Oxyuranus scutellatus scutellatus*.

SEQ ID NO: 11 is a polypeptide sequence for Factor V-like component of OsPA (or oscutarin C) from *Oxyuranus scutellatus scutellatus*.

SEQ ID NO: 12 is a polypeptide sequence for Factor V-like component of OsPA (or oscutarin C) from *Oxyuranus scutellatus*.

SEQ ID NO: 13 is a polypeptide sequence for Factor V-like component of OsPA (or oscutarin C) from *Oxyuranus scutellatus*.

SEQ ID NO: 14 is a nucleotide sequence encoding Factor V-like component of omicarin C from *Oxyuranus microlepidotus*.

SEQ ID NO: 15 is a nucleotide sequence encoding factor V from *Homo sapiens*.

SEQ ID NO: 16 is a polypeptide sequence for factor V from *Homo sapiens*.

SEQ ID NO: 17 is a nucleotide sequence encoding factor V from *Bos Taurus*.

SEQ ID NO: 18 is a polypeptide sequence for factor V from *Bos Taurus*.

SEQ ID NO: 19 is a nucleotide sequence encoding Factor X-like component of PtPA (or pseutarin C) from *Pseudonaja textilis*.

SEQ ID NO: 20 is a nucleotide sequence encoding Factor X-like component of PtPA (or pseutarin C) from *Pseudonaja textilis*.

SEQ ID NO: 21 is a nucleotide sequence encoding Factor X-like component of PtPA (or pseutarin C) from *Pseudonaja textilis*.

SEQ ID NO: 22 is a nucleotide sequence encoding Factor X-like component of PtPA (or pseutarin C) from *Pseudonaja textilis textilis*.

SEQ ID NO: 23 is a nucleotide sequence encoding Factor X-like component of PtPA (or pseutarin C) from *Pseudonaja textilis textilis*.

SEQ ID NO: 24 is a nucleotide sequence encoding Factor X-like component of PtPA (or pseutarin C) from *Pseudonaja textilis*.

SEQ ID NO: 25 is a nucleotide sequence encoding Factor X-like component of PtPA (or pseutarin C) from *Pseudonaja textilis*.

SEQ ID NO: 26 is a polypeptide sequence for Factor X-like component of PtPA (or pseutarin C) from *Pseudonaja textilis*.

SEQ ID NO: 27 is a polypeptide sequence for Factor X-like component of PtPA (or pseutarin C) from *Pseudonaja textilis*.

SEQ ID NO: 28 is a polypeptide sequence for Factor X-like component of PtPA (or pseutarin C) from *Pseudonaja textilis textilis*.

SEQ ID NO: 29 is a polypeptide sequence for Factor X-like component of PtPA (or pseutarin C) from *Pseudonaja textilis textilis*.

SEQ ID NO: 30 is a polypeptide sequence for Factor X-like component of PtPA (or pseutarin C) from *Pseudonaja textilis*.

SEQ ID NO: 31 is a nucleotide sequence encoding Factor X-like component of OsPA (or oscutarin C) from *Oxyuranus scutellatus*.

SEQ ID NO: 32 is a polypeptide sequence for Factor X-like component of OsPA (or oscutarin C) from *Oxyuranus scutellatus*.

SEQ ID NO: 33 is a nucleotide sequence encoding Factor X-like component of omicarin C from *Oxyuranus microlepidotus*.

SEQ ID NO: 34 is a polypeptide sequence for Factor X-like component of omicarin C from *Oxyuranus microlepidotus*.

SEQ ID NO: 35 is a nucleotide sequence encoding Factor X-like component of porpharin D from *Pseudechis porphyriacus*.

SEQ ID NO: 36 is a polypeptide sequence for Factor X-like component of porpharin D from *Pseudechis porphyriacus*.

SEQ ID NO: 37 is a nucleotide sequence encoding Factor X-like component of hopsarin D from *Hoplocephalus stephensii*.

SEQ ID NO: 38 is a polypeptide sequence for Factor X-like component of hopsarin D from *Hoplocephalus stephensii*.

SEQ ID NO: 39 is a nucleotide sequence encoding Factor X-like component of notecarin D from *Notechis scutatus*.

SEQ ID NO: 40 is a polypeptide sequence for Factor X-like component of notecarin D from *Notechis scutatus*.

SEQ ID NO: 41 is a nucleotide sequence encoding Factor X-like component of trocarin D from *Tropidechis carinatus*.

SEQ ID NO: 42 is a polypeptide sequence for Factor X-like component of trocarin D from *Tropidechis carinatus*.

SEQ ID NO: 43 is a nucleotide sequence encoding Factor X-like component of prothrombin activator from *Demansia vestigiata*.

SEQ ID NO: 44 is a polypeptide sequence for Factor X-like component of prothrombin activator from *Demansia vestigiata*.

SEQ ID NO: 45 is a nucleotide sequence encoding Factor X-like component of prothrombin activator from *Demansia vestigiata*.

SEQ ID NO: 46 is a polypeptide sequence for Factor X-like component of prothrombin activator from *Demansia vestigiata*.

SEQ ID NO: 47 is a nucleotide sequence encoding factor X from *Homo sapiens*.

SEQ ID NO: 48 is a polypeptide sequence for factor X from *Homo sapiens*.

SEQ ID NO: 49 is a nucleotide sequence encoding factor X from *Bos Taurus*.

SEQ ID NO: 50 is a polypeptide sequence for factor X from *Bos Taurus*.

SEQ ID NO: 51 is a partial polypeptide sequence for carinactivase-1 from *Echis carinatus* venom (prepared as described in Yamada, D., et al., (1996))—17 kDa subunit.

SEQ ID NO: 52 is a partial polypeptide sequence for carinactivase-1 from *Echis carinatus* venom (prepared as described in Yamada, D., et al., (1996))—14 kDa subunit.

SEQ ID NO: 53 is a polypeptide sequence for the uncleaved form of wild type ecarin from *Echis carinatus* venom.

SEQ ID NO: 54 is a polypeptide sequence for ecarin from *Echis carinatus* venom, wherein the signal peptide has been removed and a TEV protease site ENLYFQS has been inserted at the boundary between the propeptide and the mature domain.

SEQ ID NO: 55 is a polypeptide sequence for the mature form of wild type ecarin from *Echis carinatus* venom.

SEQ ID NO: 56 is a polypeptide sequence for a mutant form of ecarin from *Echis carinatus* venom, wherein the signal peptide has been removed and a TEV protease site ENLYFQS has been inserted at the boundary between the propeptide and the mature domain, and a P396S mutation has been introduced.

SEQ ID NO: 57 is a polypeptide sequence for the mature form of a P396S mutant ecarin from *Echis carinatus* venom.

BRIEF DESCRIPTION OF THE FIGURES

The present invention will now be described, by way of example only, with reference to the following figures.

DETAILED DESCRIPTION

Figure 1:
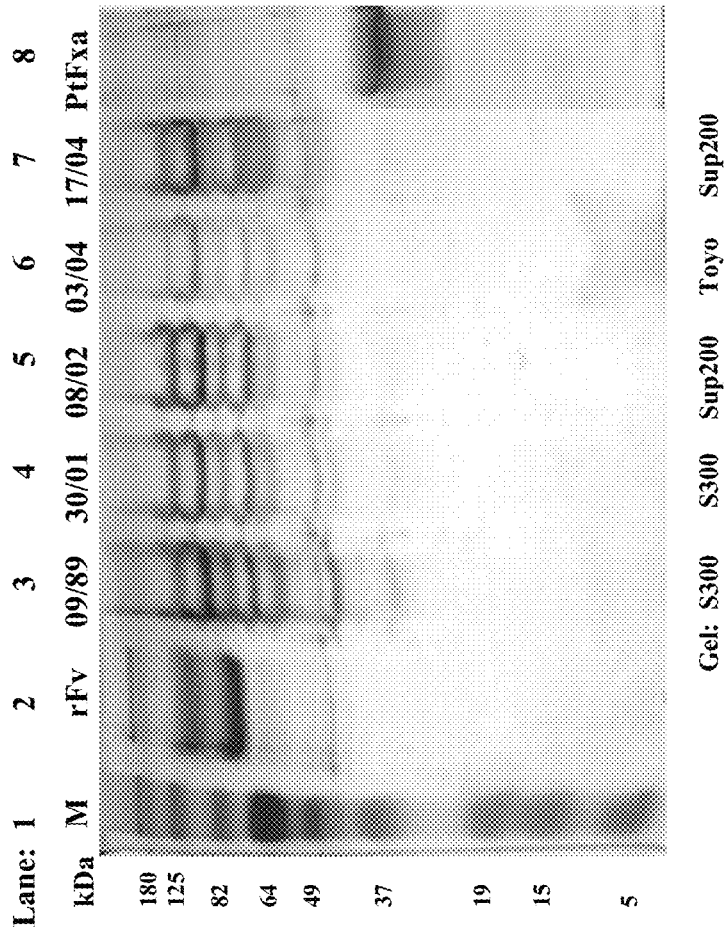
FIG. 1 shows SDS-PAGE gel patterns of rFv (Lane 2), five OsPA samples (Lanes 3, 4, 5, 6 and 7) separated by different gels and Purified Fxa (Lane 8). Markers are in Lane 1.
Figure 2:
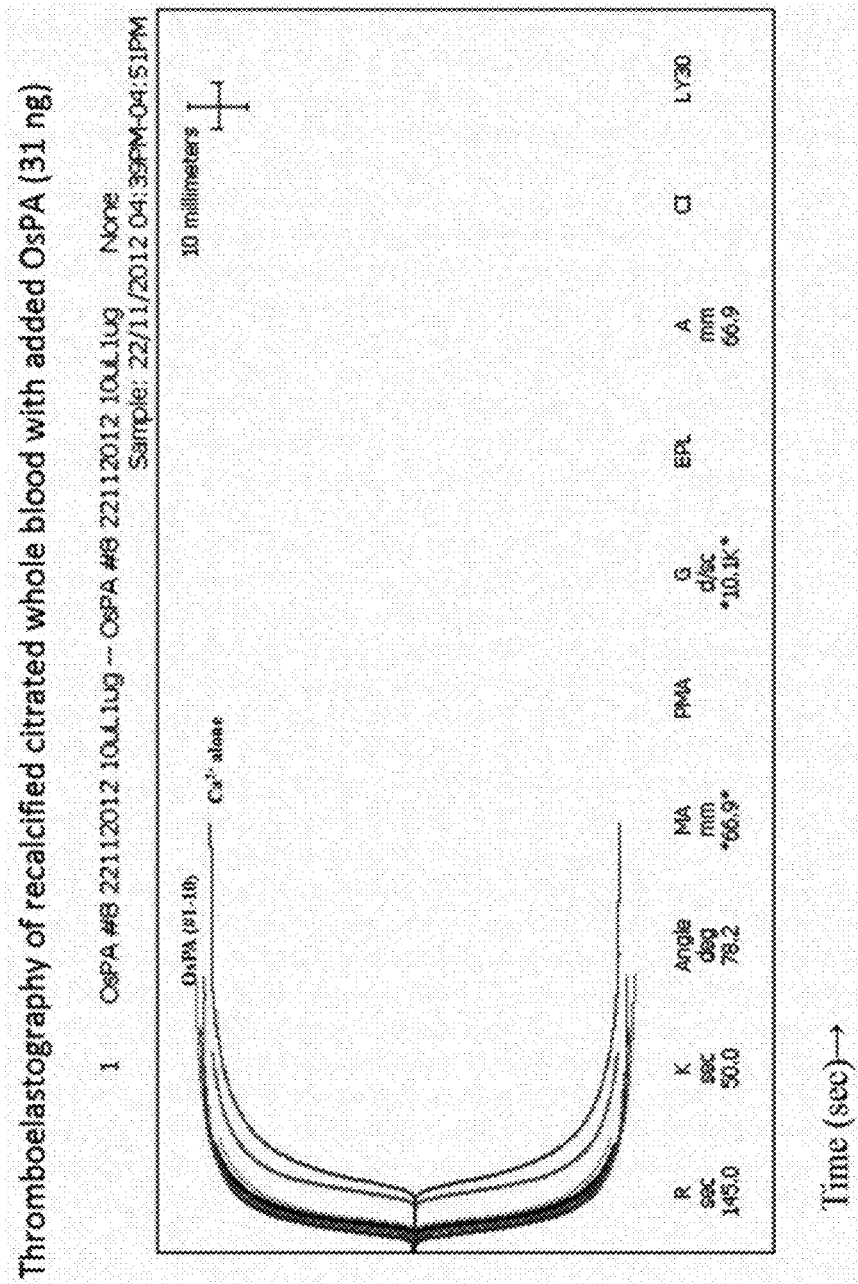
FIG. 2 shows Thromboelastograhic traces for the clotting of recalcified whole blood by 31 ng aliquots of each of the ten OsPA preparations. The 10 overlapping traces on the left (fast clotting) represent the ten preparations whereas the labelled+Ca traces represent duplicates of clotting by calcium alone.

The present inventors have found that the stability of clotting compositions comprising prothrombin activators is significantly increased when formulated in combination with one or more additional agents such as a colloid. This increased stability is significant because of the capacity to manufacture, sterilize, transport and store clotting compositions (for example, in the form of a collection tube) without significant loss of clotting activity under conditions that would previously have compromised the efficacy of such compositions. For example, the compositions of the present invention are stable after sterilisation involving radiation, storage at high temperatures and storage for extended periods of time. Dose response and ranging studies to determine the effective dose of OsPA to use in the clotting tube spray drying procedure were aimed at achieving clotting of whole blood in approximately 5 minutes. It is clearly shown that concentrations of OsPA of 0.1-1.0 ug in 4 mL of non-anti-coagulated blood will achieve this. The studies illustrate firstly in Example 1 that highly purified Coastal Taipan venom prothrombin activator (OsPA), a Group C prothrombin activator, can be purified from crude Taipan (Os) venom using gel filtration chromatography, for example, on a Superdex 200 column, the activity of which can be determined by clotting in recalcified citrated whole blood or via S-2222 chromogenic testing designed for detection of Factor Xa, or by S-2238 chromogenic testing designed for the testing of thrombin. Example 1 also details how the pooled OsPA containing fractions can then be concentrated using, for example, an Amicon ultrafiltration unit and prepared as a 50% glycerol solution for long term storage at −20° C. The glyercol stock can then be dialysed and freeze-dried as detailed in Example 1. Ecarin used in the Examples (extracted from *Echis Carinatus* venom) was purchased commercially and assayed as detailed in Example 1.

In order to achieve comparable results between experiments, standardised methods were developed. Example 2 details a standardised method of preparation of blood collection tubes with prothrombin activator solution and formulation components, involving a standard surfactant to coat the tube bottom and standardised tube drying methods. Example 3 details the standard irradiation protocols to approximate the sterilisation processes found in commercial blood collection tube manufacture. Blood samples to be used in assessing the blood collection tubes were tested using standard methods as detailed in Example 4 ensuring normal coagulation parameters and hence suitability for use in testing. Tests for clotting performance of the OsPA or other prothrombin activators were conducted using standard methods as detailed in Example 5 including a plasma clotting assay, visual assessment of clotting, Thromboerlastography (TEG) and Chromogenic assays. Standards for stability testing and analyte measurement of resultant serum are also included in Example 5, completing the standard test descriptions.

Formulations to improve the stability of OsPA in a blood collection tube are disclosed in Example 6, which compares tube drying conditions with and without the use of surfactants and a colloid, BSA. It is shown that the presence of surfactant and BSA colloid when dried with the Genevac, vacuum drying method give an improved clotting activity (reduced time to clot). Data in Example 6 also demonstrates an improvement with the addition of 0.1% BSA to OsPA without surfactant in tubes, however optimal efficacy is achieved with the addition of a surfactant coating. All subsequent Examples utilise a surfactant coating in the tube. Example 7 continues this experimental program showing a decline in clotting activity from TO when the formulation from Example 6 was stored at 25° C. for a period of 85 days. Example 8 builds on Examples 6 and 7 by testing a range of additional agents to enhance formulation stability including the colloids BSA (at a higher concentration) and Dextran. It is shown that BSA (0.5%) and dextran (0.5%), both increase the stability of OsPA at 25° C. for 99 days compared to buffer alone, with 1 μg OsPA able to clot blood in around 5 min. Example 9 uses the the colloid gelofusine (4% succinylated gelatin) and achieves stability for 1 μg OsPA after 211 days storage at 25° C. (with a 5 min clotting time). Data using fresh blood on tubes with this formulation is also included. Gelofusine was shown to have a greater effect on stability than 0.5% BSA or 0.5% Dextran, but with all colloids conferring greater stability than buffer. Example 10 shows that a combination of 0.5% Dextran and 0.5% BSA gives stability over 195 days at 25° C., and greater stability at 99 days than either colloid alone, as illustrated in Example 8. The gelofusine formulation was successfully stable at 50 C for 30 days in Example 11, indicating longer term stability is achievable. Gamma irradiation as used in the sterilisation of commercial tubes was trialed with OsPA tubes in Example 12 using the BSA/Dextran and gelofusine formulations and also a formulation with gelofusine and a non-reducing sugar (trehalose), exposing all samples to a 15 kGy dose. It was shown that OsPA formulated with either BSA/Dextran and gelofusine retained activity over baseline after irradiation, the protective effect increasing for gelofusine with the addition of trehalose. Another prothrombin activator ecarin, was successfully trialed with the gelofusine and trehalose formulation. Example 13 exposed ecarin formlated with 4% gelofusine to 25 kGy of gamma irradiation, demonstrating retention of a significant % of clotting activity. There was no significant difference in clotting activity between tubes which had been irradiated at TO and those which not been irradiated after 212 days storafe at room temperature. Example 14 tested OsPA formulated with gelofusine and a range of sugars and additional agents at room temperature and 50° C. and showed that the gelofusine and trehalose/sucrose formulations enabled acceptable clotting times after 10 weeks at 50° C. and at room temperature for over 12 m. Although with more limited stability data, lactulose shows promise as another stabilising sugar. Example 15 tested Ecarin formulated with gelofusine and a range of sugars and additional agents at room temperature and showed that the gelofusine and trehalose/sucrose formulations enabled acceptable clotting times after over 12 m at room temperature. Example 16 illustrates that there are no effects on analyte testing of the presence of gelofusine in the blood collection tubes.

In summary, the examples demonstrate the extraction processes for OsPA and the formulations required to achieve commercially acceptable stability (retention of clotting activity) for prothrombin activators such as OsPA or Ecarin in a blood collection tube with exposure to storage time, temperature and irradiation. In this regard, the stability enhancing properties of colloids were clearly demonstrated, in particular, gelofusine or BSA alone or in combination with additional agents.

Prothrombin Activators

The present invention is based in part on the finding that the stability of clotting compositions comprising prothrombin activators is significantly increased when formulated in combination with one or more additional agents such as a colloid.

In some embodiments, the prothrombin activator is an exogenous prothrombin activator. As used herein, an "exogenous prothrombin activator" means a prothrombin activator obtained from a source other than the blood sample from which the serum sample is to be prepared.

The prothrombin activators used in the present invention may comprise wild-type or naturally-occurring, recombinant, mutant or genetically engineered forms of prothrombin activators including those obtained, derived or derivable from any suitable organism, including snake, human, bovine and bacterial prothrombin activator.

In some embodiments of the present invention, the prothrombin activator is a snake prothrombin activator. Suitably, the prothrombin activator is a snake venom prothrombin activator. Snake venom prothrombin activators are generally classified in four groups (A, B, C, and D) depending on their structure, function and requirements for co-factors.

In particular embodiments, the snake venom prothrombin activator is a group A prothrombin activator. Group A prothrombin activators are metalloproteinases consisting of three domains: a metalloproteinase, a disintegrin, and a Cys-rich domain. The metalloproteinase domain contains the consensus sequence HEXXHXXGXXH, corresponding to the zinc-chelating active site. These prothrombin activators are found at least in several viper venoms, and include ecarin from *Echis carinatus* venom and basparin from *Bothrops asper* venom.

In particular embodiments, the snake venom prothrombin activator is a group B prothrombin activator. Group B prothrombin activators are metalloproteinases consisting of two subunits held non-covalently: a metalloproteinase and a C-type lectin-like disulfide-liked dimer. These prothrombin activators are found in several viper venoms, and include carinactivase-1 and carinactivase-2 from *Echis carinatus* venom and multactivase from *Echis multisquamatus* venom.

In particular embodiments, the snake venom prothrombin activator is a group C prothrombin activator. Group C prothrombin activators are serine proteases and resemble the mammalian factor Xa-factor Va complex. Pseutarin C (or PtPA) and oscutarin C (or OsPA) are group C prothrombin activators from the venoms of *Pseudonaja textilis* and *Oxyuranus scutellatus* respectively. Omicarin C is the prothrombin activator from *Oxyuranus microlepidotus* venom.

In particular embodiments, the snake venom prothrombin activator is a group D prothrombin activator. Group D prothrombin activators are serine proteases and are functionally similar to mammalian factor Xa. Porpharin D (from *Pseudechis porphyriacus*), notecarin D (from *Notechis scutatus scutatus*), trocarin D (from *Tropidechis carinatus*), hopsarin D (from *Hoplocephalus stephensi*), and notenarin D (from *Notechis ater niger*) are all group D prothrombin activators.

A review of snake prothrombin activators is provided in Kini, R. M. (2005), and of those specifically from the venom of Australian Elapids (group C and D prothrombin activators) is provided in St. Pierre et al. (2005), the contents of each are herein by reference in their entirety. These two reviews use the classification of snake prothrombin activators into groups A-D as described above. This classification supersedes the previous classification system using groups I-Ill (group I encompasses groups A and B; group II is now group D and group III is now group C), and sometimes additional groups IV (snake venom activators that cleave peptide bonds in prothrombin but do not convert the prothrombin to an enzymatically active product—i.e. thrombin or meizothrombin) and V (bacterial prothrombin activators) as described in earlier review articles, including Rosing, J. et al. (1991) and Rosing, J. et al. (1992), the contents of each being incorporated by reference in their entirety. For an explanation on the change to the classification system, see Kini, R, M., et al. (2001), the contents of which are incorporated by reference in its entirety.

In specific embodiments, the snake prothrombin activator is obtained from the Family Elapidae, illustrative examples of which include species from the genera *Demansia, Hoplocephalus, Notechis, Oxyuranus, Pseudechis, Pseudonaja, Rhinoplocephalus*, and *Tropidechis* including but not limited to *Demansia vestigiata, Hoplocephalus stephensii, Notechis ater humphreysi, Notechis ater niger, Notechis ater serventyi, Notechis flinkders, Notechis humphreysi, Notechis niger, Notechis occidentalis, Notechis scutatus, Notechis scutatus scutatus, Notechis serventyi, Oxyuranus microlepidotus, Oxyuranus scutellatus, Pseudechis porphyriacus, Pseudonaja affinis, Pseudonaja inframaculata, Pseudonaja nuchalis, Pseudonaja textilis, Rhinoplocephalus nigrescens*, and *Tropidechis carinatus*.

In specific embodiments, the snake prothrombin activator is obtained from the Family Viperidae, illustrative examples of which include species from the genera *Botrhops*, *Echis* and *Trimeresurus*, including but not limited to *Bothrops alternatus*, *Bothrops asper*, *Bothrops atrox*, *Bothrops atrox asper*, *Bothrops brasili*, *Bothrops castelnaudi*, *Bothrops columbiensis*, *Bothrops erythromelas*, *Bothrops fonsecai*, *Bothrops itapetiningae*, *Bothrops jararaca*, *Bothrops neuwiedi*, *Bothrops venezuelensis*, *Echis carinatus*, *Echis coloratus*, *Echis multisquamatus*, and *Trimeresurus okinavensis*.

In specific embodiments, the snake prothrombin activator is obtained from the Family Colubridae, illustrative examples of which include species from the genera *Dispholidus*, *Rhabdophis* and *Thelotomis*, including but not limited to *Dispholidus typus*, *Rhabdophis tigrinus tigrinus*, *Thelotomis kirtlandii*, and *Thelotomis capensis*.

In some embodiments the snake prothrombin activator is from or is obtained from snake venom. The purification and characterisation of PtPA from *P. textilis* snake venom is described in Masci (1986) and Masci et al., (1988), and OsPA from *O. scutellatus* venom is described in Speijer et al., (1986), all of which are incorporated by reference in their entirety. The purification and characterisation of ecarin from *Echis carinatus* venom is described in Morita, T et al. (1981) and Nishida, S et al. (1995), of carinactivase from *Echis carinatus* venom is described in Yamada, D et al. (1996), of multactivase from *Echis multisquamatus* is described in Yamada, D. et al., (1997), and of notecarin from *Notechis scutatus* is described in Tans, G et al., (1985), each of which are incorporated by reference in their entirety.

In certain embodiments, the prothrombin activator is a mammalian prothrombin activator. Mammalian prothrombin activators include those derived from human blood and/or tissue and those derived from bovine blood and/or tissue or recombinant versions of these proteins In certain embodiments, the prothrombin activator is a bacterial prothrombin activator. Bacterial prothrombin activators include those from *Staphylococcus aureus*, *Peptococcus indolicus*, *Bacteroides melaninogenicus*, and *Pseudomonas aeruginosa* (Rosing, J. et al. (1991).

As will be appreciated by those skilled in the art, the prothrombin activator may comprise, consist essentially of, or consist of one or more polypeptides. In some embodiments, the prothrombin activator comprises, consists essentially of, or consists of a single polypeptide. In other embodiments, the prothrombin activator comprises, consists essentially of, or consists of more than one polypeptide, including but not limited to complexes of polypeptides. Where the prothrombin activator comprises, consists essentially of, or consists of more than one polypeptide, each polypeptide may be from the organisms from the same or different genera, and/or the same or different species.

In certain embodiments, the prothrombin activator comprises an amino acid sequence selected from those set forth in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, 52, 53, 54, 55, 56 and 57 or comprises an amino acid sequence encoded by a nucleotide sequence selected from those set forth in SEQ ID NOs: 5, 6, 9, 10, 14, 15, 17, 19, 20, 21, 22, 23, 24, 25, 31, 33, 35, 37, 39, 41, 43, 45, 47, and 49.

In some embodiments, the prothrombin activator is derived or derivable from snake venom.

In some embodiments, the prothrombin activator is a serine protease Group C prothrombin activator resembling the mammalian factor Xa-factor Va complex.

In particular embodiments, the prothrombin activator is selected from the group consisting of Pseutarin C (or PtPA) and oscutarin C (or OsPA) derived or derivable from the venoms of *Pseudonaja textilis* and *Oxyuranus scutellatus*, respectively.

In a preferred embodiment, the prothrombin activator is oscutarin C (or OsPA) derived or derivable from the venom of *Oxyuranus scutellatus*.

In a particularly preferred embodiment, the prothrombin activator comprises the amino acid sequence set forth in SEQ ID NOs: 11, 12, 13 or 32, or comprises an amino acid sequence encoded by a nucleotide sequence selected from those set forth in SEQ ID NOs: 9, 10 or 31.

Chimeric Prothrombin Activators and Fusion Polypeptides

The present invention also contemplates the use of prothrombin activators comprising a chimeric polypeptide. As used herein, a "chimeric polypeptide" includes a first polypeptide component comprising a polypeptide obtained from a first organism linked to a second polypeptide component obtained from a second organism. In some embodiments, the first organism and the second organism are from different genera. In other embodiments, the first organism and the second organism are different species of the same genus. In certain embodiments, the prothrombin activator comprises a chimeric polypeptide that resembles a factor Xa-factor Va complex, wherein the first polypeptide comprises a factor Xa-like polypeptide and the second polypeptide comprises a factor Va-like polypeptide. In certain specific embodiments, the first polypeptide comprises an amino acid sequence selected from those set forth in SEQ ID NOs: 26, 27, 28, 29, 30, 32, 34, 36, 38, 40, 42, 44, 46, 48, and 50, or comprises an amino acid sequence encoded by a nucleotide sequence selected from those set forth in SEQ ID NOs: 19, 20, 21, 22, 23, 24, 25, 31, 33, 35, 37, 39, 41, 43, 45, 47, and 49, and the second polypeptide comprises an amino acid sequence selected from those set forth in SEQ ID NOs: 7, 8, 11, 12, 13, 16, and 18, or comprises an amino acid sequence encoded by a nucleotide sequence selected from those set forth in SEQ ID NOs: 5, 6, 9, 10, 14, 15, and 17.

The present invention also contemplates the use of prothrombin activators comprising a fusion polypeptide. As used herein, a "fusion polypeptide" includes a first polypeptide component linked to a second polypeptide component. The first polypeptide component may be obtained from a first organism and the second polypeptide component may be obtained from a second organism. In some embodiments, the first organism and the second organism are from different genera. In other embodiments, the first organism and the second organism are different species of the same genus. The first polypeptide component or the second polypeptide component of the fusion polypeptide can correspond to all or a portion (e.g., a fragment as described herein) of a wild-type or naturally occurring amino acid sequence. The second polypeptide component can be fused to the N-terminus or C-terminus of the first polypeptide component.

Fragments of Wild-Type or Naturally Occurring Polypeptides

The prothrombin activator may comprise a fragment of a full-length wild-type or naturally occurring polypeptide, wherein the prothrombin activator exhibits prothrombin activating activity.

Typically, fragments of a full-length polypeptide may participate in an interaction, for example an intramolecular or an intermolecular interaction. Such fragments include peptides comprising the amino acid sequences shown in SEQ ID NOs: 2, 3, 4, 51, and 52 and peptides comprising amino acid sequences sufficiently similar to or derived from the amino acid sequences of a (putative) full-length polypeptide, for example, the amino acid sequences shown in SEQ ID NOs: 1, 7, 8, 11, 12, 13, 16, 18, 26, 27, 28, 29, 30, 32, 34, 36, 38, 40, 42, 44, 46, 48, 50, 53, 54, 55, 56 and 57, or the amino acid sequences encoded by a nucleotide sequence selected from those set forth in SEQ ID NOs: 5, 6, 9, 10, 14, 15, 17, 19, 20, 21, 22, 23, 24, 25, 31, 33, 35, 37, 39, 41, 43, 45, 47, and 49, which includes less amino acids than a full-length polypeptide, and exhibit one activity of that polypeptide.

Variants of Naturally-Occurring Prothrombin Activators (Polypeptide)

The present invention also contemplates prothrombin activators comprising polypeptide(s) that is/are variant(s) of the wild-type or naturally-occurring polypeptide(s). Prothrombin activators comprising one or more variant polypeptides encompassed by the present invention are biologically active, that is, they continue to possess prothrombin activating activity.

Such "valiant" prothrombin activators include polypeptides derived from the native polypeptide, wherein the polypeptides are derived from the corresponding native polypeptide(s) by deletion (so-called truncation) or addition of one or more amino acids to the N-terminal and/or C-terminal end of the native polypeptide(s); deletion or addition of one or more amino acids at one or more sites in the native polypeptide(s); or substitution of one or more amino acids at one or more sites in the native polypeptide(s). These variant prothrombin activators may result from, for example, genetic polymorphism or human manipulation.

Further non-limiting examples of variant polypeptides include precursor polypeptide or polypeptide in zymogen form processed forms of a full-length or precursor polypeptide or polypeptide in zymogen form.

Variants of a wild-type or naturally-occurring polypeptide will have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence similarity or identity with the amino acid sequence for the wild-type or naturally-occurring polypeptide, including but not limited to the sequences in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, 52, 53 and 55 or the amino acid sequences encoded by the nucleotide sequences in SEQ ID NOs: 5, 6, 9, 10, 14, 15, 17, 19, 20, 21, 22, 23, 24, 25, 31, 33, 35, 37, 39, 41, 43, 45, 47, and 49, as determined by sequence alignment programs described elsewhere herein using default parameters. A variant of a wild-type or naturally-occurring polypeptide, which falls within the scope of a variant polypeptide, may differ from that polypeptide generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from the corresponding sequences in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, 52, 53 and 55 or the amino acid sequences encoded by the nucleotide sequences in SEQ ID NOs: 5, 6, 9, 10, 14, 15, 17, 19, 20, 21, 22, 23, 24, 25, 31, 33, 35, 37, 39, 41, 43, 45, 47, or 49, by at least 1 but by less than 15, 10 or 5 amino acid residues. In other embodiments, it differs from the corresponding sequences in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, 52, 53 and 55, or the amino acid sequences encoded by the nucleotide sequences in SEQ ID NOs: 5, 6, 9, 10, 14, 15, 17, 19, 20, 21, 22, 23, 24, 25, 31, 33, 35, 37, 39, 41, 43, 45, 47, or 49, by at least one residue but less than 20%, 15%, 10% or 5% of the residues.

A polypeptide may be altered in various ways including amino acid substitutions, deletions, truncations, and insertions. Methods for such manipulations are generally known in the art. For example, amino acid sequence variants of a polypeptide can be prepared by mutations in the DNA. Methods for mutagenesis and nucleotide sequence alterations are well known in the art. See, for example, Kunkel (1985), Kunkel et al., (1987), U.S. Pat. No. 4,873,192, Watson et al., (1987) and the references cited therein. Guidance as to appropriate amino acid substitutions that do not affect biological activity of the protein of interest may be found in the model of Dayhoff et al. (1978). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of polypeptides. Recursive ensemble mutagenesis (REM), a technique which enhances the frequency of functional mutants in the libraries, can be used in combination with the screening assays to identify polypeptide variants, see for example Arkin et al. (1992) and Delagrave et al. (1993). Conservative substitutions, such as exchanging one amino acid with another having similar properties, may be desirable as discussed in more detail below.

Variant polypeptides may contain conservative amino acid substitutions at various locations along their sequence, as compared to a parent (e.g., naturally-occurring or reference) amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g. histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g. PAM120 matrix and PAM250 matrix as disclosed for example by Dayhoff et al. (1978) and by Gonnet et al. (1992)), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 1.

TABLE 1

| Amino acid sub-classification | |
|---|---|
| Sub-classes | Amino acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and trypto- phan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants may be screened for biological activity.

TABLE 2

| Exemplary and preferred amino acid substitutions | | |
|---|---|---|
| Original residue | Exemplary substitutions | Preferred substitutions |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G. (1993).

Thus, a predicted non-essential amino acid residue in a polypeptide is typically replaced with another amino acid residue from the same side chain family. Alternatively, mutations can be introduced randomly along all or part of a polypeptide gene coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of a polypeptide without abolishing or substantially altering one or more of its activities. Suitably, the alteration does not substantially alter one of these activities, for example, the activity is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of wild-type. An "essential" amino acid residue is a residue that, when altered from the wild-type sequence of a reference polypeptide, results in abolition of an activity of the parent molecule such that less than 20% of the wild-type activity is present.

Accordingly, the present invention also contemplates variants of the naturally-occurring polypeptide sequences or their biologically-active fragments, wherein the variants are distinguished from the naturally-occurring sequence by the addition, deletion, or substitution of one or more amino acid residues. In general, variants will display at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% similarity to a parent or reference polypeptide sequence as, for example, set forth in SEQ ID NO: 1, 2, 3, 4, 7, 8, 11, 12, 13, 16, 18, 26, 27, 28, 29, 30, 32, 34, 36, 38, 40, 42, 44, 46, 48, 50, 51, 52, 53, 54, 55, 56 and 57 or the parent or reference polypeptide sequence as, for example, encoded by the nucleotide sequence set forth in SEQ ID NO: 5, 6, 9, 10, 14, 15, 17, 19, 20, 21, 22, 23, 24, 25, 31, 33, 35, 37, 39, 41, 43, 45, 47, or 49. Desirably, variants will have at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity to a parent polypeptide sequence as, for example, set forth in SEQ ID NO: 1, 2, 3, 4, 7, 8, 11, 12, 13, 16, 18, 26, 27, 28, 29, 30, 32, 34, 36, 38, 40, 42, 44, 46, 48, 50, 51, 52, 53, 54, 55, 56 and 57 or the parent polypeptide sequence as, for example, encoded by the nucleotide sequence set forth in SEQ ID NO: 5, 6, 9, 10, 14, 15, 17, 19, 20, 21, 22, 23, 24, 25, 31, 33, 35, 37, 39, 41, 43, 45, 47, or 49. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of the parent polypeptide are contemplated. Polypeptides also include polypeptides that are encoded by polynucleotides that hybridise under stringency conditions as defined herein, especially high stringency conditions, to parent-coding polynucleotide sequences, or the non-coding strand thereof, as described below. Illustrative parent polynucleotide sequences are set forth in SEQ ID NO: 5, 6, 9, 10, 14, 15, 17, 19, 20, 21, 22, 23, 24, 25, 31, 33, 35, 37, 39, 41, 43, 45, 47 and 49.

In some embodiments, variant polypeptides differ from a reference sequence by at least one but by less than 50, 40, 30, 20, 15, 10, 8, 6, 5, 4, 3 or 2 amino acid residue(s). In other embodiments, variant polypeptides differ from the corresponding sequences of SEQ ID NO: 1, 2, 3, 4, 7, 8, 11, 12, 13, 16, 18, 26, 27, 28, 29, 30, 32, 34, 36, 38, 40, 42, 44, 46, 48, 50, 51, 52, 53, 54, 55, 56 and 57, or the amino acid sequences encoded by the nucleotide sequences of SEQ ID NO: 5, 6, 9, 10, 14, 15, 17, 19, 20, 21, 22, 23, 24, 25, 31, 33, 35, 37, 39, 41, 43, 45, 47, or 49, by at least 1% but less than 20%, 15%, 10% or 5% of the residues. (If this comparison requires alignment, the sequences should be aligned for maximum similarity. "Looped" out sequences from deletions or insertions, or mismatches, are considered differences). The differences are, suitably, differences or changes at a non-essential residue or a conservative substitution.

Variants of a protein can be identified by screening combinatorial libraries of mutants, e.g., truncation mutants, of a protein. Libraries or fragments e.g., N terminal, C terminal, or internal fragments, of a protein coding sequence can be used to generate a variegated population of fragments for screening and subsequent selection of variants of a protein.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of proteins.

Some variants of the snake prothrombin activator ecarin are described in U.S. Pat. No. 6,413,737, the entire contents of which are incorporated herein by reference.

Variants of Naturally-Occurring Prothrombin Activators (Nucleotide)

The present invention also contemplates prothrombin activators comprising polypeptide(s) that is/are encoded by variant(s) of the wild-type or naturally-occurring polynucleotide(s) encoding the wild-type or naturally-occurring polynucleotide(s).

Variants of a wild-type or naturally-occurring polynucleotides will have at least at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% (and all partial integer percentages in between) sequence similarity or identity with the nucleotide sequence for the wild-type or naturally-occurring polynucleotide, including but not limited to the sequences encoded by the sequences of SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, 52, 53, 54, 55, 56 and 57 or the sequences of SEQ ID NOs: 5, 6, 9, 10, 14, 15, 17, 19, 20, 21, 22, 23, 24, 25, 31, 33, 35, 37, 39, 41, 43, 45, 47, and 49, or a complement thereof, as determined by sequence alignment programs described elsewhere herein using default parameters.

Exemplary nucleotide sequences that encode the polypeptides encompass full-length genes as well as portions of the full-length or substantially full-length nucleotide sequences of the genes or their transcripts or DNA copies of these transcripts. Portions of a nucleotide sequence may encode polypeptide portions or segments that retain the biological activity of the native polypeptide. A portion of a nucleotide sequence that encodes a biologically active fragment of a polypeptide may encode at least about 20, 21, 22, 23, 24, 25, 30, 40, 50, 60, 70, 80, 90, 100, 120, 150, 300 or 400 contiguous amino acid residues, or almost up to the total number of amino acids present in a full-length polypeptide.

Also contemplated are variants of the nucleotide sequences. Nucleic acid variants can be naturally-occurring, such as allelic variants (same locus), homologs (different locus), and orthologs (different organism) or can be non naturally-occurring. Naturally-occurring variants such as these can be identified with the use of well-known molecular biology techniques, as, for example, with polymerase chain reaction (PCR) and hybridisation techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a polypeptide. Generally, variants of a particular nucleotide sequence will have at least about at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity to that particular nucleotide sequence as determined by sequence alignment programs described elsewhere herein using default parameters.

Nucleotide sequences can be used to isolate corresponding sequences and alleles from other organisms, particularly other snakes. Methods are readily available in the art for the hybridisation of nucleic acid sequences. Coding sequences from other organisms may be isolated according to well known techniques based on their sequence identity with the coding sequences set forth herein. In these techniques all or part of the known coding sequence is used as a probe which selectively hybridises to other coding sequences present in a population of cloned genomic DNA fragments or cDNA fragments (i.e., genomic or cDNA libraries) from a chosen organism (e.g., a snake). Accordingly, the present invention also contemplates polynucleotides that hybridise to reference nucleotide sequences, or to their complements, under stringency conditions described below. As used herein, the term "hybridises under low stringency, medium stringency, high stringency, or very high stringency conditions" describes conditions for hybridisation and washing.

Guidance for performing hybridisation reactions can be found in Ausubel et al., (1992), sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridisation at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridisation at 65° C., and (i) 2×SSC, 0.1% SDS; or (ii) 0.5% BSA, 1 mM EDTA, 40 mM NaHPO4 (pH 7.2), 5% SDS for washing at room temperature. One embodiment of low stringency conditions includes hybridisation in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridisation at 42° C., and at least about 0.1 M to at least about 0.2 M salt for washing at 55° C. Medium stringency conditions also may include 1% Bovine Serum Albumin (BSA), 1 mM EDTA, 0.5 M NaHPO4 (pH 7.2), 7% SDS for hybridisation at 65° C., and (i) 2×SSC, 0.1% SDS; or (ii) 0.5% BSA, 1 mM EDTA, 40 mM NaHPO4 (pH 7.2), 5% SDS for washing at 60-65° C. One embodiment of medium stringency conditions includes hybridising in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridisation at 42° C., and about 0.01 M to about 0.02 M salt for washing at 55° C. High stringency conditions also may include 1% BSA, 1 mM EDTA, 0.5 M NaHPO4 (pH 7.2), 7% SDS for hybridisation at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridising in 6×SSC at about 45° C., followed by one or more washes in 0.2×SSC, 0.1% SDS at 65° C.

In certain embodiments, a polypeptide is encoded by a polynucleotide that hybridises to a disclosed nucleotide sequence under low, medium, high, or very high stringency conditions. One embodiment of very high stringency conditions includes hybridising 0.5 M sodium phosphate, 7% SDS at 65° C., followed by one or more washes at 0.2×SSC, 1% SDS at 65° C.

Other stringency conditions are well known in the art and a skilled addressee will recognise that various factors can be manipulated to optimise the specificity of the hybridisation. Optimisation of the stringency of the final washes can serve to ensure a high degree of hybridisation. For detailed examples, see Ausubel et al., (1992) at pages 2.10.1 to 2.10.16 and Sambrook, J. et al. (2001) at sections 1.101 to 1.104.

While stringent washes are typically carried out at temperatures from about 42° C. to 68° C., one skilled in the art will appreciate that other temperatures may be suitable for stringent conditions. Maximum hybridisation rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8). In general, the $T_m$ of a perfectly matched duplex of DNA may be predicted as an approximation by the formula:

$$T_m = 81.5 + 16.6(\log_{10} M) + 0.41(\% \ G+C) - 0.63(\% \ formamide) - (600/\text{length})$$

wherein: M is the concentration of $Na^+$, preferably in the range of 0.01 molar to 0.4 molar; % G+C is the sum of guanine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridisation procedure, a membrane (e.g., a nitrocellulose membrane or a nylon membrane) containing immobilized DNA is hybridised overnight at 42° C. in a hybridisation buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing labelled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Preparing Prothrombin Activators

Prothrombin activators may be prepared by any suitable procedure known to those of skill in the art. For example, the prothrombin activators may be produced by any convenient method such as by purifying or isolating the polypeptide from naturally-occurring reservoirs, including but not limited to snake venom, blood and blood-derived products (e.g. serum). Alternatively, the prothrombin activators used in the present invention may produced through recombinant DNA technology, or other forms of genetic engineering, including for example, using bacterial, insect, yeast, mammalian or other expression systems.

Methods of purification include affinity chromatography, including lectin (e.g. wheat germ agglutinin) affinity chromatography, anion/cation exchange chromotography or any other separation technique, for example, Hex-His tag isolation techniques. The identity and purity of derived prothrombin activator can be determined for example by SDS-polyacrylamide electrophoresis or chromatographically such as by high performance liquid chromatography (HPLC). For example, the purification and characterisation of pseutarin C (also abbreviated to PtPA) from *P. textilis* snake venom is described in Masci (1986) and Masci et al. (1988), and oscutarin C (OsPA) from *O. scutellatus* venom is described in Speijer et al. (1986), both of which are incorporated by reference in their entirety. The purification of ecarin from *E. carinatus* venom is described in Morita, T et al. (1981), the contents of which is also incorporated by reference in its entirety.

Alternatively, the prothrombin activators may be produced from venom gland cells in culture using methods known in the art, including for example the method described in Yamanouye, N., et al. (2007), which describes the primary culture of secretory cells from the venom gland of *Bothrops jararaca* for in vitro venom production, the contents of which is incorporated by reference in its entirety.

Alternatively, the prothrombin activators may be synthesised by chemical synthesis, e.g. using solution synthesis or solid phase synthesis as described, for example, in Chapter 9 of Atherton and Shephard (1989) and in Roberge et al. (1995).

Alternatively, the prothrombin activators may be prepared by recombinant techniques. For example, the prothrombin activators used in the invention may be prepared by a procedure including the steps of: (a) preparing a construct comprising a polynucleotide sequence that encodes a polypeptide and that is operably linked to a regulatory element; (b) introducing the construct into a host cell; (c) culturing the host cell to express the polypeptide; (d) isolating the polypeptide from the host cell. If the prothrombin activator comprises a complex or two polypeptides, then the prothrombin activator may be prepared by a procedure including the steps of: (a) preparing a construct comprising a polynucleotide sequence that encodes a first polypeptide and that is operably linked to a regulatory element; (b) introducing the construct into a host cell; (c) culturing the host cell to express the first polypeptide; (d) isolating the polypeptide from the host cell; repeating steps (a) to (d) for a second polypeptide; and linking the first polypeptide and the second polypeptide. The above procedures are equally applicable to preparing prothrombin activators that are fragments, variants, mutant forms or chimeric forms of wild type prothrombin activators. In illustrative examples, the nucleotide sequence that encodes a polypeptide encodes at least a biologically active portion of the sequences set forth in SEQ ID NO: 5, 6, 9, 10, 14, 15, 17, 19, 20, 21, 22, 23, 24, 25, 31, 33, 35, 37, 39, 41, 43, 45, 47, 49, or a variant thereof.

Recombinant prothrombin activators can be conveniently prepared using standard protocols as described for example in Sambrook, J. et al. (2001), in particular Chapters 16 and 17 and Ausubel et al. (1992), in particular Chapters 10 and 16. For example, the recombinant production of snake factor V and snake factor X, which can be used to produce group C and group D prothrombin activators, is described in Filippovic, I. et al (2005) and Bos, M. H. A. et al (2009), each of which is incorporated herein in its entirety. An illustrative process for the recombinant production of ecarin and variants of ecarin is provided in Yonemura, H. et al. (2004) and in U.S. Pat. No. 6,413,737, the entire contents of each of which are incorporated herein by reference.

Colloids

The present invention includes in one aspect the formulation of a clotting composition comprising a prothrombin activator and a stabilizing agent such as a colloid.

Colloids represent one of the three primary types of mixtures, with the other two being solutions and suspensions. A colloid typically has particles ranging between 1 and 1000 nanometers in diameter, with the particles able to remain evenly distributed throughout the colloid. Accordingly, a colloid involves one substance being evenly dispersed in another. Colloidal dispersions therefore remain dispersed and do not settle to the bottom of a container. The substance being dispersed is in the dispersed phase, while the substance in which it is dispersed is in the continuous phase.

If the dimensions of the substance in the dispersed phase are smaller than 1 nanometer, then the mixture is called a solution. If the dimensions of the substance in the dispersed phase are larger than 1000 nanometers, then the mixture is called a suspension.

A common method for classifying colloids is based on the phase of the dispersed substance and what phase it is dispersed in. Using this classification, types of colloids include sols, emulsions, foams and aerosols, where a sol is a colloidal suspension with solid particles in a liquid, an emulsion is one liquid dispersed in another, a foam is where gas particles are trapped in a liquid or solid, and an aerosol contains small particles of liquid or solid dispersed in a gas. When the dispersion medium is water, the collodial system may be referred to as a hydrocolloid. Table 3 exemplifies different types of colloids.

TABLE 3

Exemplary colloids

| Dispersion Medium | Dispersed Phase | Type of Colloid | Example |
| --- | --- | --- | --- |
| Solid | Solid | Solid sol | Ruby glass |
| Solid | Liquid | Solid emulsion/gel | Pearl, cheese |
| Solid | Gas | Solid foam | Lava, pumice |
| Liquid | Solid | Sol | Paints, cell fluids |
| Liquid | Liquid | Emulsion | Milk, oil in water |
| Liquid | Gas | Foam | Soap suds, whipped cream |
| Gas | Solid | Aerosol | Smoke |
| Gas | Liquid | Aerosol | Fog, mist |

Colloids are frequently used in fluid resuscitation for critical or intensive care patients. Fluid volume deficit in a patient may be the result of excessive fluid loss, insufficient fluid intake or a combination of the two, including for example blood loss, vomiting, diarrhoea and dehydration. Colloids are most typically used as plasma volume expanders in the treatment of circulatory shock. Colloids have large molecules that do not readily cross capillary walls and are retained in the blood vessels. Vascular volume can therefore be restored, circulatory haemodynamics can be stabilized and tissue perfusion can be maintained when severe haemorrhaging occurs. Common examples of colloids include the plasma substitutes Gelofusine® and Haemaccel® which consist of a modified fluid gelatin, and which promote osmotic diuresis. These colloids have a half-life of several hours, provide long-term volume replacement and are generally iso-oncotic with blood, which they typically replace on a volume-for-volume basis. Other types of colloids used in fluid resuscitation include dextran-based colloids, starch-based colloids such as Voluven® and Volulyte®, and albumin-based colloids such as human albumin. Polyvinylpyrrolidone (PVP) and other synthetic polymers are also classified as colloids.

Gelatin-based colloids have been used as plasma substitutes for almost 100 years. They are most useful as volume substitutes, with a volume effect of approximately 80%. However, they have an increased risk for anaphylactic or anaphylactoid reactions. The gelatin-based colloid Gelofusine® is 4% w/v succinylated gelatine in saline. It is generally prepared by hydrolysis and succinylation of bovine collagen, with 40 g/L gelatine, 154 mmol/L sodium, 120 mmol/l chloride, an average Mw of 30,000, an average Mn of 22,600, a pH of 7.4+/−0.3, a relative viscosity at 37° C. of 1.9, an isoelectric point of pH 4.5+/−0.3, a colloid osmotic pressure of 453 mm $H_2O$, a gel point of 0° C., an osmolarity of 274 mOsm/L and a half life of about 4 hours. Other commercially available gelatin-based colloids include Geloplasma® (a succinylated gelatin) and Isoplex® (a urea-linked modified fluid gelatin).

Starch-based colloids comprise a hydroxyethyl starch solution and have been used since the mid-1960s. Commercially available versions such as Plasmatersil® are used as volume expanders that advantageously resist biological degradation by α-amlyase through the use of high molecular weight hetastarch and chemical substitution. Other starch-based colloids such as Elo-HAES® use smaller but heavily substituted hydroxyethyl hexastarches. In addition, even smaller and less substituted hydroxyethyl starches such as HAES-Steril® pentastarch or Voluven® tetrastarch appear to have improved safety and a virtual 100% volume substitution effect that can be maintained for up to 6 hours.

Albumin-based colloids have several advantages including an absence of risk for disease transmission resulting from the manufacturing process, an absence of volume restrictions, low allergenicity, an absence of significant nephrotoxicity and an absence of intrinsic coagulopathy. However, albumin-based colloids are significantly more expensive than crystalloids, starch-based colloids and gelatin-based colloids for volume replacement. Bovine Serum Albumin is used in laboratory applications such as protein concentration standard and a nutrient in cell and microbial culture and is inexpensive.

In addition to colloids, crystalloids may also be used in fluid resuscitation. Crystalloids are balanced salt solutions that freely cross capillary walls. They are made up of water and electrolytes and are designed to remain in the intravascular compartment for a shorter time than colloids. Common examples include normal saline and sodium lactate preparations such as Hartmann's and Ringer-Lactate solutions. Crystalloids are useful for maintaining fluid balance such as during the time after an operation when a patient is not able to drink or to replace intravascular volume after sudden blood loss.

The present invention demonstrates that the stability of a clotting composition comprising a prothrombin activator is significantly improved when a stabilizing agent such as a colloid is added to the composition. In some embodiments of the present invention, the colloid is selected from the group comprising or consisting of a gelatin-based colloid, a starch-based colloid, an albumin-based colloid or a dextran-based colloid.

In some embodiments, the gelatin-based colloid is selected from the group comprising or consisting of a succinylated gelatin colloid or a urea-linked modified fluid gelatin colloid. In particular embodiments, the succinylated gelatin colloid is selected from the group comprising or consisting of Gelofusine® or Geloplasma®. In alternative particular embodiments, the urea-linked modified fluid gelatin colloid is Haemaccel®. In preferred embodiments, the succinylated gelatin colloid is Gelofusine®.

In some embodiments, the albumin-based colloid is selected from the group comprising or consisting human or bovine albumins produced by Cohn cold-ethanol treatment or chromatographic methods. In particular embodiments, the albumin-based colloid is Human Serum Albumin or Bovine Serum Albumin. In preferred embodiments, the albumin-based colloid is Bovine Serum Albumin.

In some embodiments, the starch-based colloid is selected from the group comprising or consisting of a hetastarch-based colloid, a hexastarch-based colloid, a pentastarch-based colloid or a tetrastarch-based colloid. In particular embodiments, the hetastarch-based colloid is Plasmerteril®. In alternative particular embodiments, the hexastarch-based colloid is Elo-HAES®. In alternative particular embodiments, the pentastarch-based colloid is HAES-Steril®. In alternative particular embodiments, the tetrastarch-based colloid is selected from the group consisting of Voluven®, Valvuven® and Volulyte®.

Compositions

The present invention provides clotting compositions comprising a prothrombin activator and a stabilizing agent such as a colloid.

In some embodiments, the ratio of prothrombin activator to colloid (w/w) is 1:1, 1:2, 1:3, 1:4, 1:5, 1:10, 1:20, 1:30, 1:40, 1:50, 1:60, 1:70, 1:80, 1:90, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:310, 1:320, 1:330, 1:340, 1:350, 1:360, 1:370, 1:380, 1:390, 1:400, 1:410, 1:420, 1:430, 1:440, 1:450, 1:460, 1:470, 1:480, 1:490, 1:500, 1:510, 1:520, 1:530, 1:540, 1:550, 1:560, 1:570, 1:580, 1:590, 1:600, 1:610, 1:620, 1:630, 1:640, 1:650, 1:660, 1:670, 1:680, 1:690, 1:700, 1:710, 1:720, 1:730, 1:740, 1:750, 1:760, 1:770, 1:780, 1:790, 1:800, 1:810, 1:820, 1:830, 1:840, 1:850, 1:860, 1:870, 1:880, 1:890, 1:900, 1:910, 1:920, 1:930, 1:940, 1:950, 1:960, 1:970, 1:980, 1:990, 1:1000, 1:1100, 1:1200, 1:1300, 1:1400, 1:1500, 1:1600, 1:1700, 1:1800, 1:1900, 1:2000, 1:3000, 1:400, 1:5000, 1:6000, 1:7000, 1:8000, 1:9000, or 1:10000 or more, or any integer or partial integer in between the integers stated. In particular embodiments, the ratio of prothrombin activator to colloid (w/w) is between 1:100 to 1:800.

The quantity of the composition should be sufficient to effectively clot a blood sample and to produce a serum sample by separating the serum from the clotted cells. In some embodiments, the time taken to clot the blood sample is less than 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes. In particular embodiments, the time taken to clot the blood sample is less than 2, 3, 4, 5, 6, 7, 8, 9 or 10 minutes. In a preferred embodiment, the time taken to clot the blood sample is less than 2, 3, 4 or 5 minutes.

In some embodiments, the compositions of the present invention are able to achieve clotting in an advantageously quick time after storage or transport at temperatures of less than −20, −21, −22, −23, −24, −25, −26, −27, −28, −29, −30, −31, −32, −33, −34, −35, −36, −37, −38, −39, −40, −41, −42, −43, −44, −45, −46, −47, −48, −49, −50, −51, −52, −53, −54, −55, −56, −57, −58, −59, −60, −61, −62, −63, −64, −65, −66, −67, −68, −69, −70, −71, −72, −73, −74, −75, −76, −77, −78, −79, −80, −81, −82, −83, −84, −85, −86, −87, −88, −89, −90, −91, −92, −93, −94, −95, −96, −97, −98 or −99 degrees Celsius or more than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 degrees Celsius. In a preferred embodiment, the compositions of the present invention are able to achieve clotting in an advantageously quick time after storage or transport at room temperature or at temperatures of 20, 21, 22, 23, 24 or 25 degrees Celsius or more. In another preferred embodiment, the compositions of the present invention are able to achieve clotting in an advantageously quick time after storage at elevated temperatures of 50 degrees Celsius or more.

In some embodiments, the compositions of the present invention are able to achieve clotting in an advantageously quick time after storage for a period of time of more than 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000 or 3000 or more days, or any number of day in between the integers stated. In some embodiments, the compositions of the present invention are able to achieve clotting in an advantageously quick time after storage for a period of time of more than 200 days.

In some embodiments, the compositions of the present invention are able to achieve clotting in an advantageously quick time after sterilization of the compositions by irradiation. In some embodiments, the sterilisation is via electron-beam or ethylene oxide exposure. In particular embodiments, the irradiation is gamma irradiation and the amount of irradiation the compositions are subjected to is 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 kGy. In a preferred embodiment, the irradiation is gamma irradiation and the amount of irradiation the compositions are subjected to is in a range of about 15 kGy to about 25 kGy. In a most preferred embodiment, the irradiation is gamma irradiation and the amount of irradiation the compositions are subjected to is about 15 kGy.

In some embodiments, the composition may be spray dried or otherwise adhered to an internal surface of a container suitable for collecting the blood of a subject. In other embodiments, the composition may be provided in an isolated form, suitable for addition to a blood sample previously taken from a subject. In yet other embodiments, the composition may be provided in a reaction container, to which a blood sample previously taken from a subject is added. In further embodiments, composition may be provided in an aqueous form, for example, in a container such as a blood clotting tube, to which a blood sample is added.

The amount of prothrombin activator used in the compositions of the present invention will depend upon a variety of factors including the subject being tested and the severity of any associated conditions; for example, the activity of the prothrombin activator and/or colloid, the age, body weight, general health, sex and diet of the patient, and any drugs being used by the subject, together with other related factors well known in the art, such as whether or not the subject is already being prescribed anticoagulants such as heparin or warfarin. One skilled in the art would therefore be able, by routine experimentation, to determine an effective amount of the prothrombin activator which would be required to clot a blood sample and provide a serum sample for analyte testing. The amount of prothrombin activator may be determined to ensure adequate blood clotting in a particular patient group, such as patients with normal blood to achieve rapid clotting, or to ensure adequate blood clotting from a wider patient group including, for example, patients on anticoagulant therapy.

In particular embodiments, the composition may be used as part of a stat tube, for example, for use in troponins, or in combination with cardiac procedures and/or catheterisation, or in combination with haemodialysis. In other embodiments, the composition may be used as part of a standard blood collection tube.

In some embodiments, the amount of prothrombin activator used in the compositions of the present invention is 0.00, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 µg of prothrombin activator. In other embodiments, the amount of prothrombin activator used in the compositions of the present invention is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 or 10 µg of prothrombin activator.

In other embodiments, the clotting composition is measured in units by means of an assay based on a peptide p-nitoanilide substrate or thrombin substrate. In particular embodiments, OsPA comprises 0.001-0.2 units, as measured in the hydrolysis of the chromogenic substrate S-2222 or S2238 in a standard assay.

Surfactants may also be used as part of the clotting composition in order to provide a physical barrier between blood components and the wall of a container containing the composition, such a blood collection tube. The presence of a surfactant does not affect the coagulation mechanism.

The composition may therefore also incorporate any suitable surfactant such as an anionic, cationic or non-ionic surfactant such as sorbitan esters or polyoxyethylene derivatives thereof. Suitable surfactants may also include sodium dodecyl sulphate (SDS), ammonium lauryl sulphate, sodium laureth sulphate, and sodium myreth sulphate. Surfactants are commonly used to decrease non-specific adsorption, and require careful selection and optimization. Surfactants can also improve blood flow, distribute clot activators, and prevent proteins, RBCs, and platelets from adsorbing to tube walls. Suspending agents such as natural gums, cellulose derivatives or inorganic materials such as silicaceous silicas, and other ingredients such as lanolin, may also be included.

In a preferred embodiment, the surfactant is a hydrophilic surfactant. In another embodiment, the surfactant may be a hydrophobic surfactant. Both hydrophilic and hydrophobic surfactants can have similar effectiveness in reducing interactions between blood proteins and blood cells, and the walls of containers such as blood collection tubes. In a preferred embodiment, the surfactant may be a hydrophilic polysilane polymers, such as Dow Corning 7-9245.

Compositions may be prepared according to methods which are known to those of ordinary skill in the art and may include additional carriers, excipients or diluents. Carriers, excipients and diluents must be "acceptable" in terms of being compatible with the other ingredients of the composition, and not deleterious to formation of a serum sample that possesses certain advantageous features such as decreased fibrinogen concentration, fewer microclots, fewer cells, will be able to be stored for longer periods of time if required and will result in more reproducible analyte results. Such carriers, excipients and diluents may be used for further enhancing the integrity and half-life of the compositions of the present invention.

Carriers such as polyvinylpyrrolidone (PVP), carboxymethyl cellulose, polyvinyl alcohol, and polyethylene oxide may also be used to allow addition of clotting compositions to tubes. Such carriers allow rapid clot activator suspension into blood so that the carriers dissolve into both serum and clots as the clotting is initiated. PVP and water-soluble surfactants can also release clot activators into blood specimens to reduce the need for mixing.

Further examples of acceptable carriers or diluents are demineralised or distilled water; saline solution; vegetable based oils such as peanut oil, safflower oil, olive oil, cottonseed oil, maize oil, sesame oils, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; gum tragacanth or gum acacia, and petroleum jelly.

Additional carriers that may be included in the compositions of the present invention include non-reducing sugars such as sucrose and reducing sugars such as lactulose. Such carriers, as well as sugar alcohols such as mannitol, xylitol, glycerol and sorbitol, are also useful for inclusion in the compositions of the present invention as they can act as antioxidants and potential stabilisers.

In some embodiments, the clotting composition may comprise snake venom, including but not limited to crude snake venom. In some other embodiments, the clotting composition may comprise a preparation of prothrombin activator prepared by partial or full purification of snake venom. Such preparations may be prepared by any suitable method known in the art, including chromatographic and gel filtration methods, including those described herein, and elsewhere. In some other embodiments, the clotting composition may comprise a purified prothrombin activator or an isolated prothrombin activator. Purified and isolated prothrombin activators may be prepared by any suitable method known in the art, including those described herein, and elsewhere. In yet other embodiments, the prothrombin acticvator may be recombinantly produced, wherein the prothrombin activator is derivable from snake venom.

The ability of the compositions as herein defined to activate prothrombin to thrombin may be initiated by or improved with the addition of co-factors, including but not limited to calcium, phospholipid(s) and polypeptides comprising FVa activity, as well as other clotting agents or coagulants. In one embodiment, the clotting composition is initially produced devoid of co-factors, or where the co-factors are provided separately to the clotting composition, for example, where the clotting composition and the co-factors are distributed in separate locations on the inner surface of a container such as a blood collection tube. Upon the tube being filled or partially filled with a patients blood, the co-factors then come into contact with the blood and initiate or improve the clotting reaction with the prothrombin activator.

Clotting agents or coagulants are classified as either intrinsic clotting agents or extrinsic clotting agents according to the blood cascade stimulated (see for example U.S. Pat. No. 6,686,204). Suitable clotting agents include, but are not limited to, diatomaceous earth, microparticles or particles of inorganic silicates, microsilica, glass microparticles, ellagic acid, thrombin, heparinase, thromboplastin, batroxobin, hydroyapitite, kaolin, kaolin particles, prothrombin (including microparticulated prothrombin), fibrinogen, and depolymerised collagen.

In some embodiments, the composition comprises a reversible prothrombin activator, which may remain inhibited by an additional agent until activation of the clotting process is desired. Such additional agents may include protease inhibitors such as benzamidine hydrochloride, aminobenzamidin dihydrochloride, antipain dihydrochloride, aprotinin, EGTA or leupeptin hemisulphate, all of which are commercially available, for example, from Carl Roth GmbH & Co KG, or from Sigma-Aldrich Co. LLC.

In some embodiments, the composition comprises a prothrombin activator, a colloid and a surfactant. In a particular embodiment, the composition comprises a prothrombin activator derived from or derivable from snake venom, a gelatin- or albumin based colloid and a surfactant. In preferred embodiments, the composition comprises a group C prothrombin activator derived from or derivable from snake venom or a recombinant version of same, a gelatin- or albumin based colloid and a hydrophilic surfactant. In a particularly preferred embodiment, the composition comprises the Group C prothrombin activator oscutarin C (OsPa) derived from or derivable from the venom of *Oxyuranus scutellatus*, the gelatin-based colloid Gelofusine®, being 4% w/v succinylated gelatine in saline and containing 40 g/L gelatine, 154 mmol/L sodium, 120 mmol/l chloride, and a hydrophilic surfactant.

Containers

The present invention contemplates any suitable container for preparing a suitable serum sample. Many suitable containers are well known in the art, including those described in U.S. Pat. Nos. 4,227,620; 4,256,120; 6,416,717; 6,592,613; 6,686,204; 7,488,287; 7,699,828; European patent no.

0 628 816; and commercially available containers including those used in the Examples of the present specification.

In some embodiments, the containers used in accordance with the present invention are tubes, including glass or plastic tubes. Suitable plastics include polyvinyl chloride, polypropylene, polyethylene terephthalate, and polystyrene.

The containers may be evacuated and the end sealed with an appropriate puncturable septum or cap. This allows for a double-ended needle to be used where one end is inserted into a patient's vein and the other end of the needle then punctures the septum or cap covering the end of the tube so that the vacuum in the tube draws the blood sample through the needle into the tube.

The containers may be of any suitable size. In some embodiments, the containers are designed to hold a blood sample of between 50 µL and 10 mL. Suitably, the containers are designed to hold at least 50 µL, 70 µL, 100 µL, 150 µL, 200 µL, 250 µL, 300 µL, 350 µL, 400 µL, 450 µL, 500 µL, 1 mL, 2 mL, 3 mL, 4 mL, 5 mL, 8 mL, or 10 mL of blood sample. In a particular embodiment, the containers hold a 4 mL blood sample providing a final concentration of prothrombin activator in the 4 mL blood sample of 25 ng/mL to 2.5 µg/mL.

In some embodiments, the containers contain a clotting composition comprising, consisting essentially of, or consisting of a prothrombin activator and an additional agent such as a colloid.

In some embodiments, the clotting composition may be contained within the container before the blood sample is added to the container. In some embodiments, the clotting composition may be added to the container after the blood sample is added to the container. Where the clotting composition is contained within the container before the blood sample is added, it may have been added to the container by any suitable method known in the art. In some embodiments, the clotting composition is dissolved into a suitable solvent and is then added to the container and dried onto the inner surface of the container. The solvent may be a neutral buffer. The clotting composition in solution may be dried onto the inner surface of the container by spray-drying, by freeze-drying, by heat-drying or by any other suitable method known in the art. In some embodiments, the clotting composition is dried on to an inner surface of a container such as a blood collection tube using a blast of warm air heated to 60° C.-70° C. In some other embodiments, the clotting composition is dissolved into a suitable solvent and added to the container without drying so that the container contains an aqueous solution comprising the clotting composition. The solvent may be a neutral buffer. In further embodiments, the clotting composition is contacted onto the inner surface of a container such a blood collection tube by atomisation or aerosolisation.

In some embodiments, beads are coated with the clotting composition and these beads are added to the container. The beads may be glass beads or synthetic resinous beads, including polystyrene and propylene beads. The beads may have a spherical shape. In some embodiments, the mean diameter of the beads is between 0.1 mm and 1 mm.

In a particular embodiment, the prothrombin activator is rapidly dried onto an inner surface of a container using a mild vacuum at 37° C., for example, by using a Gene-Vac machine. In a particular embodiment, the proithrombin activator is rapidly dried by a jet of heated air at 50° C. or greater directly into a container such as a blood collection tube.

In some embodiments, the container provides for separation of the serum from the clotted cells after clotting has occurred. In some embodiments, the container comprises or contains a serum separator gel that provides a barrier between the clotted cells and the serum sample. In some embodiments, the container is a suitable shape and a suitable material to permit centrifugation to separate or assist in maintaining separation of the clotted cells and the serum sample. In some embodiments, the serum sample is removed from the clotted cells, or the clotted cells are removed from the serum sample. For example, such embodiments are compatible with the use of commercially available Serum Separation Tubes and Plasma Separator Tubes.

In some embodiments, the container may comprise one or more further components. The other components may include, for example, one or more co-factors, one or more surfactants, and/or one or more clotting agents in addition to the clotting composition.

In a preferred embodiment, the containers are Greiner Bio-One White Top or Red Top tubes, or Becton Dickinson venous blood collection tubes. Such preferred collection tubes are made of polyethylene terephthalate and may have no additives at all, or may be coated with a surfactant, and contain silica as the clot activator, a gel separator and a rubber stopper coated with silicone.

Serum Samples

As discussed above, the present invention is predicated in part on the discovery that prothrombin activators, when formulated in combination with an additional agent such as a colloid, result in a clotting composition having enhanced stability, thereby preserving clotting activity and improving the quality of serum samples for use in immunoassays or analyte detection, which may be in a laboratory, at point of care or at a clinical or research situation. A serum sample that is suitable for detecting analytes is one of suitable quality as discussed herein, and/or one that is prepared within a suitable time as discussed herein.

An important factor in the preparation of a serum sample suitable for detecting analytes is the extent to which the clotting process removes fibrinogen from the serum. Serum containing residual fibrinogen or partially degraded fibrinogen, or fibrin as a result of incomplete clotting can lead to analytical accuracy problems because of the formation of precipitates (microclots or strings), latent clotting post-centrifugation and on storage of the serum. Hence, complete or substantially complete clotting is pivotal in ensuring highest quality serum and accurate test results.

Accordingly, some embodiments of the present invention provide the use of a clotting composition comprising, consisting essentially of, or consisting of a prothrombin activator and a colloid in the preparation of a serum for detecting an analyte, where the serum comprises ≤30 µg/mL of fibrinogen or fibrinogen/fibrin related products. In more specific embodiments, the serum comprises ≤25 µg/mL, ≤20 µg/mL, ≤15 µg/mL, ≤10 µg/mL, ≤8 µg/mL, or ≤6 µg/mL of fibrinogen or fibrinogen/fibrin related products.

In some embodiments, the serum comprises ≤30%, ≤20%, ≤10%, ≤9%, ≤8%, ≤7%, ≤6%, ≤5%, ≤4%, ≤3%, ≤2%, ≤1%, ≤0.5%, ≤0.2%, ≤0.1% of fibrinogen or fibrinogen/fibrin related products present in the original sample from which the serum was produced.

Levels of fibrinogen and/or fibrinogen/fibrin related products can be detected by any suitable method known in the art, including a sandwich immunoassay using antibodies from MP Biomedicals and standard fibrinogen preparations purchased from NIBSC, Potters Bar, Hertsfordshire, London, UK.

Another important factor in the preparation of a serum sample suitable for detecting analytes is the activity or number of cells or cellular debris that remain in the serum after clotting. The presence of cells can have two effects during storage and analysis of serum or plasma. Firstly, cells may lyse, releasing cellular contents (e.g. potassium, lactate dehydrogenase) into the serum or plasma. This can lead to significant differences between measurements made immediately after centrifugation and measurements after a period of storage. Secondly, cells continue to be metabolically active and may use up significant amounts of nutrients (e.g. glucose) and release metabolic products (e.g. lactate) on storage. Changes can even be observed in the samples of many tubes when the samples are stored for the usual recommended 30 minute clotting time when the samples are from healthy participants. The degree of cellular contamination is therefore an important quality criterion for serum samples and an important advantage of using serum over plasma.

Accordingly, in some embodiments, the serum sample comprises less than 50%, 40%, 30%, 20%, 10%, 5%, or 1% of cells in the blood sample from which it has been prepared.

In some embodiments, the serum sample comprises a change of lactate dehydrogenase activity or phosphate concentration (typically measured in U/L and mmol/L respectively) of <25%, <20%, <15% or <10% over a period of 24 hours, 12 hours, 8 hours, 6 hours, 5 hours, 4 hours, 3 hours, 2 hours, 1 hour or 30 minutes. In some embodiments, the serum sample comprises a change of glucose concentration or potassium concentration (both typically measured in mmol/L) of <5%, <4%, <3%, <2%, <1%, <0.5%, or <0.1% over a period of 24 hours, 12 hours, 8 hours, 6 hours, 5 hours, 4 hours, 3 hours, 2 hours, 1 hour or 30 minutes (for example, from the time of preparing the serum sample). Methods for measuring lactate dehydrogenase activity are well known in the art, see, for example, Dimeski, G., et al. (2004), the contents of which is incorporated by reference in its entirety.

The haemoglobin concentration of a serum sample can also be used to determine whether the serum sample is suitable for detecting analytes. Accordingly, in some embodiments, the serum sample comprises a haemoglobin concentration of <150 mg/L, <100 mg/L, <90 mg/L, <80 mg/L, <70 mg/L, <60 mg/L, <50 mg/L, <40 mg/L, <30 mg/L, <20 mg/L, or <10 mg/L.

As a sample for testing, serum is usually preferred over plasma unless urgent results are required and thus the clotting time for a serum tube is considered too long. Another downside to prolonged clotting time is that it can lead to clinically significant analyte concentration changes due to cellular activity in the blood sample, this problem being most pronounced in leukocytosis (Dimeski and Bird 2009).

Thus in some embodiments, the present invention provides a method of producing a serum sample for detecting an analyte of interest, the method comprising contacting a blood sample with a clotting composition comprising, consisting essentially of, or consisting of a prothrombin activator and a colloid as defined herein, where the serum sample is prepared within 25, 20, 15, 10, 8, 6, 5, 4, 3, 2, 1, or 0.5 minutes from contact with the clotting composition.

Blood Samples

As discussed herein, there is a desire to provide a clotting composition that is suitable for producing a serum sample from most, if not all, blood samples, or a container comprising a clotting composition that will clot most, if not all blood samples, in a suitable time; that is, in a period of time that allows for analyte testing to be conducted consistent with the clinical needs of a patient.

Examples of different types of blood sample for which testing may be desired include fresh blood from healthy individuals, citrated blood, blood with EDTA added, blood from patients on anti-clotting therapy such as heparin, warfarin, citrate, oral anticoagulants of the Factor Xa inhibitor (eg rivoroxaban), or direct thrombin inhibitor (eg dabigatran) classes, patients taking anti-thrombotic agents including aspirin, thrombocytopenic patients (patients with low platelet counts), and patients with prolonged PTT.

In some embodiments, the blood sample is a whole blood sample. In some other embodiments, the blood sample is a serum sample derived from a whole blood sample. Exemplary serum samples in this instance include serum samples where a better quality serum sample is desired, including those where the amount of fibrinogen or fibrinogen/fibrin related products and/or the amount of cells or cellular material in the serum sample and/or the amount of haemoglobin is considered too high for the serum sample to be a sample suitable to detect analytes. For example, the serum sample may exhibit microclots or latent clotting. In some other embodiments, the blood sample is a plasma sample derived from a whole blood sample. For example, the plasma sample may exhibit microclots or insoluble fibrin formation, or latent clotting.

Detecting Analytes

In some embodiments the present invention further provides methods of detecting an analyte, the method comprising analysing a serum sample prepared by the method of the present invention for the presence or amount of the analyte of interest.

In specific embodiments, the serum sample prepared by the method of the present invention is suitable for more than one analyte test, so that the serum sample can be used to detect more than one analyte. As discussed herein, often a clinician will desire more than one analyte test to be performed on a blood sample from a patient, and it is not uncommon for one serum sample to be used for at least 20 tests, or even more, sometimes between 50-60 or even 70-80 tests. It will be appreciated by those skilled in the art that in specific embodiments the present invention provide for the production of a serum sample where the serum sample is of sufficient volume and quality to enable all desired analyte tests to be performed on the one serum sample. The advantage of this is that both the volume of blood to be taken from the subject and the time taken to perform the analyte tests are reduced.

Illustrative analyte tests are described below. Methods for performing these analyte tests may be performed in a number of ways and are well known in the art.

Troponin: This test measures the levels of Troponin T and/or Troponin I in a serum or plasma sample, in which high levels can be indicative of acute myocardial infarction.

Sodium ($Na^+$): This test measures the amount of sodium in a serum or plasma sample. Sodium plays an important role in salt and water balance in the body. Low sodium levels may indicate too much water intake, heart failure, kidney failure, or loss of sodium from the body due to diarrhoea or vomiting. High sodium levels may indicate excessive salt intake or insufficient water intake.

Potassium ($K^+$): This test measures the amount of potassium in a serum or plasma sample. Levels of potassium that are too high (hyperkalaemia) may be the result of kidney disease, diabetes, ketoacidosis or drugs that decrease the amount of potassium excreted from the body. Levels of potassium that are too low (hypokalaemia) may be caused by dehydration, for example from diarrhoea or vomiting, or excessive sweating. Levels of potassium may also be low as a result of taking drugs that cause the kidneys to lose potassium, for example diuretics. Potassium levels are often monitored in those patients that take diuretics or heart medications, those with high blood pressure or kidney disease, critical acidosis and alkalosis conditions, and those receiving kidney dialysis or intravenous therapy on a drip.

Chloride ($Cl^-$): This test measures the amount of chloride in serum or plasma. Chloride is typically measured to assess whether there is an electrolyte imbalance in the patient. Low chloride and normal sodium and elevated bicarbonate can be indicative of vomiting or loss of gastric fluid.

Bicarbonate ($HCO_3^-$): This test measures the amount of three forms of carbon dioxide (bicarbonate, carbonic acid, and dissolved carbon dioxide) in serum or plasma. A bicarbonate/carbonic acid buffer is the most important in plasma, being very effective in regulation of body pH. This test is often performed in determining metabolic acid/base status. Buffer concentration is regulated by the kidneys. A high level may be observed in response to loss of chloride (vomiting), diuretic therapy, mineralocorticoid excess or glucocorticoid excess (e.g. Cushing's disease). A low level may be caused by production of organic acids as seen in diabetic ketoacidosis, reduced excretion of acids in renal failure, excessive loss of bicarbonate (renal disease), diarrhoea and poisons such as methanol abuse.

Glucose: This test measures the amount of glucose in serum or plasma. Glucose levels are often tested in those patients exhibiting symptoms of high blood glucose (hyperglycaemia) or hypoglycaemia, those who are pregnant, those who have diabetes.

Urea: This test measures the amount of urea in serum or plasma. This test can help evaluate kidney function and monitor the effectiveness of dialysis.

Creatinine: This test measures the amount of creatinine in serum or plasma. This test is pivotal in helping to evaluate kidney function and monitor treatment of kidney disease.

Urate: This test measures the amount of urate (or uric acid) in serum or plasma. High levels of uric acid may be a sign of gout. Uric acid levels are also monitored in patients that are undergoing chemotherapy or radiotherapy to detect tumour lysis syndromes.

Total protein (TP): This test measures the total amount of protein in serum or plasma. Although the results of a total protein test will not indicate a specific disease, a high or low protein level often indicates that additional tests are required to determine if there is a problem. Total protein tests are often used to screen for certain liver disorders, kidney disorders, multiple myeloma and hydration status.

Albumin (Alb): This test measures the amount of albumin in serum or plasma. Albumin levels are often measured to screen for liver or kidney disease, or to evaluate nutritional status, especially in hospitalised patients.

Total bilirubin: This test measures the amount of bilirubin in serum or plasma. Bilirubin levels are measured to screen for and monitor liver disorders, such as jaundice, or liver diseases, such as cirrhosis. Bilirubin levels are also measured in babies to help detect certain rare genetic disorders and to avoid brain damage in those babies with jaundice.

Alkaline phosphatise (ALP): This test measures the amount of alkaline phosphatase in serum or plasma. This test is typically performed to screen for or monitor treatment of a liver or bone disorders.

Gamma-glutamyl transferase (GGT): This test measures the amount of gamma-glutamyl transferase in serum or plasma. This test is used to screen for liver disease and alcohol abuse. It can also be used to determine if a raised level of ALP is due to liver or bone disease.

Alanine aminotransferase (ALT): This test measures the amount of alanine aminotransferase in serum or plasma. This test is used to screen for liver disease.

Aspartate aminotransferase (AST): This test measures the amount of aspartate aminotransferase in serum or plasma. This test is used to detect liver damage, muscular damage, and other conditions as the enzyme is present in many organs and tissue cells.

Lactate dehydrogenase (LDH): This test measures the amount of lactate dehydrogenase in serum or plasma. This test is typically used to identify the cause and location of tissue damage in the body, tissue ischemia, and to monitor its progress.

Creatine kinase (CK): This test measures the amount of creatine kinase in serum or plasma. Creatine kinase is measured in patients with chest pain or muscle pain or weakness to determine if they have had a heart attack and if other muscles in the body have been damaged.

Total calcium (TCa): This test measures the amount of calcium in serum or plasma. Calcium levels are often measured in patients with kidney, bone or nerve disease, or when symptoms of significantly increased or decreased calcium are present.

Phosphate: This test measures the amount of phosphate in serum or plasma. Phosphate levels may be measured as a follow-up to a test result of abnormal calcium levels. Phosphate levels may also be measured in patients with kidney disorders, uncontrolled diabetes, or where the patient is taking calcium or phosphate supplements.

Magnesium ($Mg^{2+}$): This test measures the amount of magnesium in serum or plasma. This test may be performed if the patient has symptoms of too much or too little magnesium, including weakness, irritability, cardiac arrhythmia, nausea or diarrhoea. Magnesium levels may also be measured if abnormal calcium or potassium levels have been detected.

Lipase: This test measures the amount of lipase in serum or plasma. This test is typically used to diagnose pancreatitis or other pancreatic diseases.

Cholesterol: This test measures the amount of cholesterol in serum or plasma. Cholesterol levels are measured to screen for risk of developing heart disease.

Triglycerides: This test measures the amount of triglycerides in serum or plasma. As for cholesterol levels, this test is typically used to screen for risk of developing heart disease.

High-density lipoprotein (HDL): This test measures the amount of HDL cholesterol in serum or plasma. This test is typically used to determine the risk of developing heart disease.

Iron ($Fe^{2+}$): This test measures the amount of iron in serum or plasma. Iron is measured to check if a patient has low or high iron levels. Low iron levels can cause anaemia, and is usually due to long-term or heavy bleeding, pregnancy or rapid growth (in children). High iron levels can be due to a genetic condition or extensive blood transfusions.

Transferrin: This test measures the amount of transferrin in serum or plasma. Transferrin is a plasma protein that transports iron through the blood to the liver, spleen and bone marrow. Thus the blood transferrin level is tested to determine the cause of anaemia, to examine iron metabolism (for example, in iron deficiency anaemia) and to determine the iron-carrying capacity of the blood.

C reactive protein (CRP): This test measures the amount of C reactive protein in serum or plasma. This test is used to identify the presence of inflammation, to determine its severity, and to monitor response to treatment.

Cortisol: This test measures the amount of cortisol in serum or plasma. Cortisol levels are measured to help diagnose Cushing's syndrome or Addison's disease.

Free thyroxine: This test measures the amount of free thyroxine in serum or plasma. The test is typically used to diagnose hypothyroidism or hyperthyroidism.

Thyroid stimulating hormone (TSH): This test measures the amount of thyroid stimulating hormone in serum or plasma. The test is typically used to screen for, diagnose and monitor thyroid disorders.

Ferritin: This test is used to measure ferritin in serum or plasma. Low ferritin levels are indicative of iron deficiency. Elevated levels are indicative of iron overload such as in haematochromatosis.

Haemolytic index: The haemolytic index test measures the degree of red cell lysis. Haemolysis is the most common interference encountered in a biochemistry laboratory. The test is predominantly used to detect in vitro haemolysis and sample suitability for reporting of certain or all analytes, and in detection of haemolytic anaemias (hereditary spherocytosis, spontaneous haemolysis, RBC enzyme deficiency). Haemolysis or haemolytic index (concentration of free haemoglobin in serum or plasma) is currently estimated by all general chemistry analysers. The value is then used as a guide in determining which analytes and at what haemolysis level may be affected or not reported (Dimeski et al. 2005).

Icteric index: The icteric index test returns a value indicating the relative level of bilirubin in a test sample by a purely spectrophotometric method. It is used in determining sample suitability for reporting of certain analytes and cross checking accuracy of bilirubin results in rare cases of interference with the total bilirubin photometric estimation methods. The icteric index has been shown to be of value in detecting cancer paraproteins interference (precipitation and false high total bilirubin) with Roche Total Bilirubin method (Sheppard et al., 2005), where the icteric index has stayed unaffected. Bilirubin can interfere with some creatinine assays at high concentration (e.g. >200 $\mu M/L$) as discussed in Dimeski et al., 2008.

Lipemia index: The lipemia index has been employed to predict possible interference with assays due to lipaemia (Dimeski 2009).

In addition to the above analyte tests, other assays may be performed using a serum or plasma sample by different analytical techniques such as immunoassays, including competitive, non-competitive, reverse or sandwich enzyme-linked immunoassays.

Methods of Diagnosis, Prognosis and Monitoring Responsiveness to Therapy

The present invention provides methods for diagnosing a disease or condition in a subject, wherein the methods comprise providing a blood sample from the subject, preparing a serum sample from the blood sample by contacting the blood sample with a clotting composition of the present invention, and testing the serum sample for the presence or absence of an analyte in the serum sample, or for an indicative level or concentration of an analyte in the serum sample, wherein the presence, absence or indicative level or concentration of the analyte is indicative of the disease or condition in the subject.

The present invention also provides methods for providing a prognosis for a subject, wherein the methods comprise providing a blood sample from the subject, preparing a serum sample from the blood sample by contacting the blood sample with a clotting composition of the present invention, and testing the serum sample for the presence or absence of an analyte in the serum sample, or for an indicative level or concentration of an analyte in the serum sample, wherein the presence, absence or indicative level or concentration of the analyte is indicative of the prognosis for the subject.

The present invention moreover provides methods for monitoring the responsiveness of a subject to a therapy, wherein the methods comprise providing a blood sample from the subject, preparing a serum sample from the blood sample by contacting the blood sample with a clotting composition of the present invention, and testing the serum sample for the presence or absence of an analyte in the serum sample, or for an indicative level or concentration of an analyte in the serum sample, wherein the presence, absence or indicative level or concentration of the analyte is indicative of the responsiveness of the subject to the therapy.

In some embodiments, the methods of the present invention involve comparing the result of the analyte test to a reference interval or cut off limit in order to obtain the diagnosis.

The disease or condition may be any disease or condition that is susceptible to diagnosis, prognosis or responsiveness to therapy, using a serum sample, including but not limited to, the diseases or conditions outlined above with reference to different analyte tests.

In some embodiments, the methods may comprise diagnosing the presence or absence of a disease or condition not previously presented by the subject. In other embodiments, the methods may comprise diagnosing the presence, absence or severity of a disease or condition that the subject has previously presented. The methods may comprise reference to a result obtained from the subject at an earlier time. Alternatively, the reference result may be a standard analytical reference.

In some embodiments, the methods are performed in a testing facility such as a pathology laboratory. In some other embodiments, the methods are "point-of-care" methods. As used herein, a "point-of-care method" means that the method is performed at or near the site of patient care. Point-of-care methods are increasingly popular in hospital and other environments where there is a need to obtain results rapidly. This is often accomplished through the use of transportable, portable, and hand-held instruments and test kits.

The advantages of point of care testing include the ability to obtain rapid analytical results at the bedside in hospitals, especially in emergency situations and the ability to obtain analytical results at home, in doctors' surgeries, remote areas, etc (e.g., using small volumes of arterial, venous or capillary blood).

Devices for point-of-care methods currently available on the market include the i-Stat (Abbott Diagnostics), the Retro-STATUS HIV/CD4 350 rapid test device (Millenium Biotechnology, Inc.), and the Triage PLGF test (Alere International).

Kits

The present invention provides kits for preparing a serum sample, wherein the kit comprises a prothrombin activator and a colloid.

Kits of the present invention facilitate the employment of the methods of the present invention. Typically, kits for carrying out a method of the invention contain all the necessary reagents and means to carry out the method. For example, in one embodiment, the kit may comprise a clotting composition of the present invention and, optionally, means to perform analyte detection such as devices for point of care methods as defined herein.

Typically, the kits described herein will also comprise one or more containers. In the context of the present invention, a compartmentalised kit includes any kit in which compounds or compositions are contained in separate containers, and may include small glass containers, plastic containers or strips of plastic or paper. Such containers may allow the efficient transfer of compounds or compositions from one compartment to another compartment whilst avoiding cross-contamination of samples, and the addition of agents or solutions of each container from one compartment to another in a quantitative fashion. In a preferred embodiment, the one or more containers comprising the kit is a blood collection tube.

Typically, a kit of the present invention will also include instructions for using the kit components to conduct the appropriate methods.

Methods and kits of the present invention are equally applicable to any animal, including humans, for example including non-human primate, equine, bovine, ovine, caprine, leporine, avian, feline and canine species. Accordingly, for application to different species, a single kit of the invention may be applicable, or alternatively different kits, for example containing compounds or compositions specific for each individual species, may be required.

Methods and kits of the present invention find application in any circumstance in which it is desirable to produce a serum sample.

Research Tools

The present invention also contemplates the use of research tools that employ serum samples produced in accordance with the present invention. These methods generally comprise providing a serum sample prepared according to the methods broadly described above; and employing the serum sample in a research tool study, including but not limited to a genomics, proteomics, metabolomics, systems biology, molecular imaging or assay study.

Suitable research tools are well known in the art and include those described in Scaros, O. et al., 2005, the entire contents of which are incorporated by reference. Genomics includes pharmacogenomics which studies the correlation between genetics and gene expression patterns with response to therapeutics. Proteomics permits the analysis of the abundance and distribution of proteins in a system. Metabolomics, or biochemical profiling, is the study of metabolites in a system. Systems biology looks at the entire biological system as a functional unit, producing models of behaviour that can potentially predict how that system will respond to stimulus. Molecular imaging technologies have the ability to demonstrate both the level of a specific molecular target and the functional state of that target in vivo, and can be used for diagnostic methods.

The person skilled in the art will understand and appreciate that different features disclosed herein may be combined to form combinations of features that are within the scope of the present invention.

The present invention will now be further described with reference to the following examples, which are illustrative only and non-limiting.

EXAMPLES

A requirement for using prothrombin activators in clotting compositions is that the activity of the prothrombin activator remains stable over time, and under variable conditions such as exposure to heat and/or sterilizing irradiation. For example, if a prothrombin activator is to be used in a clotting composition in combination with a container such as a blood collection tube, the clotting activity of the prothrombin activator must be retained during storage of the prothrombin activator after purification or recombinant production and before tube production.

In addition, commercially available blood collection tubes are typically made in very large numbers on a production line, where the product may be a plastic tube containing additives such as a procoagulant, a surfactant and a spacer gel. The contents of the tubes are typically dried, sealed under vacuum and sterilized. Where the procoagulant is a prothrombin activator, the prothrombin activator must therefore be capable of retaining activity after the processes of drying, sealing under vacuum and sterilizing (for example, using irradiation). Stability should typically be demonstrated across a wide range of temperatures as disclosed herein. In particular embodiments, stability at room temperature should allow for a shelf life of at least 6 months, preferably greater than 12 months, and more preferably greater than 18 months.

Example 1—Prothrombin Activators: Isolation and Characterisation

In mammals, the prothrombin-activator complex in vivo typically consists of a serine protease, Factor Xa, and a protein cofactor, Factor Va, complexed on a phospholipid membrane in the presence of calcium ions (Jackson and Suttie, 1977). Factor Xa alone activates prothrombin, but inefficiently. In the presence of Factor Va, calcium ions and phospholipid, prothrombin activation is enhanced by several orders of magnitude.

It is well known that the venoms of many snakes cause rapid coagulation of blood. The first report of a prothrombin activator complex in snake venom was by Speijer et al (1986), who reported the discovery of a prothrombin activator complex from *Oxyuranus scutellatus* (Coastal Taipan) venom with at least four polypeptide chains, two of which appeared to represent a Factor Va-like component and two, joined by a disulfide bond, that represented a Factor Xa-like component.

The methodology used in the present study for purification of the prothrombin activator is essentiallythat previously described by Masci et al 1988 and Masci et al 2000. Briefly, 10 grams of venom (purchased from Venom Supplies Pty Ltd, South Australia) was purified in 1 gram batches using a single step column chromatography process involving redissolved venom on a suitable gel filtration resin (e.g. Sephacryl S300, Superdex 200). The activity of the concentrated OsPA containing fraction was then determined in recalcified citrated whole blood and recalcified citrated plasma clotting assays as well as by using the spectrophotometric substrate designed for Factor Xa, S-2222.

Example 1.1—Purification of Prothrombin Activators

Sephacryl S-300, Superdex 200, Toyopearl H55S and Toyopearl H65Sresins were purchased from GE Healthcare Sydney and Toyo, Japan. A slurry of each resin was diluted by 150% with column buffer, 0.05 M tris-HCl, pH 7.4, containing 0.1 M NaCl and 0.01% sodium azide. Glass columns (either 5.0×95 cm; or 2.5×95 cm) were packed with each resin at 4° C. in a cold room. Columns were equilibrated overnight at flow rate 1 ml/min and absorbance at 280 nm was monitored until stable at zero (minimum of 10 column volumes of buffer between runs).

Coastal Taipan (*Oxyuranus scutellatus*, Os) venom (Venom Supplies Pty Ltd, South Australia) was purchased in 2×5 gram lots and the commercial supplier, Venom Supplies confirmed both 5 gram lots were from the same batch of venom milkings. Approximately 1.0-1.5 grams lots of Os venom were reconstituted in 45 mL of column buffer in a 37° C. water bath until completely dissolved. This took approximately 30 minutes. A 1/50 dilution of the Os venom solution was made and A280 measured and recorded for total protein concentration. From the stock solution, 2×1.0 mL aliquots, 1×0.5 mL in 50% glycerol and a 1/50 dilution were stored at −20° C. The remaining 40-42 mL of Os venom solution was then loaded onto an equilibrated gel filtration column. Chromatography was developed over 24 hours at 0.8-1.0 mL/min flow rate. Fractions were collected using an LKB Redirac fraction collection on time-base mode collecting 8-10 mL fractions. Absorbance at 280 nm ($A_{280}$) of the eluent was monitored continuously using an Alex dual UV ($A_{280}$ nm) channel monitoring system and a dual pen recorder set full scale range on 2.48 and 1.24 absorbance units.

Fractions containing OsPA clotting activity were identified by assay using the recalcified citrated plasma clotting assay and the S-2222 chromogenic hydrolytic activity assay, as described below. Fractions with high specific clotting activity were pooled and concentrated as described below.

Example 1.2—Concentration and Storage of OsPA

Fractions from Superdex 200, Sephacryl S300 and Toyopearl H55S and Toyopearl H65S chromatographies which contained plasma clotting and S-2222 hydrolytic activity were pooled (designated "pooled OsPA fractions") for characterization. Protein concentration was determined by measuring absorbance at 280 nm of the pooled OsPA fractions and using an absorption coefficient of 1.0 for 1 mg/mL solution to calculate the protein concentration in mg/mL.

Concentration of the pooled OsPA fractions was carried out using a pressurized Amicon cell Model 402 using a YM 10 membrane (mol cut off 10,000 Da) to a concentration of 2-4 mg/mL. In the initial experiments, the loss of protein in the concentration step was 20-25%. In later experiments, 5% glycerol was added to pooled OsPA containing fractions prior to concentrating with the aim of reducing losses due to protein binding. When 5% glycerol was used the loss of protein in the concentrating step was 0-5%. High purity glycerol was then added to the concentrated OsPA solution to achieve 50% glycerol concentration. The OsPA/glycerol solution was gently mixed to avoid frothing until solution was homogeneous and then stored in a dark glass bottle covered in Alfoil at −20° C. Protein concentration of the OsPA/glycerol solution was determined using a 1/10 dilution and measuring absorbance at 280 nm. OsPA Batch 17 Apr. 2012 is used for all experiments.

Table 4 shows characterisation data for 10 different preparations demonstrating that the different isolation methods yield functionally similar preparations that are suitable and all capable of producing high quality serum as can be inferred from chromogenic substrate S-2222.

TABLE 4

Characterisation data for prothrombin activator preparations

| No | Column | Date | Yield (mg/per g venom) | Total yield (mg) | SA (plasma clotting) (U/mg) | Total U/per g venom | Total U from 1 g venom | S.A. (S-2222) (U/mg)* |
|---|---|---|---|---|---|---|---|---|
| 1 | Sephacryl 300 | 30 Jan. 2012 | 118.1 | 135 | 4761.9 | 1069519 | 562380 (52.6%) | 3.80 ± 0.28 |
| 2 | Superdex 200 | 8 Feb. 2012 | 97.8 | 114 | 5586.6 | 1089325 | 546369 (50.2%) | 4.207 ± 0.28 |
| 3 | Superdex 200 | 17 Apr. 2012 | 151.4 | 159 | 3533.6 | 900901 | 534987 (59.4%) | 3.33 ± 0.18 |
| 4 | Superdex 200 | 1 May 2012 | 116.4 | 158.7 (P1&2)* | 3968.5 | 1015228 | 461933 (45.5%) | 2.45 ± 0.09 |
| 5 | Superdex 200 | 21 May 2012 | 136.2 | 221 (P1, 2, 3&4)* | 2740.0 | 677141 | 373188 (55.1%) | 1.79 ± 0.46 |
| 6 | Superdex 200 | 31 May 2012 | 128.8 | 213 (P1&2)* | 3236.2 | 1015228 | 416823 (41.1%) | 2.34 ± 0.22 |
| 7 | Superdex 200 | 8 Oct. 2012 | 134.1 | 212 | 3571.2 | 1298701 | 478898 (36.9%) | |
| 8 | Toyopearl (HW55-S) | 3 Apr. 2012 | 227.2 | 95.2 | 833.5 | 900901 | 189371 (21.0%) | 0.69 ± 0.20 |
| 9 | Toyopearl (HW65-S) | 6 Jun. 2012 | 582.2 | 161.5 | 1394.1 | 1347709 | 811994 (60.2%) | |
| 10 | Toyopearl (HW65-S) | 14 Jun. 2012 | 776.4 | 261.1 | 962.5 | 998004 | 747285 (74.8%) | |
| 11 | Mean ± SD# | | 126 ± 17 (1-7) | | 41284 ± 880 (1-4 and 7) | 1031200 ± 194000 (1-10) | 526417 ± 44433 (1-4) | |

Table 4 provides quantitative information on the ten OsPA preparations described above in terms of elution profiles and SDS PAGE banding patterns. In summary, (1) the yield of protein in the OsPA preparations using Sephacryl or Superdex was 126±17 mg per gram of dry venom, (2) the plasma clotting activity of one gram of venom was $(1.031±0.194) \times 10^6$ units, (3) the plasma clotting activity in four Sephacryl or Superdex preparations was 526,417±44433 units, giving a yield of approximately 52% of the total plasma clotting activity of the venom sample loaded onto the column, and (4) the two Toyopearl 65S runs gave higher recoveries of activity (60% and 75%) with very little purification between the prothrombin activator fraction and taipoxin fraction.

FIG. 1 shows the banding patterns obtained using samples from six preparations of OsPA, including one stored since 1989. In all cases, there is a very consistent banding pattern in the high molecular weight region. The only clear difference is the presence of a greater amount of low molecular weight material in the Toyopearl preparation. This is consistent with the much poorer resolution of venom fractions achieved using Toyopearl chromatography.

Clotting of whole blood by samples of each of these ten preparations (being the concentrated OsPA fractions stored in 50% glycerol, derived from each preparation) was studied by thromboelastography. Traces are shown in FIG. 2 and parameters for each trace are shown in Table 5.

TABLE 5

Thromboelastographic Data for 10 OsPA Preparations

| No | Column | Date | Yield (mg/per g venom) | Total yield (mg) | Angle (deg) | K (sec) | MA (mm) | G (kd/sc) | Whole blood clotting TEG (31 ng) R time (sec) |
|---|---|---|---|---|---|---|---|---|---|
| 1 | Sephacryl 300 | 30 Jan. 2012 | 118.1 | 135 | 75.6 | 60 | 72.2 | 11.6 | 55 |
| 2 | Superdex 200 | 8 Feb. 2012 | 97.8 | 114 | 76.5 | 60 | 70.4 | 11.9 | 75 |
| 3 | Superdex 200 | 17 Apr. 2012 | 151.4 | 159 | 75.8 | 60 | 71.3 | 12.4 | 85 |
| 4 | Superdex 200 | 1 May 2012 | 116.4 | 158.4 (P1/2) | 75.8 | 55 | 72.1 | 12.9 | 90 |
| 5 | Superdex 200 | 21 May 2012 | 136.2 | 221 (Total) | 76.5 | 60 | 74.3 | 14.4 | 80 |
| 6 | Superdex 200 | 31 May 2012 | 128.8 | 213 (P1/2) | 77.9 | 50 | 71.8 | 12.7 | 95 |
| 7 | Superdex 200 | 8 Oct. 2012 | 134.1 | 212 | 78.7 | 50 | 68.1 | 10.7 | 125 |
| 8 | Toyopearl (HW55-S) | 3 Apr. 2012 | 227.2 | 95.2 | 78.2 | 50 | 66.9 | 10.1 | 145 |
| 9 | Toyopearl (HW65-S) | 6 Jun. 2012 | 582.2 | 161.5 | 77.6 | 50 | 65.5 | 9.5 | 170 |
| 10 | Toyopearl (HW65-S) | 14 Jun. 2012 | 776.4 | 261.1 | 77.1 | 50 | 67.8 | 10.5 | 120 |

All OsPA preparations caused rapid and complete clotting as shown by R, K and angle values (speed) and MA values (clot strength).

Based on results achieved, the OsPA preparation designated 17/4/2012 was used in all dosage and stability experiments. The Superdex 200 chromatography elution profile for this preparation is shown in FIG. 3 and the SDS PAGE banding pattern in FIG. 1. Comparison of the elution profile and banding pattern of this preparation shows that it is a typical preparation. As shown in Table 1, the pooled fractions making up this preparation contained 159 mg, equivalent to 151 mg per gram of venom. The specific activity in the plasma clotting assay was 3534 U/mg and the total activity recovered was 534,987 U per gram of dry venom, a yield of 59%. These numbers are in general agreement with mean values achieved in several preparations as listed in Table 1. The specific activity of 3534 U/mg shows that 1 μg of OsPA, as used in many of the dosage and stability experiments, contained 3.5 plasma clotting units. Parameters for clotting of whole blood by this preparation are in Table 5.

Results for the assay of venom and the 17/4/2012 OsPA preparation against the Factor Xa selective substrate S-2222 are shown in Table 6.

TABLE 6

| | S-2222 assay data for the 17 Apr. 2012 OsPA preparation | | | | | | |
|---|---|---|---|---|---|---|---|
| | Amount of S2222 assay (µg) | Slope (Δ405/sec) | R2 | *Specific activity (U mg$^{-1}$) | Total amount (µg) | Total S2222 activity | Total S2222 activity |
| Venom | 8 | 0.0002 | 0.9914 | 1.25 | 1050 | 1312.5 | 100 |
| OsPA* | 8 | 0.0022 | 0.9999 | 13.75 | 159 | 2186.25 | 166.57 |

Example 1.3—Elution Profiles after Gel Chromatography

Figure 3:
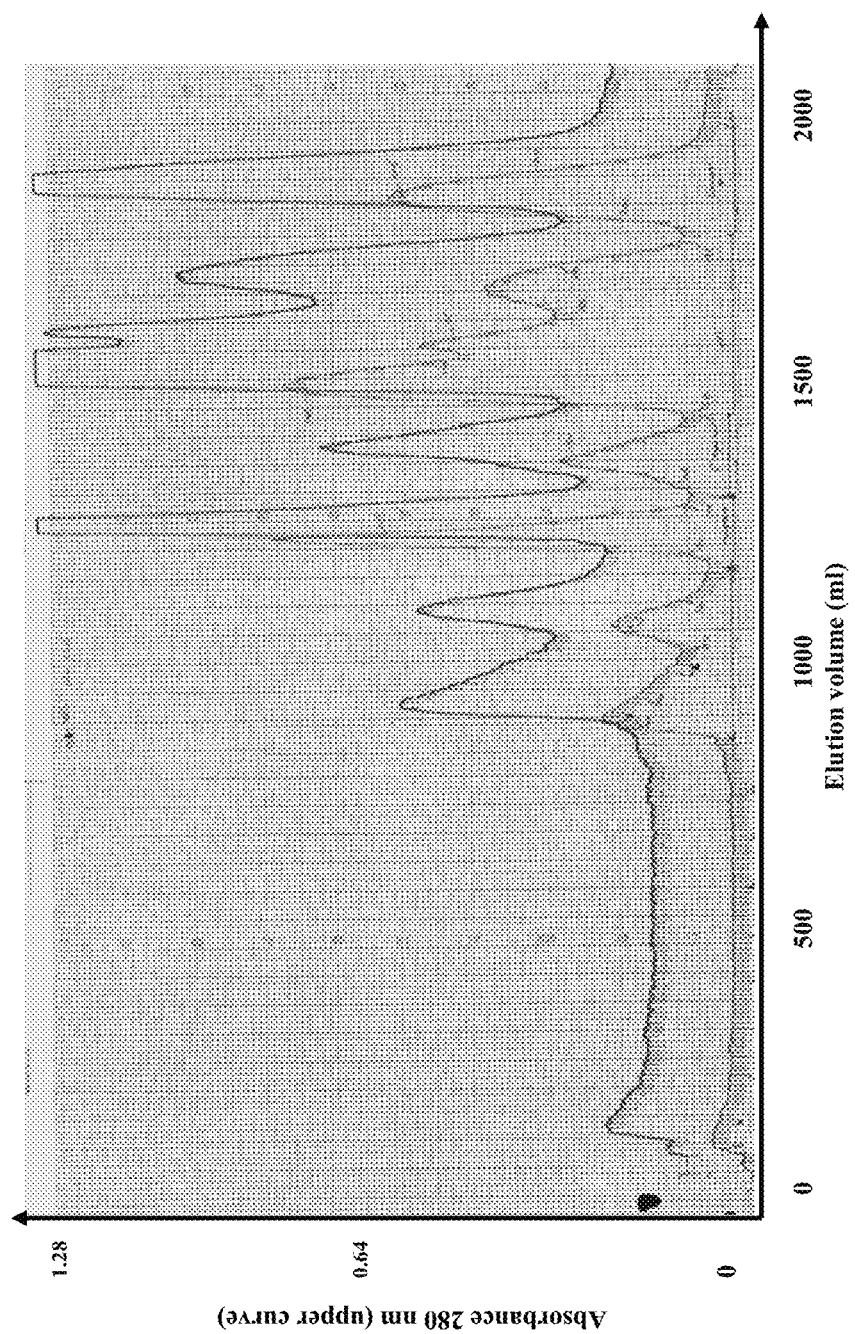
FIG. 3 shows chromatography of 1.05 gram *Oxyuranus scutellatus* venom using Superdex™ 200 (gel column: 5 cm diameter, 95 cm long) (17 Apr. 2012).

Solutions containing approximately 1-1.5 g of *O. scutellatus* venom (prepared by dissolving freeze dried venom) were subjected to gel filtration chromatography as follows: on Sephacryl 300 (once); on Superdex 200 (6 times), on Toyopearl HW55-S (once) and on Toyopearl HW65-S (twice). FIG. 3 shows the elution profile of *O. scutellatus* venom using Superdex™200 (gel column: 5 cm diameter, 95 cm long).

Example 1.4—SDS-Page

NuView Precast Mini Gels (#NB10-420, 4-20%) SDS PAGE gels with Tris-Glycine non-reducing sample buffer (#BG-145) (NuSep), and a reducing sample buffer with 5% β-mercaptoethanol were prepared. After a five minute incubation, a 40 µL aliquot from each sample was transferred into the equivalent volume of reducing sample buffer. The samples were then incubated for 10 minutes at 100° C. in a heating block. Aliquots of 25 µL of each sample and 12 µL of the pre-stained molecular weight marker (#SM0671 Page Ruler Prestained Protein Ladder, Fermentas, Hanover, Md., USA) were loaded on the gels. Gels were run at 100 V using a Mini-Protein II Cell PAGE apparatus (Bio-Rad) until the dye-front reached the bottom of the gel. The gels were stained with Coomassie Brilliant BlueG (#B-0770, Sigma) (0.25% w/v Coomassie Brilliant Blue G, 45% methanol, 10% acetic acid), and excess stain was removed by de-staining solution (45% methanol, 45% water and 10% acetic acid).

Example 1.5—Storage of OsPA Freeze-Dried as a Freeze-Dried Powder

In addition to the storage of purified OsPA in 50% glycerol, OsPA can be produced as a freeze-dried protein which can then be stored at −20 C. This can be achieved by conversion from the 50% glycerol OsPA stock solution or directly from the OsPA concentrate directly from the column.

Dialysis tubing (23 mm width, 12 kDa cut off) of 30 cm length was soaked in distilled water containing 1 mM EDTA and 0.2% sodium azide for 1-2 hours. Tubing was then washed with distilled water 10 times then each piece was filled with 80 ml 10% BSA in H$_2$O containing 0.2% sodium azide and stored in distilled water at 4° C. for 8 weeks. The tubing is ensured to be always submerged. Before use, the BSA solution was removed and the tubing washed inside with 100 volumes of distilled water.

Add OsPA glycerol stock (2.0 mg/mL in 50% glycerol-0.05 M Tris HCL Ph7.4) into each tubing, then add 10% BSA at a final concentration of 1% and 10% sodium azide to final concentration 0.2% and tie off tube. The OsPA in dialysis tubing was dialysed in 0.02 M hepes buffer pH 7.4 (dialysis buffer) at 250-300 times dialysate volume at 4° C. overnight with continuous slow magnetic stirring to giving an approximate final glycerol concentration of 10-15 mM. This ratio ensures that the final concentration of glycerol in the blood (4 mL) in a collection tube with OsPA is less than 0.1 mM.

After equilibrium was achieved (i.e. 24 hours at 4° C.), the dialyzed OsPA was carefully removed from the tubing. The OsPA was divided into dark glass bottles pretreated and dried with surfactant (2.41 g/L) with 10 mg of OsPA per bottle. The recovered OsPA/BSA suspension was shell-frozen using dry ice in preparation for freeze drying. Freeze drying was undertaken using a Christ freeze dryer as per Example 2 with setting 0.08 m Torr and −60 C for 24 hours.

After freeze drying, a sample bottle of the OsPA was reconstituted with 5 mL of Gelofusine to give an OsPA concentration 1.0-2.0 mg/mL A standard concentration curve of undialyzed OsPA at 0.125, 0.25, 0.50, 0.75, 1.0, 1.5, 2.0 and 3.0 µg was established for determining the recovery of dialyzed and freeze-dried OsPA. Four different dilutions of both dialyzed and freeze-dried OsPAs was used for recalcified whole blood clotting assay. The recovery of the OsPA at the two steps was calculated wth results showing that approximately 100% of OsPA was recovered from the dialysis and freezer-drying steps.

The freeze dried OsPA has been successfully stored with retention of activity for 6 months at −20 C.

Note that the OsPA used in the Examples is from 50% glycerol stocks.

Example 1.6 Characterisation of Ecarin

Ecarin isolated from *Echis carinatus* venom was sourced from Sigma Aldrich Catalogue Number EC0504 in a vial of 45-55 Units as a freeze-dried powder. The protein content was determined by Lowry protein assay (BioRAD DC protein Assay Catalogue number 500-01116) as 110-110 mg/vial. The ecarin was stored at −20 C.

Ecarin from *Echis carinatus* venom is the primary reagent in the ecarin clotting time (ECT) test, which is used to monitor anticoagulation and thrombin inhibition. One unit is defined as the amount required to activate prothrombin to produce one unit of amidolytic activity at pH 8.4 at 37° C. One amidolytic unit will hydrolyze 1.0 µmole of N-p-tosyl-Gly-Pro-Arg-p-nitroanilide per min at pH 8.4 at 37° C. Ecarin activity is determined using the chromotographic Assays as per Example 5.

Example 2—Tube Preparation

The tubes used in the present study were either plastic Greiner White Top plain tubes (Code #456001, Greiner Bio-One GmbH, Austria) or plastic Becton Dickinson Red Top tube plain (Code #3276916, Becton, Dickinson and Company, Franklin Lakes, USA).

Example 6 illustrates that the presence of a surfactant in the tube formulation is of benefit for optimal release from the tube wall and hence activity of the prothrombin activator. Although in this example, the addition of a colloid carrier (in this case 0.1% BSA) to the tubes with no surfactant demonstrates a benefit compared to the tubes with no BSA and no surfactant, activity is optimal in all cases with the addition of a surfactant. Hence, tubes for the examples have been produced with the addition of a surfactant.

To prepare tubes, 20 µl of surfactant solution was added to the tube as a liquid formulation, followed by vortexing for 10 seconds to ensure bottom of tube was coated. This process mimicked the commercial spraying process typically employed by tube manufacturers. Tubes were then dried in a vacuum dessicator overnight or using a GeneVac centrifuge drier. 20 µL of prothrombin activator was then dissolved in buffer or other formulation (as per Example 1) and added to the tube, followed by drying by centrifugal vacuum drying using a Genevac Z-22 for 30 minutes at 0.1 T vacuum at 29-30° C. Tubes were then re-capped with the original lid and cling wrapped to protect from dust and moisture and stored at room temperature until required.

Alternatively, tube samples were air-dried overnight without the lid at a controlled ambient temperature. Tubes were then re-capped with the original lid and cling wrapped to protect from dust and moisture and stored at room temperature until required.

Freeze-drying was conducted using a Christ freeze-dryer. Samples were dried at 0.01 T vacuum at −60° C. for 1 hour. Tubes were then re-capped with the original lid and cling wrapped to protect from dust and moisture and stored at room temperature until required.

Example 3—Irradiation

Irradiation of prepared tubes was undertaken to ensure the sterility of the final product. Irradiation can be accomplished by either exposure to gamma radiation or electon beam (E-beam) technology. In the present study, irradiation was undertaken by a commercial facility utilising a Gammacel 220 system (GC220) utilising gamma irradiation.

Blood collection tubes containing prepared clotting compositions were placed in a calibration rig (GC220), and then into the GC220 irradiation chamber and subject to gamma irradiation (Cobalt −60). Based on the known dose rate in this calibration rig, the product was then irradiated for a time expected to ensure the required dose was achieved. Results are expressed as target dose (kGv); actual dose; (kGv) and irradiation time.

Measurement traceability and uncertainty were validated as follows. Dosimeters were calibrated in a cobalt-60 radiation field, in which the dose rate was determined from reference dosimeter measurements made under similar conditions. The reference dosimeter measurements are traceable to the Australian standard for absorbed dose. This irradiation was performed based on the reference dose rate determined in the calibrated radiation field.

The overall uncertainty associated with the reference dose rate includes both the uncertainty of calibration of the batch of dosimeters and the uncertainty due to variation within the batch, and was calculated to be 2.0%. This expanded uncertainty was based on the standard uncertainty multiplied by a coverage factor of two, providing a level of confidence of approximately 95%. The uncertainty evaluation was carried out in accordance with the ISO Guide to the Expression of Uncertainty in Measurement. Quality management systems were compliant with the following licences and standards: TGA Licence No. 1182; ISO 13485:2003 (excluding design and development) of ISO 9001:2008. The quality management system also adhered to the principles of the following standards and guidelines: RSO 11137 International best practice for dosimetry (ISO 17025 and ISO/ASTM standards for dosimetry for radiation processing).

Example 4—Standardised Methods for Assessing Blood Samples

Citrated whole blood collected for all examples was taken from both healthy individuals and patients who were undertaking oral anticoagulant therapies, with written consent. The coagulation parameters used were: prothrombin time (PT), activated partial thromboplastin time (aPTT) and plasma fibrinogen concentration.

Platelet numbers were also measured on a Sysmex XE-5000 haematology analysers (Sysmex, Kobe Japan):

Normal coagulation parameters are: PT: 10-12 seconds; aPTT: 30-35 seconds; fibrinogen plasma concentration 1.5-2.5 g/L and platelet count 150-450×10$^9$ per mL of blood.

Patients undertaking oral warfarin therapy were monitored using International Normalized ratio (INR). The INR was determined by plotting the ratio of PT of patients on anticoagulation therapies versus healthy individuals. INR for effective warfarin therapy is 2.0-3.0.

Citrated whole blood from healthy individuals was either pooled at approximately n=50 or used on an individual basis. Healthy individuals donated ~500 mL of blood which were checked for recalcified whole blood clotting time, PT, aPTT, fibrinogen concentration and platelet count.

Whole blood recalcification time was measured in every example and data recorded for each batch of citrated whole blood. Normal whole blood recalcification time is between 15-20 minutes. Pooled or single samples with normal clotting profile or anticoagulated patients were suitable for use in blood clotting testing.

Fresh blood was used in some examples, taking single or multiple samples directly from volunteers with no citration/recalcification. The samples were tested for normal clotting profile by the use of a control tube in parallel to the tubes being tested. In some studies, blood from the same volunteer was also citrated and tested in parallel including TEG measurements as per Example 5.

Example 5—Clotting Composition Performance Assessment

Example 5.1—Plasma Clotting Assay

A recalcified citrated plasma clotting assay was performed using a Hyland-Clotek instrument as described by Austen et al (1975). Freshly pooled citrated plasma from normal volunteers was used for each group of experiments. The assay volume was 250 µL. Citrated normal human plasma (100 µL) was added to a glass clotting tube (1 mL) with 100 µL of 0.2 M Hepes buffer and 0.1 M NaCl (pH 7.4). Samples were placed in the 37° C. heating block of a Hyland-Clotek plasma clotting machine, and after at least 1 min, 25 µL of 0.2 M $CaCl_2$) (to a final concentration 20 mM) was added (when required), immediately followed by 20 µL of a solution containing OsPA activity, at which point the timer was started.

The concentrations of OsPA, based on protein concentration and a molecular weight for the Factor V-Factor Xa complex of 250,000, ranged between 0.01 pM and 1.9 µM. Citrated plasma typically contains 20 mM citrate (as trisodium citrate) and after dilution, the citrate concentration in the reaction mixture was 8 mM, giving a net calcium concentration (molar excess over citrate) in the reaction mixture of 12 mM. Clotting time was recorded in seconds. Each assay was carried out in duplicate.

Figure 4:
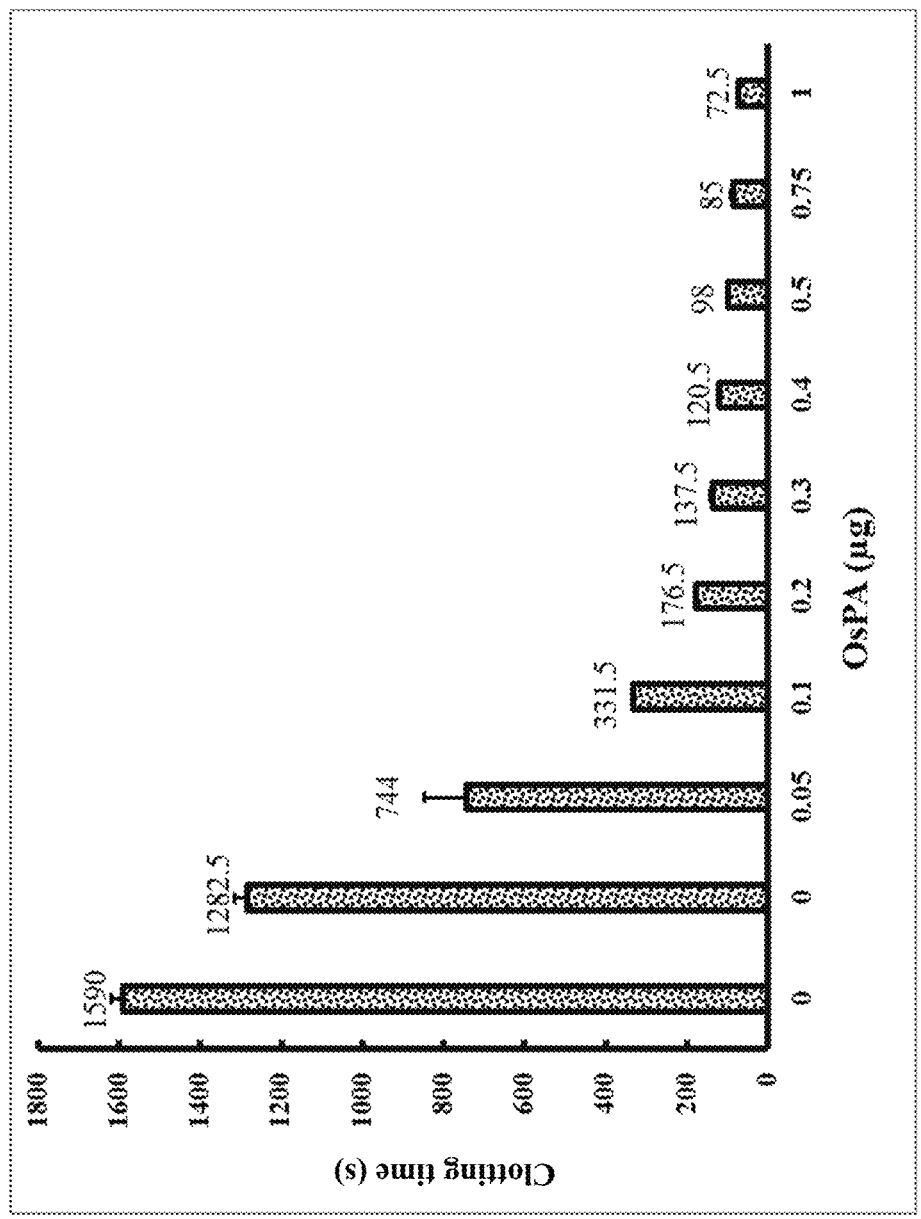
FIG. 4 shows whole blood clotting activity curve of concentrated OsPA fraction purified on Superdex resin.

FIG. 4 shows standard curves, plotting clotting time against amount of protein from the Apr. 17, 2012 OsPA fraction.

Example 5.2—Visual Assessment of Clotting

Pooled citrated normal blood having a PT=10-12 seconds; an aPTT=35-40 seconds; fibrinogen concentration=1.5-4.0 g/L and platelet count of 150-400×$10^9$/mL was placed in a plastic bottle in a biohazard hood. Greiner white top tubes or BD plain red top tubes containing vacuum dried hydrophilic surfactant (20 μL of 2.41 g/L surfactant in RO water) were used. In addition, either OsPA or ecarin, with or without Gelofusine (20 μL), was added to the tubes. The OsPA or ecarin was added either as a wet solution or as a Genevac/vacuum desiccator dried composition, to which 50 μL of 1 M calcium chloride was added. 3.95 mL of citrated blood was then dispensed using a Gilson P5000 pipette into the tubes and the timer was started. The tubes were immediately recapped and then gently tilted by inversion. Duplicate test blood samples were carried out by two investigators. Blood containing tubes were continually inverted until an initial clot lump was observed, at which point the time was recorded as "start clotting time". When a solid clot was observed on inversion, the time was recorded as "completed clotting time".

Example 5.3—Thromboelastography (TEG) Assay

The operating procedures for the thrombelastograph (TEG) machine and parameters generated from each assay are provided in the TEG® Haemostasis Analyser 5000 series (Haemscope Corporation, IL, USA) Operating Manual and accompanying software.

Each reaction mix was made up directly into a purpose-made disposable cup (Cat no. 6211, Haemscope Corporation) and consisted of a maximum volume of 360 μL. Whole citrated blood was a component of all of the assays and was kept at a constant volume of 320 μL.

Other components were added in the following order: 1. OsPA dilutions, 2. Calcium when present (final concentration 20 mM=3.6 μL of 2 M solution), and 3. Citrated whole blood (320 μL), giving an excess of calcium over citrate of about 10 mM depending on the haematocrit of the pool of 10 blood samples.

Figure 5:
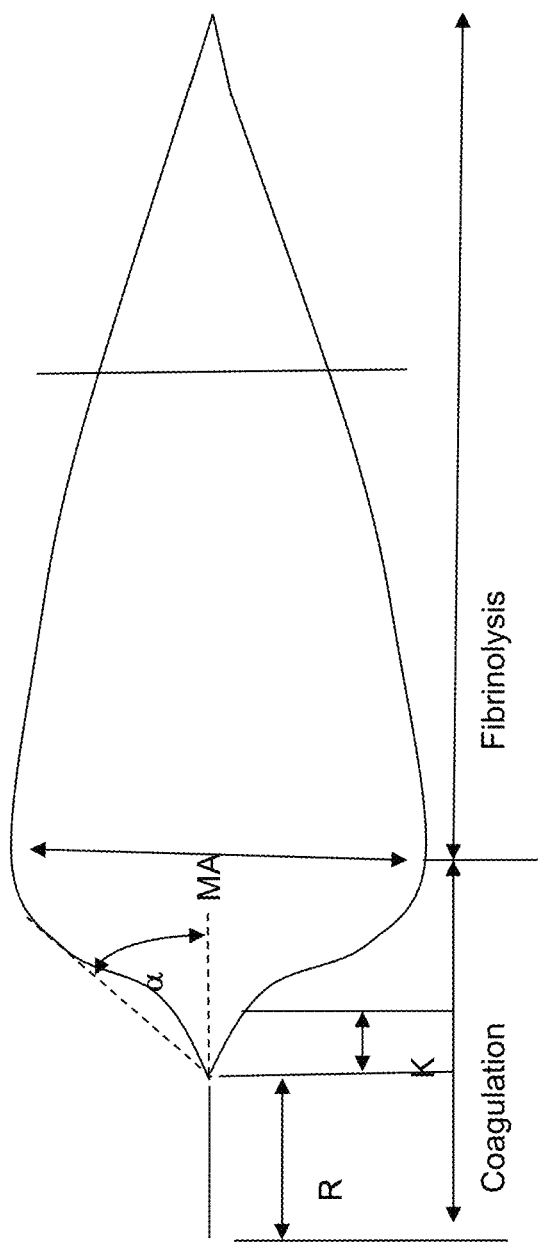
FIG. 5 shows a diagram representing a graph from the Thrombelastograph® during the clotting of whole blood (from TEG® Haemostasis Analyser 5000 Series Manual).

FIG. 5 shows a diagram of a trace from a thrombelastography experiment. Each test was monitored until the maximum amplitude (MA) value was established. Graphs were generated by the TEG companion software. The TEG® analyzer measures the shear elasticity of a clot as it forms or lyses. The relevant parameters calculated by the companion software were: R—Reaction time. The time from the start of a sample run until the first detectable clot formation. This is the point at which most traditional plasma clotting assays reach their end point, measured in seconds; Angle—α. Measurement of the rapidity of fibrin build-up and cross-linking (clot strengthening); MA—Maximum amplitude. Maximum stiffness or strength (maximum shear modulus) of the developed clot; A—Amplitude. The width of the trace at any point and is equal to MA until MA is established; G—The shear elastic modulus strength (SEMS). This value can be calculated from the maximum amplitude value using the relationship G=5000*MA/(100−MA).

The amplitude of the Thrombelastograph profile at 5 second intervals was recorded and retrieved using the lysis Tracker function in the TEG software. These data were then used to calculate the kinetic parameters of clot formation and lysis. The parameters for each sample were recorded and averaged for replicates. Standard error was determined by first calculating the standard deviation then dividing this value by the square root of the replicate number.

Example 5.4—Chromogenic/S-2222 Assay

S-2222 is a peptide-based chromogenic substrate which releases p-nitroaniline on hydrolysis, which can be measured at 405 nm. S-2222 was designed to be specific for hydrolysis by Factor Xa.

Using a spectromphotometer, the assay mixture in the cell had a total volume of 1 mL, made up of: (1) 900 μL Hepes buffer, pH 7.4; (2) 50 μL S-2222 (3 mM solution in water), giving an initial substrate concentration of 150 μM; and 50 μL prothrombin activator, such as OsPA. This was diluted to a final working concentration of 10 nM. The molar extinction coefficient A405 for p-nitroaniline is 9600 $M^{-1}$, with the spectrophotometer providing the rate of increase in A405 in absorbance units/sec.

Figure 6:
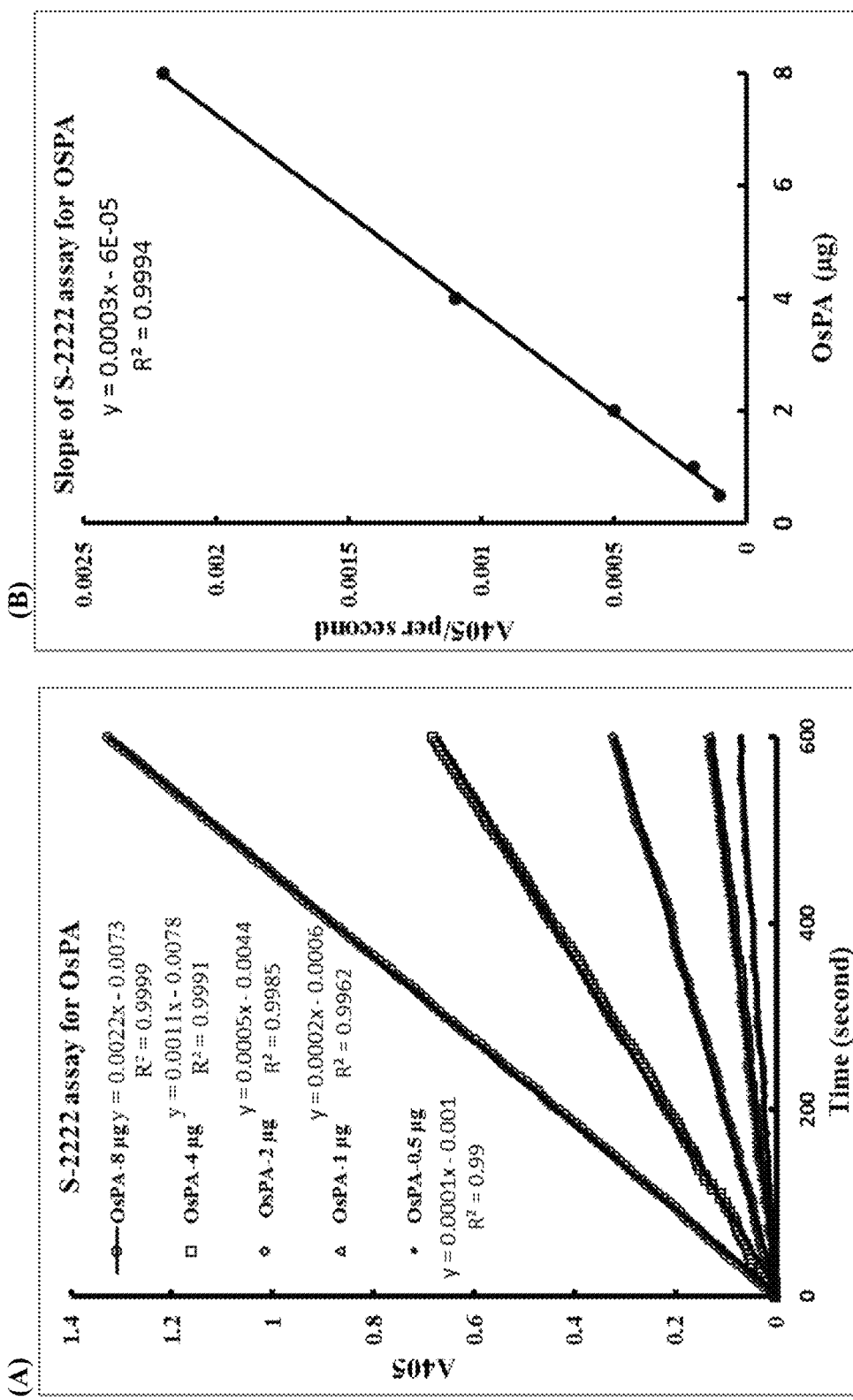
FIG. 6 shows progress curves for the S-2222 assay using pooled OsPA (17/4/12) (A) and standard curve (B).

FIG. 6 shows progress curves for the release of p-nitroaniline at different concentrations of OsPA (using the OsPA fraction designated 17/04/2012). The progress curves are linear. A replot of rate against amount of OsPA was linear and constituted the standard curve for this assay. From the rate, and the amount of prothrombin activator in the assay, a specific activity of prothrombin activator can be calculated, as Units/mL of protein where 1 Unit (U) is the amount of protein required to hydrolyse 1 micromole of S-2222 per minute in the standard assay.

Example 5.5—Chromogenic/S-2238 Two Stage Assay

Another chromogenic assay which can be used is the S-2238, a peptide-based chromogenic substrate which releases p-nitroaniline on hydrolysis, which is measured at 405 nm. S-2238 was designed to be specific for hydrolysis by thrombin (Factor IIa). The assay depends on sampling timed aliquots from a first stage assay mixture (Prothrombin and Activator) into a second stage assay mixture containing S-2238 to measure the thrombin produced in the first stage.

The assay is performed in a 96 well microtitre plate and absorbances read on a Plate reader. The first stage assay mixture had a total volume of 100 uL, made up of: (1) 25 μL Hepes buffer, pH 7.4, 5 mM $CaCl_2$), 0.1% BSA; (2) 25 uL activator (0.25 ug OsPA/mL); (3) and 50 uL prothrombin (2 uM) to start the reaction.

At 5 min intervals 10 uL of the first stage assay mixture are added to 90 uL 0.2 mM S2238 in an adjacent well of the microplate and the absorbance monitored for 2 minutes. The effective extinction coefficient A405 for p-nitroaniline under these conditions was determined as 2271 $M^{-1}$, using p-nitroaniline standards. This factor is used to convert the rate of increase in absorbance units/s to umol S2238 hydrolysed per second.

Linear progress curves were produced the slopes of which give the rate of S2238 hydrolysis in Stage 1. These are converted to thrombin concentrations using the Michaelis-Menten equation substituted with literature values for kcat and Km (Sonder S A and Fenton J W, Clin. Chem. 1986, 32

(6), 934-937A). A replot of these thrombin concentrations against sampling time was also linear, the slope of which gives the concentration of prothrombin activator in the Stage 2 assay as Units/mL, where 1 Unit (U) is the amount of activator required to hydrolyse 1 micromole of prothrombin per minute in the standard assay (eg) (9.98e-6 umol/min). Linearity of the rate of thrombin production against OsPA concentration was also demonstrated, the slope of which gives the specific activity of the prothrombin activator as Units/mg of protein (eg) (5.0e-3 units/mg).

Example 5.6—Stability Testing

In order to determine the stability of formulations under usage conditions, the samples were stored at the following conditions: (1) for refrigerated stability testing: 4° C. in a refrigerated environment (thermostat controlled cold room); (2) for room temperature stability testing, defined as 25° C. (23.5-26.5° C.) samples were stored at ambient temperature; (3) for accelerated stability testing: 50° C. in a thermostat controlled oven (49-51° C.).

Example 5.7—Analyte Measurement

The following panel of analytes was measured in serum prepared as described herein. The equipment used was a Beckman DxC800 general chemistry analyser and Beckman DxI800 immunoassay analyser (Beckman Coulter, Brea, Calif., USA):

| Biochemical Assay | Unit measured |
| --- | --- |
| Sodium | mmol/L |
| Potassium | mmol/L |
| Chloride | mmol/L |
| Glucose | mmol/L |
| Urate | mmol/L |
| Total Protein | g/L |
| Albumin | g/L |
| Bilirubin | µm/L |
| Alkaline Phosphatase (ALP) | U/L |
| Gamma Glutamyl Transferase (GGT) | U/L |
| Aspartate Aminotransferase (AST) | U/L |
| Lactase dehydrogenase (LD) | U/L |
| Calcium | mmol/L |
| Phosphate | mmo/L |
| Magnesium | mmol/L |
| Lipase | U/L |
| Cholstrerol | mmol/L |
| HDL Cholstrol | mmol/L |
| Haemolytic Index | 1 = 0-50 mg/dL |

Example 6. Stability of Clotting Compositions Relative to Drying Conditions and Surfactant Example 6.1—Introduction This experiment aimed to investigate the effects of drying conditions and the use of surfactants on clotting time. In this example, samples of freshly diluted prothrombin activator (OsPA, either 0.25 µg or 1 µg) were placed in Greiner White Top plain (Code #456001) blood collection tubes (+/− hydrophilic surfactant (20µ of 2.41 g/L in water); +/−0.1% BSA) in HEPES buffer. These tubes were prepared as per Example 2, then tested with 4 mL of blood from a pool of 50 healthy donors or individual patients as per Example 4 and subjected to the visual clotting assay and TEG analysis as per Example 5. The tubes were dried either by vacuum dessicator or Genevac as per Example 2 prior to blood clotting experiments. All steps were carried out at room temperature.

Example 6.2—Results and Discussion

Figure 7:
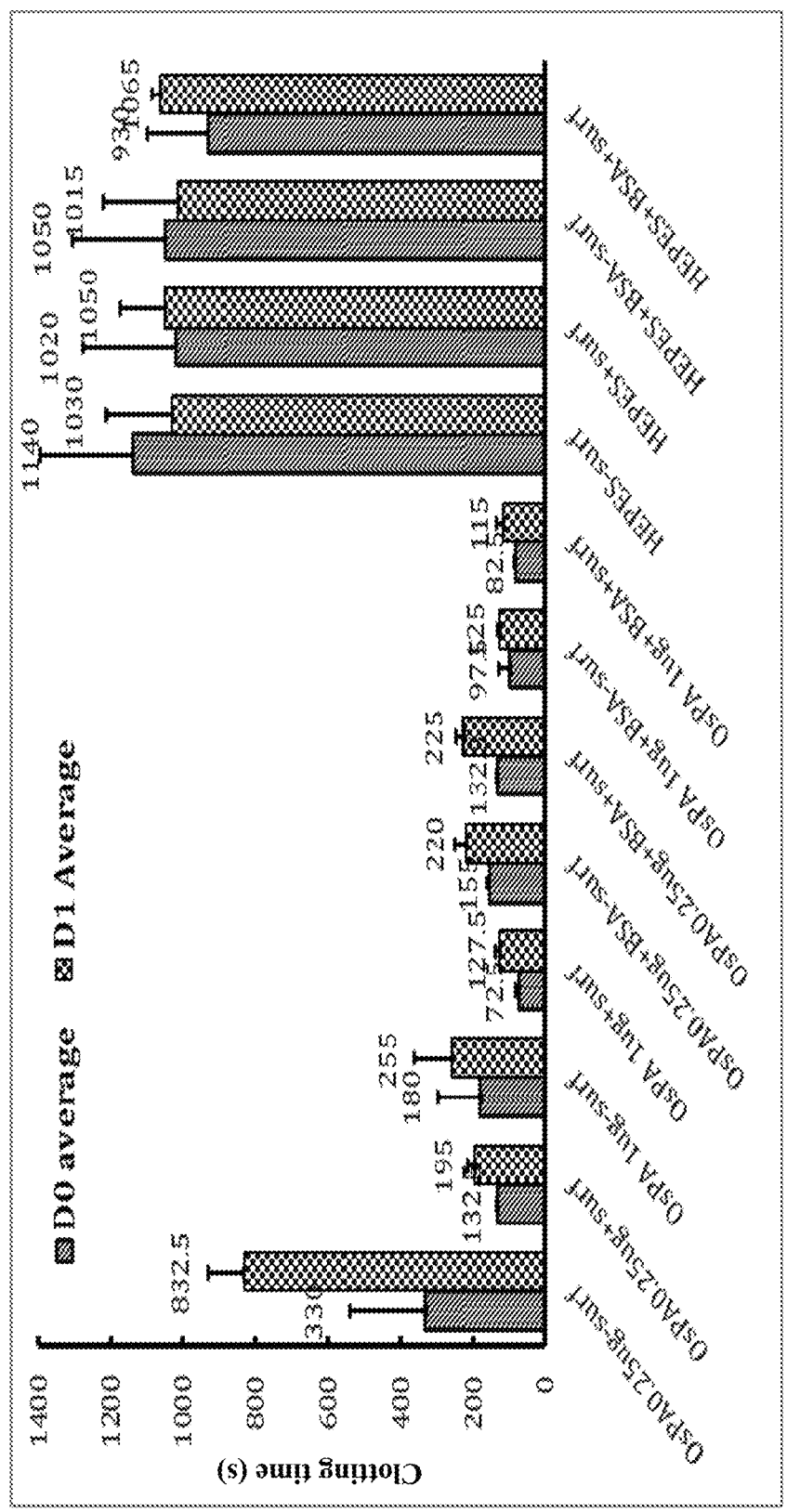
FIG. 7 shows whole blood clotting activity of freshly diluted OsPA compared with that of desiccator-dried OsPA. D0 data are for freshly diluted liquid samples of OsPA added to blood collection tubes; D1 data are for samples dried overnight at room temperature in blood collection tubes in a vacuum desiccator.

The results in FIG. 7 show whole blood clotting activity of freshly diluted OsPA compared with that of vacuum dessicator-dried OsPA. D0 data are for freshly diluted liquid samples of OsPA added to blood collection tubes. D1 data are for samples dried overnight at room temperature in blood collection tubes in a vacuum desiccator as per Example 2. Upon comparison of the dark columns (D0), the effect of including a surfactant and BSA on fresh samples can be seen. For the control blood samples (no OsPA), adding surfactant and/or BSA to the tube prior to the blood had no significant effect on the clotting time as measured using the Standard Clotting Assays as per Example 5. For the samples containing 0.25 µg OsPA, the presence of surfactant reduced the clotting time from 330 to 132 seconds; with 1 µg OsPA, the values were 180 and 72.5 seconds respectively. BSA alone also reduced the clotting times substantially (but not as much as the surfactant) but the effect of BSA and surfactant was not additive. Without wishing to be bound by theory, the likely explanation for the effects of the surfactant is that it prevents binding of OsPA to the tube surface in such a way that it is unavailable to function.

Comparing the checkered and dark columns in FIG. 7 (D0 and D1) for each set of conditions shows the effect of drying in a vacuum desicator as undertaken per Example 2 compared to a freshly diluted OspA sample. There was generally a loss of clotting activity caused by the drying process. For example, using 1 µg OsPA, drying increased the clotting time from 180 to 255 seconds in the absence of surfactant and from 72.5 to 127.5 sec in the presence of surfactant. The presence of surfactant and BSA separately or together led to lower clotting times on drying but losses remained substantial. In all cases, tubes with surfactant clotted faster than tubes with no surfactant. For example, a wet sample of 1 µg OspA without surfactant clotted in 180 seconds, and with the addition of a surfactant in 72 seconds. The same tube with the OsPA dissolved in a 0.1% BSA and no added surfactant clotted in 97 seconds. This pattern is repeated across the wet and dried samples and shows that although colloids such as BSA may improve activity if the prothrombin activator in a tube environment, the addition of a surfactant is optimal.

Figure 8:
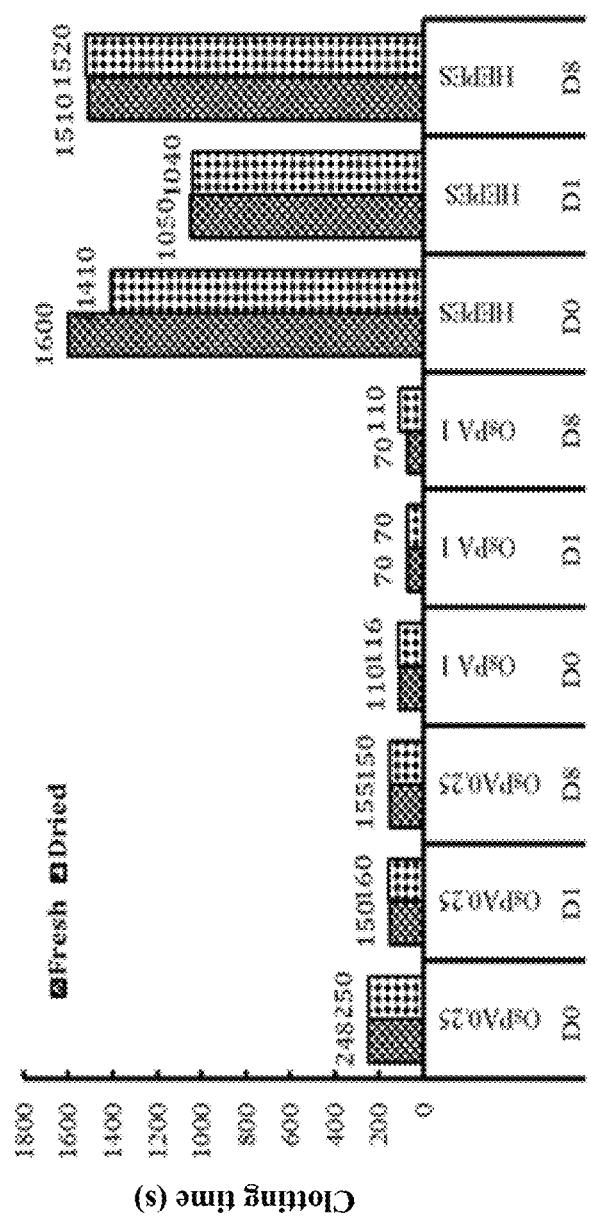
FIG. 8 shows whole blood clotting times in blood collection tubes containing freshly diluted OsPA and in similar tubes in which OsPA had been dried using a Genevac.

The results in FIG. 8 involved use of a Genevac vacuum drier as per Example 2 which achieved faster drying of the OsPA sample than the vacuum dessicator used in FIG. 7. The drying time was 30 min for a total volume of 50 µL as per Example 2. FIG. 8 shows that dried samples had the same clotting times as the corresponding fresh samples. HEPES controls were also included. This experiment demonstrates that drying in a Genevac gave 100% retention of clotting activity. Accordingly, Genevac drying was used in the majority of subsequent experiments to prepare blood collection tubes containing dried OsPA.

FIG. 8 also shows that samples maintained activity, as evidenced by clotting time, after storage at room temperature for 8 days.

Example 7—Stability of Clotting Compositions Relative to Storage Time

Example 7.1—Introduction

This experiment aimed to investigate the effects of storage time on clotting time. Samples of freshly diluted prothrombin activator (OsPA, either 0.25 μg or 1 μg) were placed in Greiner White Top plain (Code #456001) blood collection tubes (+/− hydrophilic surfactant (20l of 2.41 g/l in water); +1-0.1% BSA) in HEPES buffer. The tubes were then dried using a Genevac vacuum drier as Per Example 2 and stored at room temperature in a dry environment as per Example 2 for up to 85 days. Whole blood clotting assays were performed as per Example 5 weekly using citrated, pooled blood collected as per Example 4. After storage, the tubes were used for blood clotting assay via the visual clotting and TEG analyses (see Example 5). All steps were carried out at room temperature. Controls using freshly diluted OsPA in liquid form were performed each week, as well as controls using Hepes buffer only.

Example 7.2—Results

Table 7 shows a loss of clotting activity by Day 85 for both 0.25 μg and 1 μg OsPA samples. Loss of activity occurs sometime between Day 15 and Day 22.

Example 8—Stability of Clotting Compositions Relative to Storage Time and Other Additives Example 8.1—Introduction This experiment aimed to investigate the effects on clotting time of ten reagents known to stabilize proteins under some conditions. Samples of freshly diluted prothrombin activator (OsPA, either 0.25 μg or 1 μg+/−ammonium-acetate pH 6.8) were placed in Greiner White Top plain (Code #456001) blood collection tubes (+/− hydrophilic surfactant (20 μl of 2.41 g/L in water)+/−0.5% BSA; and other potential stabilizing agents: +/−0.1% PEG; +/−0.5% Prionex®; +/−1 mM Glycine/Arginine; +/−534 nm Textilinin; +/−1 mM trisodium citrate; +/−0.5% mannitol; +/−0.5% sorbitol; +/−0.5% dextran; +/−0.5% gelatin) in HEPES buffer. The tubes were prepared as per Example 2, being dried using a Genevac® and stored at room temperature in a dry environment for up to 99 days. Whole blood clotting

TABLE 7

Clotting of recalcified citrated whole blood in dry OsPA-containing blood collection tubes (χlotting times in seconds)

| No. Formulation | D0 | D1 | D8 | D15 | D22 | D29 | D36 | D43 | D50 | D57 | D64 | D71 | D78 | D85 |
|---|---|---|---|---|---|---|---|---|---|---|---|---|---|---|
| 1 OsPA (0.25 μg) − 0.1% BSA(Fresh) | 248 | 150 | 155 | 160 | 180 | 150 | 190 | 185 | 235 | 220 | 260 | 170 | 230 | 220 |
| 2 OsPA (0.25 μg) + 0.1% BSA(Fresh) | 245 | 150 | 130 | 140 | 145 | 118 | 185 | 170 | 190 | 225 | 230 | 160 | 235 | 225 |
| 3 OsPA (0.25 μg) − 0.1% BSA(Dried) | 250 | 160 | 150 | 150 | 370 | 425 | 610 | 588 | 1040 | 890 | 1320 | 660 | 909 | 1110 |
| 4 OsPA (0.25 μug) + 0.1% BSA(Dried) | 265 | 125 | 270 | 220 | 370 | 405 | 510 | 358 | 450 | 600 | 820 | 460 | 660 | 910 |
| 5 OsPA (1 μug) − 0.1% BSA(Fresh) | 110 | 70 | 70 | 80 | 85 | 90 | 75 | 85 | 100 | 88 | 90 | 101 | 76 | 85 |
| 6 OsPA (1 μg) + 0.1% BSA(Fresh) | 103 | 90 | 70 | 60 | 95 | 95 | 90 | 88 | 95 | 59 | 105 | 90 | 75 | 82 |
| 7 OsPA (1 μg) − 0.1% BSA(Dried) | 116 | 70 | 110 | 100 | 320 | 400 | 490 | 565 | 935 | 730 | 940 | 568 | 909 | 1143 |
| 9 OsPA (1 μg) + 0.1% BSA(Dried) | 98 | 85 | 160 | 90 | 225 | 245 | 315 | 275 | 370 | 540 | 510 | 390 | 670 | 970 |
| 9 Hepes − 0.1% BSA(Fresh) | 1600 | 1050 | 1510 | 1040 | 990 | 970 | 1010 | 1045 | 1230 | 1075 | 1320 | 470 | 1160 | 1270 |
| 10 Hepes + 0.1% BSA(Fresh) | 1560 | 840 | 1390 | 810 | 650 | 990 | 990 | 965 | 1340 | 1010 | 920 | 450 | 1260 | 1260 |
| 11 Hepes − 0.1% BSA(dried) | 1410 | 1040 | 1520 | 1040 | 955 | 1000 | 1230 | 1030 | 1140 | 1100 | 1140 | 480 | 1170 | 1230 |
| 12 Hepes + 0.1% BSA(dried) | 1460 | 1120 | 1590 | 830 | 740 | 1000 | 1090 | 980 | 1170 | 980 | 1090 | 510 | 1190 | 1250 |

Example 7.3—Conclusion

From Table 7, it can be seen that control tubes using freshly prepared liquid OsPA consistently gave the expected clotting times throughout the 85 days of the experiment (see rows 1, 2, 5 and 6). For the dried samples, clotting times remained stable for the first three measurements (Days 1, 8 and 15). However, there was a marked increase in clotting time at the 22 day time point and this loss of clotting activity continued through until Day 85 (see Rows 3, 4, 5 and 6). This example therefore demonstrated a gradual loss of OsPA activity when formulated with surfactant only over time when the OsPA containing blood collection tubes were stored at room temperature.

assays were performed weekly using citrated, pooled blood prepared as per Example 4. After storage, the tubes were used for blood clotting assay using the visual clotting method as per Example 5. All steps were carried out at room temperature. Controls using freshly diluted OsPA in liquid form were performed each week, as well as controls using Hepes buffer only.

Example 8.2—Results

Table 8 shows a loss of clotting activity by Day 85 for the 1 μg OsPA samples. Loss of activity occurs some time between Day 15 and Day 22.

TABLE 8

Clotting of recalcified citrated whole blood in dry OsPA-containing blood collection tubes

| Formulation<br>Blood collection tube condition | Day 0 | Day 1 | Day 8 | Day 15 | Day 22 | Day 29 | Day 57 | Day 99 |
|---|---|---|---|---|---|---|---|---|
| Recalcification control | 590 | 575 | 1070 | 1200 | 820 | 1305 | 945 | 710 |
| Fresh OsPA (1 µg) in 0.01M Am-Ac pH 6.8 | | | 95 | 90 | 80 | 95 | 95 | 95 |
| OsPA (1 µg) dried in 0.01M Am-Ac pH 6.8 | 62 | 135 | 105 | 205 | 490 | 980 | 545 | 510 |
| OsPA (1 µg) + 0.5% BSA | 81 | 180 | 130 | 180 | 315 | 370 | 210 | 380 |
| OsPA (1 µg) + 0.5% Dextran | 73 | 105 | 150 | 270 | 270 | 310 | 240 | 310 |

Table 8 shows the results of the experiment covering storage for up to 99 days (over 3 months) at room temperature. Figures shown are the number of seconds required for clot formation. BSA and dextran separately stabilized the blood clotting activity of OsPA compared with buffer alone. For example, after 99 day storage, the clotting time for the OsPA/BSA and OsPA/dextran tubes was 380 and 310 seconds, respectively, compared with the fresh control (95 seconds), OsPA only (510 seconds) and the the control without OsPA (710 seconds). This result demonstrated the ability of 1 µg of OsPA to clot 4 mL of recalcified citrated whole blood in approximately 5 minutes after storage at room temperature for three months, with either dextran or BSA. Other reagents which gave some degree of stabilization were sorbitol, Prionex®, gelatin and mannitol.

Example 9—Stability of Clotting Compositions Relative to Storage Time, Temperature and Addition of the Colloid Gelofusine Example 9.1—Introduction In seeking to further improve the stability of the clotting activity of dried prothrombin activators such as OsPa, the plasma extender Gelofusine was tested. The colloid Gelofusine (B. Braun) is a sterile solution of succinylated gelatin (4% w/v) in isotonic saline and is low cost and readily available.

Figure 9:
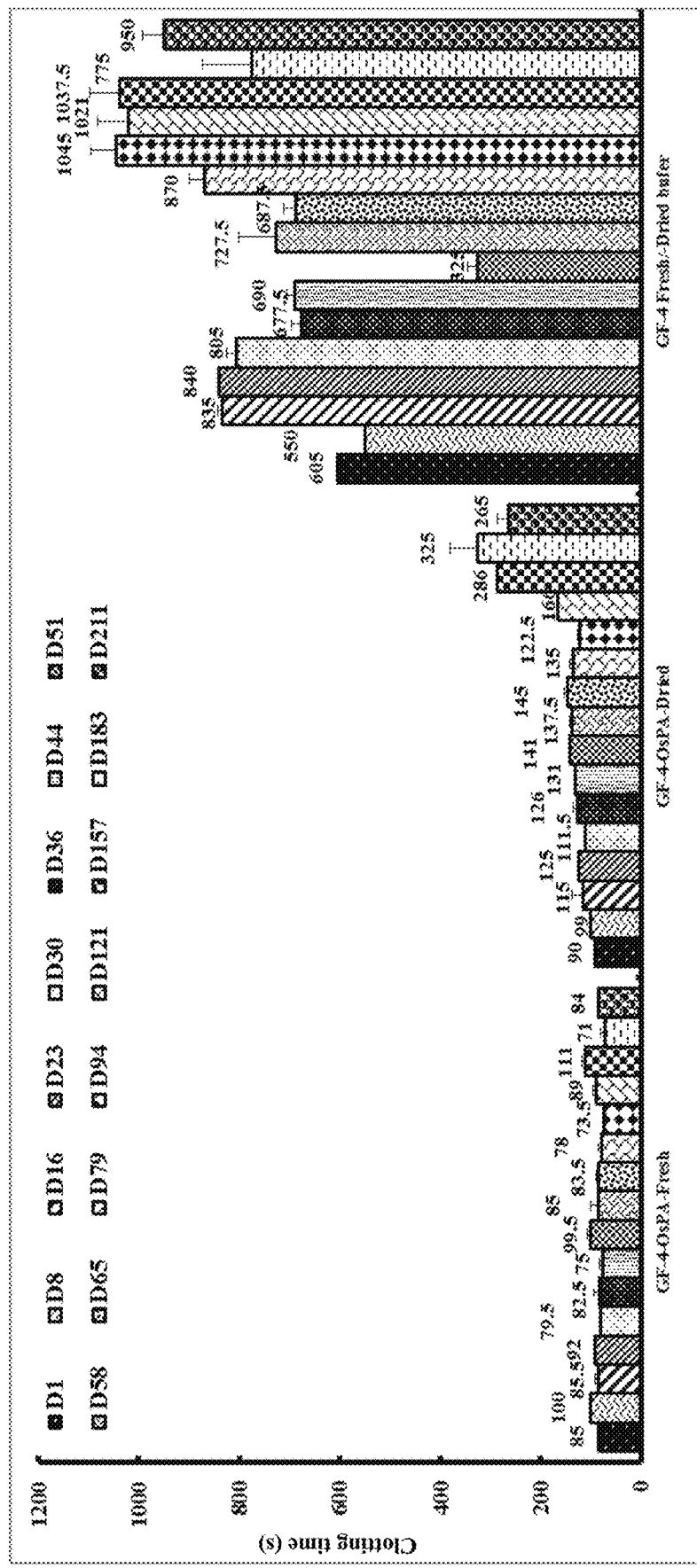
FIG. 9 shows stability of dried OsPA in Gelofusine at room temperature for 211 days in whole blood clotting time. Left hand series: controls using 1 µg freshly diluted OsPA in buffer ph 7.4; middle series: test samples in which 1 µg OsPA was dried in the presence of Gelofusine (20 µl); right hand series: clotting times of recalcified blood samples with no OsPA.
Figure 10:
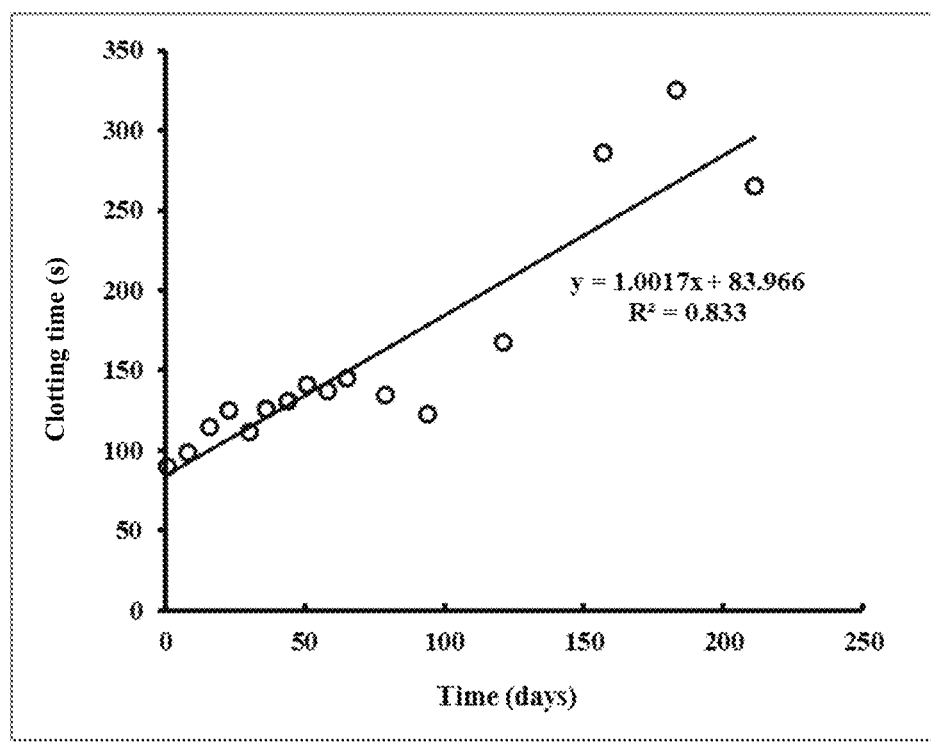
FIG. 10 shows line graphs using data from FIG. 9. A: all points from zero to 211 days; B: points from zero to 65 days.
Figure 10:
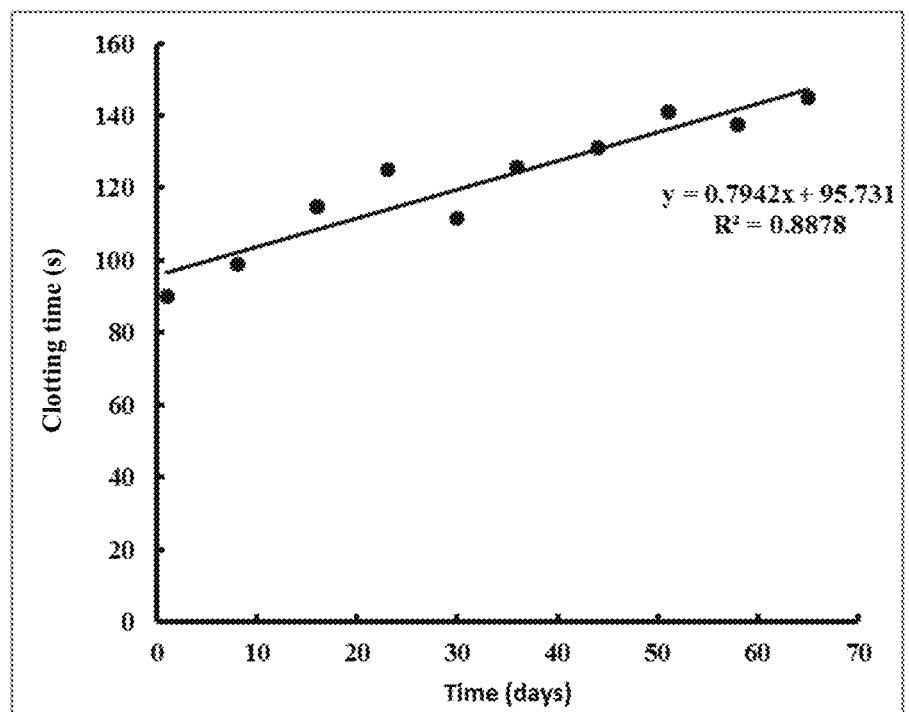

This experiment aimed to investigate the effects of a protein colloid as a stabilizer to preserve clotting time function over time. Tubes were prepared as per Example 2, wherein the colloid was rolled onto the inside surface of the tube. Samples of freshly diluted prothrombin activator (OsPA, 1 µg+/−ammonium-acetate pH 6.8) in 20 µL Gelofusine pH 7.4 were placed in Greiner White Top plain (Code #456001) blood collection tubes (+/− hydrophilic surfactant (204 of 2.41 g/L in water). The tubes were then dried using a Genevac® as per Example 2 and stored at room temperature for up to 211 days (FIGS. 9 and 10). Whole blood prepared as per Example 4 was used in whole blood clotting assays and assessed in this example by the Visual Clotting Assessment method as per Example 5. After storage and at each time point, blood samples (citrated, pooled) were aliquoted into the tubes with a final volume of 4 mL, and the tube containing the sample subjected to the standard whole blood clotting assay as per Example 5. All steps were carried out at room temperature. Controls using freshly diluted OsPA in liquid form were performed at each time point in addition to appropriate controls that were devoid of OsPA.

In addition, 12 tubes were tested using fresh blood as per Example 4 with Visual Clotting Assessment conducted as per Example 5. The tubes were prepared as per Example 2, with samples of freshly diluted prothrombin activator (OsPA, 1 µg in 20 µL Gelofusine pH7.4) placed in Becton Dickinson plain (Code #3276916) blood collection tubes+ hydrophilic surfactant (204 of 2.41 g/L in water). The tubes were then dried using a Genevac® as per Example 2. The visual clotting time at TO was 158.9+/−95 seconds, comparable to the experiments with citrated blood in BD plain tubes.

Example 9.2—Results and Discussion

Results are shown in FIGS. 9 (histogram) and 10 (line graphs). After seven months (211 days) at room temperature, the clotting time using 1 µg OsPA of 4 mL blood was 265 seconds, compared with 84 seconds for the fresh control and 950 seconds for recalcified citrated blood sample control with no additions. Excellent stability was observed up to 121 days but then there was a loss of activity between 121 and 157-day measurements. The slope of the 'dried OsPA' line graph is 1.0 seconds/day if all time points are considered and 0.79 seconds/day if points from day 1 to day 121 only are considered.

The rates of loss of clotting activity in Example 10 and the present example were then compared. The initial rates of activity loss were 1.67 seconds per day in Example 10 (presence of BSA and dextran) and 0.79 seconds per day in Example 9 (presence of Gelofusine as an exemplary colloid). If all data points in each trial are considered, the corresponding rates were 1.29 in Example 11 and 1.0 in Example 10. These data therefore show that the colloids dextran, BSA and Gelofusine are effective in stabilising OsPA, with Gelofusine appearing to have the greatest effect out of the samples tested.

Figure 11:
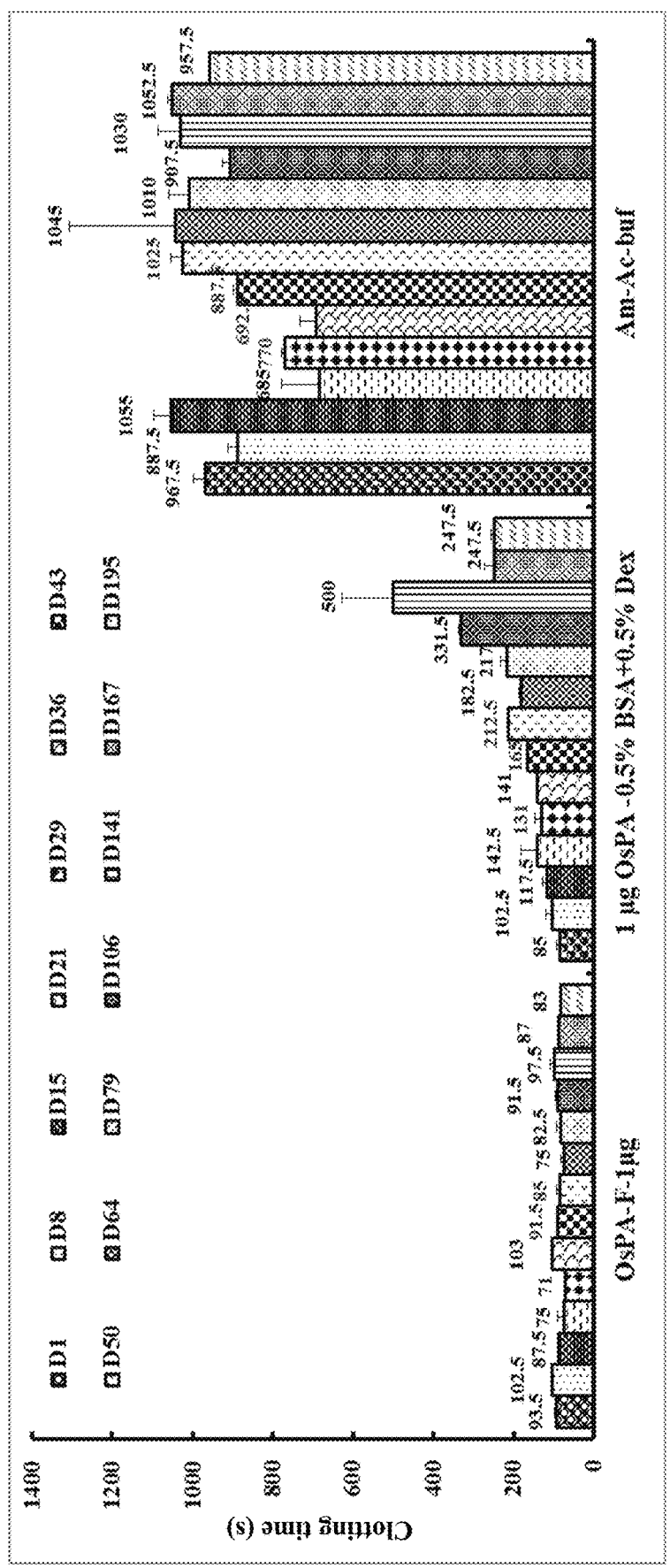
FIG. 11. Clotting times (means of duplicates) for the clotting of recalcified citrated whole blood by OsPA in blood collection tubes after storage at room temperature for up to 195 days. Left hand series: controls using 1□g freshly diluted OsPA in 0.1 M Ammonium Acetate buffer pH 6.8; middle series: test samples in which 1 µg OsPA was dried in the presence of 0.5% w/v bovine serum albumin and 0.5% w/v dextran; right hand series: clotting times of recalcified blood samples with no OsPA.
Figure 12:
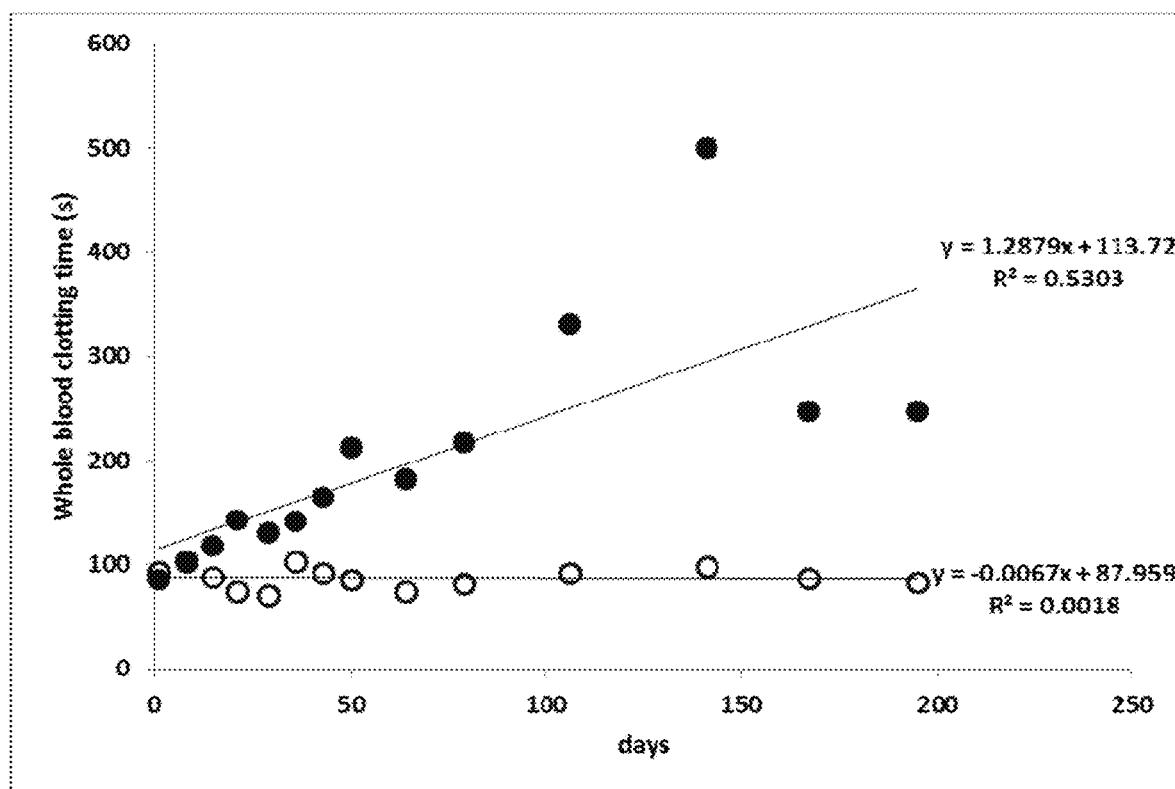
FIG. 12 shows line graphs of the clotting times for the fresh control and OsPA/BSA/dextran tubes. Data from FIG. 11.

Example 10—Stability of Clotting Compositions Relative to Storage Time, Temperature and Addition of BSA and Dextran Example 10.1—Introduction This experiment aimed to investigate the effects of BSA and Dextran combined as a stabiliser to preserve clotting function over time (FIGS. 11 and 12). Tubes were prepared as per Example 2. Samples of freshly diluted prothrombin activator (OsPA, 1 µg in 20 µL ammonium-acetate solution containing +/−0.5% dextran, +/−0.5% BSA pH 6.8) were placed in Greiner White Top plain (Code #456001) blood collection tubes (+/−hydrophilic surfactant (20µ of 2.41 g/l in water) The tubes were then dried using a Genevac® as per Example 2 and stored at room temperature for up to 195 days as per Example 5. Whole blood prepared as per Example 4 was used in whole blood clotting assays, assessed in this example by the Visual Clotting Assessment method as per Example 5. After storage and at each time point, blood samples (citrated, pooled) were aliquoted into the tubes, final volume of 4 ml and the tube containing the sample subjected to the standard whole blood clotting assay as per Example 5. All steps were carried out at room temperature. Controls using freshly diluted OsPA in liquid form were performed at each time point in addition to appropriate controls that were devoid of OsPA.

Example 10.2—Results and Discussion

FIG. 11 shows the results of the experiment covering storage for up to 195 days (about 6.5 months) at room temperature as a histogram, and FIG. 12 shows the corresponding line graphs. Comparing these results with those in Table 8 shows that BSA and dextran together gave greater stabilization than either material alone. After 6.5 months storage, the clotting time for the OsPA/BSA/dextran tubes was 247 seconds compared with the fresh control (83 seconds) and the control without OsPA (957 seconds). The slope of the line graph in FIG. 12 including all time points is 1.29 seconds per day (increase in clotting time per day). If the last four time points are excluded, the slope is 1.67 seconds per day (R2=0.87).

Example 11—Stability of Clotting Compositions Relative to Temperature and Addition of the Colloid Gelofusine Example 11.1—Introduction The aim of this study was to determine the stability of the whole blood clotting activity of OsPA dried in Gelofusine when stored at 5000. Forced degradation at higher than the normal storage temperature has often been used to obtain stability data more rapidly than by storing samples for a defined period at the elevated storage temperature. The rate of loss of activity at the higher temperature can then be extrapolated to the normal storage temperature, for example, by using the Arrhenius equation.

As well as testing stability when OsPA was dried in Gelofusine at pH 7.4, the effect of adjusting the Gelofusine pH to 6.0 was also determined. The reason for studying the effect of a lower pH was to investigate the possibility that the Factor Xa component of OsPA is able to catalyse the proteolysis of OsPA with concomitant loss of activity. The catalytic activity of OsPA is lower at pH 6.0 than at pH 7.4.

Tubes were prepared as per Example 2. Two sets of samples were prepared, one set with Greiner White Top plain (Code #456001) blood collection tubes and one with BD red top plain blood collection tubes (Code #3276916). For each set of samples, freshly diluted prothrombin activator (OsPA, either 1 µg, 2 µg or 5 µg,) were placed in the tubes+/−hydrophilic surfactant (204 of 2.41 g/L in water)+/− 50 µl of 4% w/v Gelofusine; and buffered to either pH 7.4 or pH 6.0. The tubes were then dried using a Genevac® as per Example 2 and stored at room temperature for up to 211 days as per Example 2. Whole blood prepared as per Example 4 was used in whole blood clotting assays, assessed in this example by the Visual Clotting Assessment method as per Example 5. After storage and at each time point, blood samples (citrated, pooled) were aliquoted into the tubes, final volume of 4 ml and the tube containing the sample subjected to the standard whole blood clotting assay as per Example 5. All steps were carried out at room temperature. Controls using freshly diluted OsPA in liquid form were performed at each time point in addition to appropriate controls that were devoid of OsPA.

Example 11.2—Results and Discussion

Figure 13:
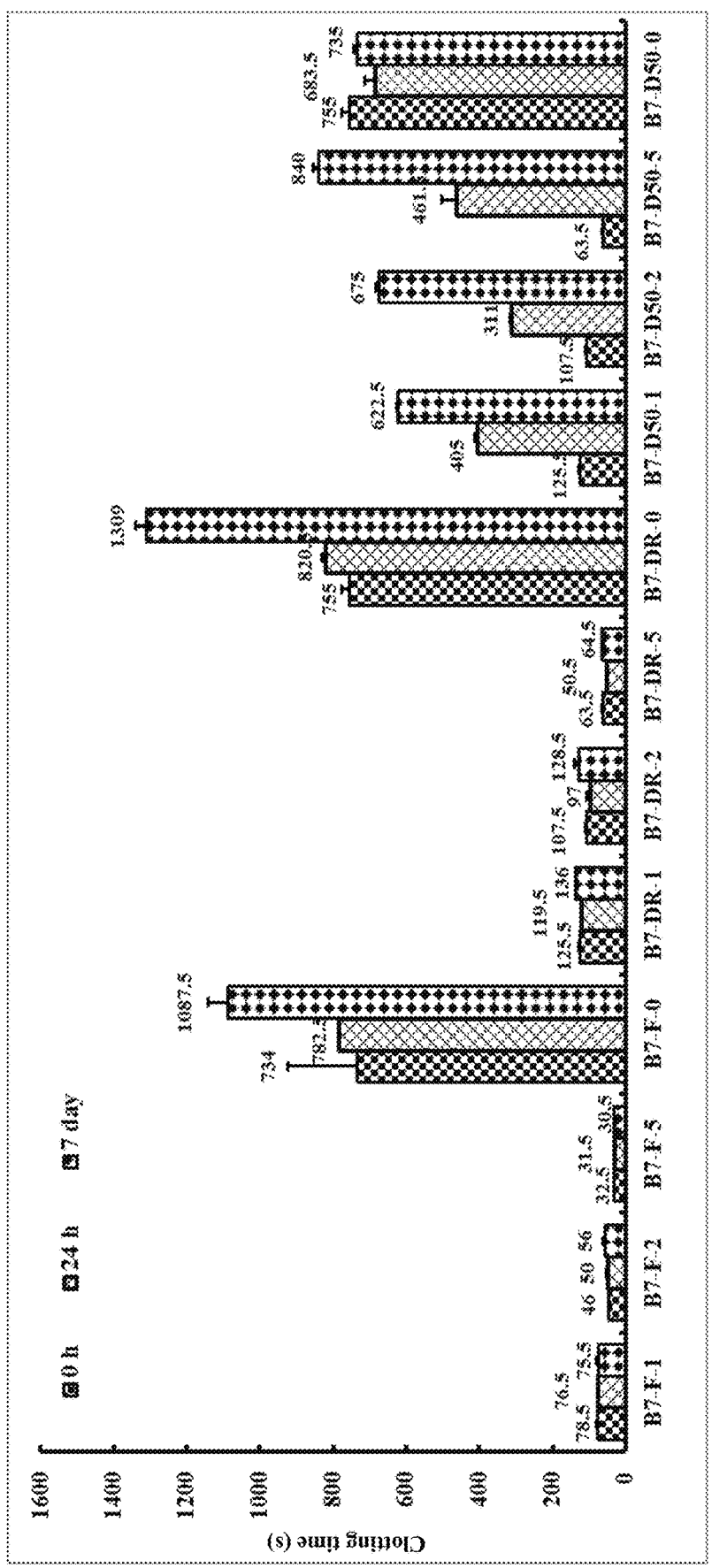
FIG. 13 shows clotting times in seconds for recalcified citrated blood after incubation at 50 C. Identifying code for samples: 'B'=BD tube; '7'=pH 7.4; 'F'=freshly diluted OsPA, not dried; DR'=dried and kept at room temperature; 'D50'=dried and kept at 50 C; '0, 1, 2 or 5'=0, 1, 2 or 5 µg OsPA. Vertical bars represent storage for zero, one and seven days.
Figure 14:
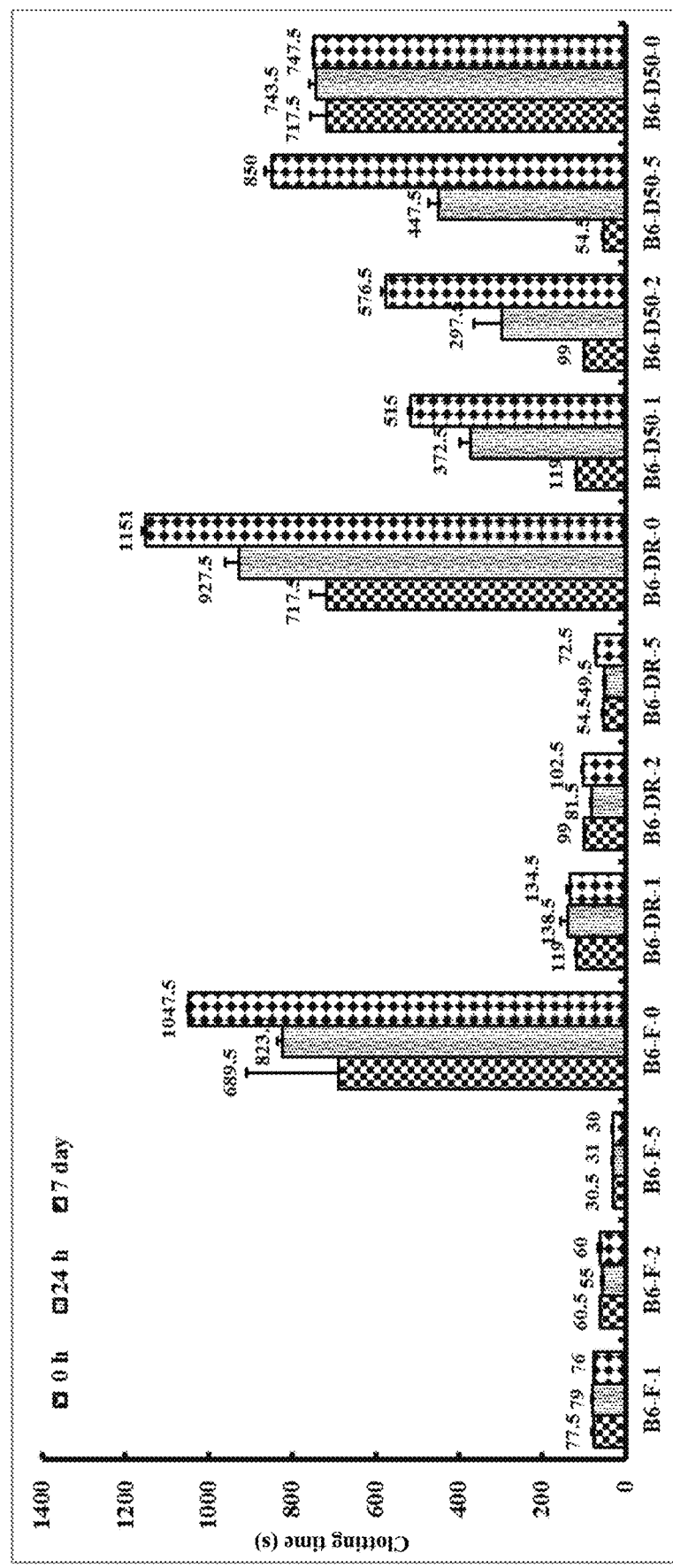
FIG. 14. Clotting times in seconds for recalcified citrated whole blood after incubation at 50° C. Identifying code for samples: 'B'=BD tube; '6'=pH 6.0; 'F'=freshly diluted OsPA, not dried; DR'=dried and kept at room temperature; 'D50'=dried and kept at 50° C.; '0, 1, 2 or 5'=0, 1, 2 or 5 µg OsPA. Vertical bars represent storage for zero, one and seven days.

FIGS. 13 and 14 show the results of the 50° C. stability trial with BD tubes. FIGS. 15-18 show results with Greiner tubes.

Based on these results, the corresponding experiment in Greiner tubes was modified so as to use a single amount of OsPA (1 µg). Results in FIGS. 15 (pH 7.4) and 18 (pH 6.0) showed that the OsPA was much more stable in the Greiner tubes than in the BD tubes (compare FIGS. 13 and 15 and FIGS. 14 and 16). Accordingly, the experiment was continued for 30 days rather than the 7 day cut off for the BD experiment.

Figure 15:
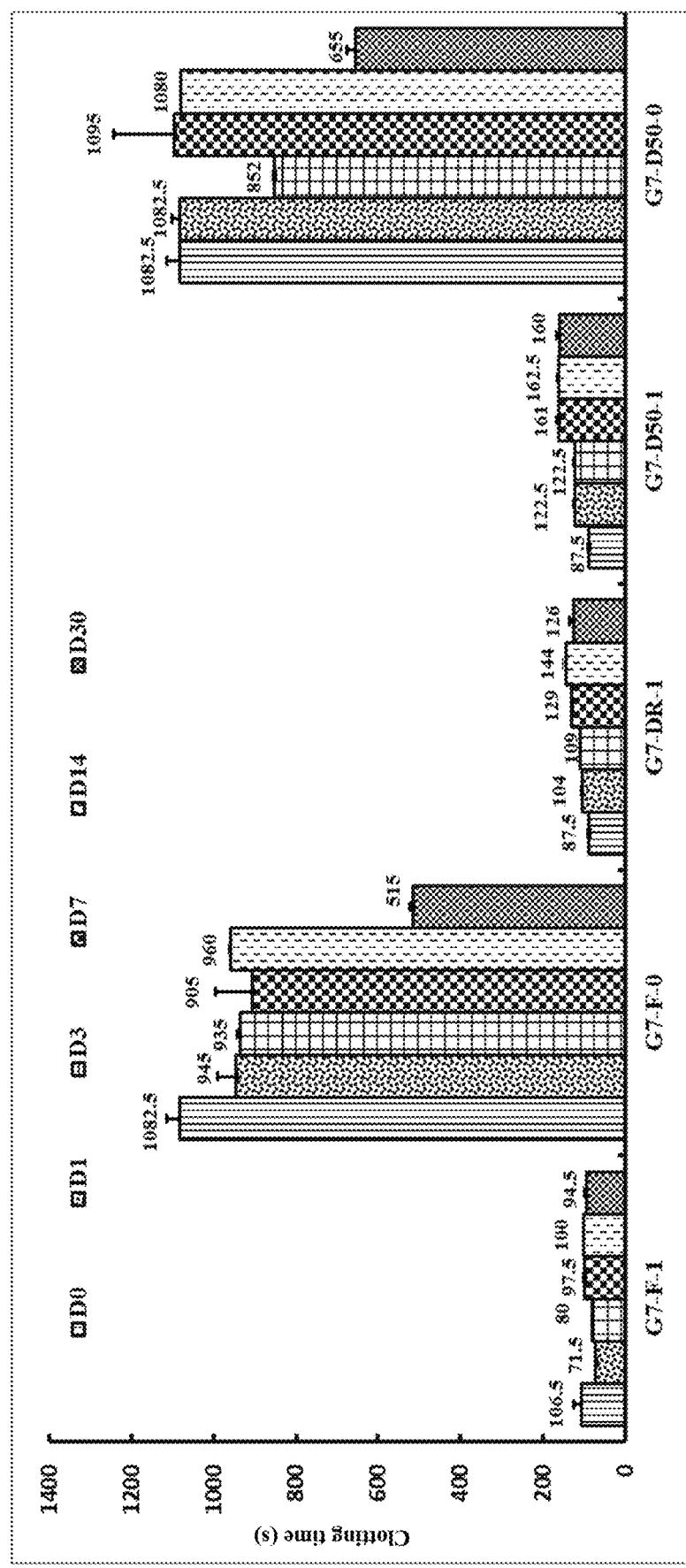
FIG. 15 shows clotting times in seconds for recalcified citrated blood after incubation at 50° C. Identifying code for samples: 'G'=Greiner tube; '7'=pH 7.4; 'F'=freshly diluted OsPA, not dried; DR'=dried and kept at room temperature; 'D50'=dried and kept at 50° C.; '0, 1'=0 or 1 µg OsPA. Vertical bars represent storage for zero, 1, 3, 7, 14 and 30 days respectively.
Figure 16:
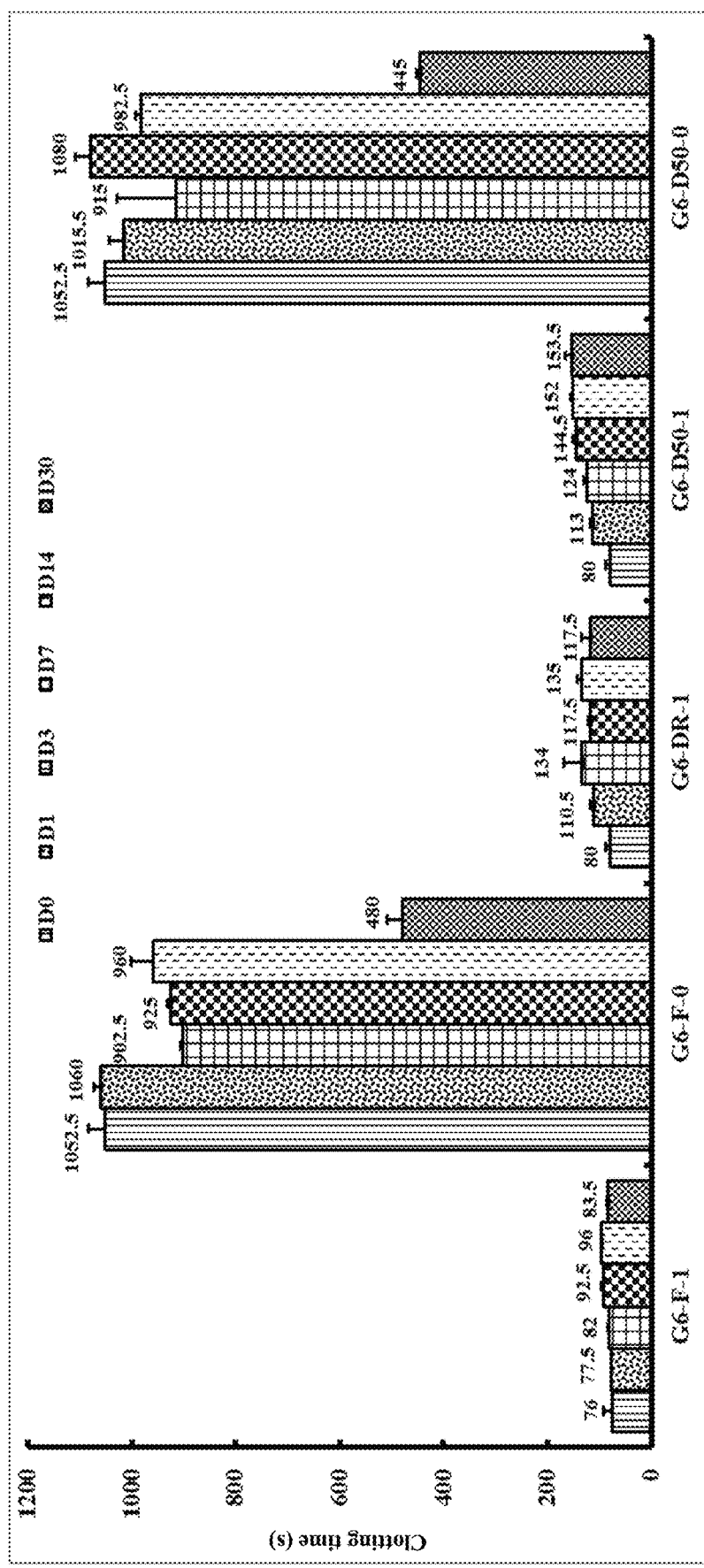
FIG. 16 shows clotting times in seconds for recalcified citrated blood after incubation at 50° C. Identifying code for samples: 'G'=Greiner tube; '6'=pH 6.0; 'F'=freshly diluted OsPA, not dried; DR'=dried and kept at room temperature; 'D50'=dried and kept at 50° C.; '0 or 1'=0 or 1 μg OsPA. Vertical bars represent storage for zero, 1, 3, 7, 14 and 30 days respectively.

After 30 days, the clotting time for the 50° C. tube was 153.5 seconds compared with 117.5 seconds for the tube kept at room temperature and 83.5 seconds for the fresh control (FIG. 16). Comparison of the FIGS. 15 and 16 data also shows that adjusting the pH to 6 had a small beneficial effect (cf. FIGS. 13 and 14).

The results in FIG. 13 show that maintaining the OsPA-containing BD tubes at 50° C. led to a progressive loss of activity, such that a high percentage of the original activity had been lost by 7 days. Similar results were obtained using 1, 2 or 5 µg OsPA except that a higher percentage of the original activity was lost in the 5 µg tubes than in the 2 µg tubes which in turn lost more activity than the 1 µg tubes. This result is consistent with earlier suggestions that the proteolytic activity of OsPA may result in self-degradation, which would occur faster at higher concentrations. Another possible reason for this concentration dependence of activity loss is that the amount of Gelofusine per tube was the same in all tubes whereas the OsPA amount changed from 1-5 µg. A higher Gelofusine to OsPA ratio may give better protection. FIG. 14 shows that similar results were obtained when the pH of the Gelofusine was adjusted from 7.4 to 6.0 prior to addition of OsPA and drying. However, comparison of the clotting times after 1 and 7 days storage at 50° C. suggests that there was slightly slower loss of activity at pH 6 than at pH 7.4. This also fits the "proteolytic loss of activity" hypothesis.

The results clearly show that the loss of activity was greater in the BD than in the Greiner tubes. One possible reason is that the surfactant used may not have been suited to the type of plastic in the BD tubes. It should be noted that the rate of loss of activity in the Greiner tubes at 50° C. was not much greater than the rate of loss in the corresponding experiment at room temperature. This may be due to excess moisture in the film at the lower temperature. It should be noted that commercially produced blood collection tubes are sealed under vacuum, which may limit the amount of moisture within the surface film.

Figure 17:
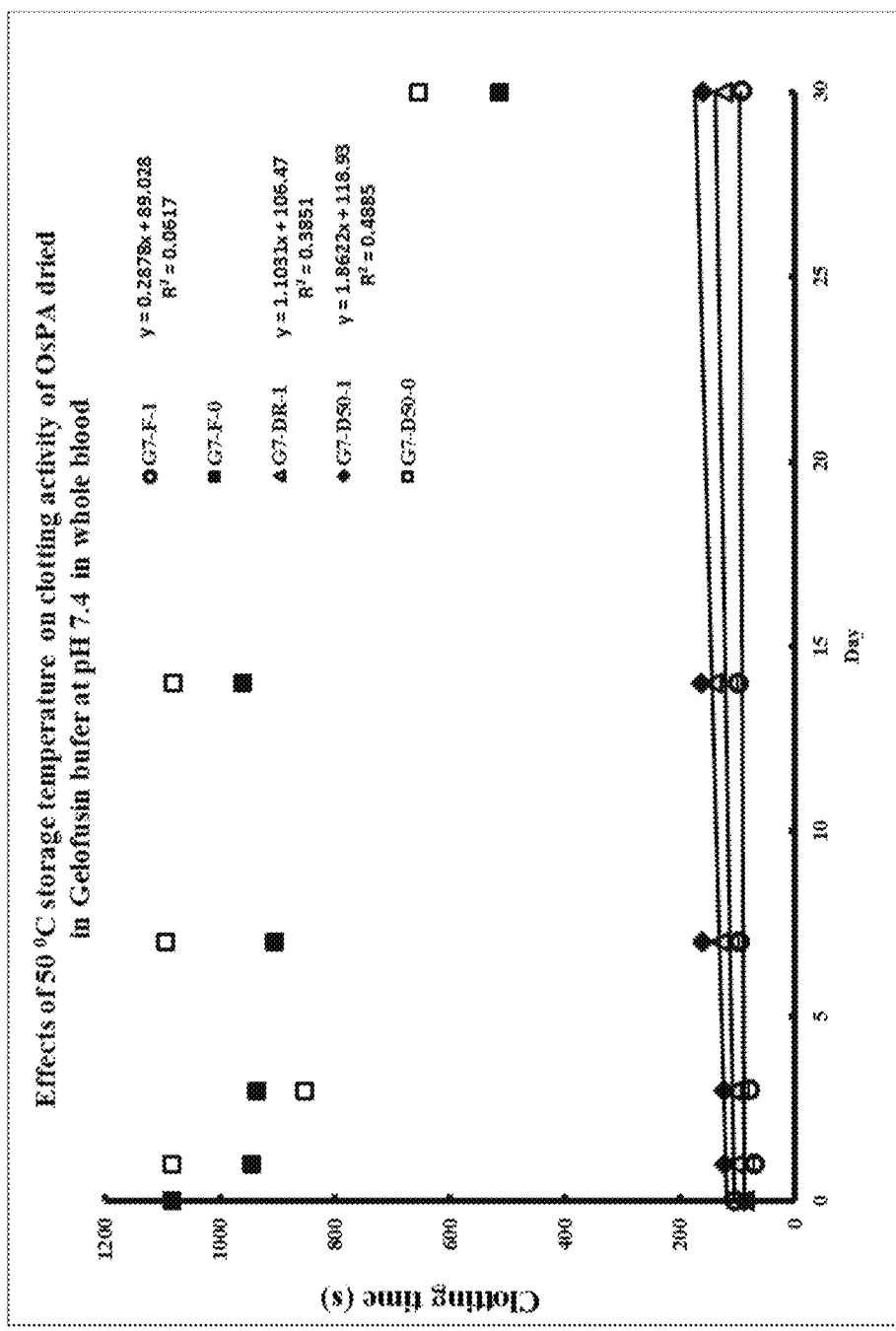
FIG. 17 shows line graphs of data from FIG. 15.
Figure 18:
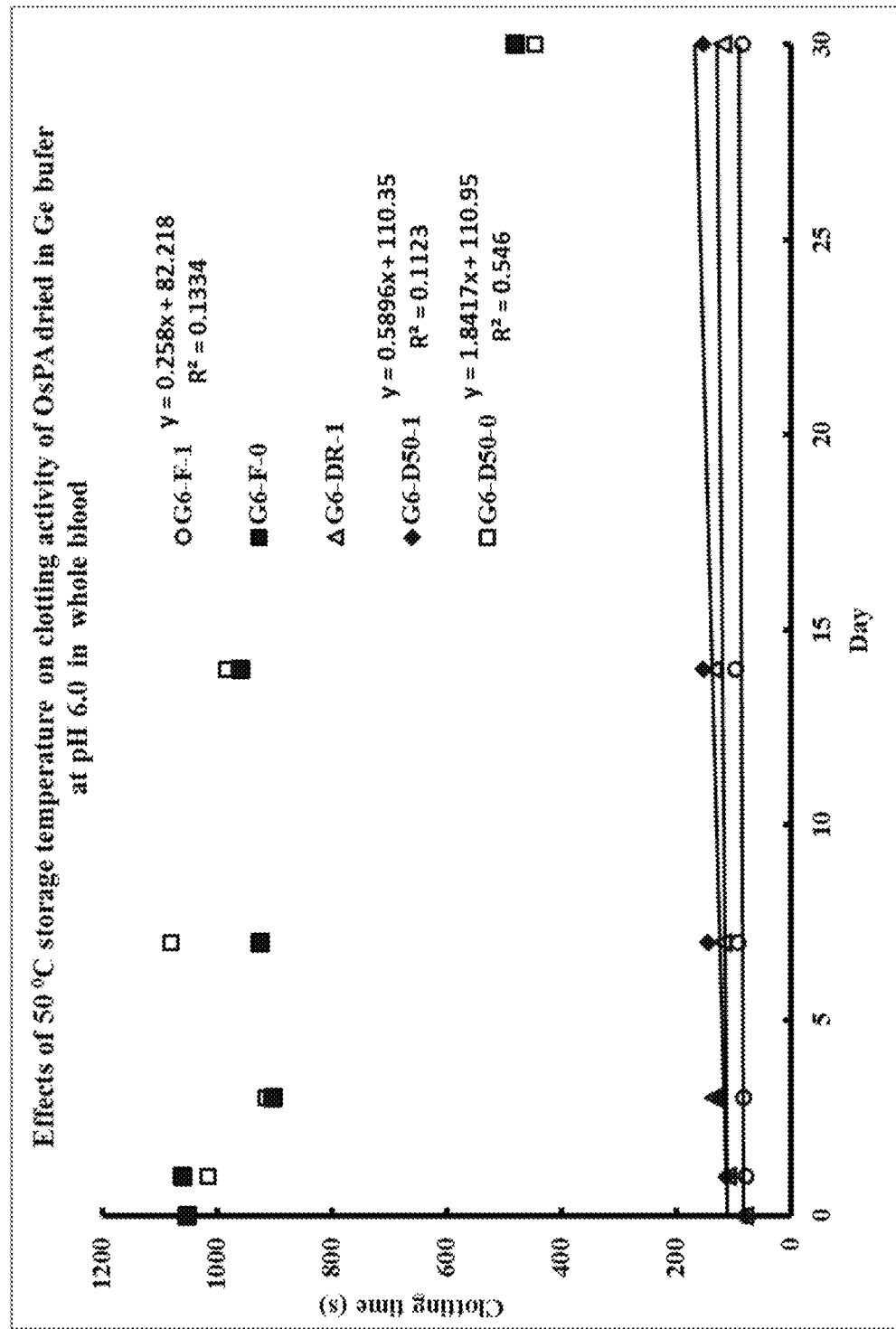
FIG. 18 shows line graphs for data from FIG. 16.

The clotting times in FIGS. 15 and 16 were plotted as line graphs in an attempt to determine the rate of loss of activity at 50° C., per FIGS. 17 and 18, respectively. The slope of the line of best fit for the 50° C. data in FIG. 17 was an increase in clotting time of 1.86 seconds per day of storage. The corresponding slope for the room temperature storage in Example 9 was 0.79 seconds per day (based on the initial rate).

Example 12—Stability of Clotting Compositions Relative to Irradiation

Example 12.1—Introduction

Irradiation is routinely used in the commercial production of standard blood collection tubes as a means of sterilization.

This experiment aimed to investigate the effect on OsPA of gamma irradiation at an industrially relevant dose of 15 kGy. The experiment was conducted in two parts: Part 1: OsPA with gelofusine, Part 2: OsPA and snake-venom derived ecarin with gelofusine and trehalose.

In Part 1, tubes were prepared as per Example 2. Freshly diluted prothrombin activator (OsPA, either 1 μg, or 5 μg,) was placed in Greiner White top blood collection tubes (Code #456001)+hydrophilic surfactant (20 μL of 2.41 g/L in water) and either 50 μL of 4% w/v Gelofusine; Hepes buffer pH7.4, or Hepes buffer pH 7.4+0.5% Dextran+0.5% BSA. The tubes were then dried using a vacuum dessicator as per Example 2 and stored at room temperature while irradiation was done as per Example 3. Eight tubes were manufactured with each formulation, being four tubes for irradiation as per Example 3 and four tubes to be stored at room temperature as per Example 2.

Tubes to be irradiated were sent to the irradiation facility on Day 1 after preparation. After irradiation with 15 kGy, the tubes were returned and assayed on Day 8. Irradiation was conducted as per Example 3 at the Gammacell 220 irradiation facility (ANSTO, Building 23, New Illawarra Road, Lucas Heights, NSW 2234, Australia) at 1.92 kGy/h for 7.88 hours at 23.4° C. for 7.88 hours, delivering a total dose of 15.1 kGy.

For Part 2, tubes were prepared as per Example 2 including coating with hydrophilic surfactant. Prothrombin activator (OsPA or ecarin), was prepared by diluting concentrated solutions into Gelofusine containing 6% or 10% trehalose. Twenty μL aliquots containing either 1 μg, or 5 μg, of OsPA or 2 IU of ecarin, were placed in Greiner White top plain tubes (Code number 456001) and BD Red top no additive tubes (Code number 366408). The tubes were then dried using a Genevac as per Example 2 and stored at room temperature while irradiation was done as per Example 3. Thirty-two OsPA-containing tubes and eight ecarin-containing tubes were manufactured, being twenty tubes for irradiation as per Example 3 and twenty tubes to be stored at room temperature as per Example 2.

Tubes to be irradiated were again sent to the irradiation facility on Day 1 after preparation. After irradiation on Day 8 with 15 kGy, the tubes were returned and assayed on Day 20. Irradiation was conducted as per Example 3 at the Gammacell 220 irradiation facility (ANSTO, Building 23, New Illawarra Road, Lucas Heights, NSW 2234, Australia) at 1.92 kGy/h for 7.88 hours at 23.4° C. for 7.88 hours, delivering a total dose of 15.1 kGy.

Whole blood prepared as per Example 4 was used in whole blood clotting assays, assessed in this example by the Visual Clotting Assessment method as per Example 5. All steps were carried out at room temperature. Controls using freshly diluted OsPA in liquid form were performed in addition to appropriate controls that were devoid of OsPA. All tubes with clotted blood were centrifuged after 35 minutes. Serum from individual tubes was imaged and collected for biochemical analyte testing.

Example 12.2—Part 1 Results and Discussion

The results in FIG. 19 show that irradiation with 15 kGy led to a loss of most of the clotting activity in all samples with 1 μg OsPA. Gelofusine gave significant protection of the clotting activity, that is, tubes retained ~20% activity of non-irradiated tubes whereas in the Hepes buffer alone, nearly all of the activity was lost. Both Dextran and BSA in the Hepes buffer and Gelofusine gave protection of the clotting activity, Gelofusine doing so to a greater extent.

There was also some loss of activity in the tubes which had been dried and stored at room temperature but not irradiated (FIG. 19A), consistent with earlier experiments which showed loss of activity when samples were dried by vacuum dessicator. This did not significantly affect the results in the Gelfusine tubes or in the tubes containing Hepes with BSA and dextran. However, with Hepes alone, the tubes containing 1 μg OsPA lost most activity without irradiation, confirming earlier tests.

Figure 19A:
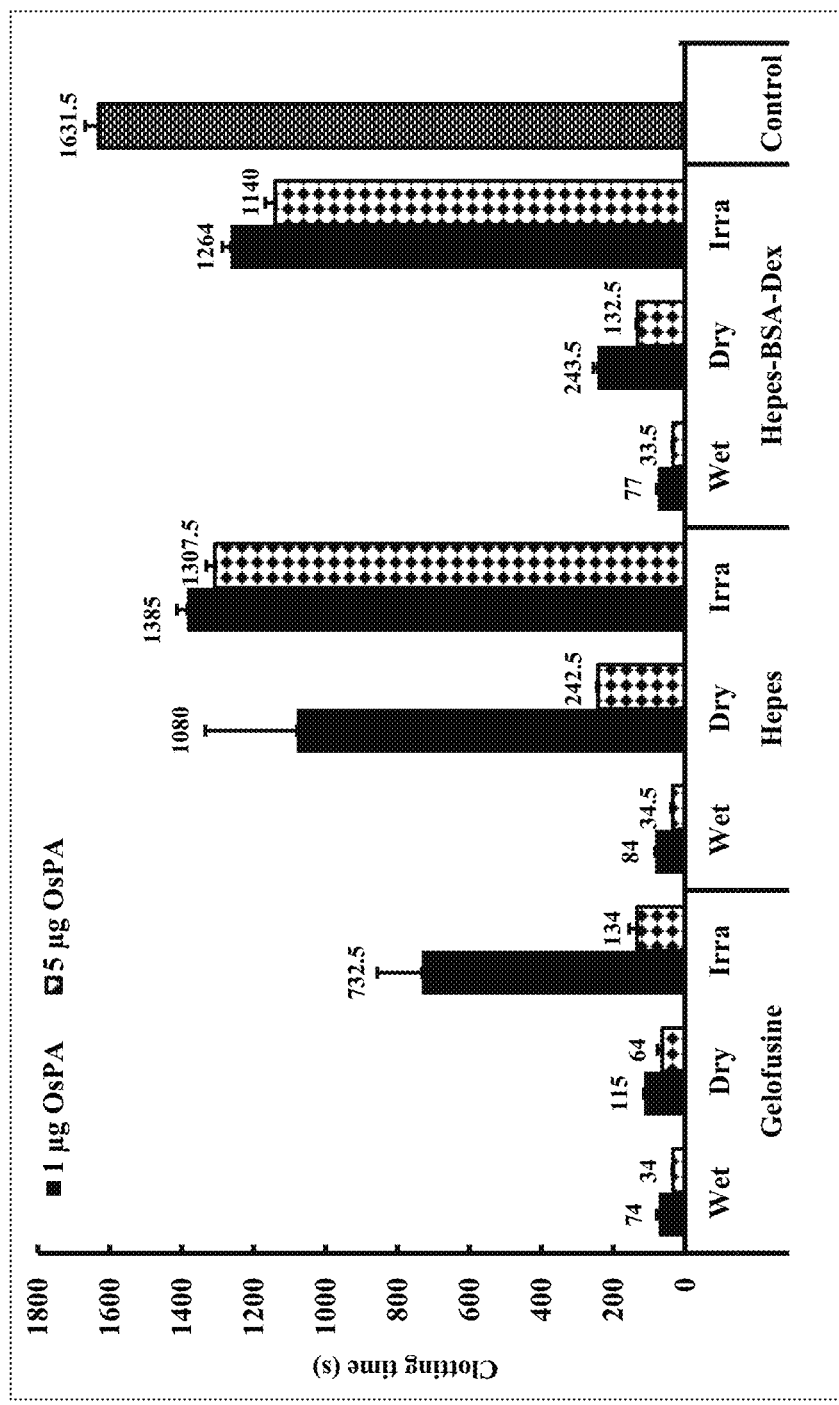
FIG. 19A shows clotting times in whole blood clotting assay for the tubes as listed above and for fresh controls and OsPA devoid control. Irradiated tubes were treated with 15 kGy gamma radiation. Each bar represents the mean of two estimates.

The concentration dependence of clotting times shown in FIG. 4 allows an estimation to be made of how much of the clotting activity had been lost due to irradiation. For example, the clotting time of the irradiated tubes containing 5 μg OsPA was 134 seconds (FIG. 19a). The clotting time in a tube containing 0.3 μg OsPA was 137 seconds (FIG. 4). Therefore the activity of the 5 μg OsPA after irradiation was approximately the same as the activity of 0.3 μg of fresh OsPA. Similarly, 1 μg of irradiated OsPA in Gelofusine gave a clotting time of 733 seconds compared with 744 seconds for 0.05 μg of fresh OsPA.

Example 12.3—Part 2 Results and Discussion

Figure 19B:
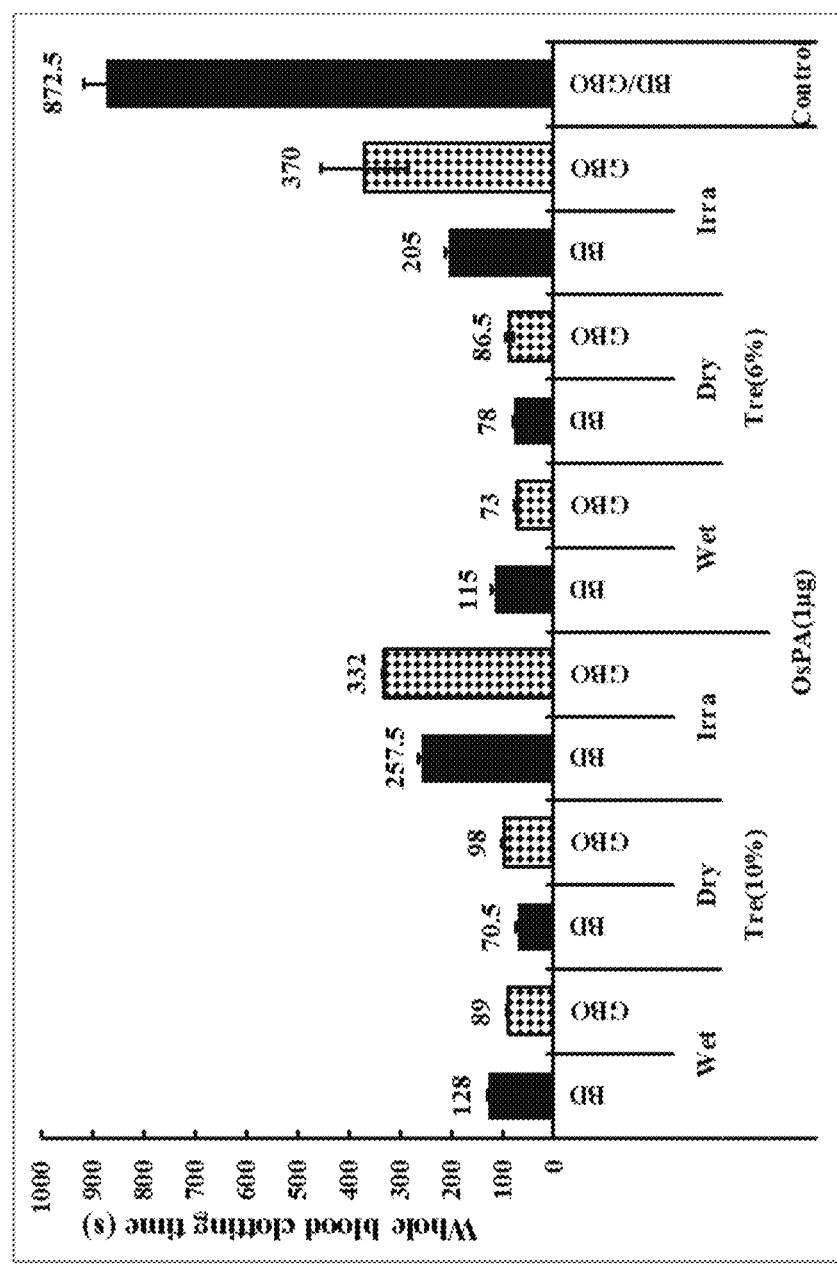
FIG. 19B shows clotting times in whole blood clotting assay for the tubes as listed above and for fresh controls and OsPA devoid control. Irradiated tubes were treated with 15 kGy gamma radiation. Each bar represents the mean of two estimates (BD and GBO are codes for two different plain blood collection plastic tubes). All tubes apart from controls were formulated with trehalose dissolved in gelofusine.

FIG. 19B shows the results of the trials with OsPA tubes formulated with Gelofusine and 6% or 10% trehalose. The results show that irradiation with 15 kGy led to some loss of the clotting activity in all samples at day 12 after irradiation. However, Gelofusine containing 6% and 10% trehalose gave significant protection of the clotting activity of OsPA compared with the results shown in FIG. 19A. Furthermore, the clotting time of 1 μg OsPA dried in Gelofusine with 10% trehalose was about 5 min after irradiation.

Figure 19C:
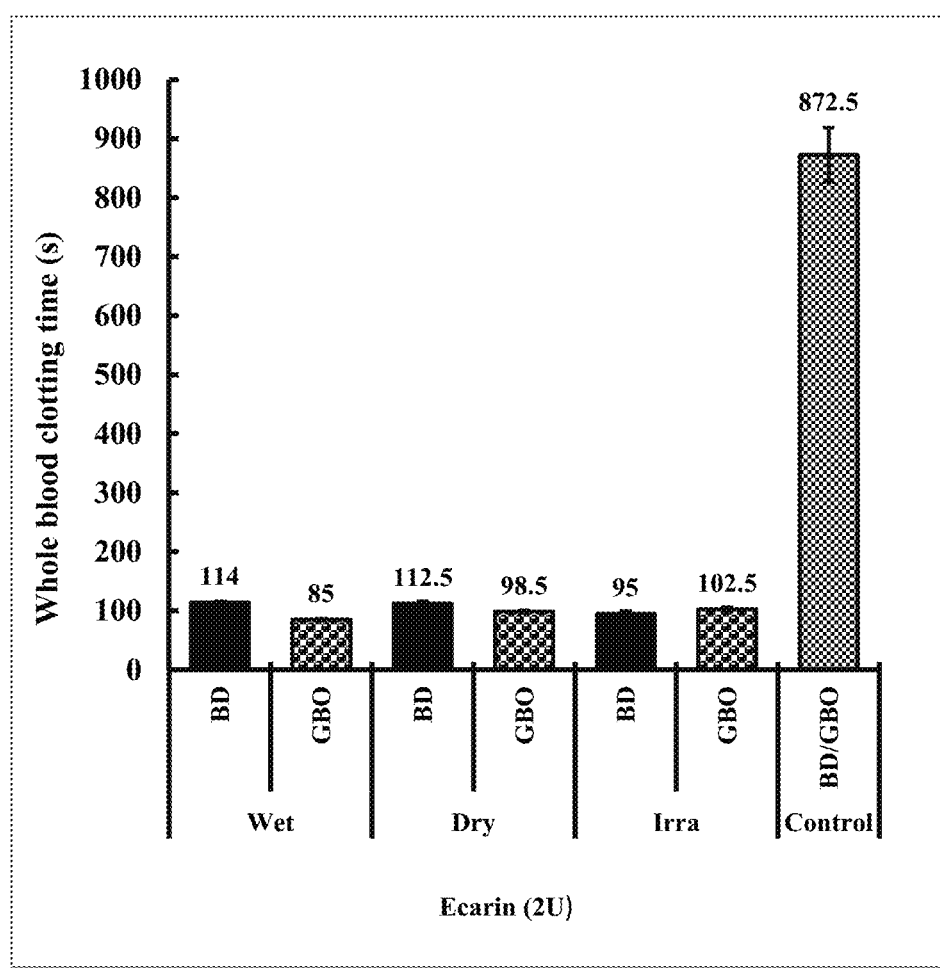
FIG. 19C shows clotting times for the tubes as listed above and for fresh controls and OsPA devoid control. Irradiated tubes were treated with 15 kGy gamma radiation. Each bar represents the mean of two estimates (BD and GBO are codes for two different plain blood collection plastic tubes). All tubes apart from controls were formulated with trehalose dissolved in gelofusine.

The results in FIG. 19C show that irradiation with 15 kGy did not affect the clotting activity of ecarin at 2 IU dried in Gelofusine containing 10% trehalose.

Example 13—Stability of Clotting Compositions Relative to Irradiation II

This experiment aimed to investigate the effect on OsPA of gamma irradiation at an industrially relevant dose of 25 kGy with tubes formulated with Ecarin. The experiment was conducted in two parts: Part 1: Ecarin with gelofusine, Part 2: Stability at room temperature of irradiated tubes.

In Part 1, tubes were prepared as per Example 2. Freshly diluted Ecarin 2U was placed in Greiner White top blood collection tubes (Code #456001)+hydrophilic surfactant (20 μL of 2.41 g/L in water) and 20 μL of 4% w/v Gelofusine. The tubes were then dried using a Genevac as per Example 2 and stored at room temperature while irradiation was done as per Example 3.

Tubes to be irradiated were sent to the irradiation facility on Day 1 after preparation. After irradiation with 25 kGy, the tubes were returned and assayed on Day 7. Irradiation was conducted as per Example 3 at the Gammacell 220 irradiation facility (ANSTO, Building 23, New Illawarra Road, Lucas Heights, NSW 2234, Australia)

For Part 2, tubes with and without irradiation treatment were stored at room temperature as per Example 2.

Whole blood prepared as per Example 4 was used in whole blood clotting assays, assessed in this example by the Visual Clotting Assessment method as per Example 5. All steps were carried out at room temperature. Controls using freshly diluted OsPA in liquid form were performed in addition to appropriate controls that were devoid of OsPA. All tubes with clotted blood were centrifuged after 35 minutes.

Example 13.1—Results and Discussion

Figure 20:
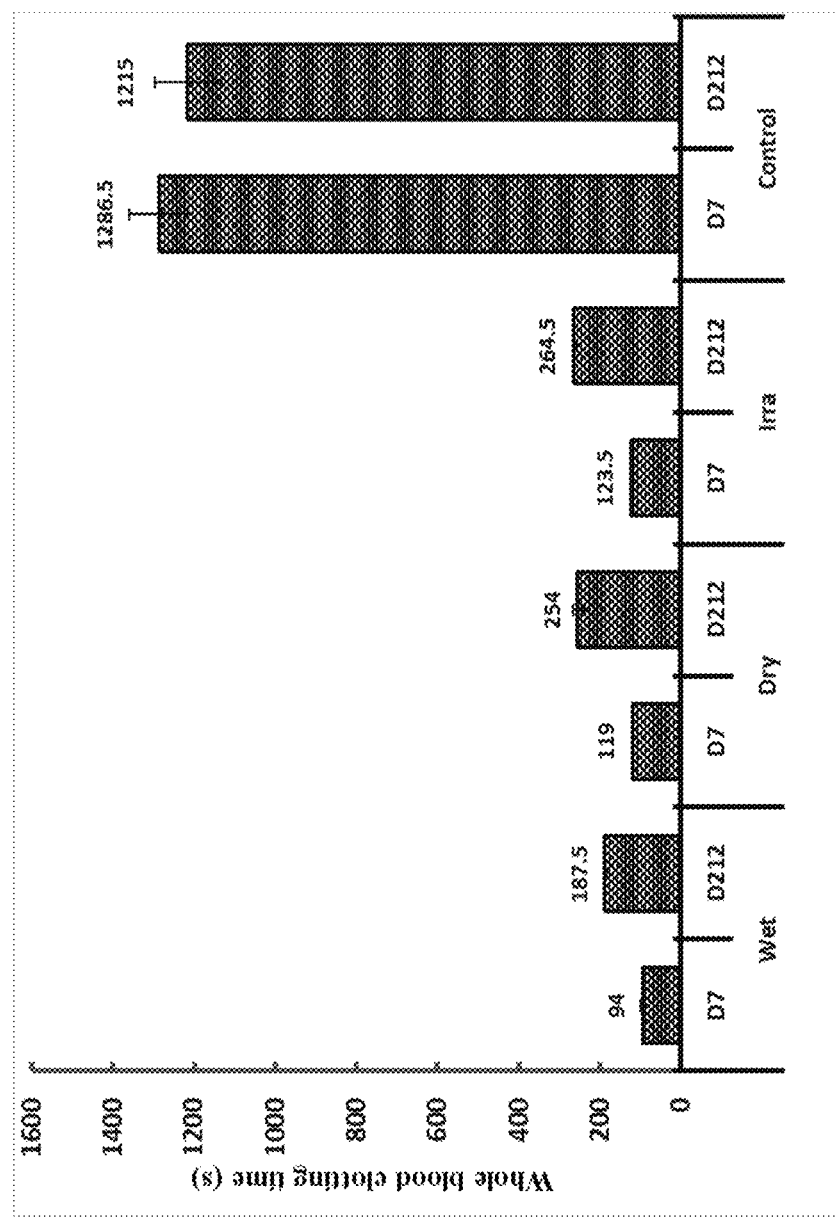
FIG. 20 shows clotting times in whole blood for Ecarin containing tubes and for fresh controls and OsPA devoid control. Irradiated tubes were treated with 25 kGy gamma radiation and stored at Room Temperature for 212 days. All tubes apart from controls were formulated with gelofusine.

The results in FIG. 20 show that irradiation with 25 kGy led to a minor loss of clotting activity at Day 7 in samples with 2U Ecarin (123 seconds) compared to dried and not irradiated (119 seconds). After 212 days at room temperature, there was again a minor difference between tubes which has been irradiated compared to those tubes which had not been irradiated (264 seconds compared to 254 seconds). This example illustrates that the prothrombin activator Ecarin in an appropriate formulation exhibits stability in the presence of irradiation and after subsequent long term storage at room temperature.

Example 14—Stability of Clotting Compositions Relative to Storage Time, Temperature and Other Additives II

Example 14.1—Introduction

Experiments were carried out to determine if the stability of OsPA when stored or transported at room temperature and at elevated temperatures such as at 50° C. could be enhanced by the use of sugars and other additives. Tubes were prepared as per Example 2. Freshly diluted OsPA 1 µg was placed in Greiner White top plain blood collection tubes (Code #456001) (+hydrophilic surfactant (20 µL of 2.41 g/L in water)+/−20 µL of 4% w/v Gelofusine, and containing 10% of trehalose, mannose, sucrose and sorbitol, 1 mM benzamidine and 0.1 mM EDTA. In part 1, the tubes were then dried using a vacuum dessicator as per Example 2 and stored at 50° C. for up to 71 days (see FIG. 21). In part 2, the tubes were then dried using a vacuum dessicator as per Example 2 and stored at room temperature for up to 392 days (see FIG. 22). In part 3, additional tubes were prepared as per Example 2 using OsPA 1 µg placed in BD red top plain blood collection tubes (Code #3276916) (+hydrophilic surfactant (20 µL of 2.41 g/L in water)+20 µL of 4% w/v Gelofusine, and containing 6 or 10% of lactulose. In part 3, the tubes were then dried using a Genevac vacuum drier as per Example 2 and stored at room temperature for 22 days (see FIG. 23).

Whole blood prepared as per Example 4 was used in whole blood clotting assays, and assessed by the Visual Clotting Assessment method as per Example 5. After storage, blood samples (citrated, pooled) were aliquoted into tubes, with a final volume of 4 mL. Tubes containing the samples were then subjected to the standard whole blood clotting assay as per Example 5. All steps were carried out at room temperature. Controls using freshly diluted OsPA were performed at each time point in addition to appropriate controls that were devoid of prothrombin activator.

Example 14.2—Part 1—Results and Discussion

Figure 21:
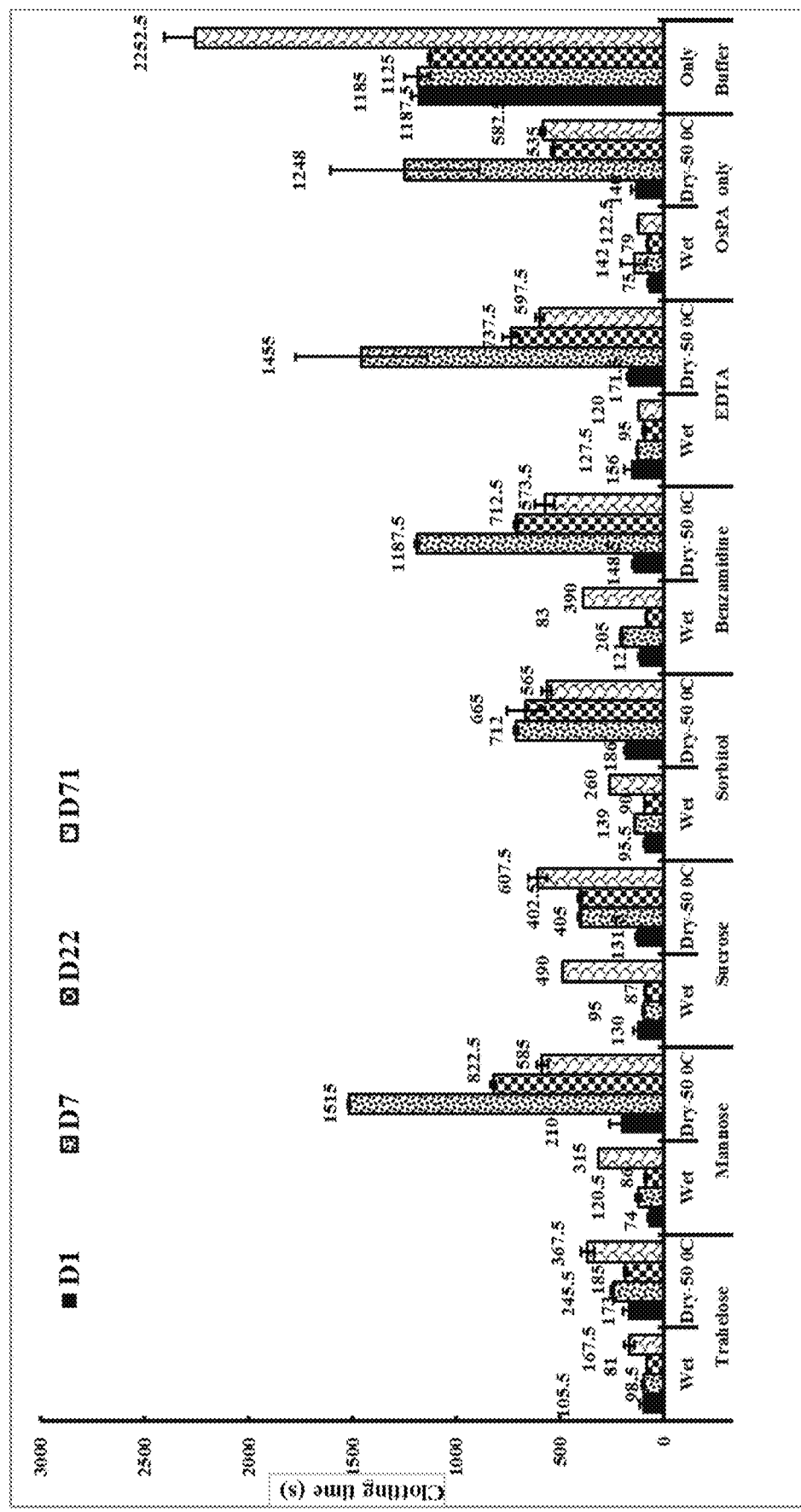
FIG. 21 shows activity of dried OsPA in different sugar and other formulations in plain blood collection plastic tubes at 50° C. in clotting recalcified whole blood.

FIG. 21 shows a time course in which major loss of activity with OsPA was found at 7 days in all samples when the samples were dried in a vacuum-dessicator. Subsequent storage at 50° C. gave no further loss of activity. Indeed, some samples showed partial recovery of activity. It is possible that the initial loss of activity may have been due to incomplete drying of samples, such that the presence of moisture was the cause of the initial loss of activity. The trehalose-containing sample had a clotting time of 367 seconds after 10 weeks at 50° C. and the other sugars around 580-600 seconds after the same period. This is very encouraging assuming that the initial loss of activity can be prevented, and suggests that agents such as colloids with stabilising additives can effectively stabilize the activity of prothrombin activators when stored at elevated temperatures over extended periods of time.

Example 14.3—Part 2—Results and Discussion

Figure 22:
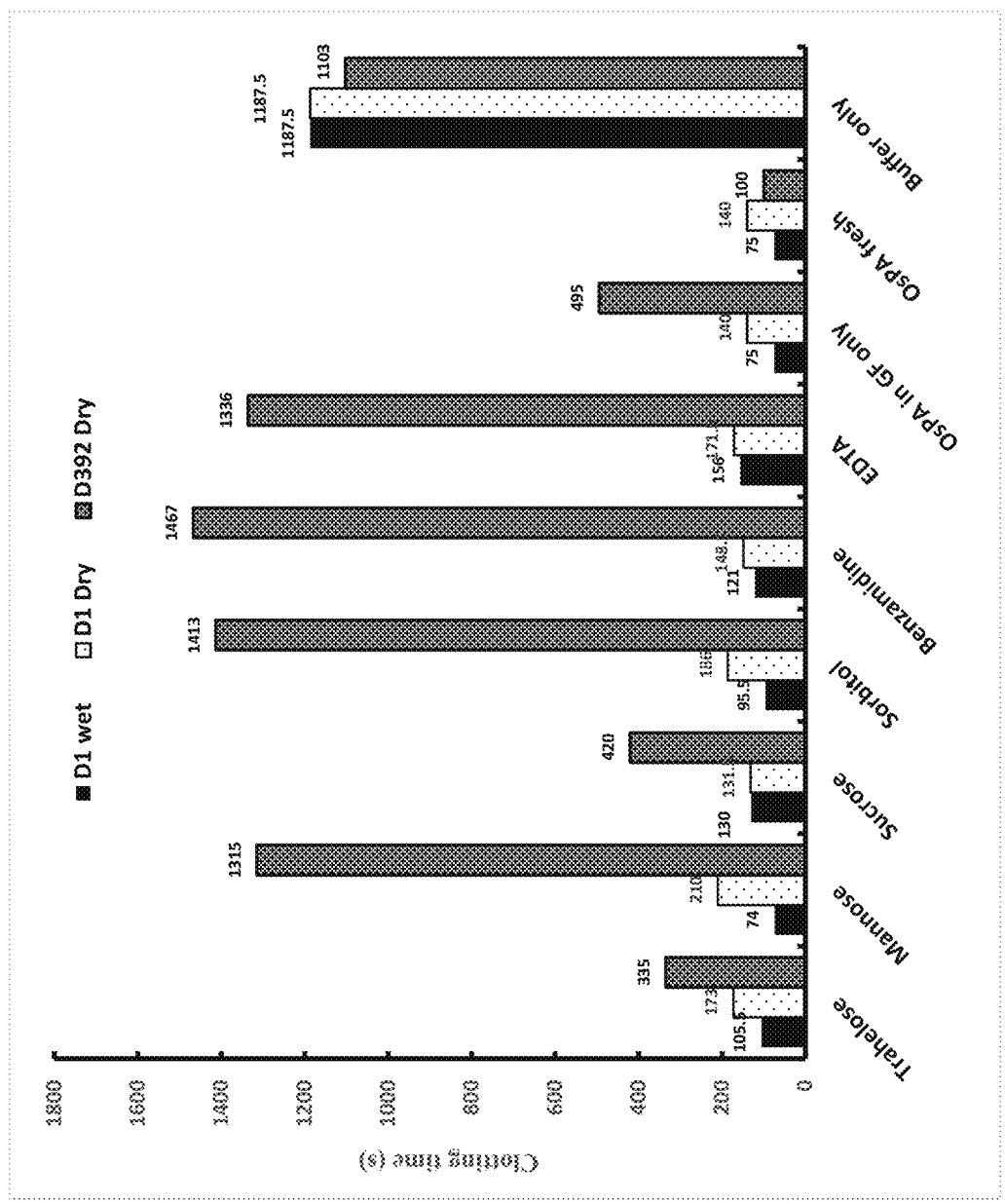
FIG. 22 shows activity of dried OsPA in different sugar and other formulations in plain blood collection plastic tubes at Room Temperature in clotting recalcified whole blood.

FIG. 22 illustrates that although the drying process leads to a decrease in activity at T0, subsequent storage at room temperature for 392 days showed retention of activity within 425 seconds in samples formulated with Trehalose and sucrose. Formulations with other additives appeared to have a negative effect on clotting activity. This is also very encouraging assuming that the initial loss of activity can be prevented, and suggests that agents such as colloids with stabilising additives can effectively stabilize the activity of prothrombin activators when stored at commercially relevant temperatures over extended periods of time.

Example 14.4 Part 3—Results and Discussion

Figure 23:
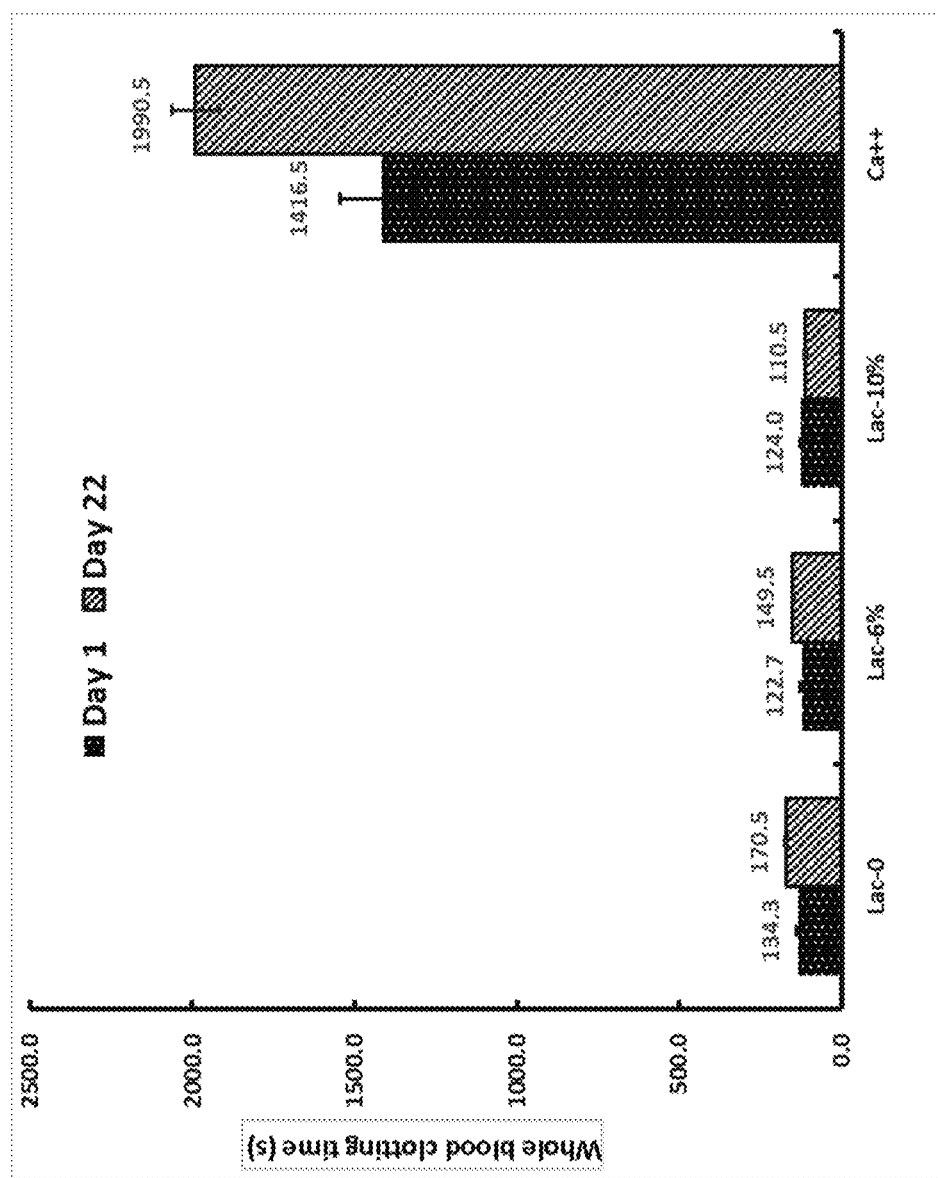
FIG. 23 shows activity of dried OsPA formulated in gelofusine and lactulose 6 and 10% in plain blood collection tubes at Room Temperature in clotting recalcified whole blood.

FIG. 23 illustrates that lactulose when formulated with gelofusine appears to have a protective effect from the drying process at T0. Although only stored for 22 days at Room Temperature, the results show an improvement in clotting time with 10% lactulose, indicating that there may be a stabilising effect on OsPA over extended periods of time.

Example 15: Stability of Clotting Compositions Relative to Storage Time, Temperature and Other Additives III

Example 15.1—Introduction

Experiments were carried out to determine if the stability of Ecarin when stored or transported at room temperature could be enhanced by the use of sugars and other additives. Tubes were prepared as per Example 2. Freshly diluted Ecarin 1U was placed in Greiner White top plain blood collection tubes (Code #456001) (+hydrophilic surfactant (20 µL of 2.41 g/L in water)+/−20 µL of 4% w/v Gelofusine, and containing 10% of trehalose, mannose, sucrose and sorbitol, 1 mM benzamidine and 0.1 mM EDTA. The tubes were then dried using a vacuum dessicator as per Example 2 and stored at room temperature for up to 392 days (see FIG. 23)

Recalcified, citrated whole blood prepared as per Example 4 was used in whole blood clotting assays, and assessed by the Visual Clotting Assessment method as per Example 5. After storage, blood samples (citrated, pooled) were aliquoted into tubes, with a final volume of 4 mL. Tubes containing the samples were then subjected to the standard whole blood clotting assay as per Example 5. All steps were carried out at room temperature. Controls using freshly diluted OsPA were performed at each time point in addition to appropriate controls that were devoid of prothrombin activator.

Example 15.2—Results and Discussion

Figure 24:
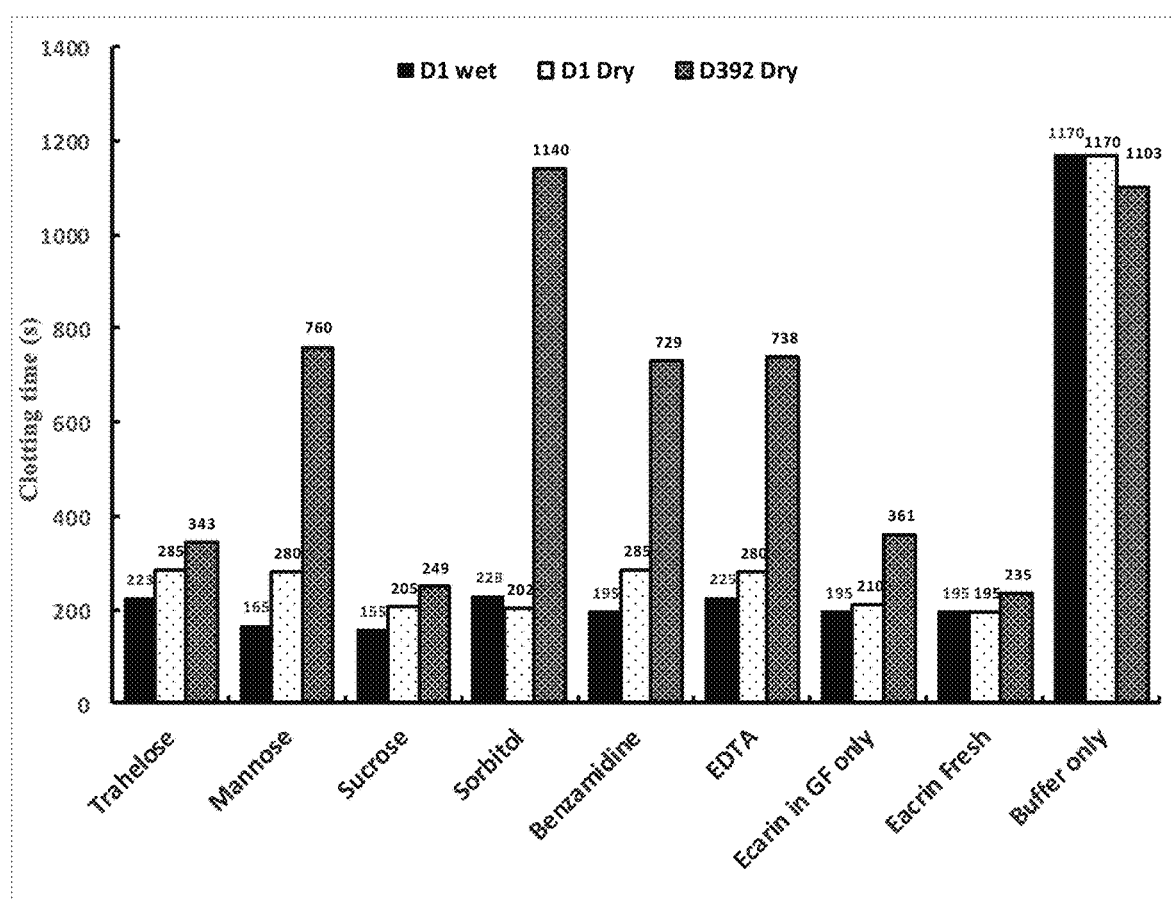
FIG. 24 shows activity of dried Ecarin in different sugar and other formulations in plain blood collection plastic tubes at Room Temperature in clotting recalcified whole blood.

FIG. 24 illustrates that although the drying process leads to a decrease in activity at T0, subsequent storage at room temperature for 392 days showed retention of activity within 350 seconds in samples formulated with Trehalose and Sucrose. Formulations with other additives appeared to have a negative effect on clotting activity although not as much as in Example 13 when OspA was used as the active. This is also very encouraging assuming that the initial loss of activity can be prevented, and suggests that agents such as colloids with stabilising additives can effectively stabilize the activity of prothrombin activators when stored at commercially relevant temperatures over extended periods of time.

Example 16—Effect of Gelofusine on Analyte Detection

Example 16.1—Introduction

This study aimed to determine whether or not the addition of gelofusine to blood collection tubes had any clinically significant effect on the ability to detect range of biochemical analytes.

The following tube samples were prepared according to Example 2 in the following tubes: Greiner White top plain tube (Code number 456001, Greiner Red top serum tube (Code number 456092), BD Red top plain tube (Code number #3276916) and BD no additive tube (Code number 366408): (1) Greiner plain tube with OsPA in Hepes buffer+hydrophilic surfactant A, (2) Greiner plain tube with OsPA+gelofusine+hydrophilic surfactant A, (3) BD plain tube with OsPA in Hepes buffer+hydrophobic surfactant; (4) BD plain tube with OsPA+gelofusine+hydrophobic surfactant, (5) Greiner serum tube, (6) Greiner serum tube+gelofusine, (7) Greiner serum tube+OsPA in Hepes buffer, (8) Greiner serum tube+OsPA+gelofusine, (9) BD serum tube, (10) BD serum tube+gelofusine, (11) BD serum tube+OsPA in Hepes buffer, and (12) BD serum tube+OsPA+gelofusine.

Each of these tube samples was then used to detect a range of analytes as shown in Table 9. Analytes were tested as per Example 5.

Example 16.2—Results and Discussion

Results are shown in Table 9. OsPA added on top of the commercial serum tubes (both Greiner tubes 7 and 8 and BD tubes 11 and 12) maintained normalanalyte detection. The addition of gelofusine had no clinical impact on any of the measured analytes. The addition of gelofusine to blood collection tubes therefore appears to have no impact on the ability to detect analytes.

TABLE 9

Detection of analytes using Gelofusine in blood collection tubes

| | 1 | 2 | 3 | 4 | 5 | 6 | 7 | 8 | 9 | 10 | 11 | 12 |
|---|---|---|---|---|---|---|---|---|---|---|---|---|
| Clotting Time | <2 min | <2 min | <2 min | <2 min | ~10 min | ~8 min | <2 min | <2 min | ~10 min | ~8 min | <12 min | <2 min |
| Na | 138 | 137 | 137 | 138 | 139 | 138 | 138 | 138 | 137 | 138 | 138 | 139 |
| K | 3.8 | 3.7 | 3.6 | 3.7 | 3.8 | 3.6 | 3.7 | 3.7 | 3.7 | 3.6 | 3.7 | 3.8 |
| Cl | 103 | 103 | 104 | 103 | 105 | 104 | 105 | 104 | 104 | 105 | 105 | 106 |
| Glu | 4.6 | 4.7 | 4.7 | 4.6 | 4.7 | 4.6 | 4.5 | 4.6 | 4.6 | 4.7 | 4.7 | 4.8 |
| Urea | 4.9 | 6.8 | 6.7 | 6.8 | 6.7 | 6.8 | 6.5 | 7.1 | 6.9 | 7.1 | 6.7 | 7 |
| Crea | 101 | 98 | 99 | 100 | 103 | 101 | 101 | 104 | 102 | 105 | 102 | 101 |
| Urate | 0.22 | 0.21 | 0.21 | 0.21 | 0.22 | 0.22 | 0.22 | 0.22 | 0.22 | 0.21 | 0.22 | 0.22 |
| T Prot | 64 | 62 | 65 | 65 | 62 | 64 | 63 | 63 | 64 | 64 | 64 | 65 |
| Alb | 39 | 39 | 39 | 39 | 39 | 40 | 39 | 40 | 40 | 40 | 40 | 40 |
| Bili | 16 | 17 | 16 | 17 | 21 | 17 | 17 | 17 | 18 | 14 | 18 | 17 |
| ALP | 57 | 62 | 57 | 58 | 57 | 52 | 56 | 60 | 52 | 53 | 56 | 57 |
| GGT | 15 | 10 | 7 | 9 | 8 | 7 | 7 | 8 | 10 | 7 | 9 | 9 |
| AST | 14 | 15 | 13 | 15 | 13 | 18 | 14 | 13 | 13 | 12 | 14 | 14 |
| LD | 230 | 238 | 218 | 209 | 219 | 223 | 212 | 216 | 233 | 233 | 233 | 239 |
| Ca | 2.12 | 2.27 | 2.32 | 2.14 | 2.16 | 2.14 | 2.31 | 2.14 | 2.16 | 2.16 | 2.29 | 2.16 |
| Phos | 1.11 | 1.11 | 1.11 | 1.11 | 1.12 | 1.11 | 1.12 | 1.12 | 1.12 | 1.08 | 1.12 | 1.12 |
| Mg | 0.89 | 0.9 | 0.99 | 0.88 | 0.91 | 0.92 | 0.88 | 0.91 | 0.89 | 0.88 | 0.88 | 0.88 |
| Lipase | 29 | 29 | 30 | 30 | 30 | 31 | 31 | 30 | 29 | 29 | 32 | 30 |
| Chol | 5.7 | 5.7 | 5.6 | 5.6 | 5.8 | 5.7 | 5.8 | 5.6 | 5.8 | 5.9 | 5.9 | 5.9 |
| HDL | 1.4 | 1.4 | 1.39 | 1.4 | 1.4 | 1.5 | 1.4 | 1.4 | 1.4 | 1.4 | 1.4 | 1.4 |
| Haem Index | 0 | 0 | 0 | 0 | 0 | 0 | 0 | 0 | 0 | 0 | 0 | 0 |

REFERENCES

1. Arkin, A. P., Youvan, D. C., "An algorithm for protein engineering: simulations of recursive ensemble mutagenesis" 1992 Proc. Natl. Acad. Sci. USA 89: 7811-7815.
2. Atherton, E., Shephard, R. C., Solid Phase Peptide Synthesis—A Practical Approach 1989, IRL Press, Oxford England.
3. Ausubel et al., *Current Protocols in Molecular Biology*, Greene Publ. Assoc. and Wiley-Intersciences, 1992.
4. Bos, M. H. A., Boltz, M., St Pierre, L., Masci, P. P., de Jersey, J., Lavin, M. F., Camire, R. M., "Venom factor V from the common brown snake escapes hemostatic regulation through procoagulant adaptations" Blood 16 Jul. 2009; 114(3): 686-692.
5. Dayhoff, M. O., Schwartz, R. M., Orcutt, B. C., et al., "A model of evolutionary change in proteins. Matrices for determining distance relationships" 1978 In Atlas of protein sequence and structure (Dayhoff, M. O. ed.), vol 5, pp 345-358, National Biomedical Research Foundation, Washington D.C.
6. Delagrave, S., Goldman, E. R., Youvan, D. C., "Recursive ensemble mutagenesis" April 1993 Protein Eng. 6(3): 327-31.
7. Dimeski G. *A commentary on the effect of lipid emulsions on pathology tests.* Br J Anaesth 2009; 64:1033-6.
8. Dimeski G, Bird R. Hyperleukocytosis: *Pseudohyperkalaemia and other biochemical abnormalities in hyperleukocytosis.* Clin Chem Lab Med 2009; 47:880-1.
9. Dimeski G, McWhinney B, Jones B, Mason, R, Carter A. *Extent of bilirubin interference in Beckman-Coulter creatinine methods.* Ann Clin Biochem 2008; 45:91-2.
10. Dimeski G, Masci P P, Trabi M, Lavin M F, de Jersey J. *Evaluation of the Becton-Dickinson Rapid Serum Tube: Does it provide a suitable alternative to lithium heparin plasma tubes?* Clin Chem Lab Med 2010; 48:651-6.
11. Dimeski G, Badrick T, Flatman R, Ormiston B. *The Roche IFCC Methods for Lactate Dehydrogenase tested for duplicate errors using Greiner and BD Lithium-Heparin and Greiner serum samples.* Clin Chem 2004; 50:2391-2.
12. Dimeski G, Clague A E, Hickman P E. *Correcting and reporting of potassium results in haemolysed samples.* Ann Clin Biochem 2005; 42:119-123.
13. Filippovich, I., Sorokina, N., St Pierre, L., Filght, S., de Jersey, J., Perry, N., Masci, P. P., Lavin, M. F. "Cloning and functional expression of venom prothrombin activator protease from *Pseudonaja textilis* with whole blood procoagulant activity" British Journal of Haematology 2005; 131: 237-246.
14. Gonnet, G. H., Cohen, M. A., Benner, S. A., "Exhaustive matching of the entire protein sequence database" Jun. 5, 1992 Science 256(5062): 1443-5.
15. Jackson C M, Suttie J W, "Recent developments in understanding the mechanism of vitamin K and vitamin K-antagonist drug action and the consequences of vitamin K action in blood coagulation", *Prog Hematol.* 1977; 10:333-59.
16. Kini R M, Morita T, Rosing J. Classification and nomenclature of prothrombin activators isolated from snake venoms. Throm Haemost 2001; 86:710-711.
17. Kini R M. The intriguining world of prothrombin activators from snake venom. Toxicon 2005; 45:1133-45.
18. Kunkel, T. A., "Rapid and Efficient site-specific mutagenesis without phenotypic selection" 1985 Proc. Natl. Acad. Sci. USA, 82: 488-492.
19. Kunkel, T. A., Roberts, J. D., Zakour, R. A., "Rapid and Efficient site-specific mutagenesis without phenotypic selection" 1987 Methods in Enzymol. 154: 367-382.
20. Masci, P. P., "The Effects of Australian Snake Venoms on Coagulation and Fibrinolysis" Thesis for Masters of Science in the subject of Biochemistry, July 1986, University of Queensland, St Lucia, Brisbane, Australia.
21. Masci P P, Whitaker A N, de Jersey J. Purification and characterization of a prothrombin activator from the venom of the Australian brown snake *Psuedonaja textilis textilis*. Biochem Int 1988; 17:825-835.
22. Masci P P, Whitaker A N, Sparrow L G, de Jersey J, Winzor D J, Watters D J, Lavin M F, Gaffney P J, "Textilinins from *Pseudonaja textilis textilis*. Characterization of two plasmin inhibitors that reduce bleeding in an animal model", 2000 June; 11 (4):385-93.
23. Morita T, Iwanaga S. Purification and properties of prothrombin activator from venom of *Echis carinatus*. J Biochem 1978; 83:559-570.
24. Morita, T., Iwanaga, S., "Prothrombin activator from *Echis carinatus* venom" Meth Enzymol 1981; 80-pt. C: 303-311.
25. Nishida, S., Fujita, T., Kohno, N., Atoda, H., Morita, T., Takeya, H., Kido, I., Paine, M. J. I., Kawabata, S-i., Iwanaga, S. "cDNA Cloning and Deduced Amino Acid Sequence of Prothrombin Activator (Ecarin) from Kenyan *Echis carinatus* venom." Biochemistry 1995; 34: 1771-1778.
26. Rao V S, Kini R M. Pseutarin C, a prothrombin activator from *Pseudonaja textilis* venom: its structural and functional similarity to mammalian coagulation factor Xa-Va complex. Thromb Haemost 2002; 88:611-9.
27. Roberge, J. Y., Beebe, X., Danishefsky, S. J., "A strategy for a convergent synthesis of N-linked glycopeptides on a solid support" Science 1995 269(5221); 202-204.
28. Rosing J, Tans G. Inventory of exogenous prothrombin activators. For the Subcommittee on Nomenclature of Exogenous Hemostatic Factors of the Scientific and Standardization Committee of the International Society on Thrombosis and Haemostasis. Thromb Haemost 1991; 65:627-30.
29. Rosing J, Tans G. Structural and functional properties of snake venom prothrombin activators. Toxicon 1992; 30:1515-27.
30. Sambrook et al., *Molecular Cloning: A Laboratory Manual*, Cold Spring Harbor, N. Y., 2001
31. Scaros, O. and Fisler, R. "Biomarker technology roundup: from discovery to clinical applications, a broad set of tools is required to translate from the lab to the clinic" Biotechniques 2005; 38; S30-S32.
32. Speijer H, Govers-Riemslag J W, Zwaal R F, Rosing J. Prothrombin activation by an activator from the venom of *Oxyuranus scutellatus* (Taipan snake). J Biol Chem 1986; 261:13258-67.
33. St Pierre L, Masci P P, Filippovich I, Sorokina N, Marsh N, Miller D J, Lavin M F. Comparative analysis of prothrombin activators from the venom of Australian elapids. Mol Biol Evol 2005; 22:1853-64.
34. Tans, G., Govers-Riemslag, J. W., van Rijn, J. L., Rosing, J. J., "Purification and properties of a prothrombin activator from the venom of *Notechis scutatus scutatus*" Biol. Chem. 1985 Aug. 5; 260(16): 9366-72.
35. Watson, J. D., Hopkins, N. H., Roberts, J. W., Steitz, J. A., Weiner, A. M. Molecular Biology of the Gene. fourth edition, 1987 The Benjamin/Cummings Publishing Co., Inc., Menlo Park, Calif.

36. Yamada D, Sekya F and Morita T. Isolation and characterization of carinactivase, a novel prothrombin activator in *Echis carinatus* venom with a unique catalytic mechanism. J Biol Chem 1996; 271:5200-7.
37. Yamada, D., Morita, T., "Purification and Characterization of a $Ca^{2+}$-Dependent Prothrombin Activator, Multactivase, from the Venom of *Echis multisquamatus*" J. Biochem. 1997; 122: 991-997.
38. Yamanouye, N., Kerchove, C. M., Moura-da-Silva, A. M., Carneiro, S. M., Markus, R. P., "Long-term primary culture of secretory cells of *Bothrops jararaca* gland for venom production in vitro" Nature Protocols 2007; 1: 2763-2766.
39. Yonemura, H., Imamura, T., Soejima, K., Nakahara, Y., Morikawa, W., Ushio, Y., Kamachi, Y., Nakatake, H., Sugawara, K., Nakagaki, T., Nozaki, C., "Preparation of Recombinant α-Thrombin: High-Level Expression of Recombinant Human Prethrombin-2 and Its Activation by Recombinant Ecarin" J. Biochem. 2004; 135: 577-582.
40. EP 0 628 816
41. U.S. Pat. No. 4,227,620
42. U.S. Pat. No. 4,256,120
43. U.S. Pat. No. 4,873,192
44. U.S. Pat. No. 6,187,553
45. U.S. Pat. No. 6,413,737
46. U.S. Pat. No. 6,416,717
47. U.S. Pat. No. 6,592,613
48. U.S. Pat. No. 6,686,204
49. U.S. Pat. No. 7,488,287
50. U.S. Pat. No. 7,699,828
51. U.S. Pat. No. 8,586,323

The invention claimed is:

1. A clotting composition for preparing a serum sample, wherein the clotting composition comprises a prothrombin activator and a colloid, wherein the prothrombin activator and the colloid are present in an amount that is sufficient to produce a serum sample when the clotting composition is added to a blood sample, wherein the prothrombin activator is a group A snake venom prothrombin activator or a group C snake venom prothrombin activator, and the colloid is a gelatin-based colloid, an albumin-based colloid or a dextran-based colloid.

2. A clotting composition as claimed in claim 1, wherein the clotting composition comprises a ratio of prothrombin activator to colloid in the range of about 1:100 to about 1:800.

3. A method for preparing a serum sample comprising contacting a blood sample with a clotting composition under conditions sufficient to cause clotting of the blood sample, thereby preparing a serum sample, wherein the clotting composition comprises a prothrombin activator and a colloid, wherein the prothrombin activator is a group A snake venom prothrombin activator or a group C snake venom prothrombin activator, and the colloid is a gelatin-based colloid, an albumin-based colloid or a dextran-based colloid.

* * * * *